(12) United States Patent  
Bhatia et al.

(10) Patent No.: US 8,044,069 B2  
(45) Date of Patent: Oct. 25, 2011

(54) COMPOUNDS AS CALCIUM CHANNEL BLOCKERS

(75) Inventors: Pramila A. Bhatia, Libertyville, IL (US); George A. Doherty, Libertyville, IL (US); Irene Drizin, Wadsworth, IL (US); Helmut Mack, Ludwigshafen (DE); Richard J. Perner, Gurnee, IL (US); Andrew O. Stewart, Libertyville, IL (US); Qingwei Zhang, Grayslake, IL (US)

(73) Assignees: Abbott Laboratories, Abbott Park, IL (US); Abbott GmbH & Co. KG, Wiesbaden (DE)

( * ) Notice: Subject to any disclaimer, the term of this patent is extended or adjusted under 35 U.S.C. 154(b) by 0 days.

(21) Appl. No.: 12/571,862

(22) Filed: Oct. 1, 2009

(65) Prior Publication Data

US 2010/0093730 A1    Apr. 15, 2010

Related U.S. Application Data

(60) Provisional application No. 61/102,132, filed on Oct. 2, 2008.

(51) Int. Cl.
```
A61K 31/4015      (2006.01)
A61K 31/4025      (2006.01)
A61K 31/45        (2006.01)
A61K 31/4523      (2006.01)
C07D 207/12       (2006.01)
C07D 211/40       (2006.01)
```
(52) U.S. Cl. ........ 514/317; 514/327; 514/422; 514/424; 546/290; 548/543

(58) Field of Classification Search .................. 514/317, 514/327, 422, 424; 546/290; 548/543  
See application file for complete search history.

(56) References Cited

U.S. PATENT DOCUMENTS

| | | | |
|---|---|---|---|
| 5,229,388 A | 7/1993 | Hrib et al. | |
| 2005/0148587 A1 | 7/2005 | Fraser et al. | |

FOREIGN PATENT DOCUMENTS

| | | |
|---|---|---|
| WO | WO-0059882 A1 | 10/2000 |
| WO | WO-2007125398 A2 | 11/2007 |
| WO | WO-2008043533 A2 | 4/2008 |
| WO | WO-2008046527 A1 | 4/2008 |

OTHER PUBLICATIONS

Schafer et al. Drug Discovery Today, vol. 13, p. 913 (2008).*
Horig et al. Journal of Translational Medicine, vol. 2, p. 44 (2004).*
Angeli F. et al., "Calcium channel blockade to prevent stroke in hypertension," American Journal of Hypertension, 2004, vol. 17 (9), pp. 817-822.
Arulmoshi D. K. et al., "Migraine: Current concepts and emerging therapies," Vascular Pharmacology, 2005, vol. 43, pp. 176-187.
Bao J. et al., "Differences in Ca2+ channels governing generation of miniature and evoked excitatory synaptic currents in spinal laminae I and II," J Neurosci, 1998, vol. 18 (21), pp. 8740-8750.
Barberis M. et al., "Systhesis of a novel series of 4,4-disubstituted 2,3,4,7—tetrahydroazepines," Tetrahedron Letters, 2005, vol. 146, pp. 4847-4850.
Barnette Mary S. et al., "Association of the anti-inflammatory activity of phosphodiesterase 4 (PDE4) inhibitors with either inhibition of PDE4 catalytic activity or competition for (3H)rolipram binding," Biochemical Pharmacology, 1996, vol. 51, pp. 949-956.
Barone F. C. et al., "SB 201823-A antagonizes calcium currents in central neurons and reduces the effects of focal ischemia in rats and mice," Stroke, 1995, vol. 26, pp. 1683-1690.
Bell, "Cell specific alternative splicing increases calcium channel density in the pain pathway," Neuron, 2004, vol. 41 (1), pp. 127-138.
Berge S. M. et al., "Describe pharmaceutically acceptable salts in detail," J. Pharmaceutical Sciences, 1977, vol. 66, pp. 1.
Beuckmann C. et al., "N-type calcium channel alpha1B subunit(Cav2.2) knock-out mice display hyperactivity and vigilance state differences," J. Neurosci, 2003, vol. 23 (17), pp. 6793-6797.
Bhatia R. et al., "Fresh and globular amyloid beta protein (1-42) induces rapid cellular degeneration: evidence for AbP channel-mediated cellular toxicity," FASEB J, 2000, vol. 14 (9), pp. 1233-1243.
Bhattacharjee A. et al., "T-Type calcium channels facilitate insulin secretion by enhancing general excitability in the insulin-secreting b-cell line, INS-1," Endocrinology, 1997, vol. 138 (9), pp. 3735-3740.
Bilici D. et al., "Protective effect of T-type calcium channel blocker in histamine-induced paw inflammation in rat," Pharmacological Research, 2001, vol. 44 (6), pp. 527-531.
Bowersox S. S. et al., "Selective N-type neuronal voltage-sensitive calcium channel blocker SNX-111 produced spinal antinociception in rat models of acute persistent and neuropathic pain," J. Pharmacol. Exp. Ther, 1996, vol. 279 (3), pp. 1243-1249.
Castiglioni et al., "Alternative splicing in the C-terminus of CaV2.2 controls expression and gating of N-type calcium channels," J. Physiol, 2006, vol. 576 (Pt 1), pp. 119-134.
Cavalli, A. et al., "Multi-target directed ligands to combat neurodegenerative diseases," J. Med. Chem., 2008, vol. 51 (3), pp. 347-372.

(Continued)

*Primary Examiner* — Yong Chu  
(74) *Attorney, Agent, or Firm* — Lisa V. Mueller; Michael Best & Friedrich LLP

(57) ABSTRACT

The present application relates to calcium channel inhibitors containing compounds of formula (I)

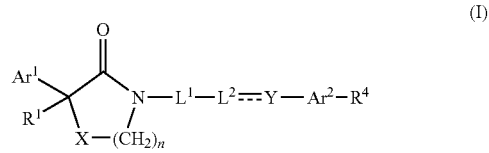

wherein $Ar^1$, $Ar^2$, $L^1$, $L^2$, n, $R^1$, $R^4$, X and Y are as defined in the specification. The present application also relates to compositions comprising such compounds, and methods of treating conditions and disorders using such compounds and compositions.

17 Claims, No Drawings

OTHER PUBLICATIONS

Chaplan S. R. et al., "Role of voltage-dependent calcium channel subtypes in experimental tactile allodynia," J. Pharmacol. Exp. Ther, 1994, vol. 269 (3), pp. 1117-1123.

Chaplan S. R. et al., "Quantitative assessment of tactile allodynia in the rat paw," Journal of Neuroscience Methods, 1994, vol. 53, pp. 55-63.

Cizkova, "Localization of N-type Ca2+ channels in the rat spinal cord following chronic constrictive nerve injury," Exp. Brain Res, 2002, vol. 147, pp. 456-463.

Colbourne F. et al., "Continuing postischemic neuronal death in CA1: Influence of ischemia duration and cytoprotective doses of NBQX and SNX-111 in rats," Stroke, 1999, vol. 30 (3), pp. 662-668.

Croom K. F. et al., "A review of the use of modified-release formulations in the treatment of hypertension and angina pectoris," Drugs, 2006, vol. 66 (4), pp. 497-528.

Darszon A. et al., "Ion channels in sperm physiology," Physiological Reviews, 1999, vol. 79 (2), pp. 481-510.

de Filippis A. et al., "Palladium-catalyted [alpha]-arylation of N-protected 2-piperidinones," Tetrahedron, 2004, vol. 60, pp. 9757-9767.

Dolphin A. C., "A short history of voltage-gated calcium channels," British Journal of Pharmacology, 2006, vol. 147, pp. S56-S62.

Eliel, E. L. et al., "Stereochemistry of Organic Compounds," 1994, pp. 119-120, 1206, John Wiley & Sons, Inc. New York.

Evans A. R et al., "Differential regulation of evoked peptide release by voltage-sensitive calcium channels in rat sensory neurons," Brain Res, 1996, vol. 712 (2), pp. 265-273.

Feng Z. P. et al., "Determinants of inhibition of transiently expressed voltage-gated calcium channels by omega-conotoxins GVIA and MVIIA," J. Biol. Chem, 2003, vol. 278 (22), pp. 20171-20178.

Geldenhuys W. J. et al., "Structure-activity relationships of pentacycloundecylamines at the N-methyl-D-aspartate receptor," Bioorganic and Medicinal Chemistry, 2007, vol. 15, pp. 1525-1532.

Gitlin M., "Treatment-resistant bipolar disorder," Molecular Psychiatry, 2006, vol. 11, pp. 227-240.

Gladstone J. P. et al., "Current and emerging treatment options for migraine and other primary headache disorders," Expert Rev. Neurotherapeutics, 2003, vol. 3 (6), pp. 845-872.

Gould R. J. et al., "Antischizophrenic drugs of the diphenylbutylpiperidine type act as calcium channel antagonists," Proc. Natl. Acad. Sci, 1983, vol. 80, pp. 5122-5125.

Gray et al., "Neuronal calcium channels: splicing for optimal performance," Cell Calcium, 2007, vol. 42 (4-5), pp. 409-417.

Greene T. W. et al., "Protective Groups in Organic Synthesis," 1999, Ed. 3, John Wiley & Sons, pp. 494-653.

Hatakeyama, "Differential nociceptive responses in mice lacking the alpha1B subunit of N-type Ca2+ channels," Neuroreport, 2001, vol. 12 (11), pp. 2423-2427.

Heinemann U. et al., "Extracellular free calcium and potassium during paroxysmal activity in the cerebral cortex of the cat," Brain Res, 1977, vol. 27, pp. 237-243.

Heinke B. et al., "Pre- and postsynaptic contributions of voltage-dependent Ca2+ channels to nociceptive transmission in rat spinal lamina I neurons," Eur. J. Neurosci, 2004, vol. 19 (1), pp. 103-111.

IUPAC Commission on Nomenclature of Organic Chemistry: Rules for the Nomenclature of Organic Chemistry Section E: Stereochemistry, Pure Appl Chem, 1976, vol. 45, pp. 13-30.

Kim, "Altered nociceptive response in mice deficient in the alpha1B subunit of the voltage-dependent calcium channel," Mol. Cell. Neurosci, 2001, vol. 18 (2), pp. 235-245.

Levy N. A. et al., "Calcium channel antagonists for the treatment of bipolar disorder," Bipolar Disorders, 2000, vol. 2 (2), pp. 108-119.

Little H. J. et al., "Calcium channel antagonists decrease the ethanol withdrawal syndrome," Life Sciences, 1986, vol. 39, pp. 2059-2065.

Liu, "In vivo analysis of voltage-dependent calcium channels," J. Bioenerg. Biomembr, 2003, vol. 35 (6), pp. 671-685.

Lorton D., "beta-Amyloid-induced IL-1 beta release from an activated human monocyte cell line is calcium- and G-protein-dependent," Mech Ageing Dev, 1997, vol. 94 (1-3), pp. 199-211.

Lubin M. L. et al., "A nonadherent cell-based HTS assay for N-type calcium channel using calcium 3 dye," Assay and Drug Development Technologies, 2006, vol. 4 (6), pp. 689-694.

Luebke J. I. et al., "Multiple calcium channel types control glutamatergic synaptic transmission in the hippocampus," Neuron, 1993, vol. 11 (5), pp. 895-902.

Luo, "Upregulation of dorsal root ganglion a2d calcium channel subunit and its correlation with allodynia in spinal nerve-injured rats," J. Neurosci, 2001, vol. 21 (6), pp. 1868-1875.

Malmberg A. B. et al., "Voltage-sensitive calcium channels in spinal nociceptive processing: blockade of N- and P-type channels inhibits formalin-induced nociception," J. Neurosci, 1994, vol. 14 (8), pp. 4882-4890.

Mason R. P. et al., "Antioxidant and cytoprotective activities of the calcium channel blocker mibefradil," Biochemical Pharmacology, 1998, vol. 55, pp. 1843-1852.

Matthews E. A. et al., "Effects of spinally delivered N- and P-type voltage-dependent calcium channel antagonists on dorsal horn neuronal responses in a rat model of neuropathy," Pain, 2001, vol. 92 (1-2), pp. 235-246.

McGivern J. G., "Targeting N-type and T-type calcium channels for the treatment of pain," Drug Discovery Today, 2006, vol. 11, pp. 245-253.

Miljanich G. P. et al., "Antagonists of neuronal calcium channels: structure function and therapeutic implications," Annu. Rev. Pharmacol Toxicol, 1995, vol. 35, pp. 707-734.

Newton et al., "Dorsal root ganglion neurons show increased expression of the calcium channel a2d-1 subunit following partial sciatic nerve injury," Mol. Brain Res, 2001, vol. 95 (1-2), pp. 1-8.

Olivera et al., "Calcium channel diversity and neurotransmitter release: the omega-conotoxins and omega agatoxins," Annu. Rev. Biochem, 1994, vol. 63, pp. 823-867.

Otoom S. et al., "Nifedipine inhibits picrotoxin-induced seizure activity: further evidence on the involvement of L-type calcium channel blockers in epilepsy," Fundamental & Clinical Pharmacology, 2006, vol. 20, pp. 115-119.

PCT international search report and written opinion for the application PCT/US2009/059215, mailed on Feb 22, 2010, 12 pages.

Pietrobon D. et al., "Function and dysfunction of synaptic calcium channels: insights from mouse models," Curr. Opin. Neurobiol, 2005, vol. 15 (3), pp. 257-265.

Prescott et al., "Lipid Vesicles as Carriers for Introducing Biologically Active Materials into Cells," Methods in Cell Biology, 1976, vol. 14, Academic Press, pp. 33-71.

Raingo J., "Alternative splicing controls G protein-dependent inhibition of N-type calcium channels in nociceptors," Nat. Neurosci, 2007, vol. 10 (3), pp. 285-292.

Rodnitzky R. L. et al., "Can calcium antagonists provide a neuroprotective effect in Parkinson's disease," Drugs, 1999, vol. 57 (6), pp. 845-849.

Saade S. et al., "The L-type calcium channel blocker nimodipine mitigates "learned helplessness" in rats," Pharmacology, Biochemistry and Behavior, 2003, vol. 74, pp. 269-278.

Saegusa, "Suppression of inflammatory and neuropathic pain symptoms in mice lacking the N-type calcium channel," EMBO J, 2001, vol. 20 (10), pp. 2349-2356.

Scott D. A. et al., "Actions of intrathecal omega-conotoxins CVID GVIA MVIIA and morphine in acute and neuropathic pain in the rat," Eur. J. Pharmacol, 2002, vol. 451 (3), pp. 279-286.

Shin H.S. et al., "T-type Ca2+ channels as therapeutic targets in the nervous system," Curr. Opin. in Pharmacology, 2008, pp. 33-41.

Smith M. T. et al., "The novel N-type calcium channel blocker, AM336, produces potent dose-dependent antinociception after intrathecal dosing in rats and inhibits substance P release in rat spinal cord slices," Pain, 2002, vol. 96 (1-2), pp. 119-127.

Takahashi T. et al., "Different types of calcium channels mediate central synaptic transmission," Nature, 1993, vol. 366 (6451), pp. 156-158.

Takei R. et al., "Increased sensitivity to halothane but decreased sensitivity to propofol in mice lacking the N-type Ca2+ channel," Neurosci. Lett, 2003, vol. 350 (1), pp. 41-45.

Tort A. B. L. et al., "Atypical antipsychotic profile of flunarizine in animal models," Psychopharmacology, 2005, vol. 177, pp. 344-348.

Urban M. et al., "Medullary N-type and P/Q-type calcium channels contribute to neuropathy-induced allodyni," Neuroreport, 2005, vol. 16 (6), pp. 563-566.

Vagnucci A. H. et al., "Alzheimer's disease and angiogenesis," The Lancet, 2003, vol. 361 (9357), pp. 605-608.

Veng L. M. et al., "Age-related working memory impairment is correlated with increases in the L-type calcium channel protein a1D (Cav1.3) in area CA1 of the hippocampus and both are ameliorated by chronic nimodipine treatment," Molecular Brain Research, 2003, vol. 110, pp. 193-202.

Vezzani A. et al., "Effects of various calcium channel blockers on three different models of limbic seizures in rats," Neuropharmacology, 1988, vol. 27 (5), pp. 451-458.

Wang Y. et al., "Effects of intrathecal administration of ziconotide a selective neuronal N-type calcium channel blocker on mechanical allodynia and heat hyperalgesia in a rat model of postoperative pain," Pain, 2000, vol. 84 (2-3), pp. 151-158.

Westenbroek R. et al., "Localization of Ca2+ channel subtypes on rat spinal motor neurons interneurons and nerve terminals," J. Neurosci, 1998, vol. 18 (16), pp. 6319-6330.

Yamamoto T. et al., "Differential effects of intrathecally administered N- and P-type voltage-sensitive calcium channel blockers upon two models of experimental mononeuropathy in the rat," Brain Res, 1998, vol. 794 (2), pp. 329-332.

Yokoyama, "Plastic change of N-type calcium channel expression after preconditioning is responsible for prostaglandin E2-induced long-lasting allodynia," Anesthesiology, 2003, vol. 99 (6), pp. 1364-1370.

Yoshinaga et al., "Functional disorders of the sympathetic nervous system in mice lacking the a1B subunit (Cav2.2) of N-type calcium channels," Proc. Natl. Acad. Sci. USA, 2001, vol. 98 (9), pp. 5323-5328.

Zanchetti A. et al, "Calcium antagonist lacidipine slows down progression of asymptomatic carotid atherosclerosis. Principal results of the European lacidipine study on atherosclerosis (ELSA), a randomized, double-blind, long-term trial," Circulation, 2002, vol. 106, pp. r47-r52.

\* cited by examiner

COMPOUNDS AS CALCIUM CHANNEL BLOCKERS

CROSS-REFERENCE TO RELATED APPLICATIONS

This patent application claims priority to U.S. Provisional Patent Application No. 61/102,132, filed on Oct. 2, 2008, the entirety of which is incorporated herein by reference.

TECHNICAL FIELD

The present application relates to compounds that are calcium channel blockers, compositions comprising such compounds, and methods of treating conditions and disorders using such compounds and compositions.

BACKGROUND OF THE INVENTION

Voltage-gated calcium channels (VGCC) play an integral role in the regulation of membrane ion conductance, neurotransmitter release, and cellular excitability. VGCC are composed of the pore-forming α1 subunit and auxiliary α2δ and β subunits that modulate channel expression and functional properties (Dolphin, A. C. A short history of voltage-gated calcium channels. British Journal of Pharmacology 2006, 147 (Suppl. 1), S56-S62). These channels can be classified into low-voltage activated (LVA; T-type or $Ca_v3.x$) and high-voltage activated (HVA; L-type or $Ca_v1.x$ and N-, P/Q- and R-types or $Ca_v2.x$) channels. N-, P/Q and R channels typically activate at more positive membrane potentials (~−30 mV) and are involved in "presynaptic" neurotransmission (McGivern J. G. Targeting N-type and T-type calcium channels for the treatment of pain. Drug Discovery Today 2006, 11, 245-253). T-type channels are activated at relatively negative membrane potentials (~−60 mV) and are primarily involved in "postsynaptic" excitability (Shin, H.-S.; Cheong, E.-J.; Choi, S.; Lee, J.; Na, H. S. T-type $Ca^{2+}$ channels as therapeutic targets in the nervous system. Curr. Opin. in Pharmacology 2008, 8, 33-41).

N-type channel $\alpha_\delta$ subunits are encoded by a single gene ($\alpha_1 B$ or $Ca_v2.2$) in contrast to pharmacologically defined L- and T-type currents that are encoded by multiple $\alpha_1$-subunit genes. A diversity of N-type channels arises due to extensive alternative splicing of the α subunit gene that generates variants with different expression patterns and GPCR-modulated biophysical properties (Gray, A. C.; Raingo, J.; Lipscombe, D. Neuronal calcium channels: splicing for optimal performance. Cell Calcium, 2007, 42(4-5), 409-417). The primary sequence for $Ca_v2.2$ is highly conserved across species (rat and human share 91% identity at the amino acid level).

N-type channels are widely expressed in the central nervous system (CNS) (cortex, hippocampus, striatum, thalamus, brain stem nuclei and spinal cord) and in the peripheral nervous system (PNS) (adult sympathetic nervous system and dorsal root ganglia) (Ino, M.; Yoshinaga, T.; Wakamori, M.; Miyamoto, N.; Takahashi, E.; Sonoda, J.; Kagaya, T.; Oki, T.; Nagasu, T.; Nishizawa, Y.; Tanaka, I.; Imoto, K.; Aizawa, S.; Koch, S.; Schwartz, A.; Niidome, T.; Sawada, K.; Mori, Y. Functional disorders of the sympathetic nervous system in mice lacking the $\alpha_{1B}$ subunit ($Ca_v2.2$) of N-type calcium channels. Proc. Natl. Acad. Sci. USA 2001, 98(9), 5323-5328). In pain pathways, N-type channels are expressed in the rostral ventral medulla, an important site of descending pain modulation (Urban, M. O.; Ren, K.; Sablad, S.; Park, K. T. Medullary N-type and P/Q-type calcium channels contribute to neuropathy-induced allodynia. Neuroreport 2005, 16(6), 563-566) and are a major contributor to the synaptic neurotransmission that occurs between C/Aδ nociceptors and spinal lamina I neurons (Bao, J.; Li, J. J.; Perl, E. R. Differences in $Ca^{2+}$ channels governing generation of miniature and evoked excitatory synaptic currents in spinal laminae I and II. J. Neurosci. 1998, 18(21), 8740-50. Heinke, B.; Balzer, E.; Sandkuhler, J. Pre- and postsynaptic contributions of voltage-dependent $Ca^{2+}$ channels to nociceptive transmission in rat spinal lamina I neurons. Eur. J. Neurosci. 2004, 19(1), 103-111). In contrast, P/Q type channels are expressed almost exclusively in laminae II-IV of the spinal cord and show little co-localization with Substance P and N-type channels (Westenbroek, R. E.; Hoskins, L.; Catterall, W. A. Localization of $Ca^{2+}$ channel subtypes on rat spinal motor neurons, interneurons, and nerve terminals. J. Neurosci. 1998, 18(16), 6319-6330).

Following nerve injury there is increased expression of $Ca_v2.2$ (Westenbroek, R. E.; Hoskins, L.; Catterall, W. A. Localization of $Ca^{2+}$ channel subtypes on rat spinal motor neurons, interneurons, and nerve terminals. J. Neurosci. 1998, 18(16), 6319-6330. Cizkova, D.; Marsala, J.; Lukacova, N.; Marsala, M.; Jergova, S.; Orendacova, J.; Yaksh, T. Localization of N-type $Ca^{2+}$ channels in the rat spinal cord following chronic constrictive nerve injury. Exp. Brain Res. 2002, 147, 456-463. Yokoyama, K.; Kurihara, T.; Makita, K.; Tanabe, T. Plastic change of N-type calcium channel expression after preconditioning is responsible for prostaglandin E2-induced long-lasting allodynia. Anesthesiology 2003, 99(6), 1364-1370) and α2δ1 subunits (Luo, Z. D.; Chaplan, S. R.; Higuera, E. S.; Sorkin, L. S.; Stauderman, K. A.; Williams, M. E.; Yaksh, T. L. Upregulation of dorsal root ganglion α2δ calcium channel subunit and its correlation with allodynia in spinal nerve-injured rats. J. Neurosci. 2001, 21(6), 1868-1875. Newton, R. A.; Bingham, S.; Case, P. C.; Sanger, G. J.; Lawson, S. N. Dorsal root ganglion neurons show increased expression of the calcium channel α2δ-1 subunit following partial sciatic nerve injury. Mol. Brain. Res. 2001, 95(1-2), 1-8) in addition to increases in the superficial layers of the dorsal horn of the spinal cord supporting a role for N-type channels in neuropathic pain. Recently a nociceptor-specific $Ca_v2.2$ splice variant has been identified in the dorsal root ganglion (Bell, T. J.; Thaler, C.; Castiglioni, A. J.; Helton, T. D.; Lipscombe, D. Cell specific alternative splicing increases calcium channel density in the pain pathway. Neuron 2004, 41(1), 127-138). These channels have distinct electrophysiological properties and current densities (Castiglioni, A. J.; Raingo, J.; Lipscombe, D. Alternative splicing in the C-terminus of $Ca_v2.2$ controls expression and gating of N-type calcium channels. J. Physiol. 2006, 576(Pt 1), 119-134) compared to wildtype $Ca_v2.2$ channels. While G-protein coupled receptor inhibition of wildtype N-type channels is typically mediated by Gβγ and is voltage-dependent, the nociceptor specific splice variant is inhibited by GPCR activation (e.g. opioids) in a voltage-independent fashion (Raingo, J.; Castiglioni, A. J.; Lipscombe, D. Alternative splicing controls G protein-dependent inhibition of N-type calcium channels in nociceptors. Nat. Neurosci. 2007, 10(3), 285-292). This mechanism substantially increases the sensitivity of $Ca_v2.2$ channels to opiates and gamma-aminobutyric acid (GABA) suggesting that cell-specific alternative splicing of mRNA for $Ca_v2.2$ channels serves as a molecular switch that controls the sensitivity of N-type channels to neurotransmitters and drugs that modulate nociception. Collectively these data provide further support for the role of $Ca_v2.2$ channels in pain states.

The relative contributions of various HVA $Ca^{2+}$ channels in nociceptive signaling have been evaluated using knockout mice studies. $Ca_v2.2$ knockout mice are healthy, fertile, and do not display overt neurological deficits (Ino, M.; Yoshinaga, T.; Wakamori, M.; Miyamoto, N.; Takahashi, E.; Sonoda, J.; Kagaya, T.; Oki, T.; Nagasu, T.; Nishizawa, Y.; Tanaka, I.; Imoto, K.; Aizawa, S.; Koch, S.; Schwartz, A.; Niidome, T.; Sawada, K.; Mori, Y. Functional disorders of the sympathetic nervous system in mice lacking the alpha 1B subunit ($Ca_v2.2$) of N-type calcium channels. Proc. Natl. Acad. Sci. USA 2001, 98(9), 5323-5328. Kim, C.; Jun, K.; Kim, S. S.; McEnery, M. W.; Chin, H.; Kim, H. L.; Park, J. M.; Kim, D. K.; Jung, S. J.; Kim, J.; Shin, H. S. Altered nociceptive response in mice deficient in the $alpha_{1B}$ subunit of the voltage-dependent calcium channel. Mol. Cell. Neurosci. 2001, 18(2), 235-245. Hatakeyama, S.; Wakamori, M.; Ino, M.; Miyamoto, N.; Takahashi, E.; Yoshinaga, T.; Sawada, K.; Imoto, K.; Tanaka, I.; Yoshizawa, T.; Nishizawa, Y.; Mori, Y.; Niidome, T.; Shoji, S. Differential nociceptive responses in mice lacking the $alpha_{1B}$ subunit of N-type $Ca^{2+}$ channels. Neuroreport 2001, 12(11), 2423-2427. Liu; L.; Zwingman, T. A.; Fletcher, C. F. In vivo analysis of voltage-dependent calcium channels. J. Bioenerg. Biomembr. 2003, 35(6), 671-685). This finding suggests that other types of $Ca_v$ channels are able to compensate for the lack of $Ca_v2.2$ channels at most synapses in these mice (Pietrobon, D. Function and dysfunction of synaptic calcium channels: insights from mouse models. Curr. Opin. Neurobiol. 2005, 15(3), 257-265). $Ca_v2.2$ deficient mice are resistant to the development of inflammatory and neuropathic pain (Kim, C.; Jun, K.; Kim, S. S.; McEnery, M. W.; Chin, H.; Kim, H. L.; Park, J. M.; Kim, D. K.; Jung, S. J.; Kim, J.; Shin, H. S. Altered nociceptive response in mice deficient in the $alpha_{1B}$ subunit of the voltage-dependent calcium channel. Mol. Cell. Neurosci. 2001, 18(2), 235-245. Hatakeyama, S.; Wakamori, M.; Ino, M.; Miyamoto, N.; Takahashi, E.; Yoshinaga, T.; Sawada, K.; Imoto, K.; Tanaka, I.; Yoshizawa, T.; Nishizawa, Y.; Mori, Y.; Niidome, T.; Shoji, S. Differential nociceptive responses in mice lacking the $alpha_{1B}$ subunit of N-type $Ca^{2+}$ channels. Neuroreport 2001, 12(11), 2423-2427. Saegusa, H.; Kurihara, T.; Zong, S.; Kazuno, A.; Matsuda, Y.; Nonaka, T.; Han, W.; Toriyama, H.; Tanabe, T. Suppression of inflammatory and neuropathic pain symptoms in mice lacking the N-type calcium channel. EMBO J. 2001, 20(10), 2349-2356), have decreased sympathetic nervous system function (Ino, M.; Yoshinaga, T.; Wakamori, M.; Miyamoto, N.; Takahashi, E.; Sonoda, J.; Kagaya, T.; Oki, T.; Nagasu, T.; Nishizawa, Y.; Tanaka, I.; Imoto, K.; Aizawa, S.; Koch, S.; Schwartz, A.; Niidome, T.; Sawada, K.; Mori, Y. Functional disorders of the sympathetic nervous system in mice lacking the alpha 1B subunit ($Ca_v2.2$) of N-type calcium channels. Proc. Natl. Acad. Sci. USA 2001, 98(9), 5323-5328), and altered responses to both ethanol and anesthetics (Newton, R. A.; Bingham, S.; Case, P. C.; Sanger, G. J.; Lawson, S. N. Dorsal root ganglion neurons show increased expression of the calcium channel alpha2delta-1 subunit following partial sciatic nerve injury. Brain Res. Mol. Brain. Res. 2001, 95(1-2), 1-8. Takei, R. Saegusa, H.; Zong, S.; Murakoshi, T.; Makita, K.; Tanabe, T. Increased sensitivity to halothane but decreased sensitivity to propofol in mice lacking the N-type $Ca^{2+}$ channel. Neurosci. Lett. 2003, 350(1), 41-45). Additional behavioral studies indicate that $Ca_v2.2$ knockout mice are less anxious, are hyperactive, and show enhanced vigilance compared to wild-type littermates (Beuckmann, C. T.; Sinton, C. M.; Miyamoto, N.; Ino, M.; Yanagisawa, M. N-type calcium channel $alpha_{1B}$ subunit ($Ca_v2.2$) knock-out mice display hyperactivity and vigilance state differences. J. Neurosci. 2003, 23(17), 6793-6797).

N- and P/Q-type channels are localized at neuronal synaptic junctions and contribute significantly to neurotransmitter release (Olivera, B. M.; Miljanich, G. P.; Ramachandran, J.; Adams, M. E. Calcium channel diversity and neurotransmitter release: the omega-conotoxins and omega agatoxins. Annu. Rev. Biochem. 1994, 63, 823-867. Miljanich, G. P.; Ramachandran, J. Antagonists of neuronal calcium channels: structure, function, and therapeutic implications. Annu Rev. Pharmacol. Toxicol. 1995, 35, 707-734). N-type channels play a major role in the release of glutamate, acetylcholine, dopamine, norepinephrine, GABA and calcitonin gene-related protein (CGRP). P/Q-type channels may be involved in the release of glutamate, aspartate, 5HT, GABA and probably glycine (Pietrobon, D. Function and dysfunction of synaptic calcium channels: insights from mouse models. Curr. Opin. Neurobiol. 2005, 15(3), 257-265).

L, P/Q and N-type channels are blocked by channel specific antagonists i.e., dihydropyridines, ω-agatoxin IVA and ω-conotoxin MVIIA/ziconotide, respectively. Agatoxin IVa has been shown to block excitatory (Luebke, J. I.; Dunlap, K.; Turner, T. J. Multiple calcium channel types control glutamatergic synaptic transmission in the hippocampus. Neuron 1993, 11(5), 895-902) as well as inhibitory neurotransmission (Takahashi, T.; Momiyama, A. Different types of calcium channels mediate central synaptic transmission. Nature 1993, 366(6451), 156-158). Intrathecal injection of selective N-type channel blockers (e.g. conotoxin-derived peptides such as GVIA, MVIIA (ziconotide), and CVID) significantly attenuates pain responses in animal models of neuropathic pain, formalin-induced pain, and post-operative pain (Chaplan, S. R.; Pogrel, J. W.; Yaksh, T. L. Role of voltage-dependent calcium channel subtypes in experimental tactile allodynia. J. Pharmacol. Exp. Ther. 1994, 269(3), 1117-1123. Malmberg, A. B.; Yaksh, T. L. Voltage-sensitive calcium channels in spinal nociceptive processing: blockade of N- and P-type channels inhibits formalin-induced nociception. J. Neurosci. 1994, 14(8), 4882-4890. Bowersox, S. S.; Gadbois, T.; Singh, T.; Pettus, M.; Wang, Y. X.; Luther, R. R. Selective N-type neuronal voltage-sensitive calcium channel blocker, SNX-111, produced spinal antinociception in rat models of acute, persistent and neuropathic pain. J. Pharmacol. Exp. Ther. 1996, 279(3), 1243-1249. Wang, Y. X.; Pettus, M.; Gao, D.; Phillips, C.; Bowersox, S. S. Effects of intrathecal administration of ziconotide, a selective neuronal N-type calcium channel blocker, on mechanical allodynia and heat hyperalgesia in a rat model of postoperative pain. Pain 2000, 84(2-3), 151-158. Scott, D. A.; Wright, C. E. Angus, J. A. Actions of intrathecal omega-conotoxins CVID, GVIA, MVIIA, and morphine in acute and neuropathic pain in the rat. Eur. J. Pharmacol. 2002, 451(3), 279-286). These peptide blockers bind to the pore region of the channel, do not show voltage- or frequency-dependent activity, and show irreversible channel block (Feng, Z. P.; Doering, C. J.; Winkfein, R. J.; Beedle, A. M.; Spafford, J. D.; Zamponi, G. W. Determinants of inhibition of transiently expressed voltage-gated calcium channels by omega-conotoxins GVIA and MVIIA. J. Biol. Chem. 2003, 278(22), 20171-20178). Ziconotide potently blocks neurotransmitter release in the spinal cord dorsal horn (Matthews, E. A.; Dickenson, A. H. Effects of spinally delivered N- and P-type voltage-dependent calcium channel antagonists on dorsal horn neuronal responses in a rat model of neuropathy. Pain 2001, 92(1-2), 235-246. Smith, M. T.; Cabot, P. J.; Ross, F. B.; Robertson, A. D.; Lewis, R. J. The novel N-type calcium channel blocker, AM336, produces potent dose-dependent antinociception after intrathecal dosing in rats and inhibits substance P release in rat spinal cord slices. Pain 2002, 96(1-2), 119-127. Heinke, B.; Balzer, E.; Sandkuhler, J. Pre- and postsynaptic contributions of voltage-dependent $Ca^{2+}$ channels to nociceptive transmission in rat spinal lamina I neurons. Eur. J. Neurosci. 2004, 19(1), 103-111) and in dorsal root ganglion (DRG) neurons (Evans, A. R.; Nicol, G. D.; Vasko, M. R. Differential regulation of evoked peptide release by voltage-sensitive calcium channels in rat sensory neurons. Brain Res. 1996, 712(2), 265-273. Smith, M. T.; Cabot, P. J.; Ross, F. B.; Robertson, A. D.; Lewis, R. J. The novel N-type calcium channel blocker, AM336, produces potent dose-dependent antinociception after intrathecal dosing in rats and inhibits substance P release in rat spinal cord slices. Pain 2002, 96(1-2), 119-127). It also potently and fully blocks depolarization-induced release of substance P from rat spinal cord slices. In contrast, intrathecal delivery of the selective P/Q type blocker ω-agatoxin IVA had no effects on mechanical allodynia in the spinal nerve ligation model (Chaplan, S. R.; Pogrel, J. W.; Yaksh, T. L. Role of voltage-dependent calcium channel subtypes in experimental tactile allodynia. J. Pharmacol. Exp. Ther. 1994, 269(3), 1117-1123) or thermal hyperalgesia in the chronic constriction injury model (Yamamoto, T.; Sakashita, Y. Differential effects of intrathecally administered N- and P-type voltage-sensitive calcium channel blockers upon two models of experimental mononeuropathy in the rat. Brain Res. 1998, 794(2), 329-332) of neuropathic pain.

Pain is the most common symptom of disease and the most frequent complaint with which patients present to physicians. Inadequate pain management across the spectrum of pain etiologies remains a major public health problem. Going forward, the development of novel therapeutics with new mechanisms of action for the treatment of pain including calcium channel blockade will have a significant impact on the ongoing struggle to balance efficacy and safety for those patients most in need. The compounds of the present invention are novel calcium channel blockers that have utility in treating pain, amongst other conditions.

SUMMARY OF THE INVENTION

The invention is directed to compounds of formula (I)

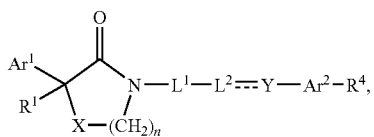

(I)

or a pharmaceutically acceptable salt thereof, wherein
═════ is a single or double bond;
n, at each occurrence, is independently 1 or 2;
X is $CH_2$, NC(O)OtBu, NH, N-alkyl, O, or $S(O)_r$;
r, at each occurrence, is independently 0, 1, or 2;
$Ar^1$ and $Ar^2$ are independently aryl or heteroaryl; wherein each $Ar^1$ and $Ar^2$ is independently unsubstituted or further substituted with 1, 2, 3, 4, or 5 substituents independently selected from the group consisting of alkyl, alkenyl, alkynyl, halogen, —CN, —$NO_2$, —$OR^a$, —$S(R^c)$, —$S(O)(R^c)$, —$S(O)_2R^c$, —$S(O)_2N(R^b)_2$, —$C(O)R^b$, —$C(O)OR^b$, —$C(O)N(R^b)_2$, —$N(R^b)_2$, —$N(R^b)C(O)R^b$, —$N(R^b)C(O)O(R^b)$, —$N(R^b)S(O)_2R^c$, haloalkyl, —$(CR^dR^e)_m$—$OR^a$, —$(CR^dR^e)_m$—$S(R^c)$, —$(CR^dR^e)_m$—$S(O)(R^c)$, —$(CR^dR^e)_m$—$S(O)_2R^c$, —$(CR^dR^e)_m$—$S(O)_2N(R^b)_2$, —$(CR^dR^e)_m$—$C(O)R^b$, —$(CR^dR^e)_m$—$C(O)OR^b$, —$(CR^dR^e)_m$—$C(O)N(R^b)_2$, —$(CR^dR^e)_m$—$N(R^b)_2$, —$(CR^dR^e)_m$—$N(R^b)C(O)R^b$, —$(CR^dR^e)_m$—$N(R^b)C(O)O(R^b)$, —$(CR^dR^e)_m$—$N(R^b)S(O)_2R^c$, and —CH═CH-heteroaryl-$(CR^dR^e)_m$—O(alkyl);

$R^a$, at each occurrence, is independently hydrogen, alkyl, haloalkyl, or —$(CR^dR^e)_m$—O(alkyl);
$R^b$, at each occurrence, is independently hydrogen, alkyl, haloalkyl, or $G^1$;
$R^c$, at each occurrence, is independently alkyl or haloalkyl;
$R^d$ and $R^e$, at each occurrence, are each independently hydrogen, halogen, alkyl, or haloalkyl;
m, at each occurrence, is independently 1, 2, 3, 4, 5, or 6;
$L^1$ is —$(CH_2)_pC(O)$— or —$(CH_2)_p$—; wherein
p, at each occurrence, is independently 1, 2, 3, or 4;
$L^2$ is —$N(R^5)$—, —$N(R^5)$—$(CH_2)_q$—, —NH—CH$(R^5)$—, —NH—CH$(R^5)$—$(CH_2)_q$—, —$N(R^5)$—$CH_2$CH$(OH)CH_2$—, —$N(R^5)$—CH$(R^6)$—, (i), (ii), (iii), (iv), (v), (vi), (vii), (viii), (ix), (x), (xi) or (xii);

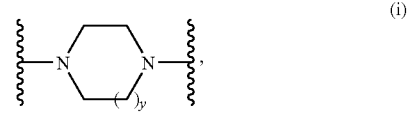

(i)

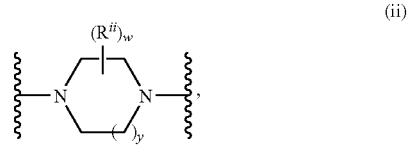

(ii)

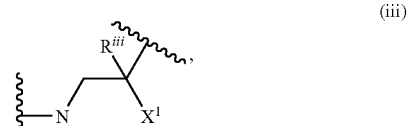

(iii)

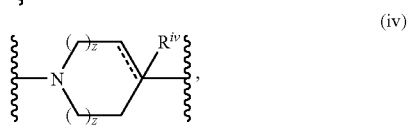

(iv)

(v)

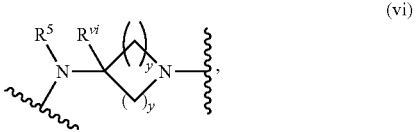

(vi)

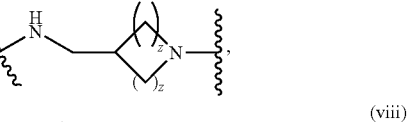

(vii)

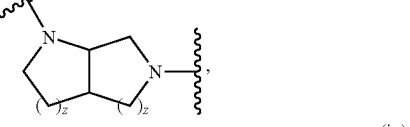

(viii)

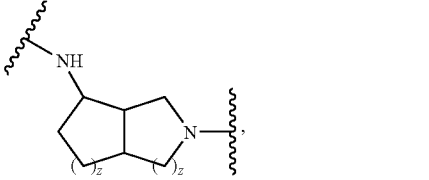

(ix)

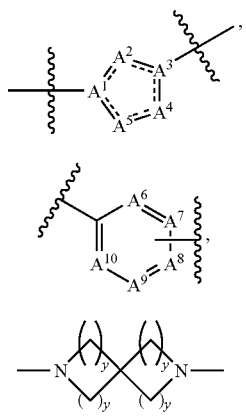

q, at each occurrence, is independently 1, 2, or 3;
w is 1, 2, 3, or 4;
x is 2, 3, 4, or 5;
y at each occurrence, is independently 1, 2, or 3;
z at each occurrence, is independently 0, 1, 2, or 3;
$R^5$ at each occurrence, is hydrogen alkyl, or $G^1$;
$R^{ii}$ at each occurrence, is independently oxo or alkyl;
$R^{iii}$ is hydrogen, alkyl, or aryl;
$R^{iv}$ is hydrogen, aryl, $OR^a$ or part of double bond between $L^2$ and Y;
$R^{vi}$ is hydrogen or alkyl;
$X^1$ is $CH_2$, NH, O, or a bond;
$A^1$ and $A^3$ are independently C or N;
$A^2$, $A^4$, and $A^5$ are each independently CH, $CR^5$, N, O, or S;
one of $A^6$, $A^7$, $A^8$, $A^9$, and $A^{10}$ is C and the others are each independently CH or N;
Y is a bond, $CH_2CR^2R^3$, $CR^2R^3$, $CR^2$, $CR^2R^3O$, C(O), C(O)OCR$^2$R$^3$, N—O—CR$^2$R$^3$, O, or S(O)$_r$;
$R^2$ is hydrogen or $G^1$;
$R^3$ is hydrogen, alkyl, cycloalkyl, or hydroxyl; or
$R^2$ and $R^3$ taken together with the carbon atom to which they are attached form a cycloalkyl;
$G^1$, at each occurrence, is independently aryl, heteroaryl, heterocycle, cycloalkyl, or cycloalkenyl; wherein each $G^1$ is independently unsubstituted or further substituted with 1, 2, 3, 4, 5, or 6 substituents independently selected from the group consisting of alkyl, alkenyl, alkynyl, halogen, oxo, —CN, —NO$_2$, —OR$^a$, —S(R$^c$), —S(O)(R$^c$), —S(O)$_2$R$^c$, —S(O)$_2$N(R$^b$)$_2$, C(O)R$^b$, —C(O)O(R$^b$), —C(O)N(R$^b$)$_2$, —N(R$^b$)$_2$, —N(R$^b$)C(O)R$^b$, —N(R$^b$)C(O)O(R$^b$), —N(R$^b$)S(O)$_2$R$^c$, haloalkyl, —(CR$^d$R$^e$)$_m$—OR$^a$, —(CR$^d$R$^e$)$_m$—S(R$^c$), —(CR$^d$R$^e$)$_m$—S(O)(R$^c$), —(CR$^d$R$^e$)$_m$—S(O)$_2$R$^c$, —(CR$^d$R$^e$)$_m$—S(O)$_2$N(R$^b$)$_2$, —(CR$^d$R$^e$)$_m$—C(O)R$^b$, —(CR$^d$R$^e$)$_m$—C(O)O(R$^b$), —(CR$^d$R$^e$)$_m$—C(O)N(R$^b$)$_2$, —(CR$^d$R$^e$)$_m$—N(R$^b$)$_2$, —(CR$^d$R$^e$)$_m$—N(R$^b$)C(O)R$^b$, —(CR$^d$R$^e$)$_m$—N(R$^b$)C(O)O(R$^b$), and —(CR$^d$R$^e$)$_m$—N(R$^b$)S(O)$_2$R$^c$;
$R^1$ is hydrogen, alkyl, or $G^1$; and
$R^4$ is hydrogen; or
$R^3$ and $R^5$ taken together are —(CH$_2$)$_p$— or —O—(CH$_2$)$_p$—; or
$R^4$ and $R^5$ taken together are a bond, —(CH$_2$)$_s$—, or —O—(CH$_2$)$_s$—; wherein
s, at each occurrence, is independently 1 or 2;
$R^4$ and $R^6$ taken together are —CH$_2$—; or
$L^1$-$L^2$=====Y taken together are S(O)$_r$;

with the provisos that
$Ar^2$ is other than a pyrazole substituted with 1 or 2 groups independently selected from aryl and heteroaryl; or
when $Ar^1$ is aryl or heteroaryl, $R^1$ is aryl or heteroaryl, X is CH$_2$, n is 1, $L^1$ is —(CH$_2$)$_p$—, Y is CR$^2$R$^3$, Ar$^2$ is aryl, and $R^4$ is H, then $L^2$ is other than —N(R$^5$)—, —N(R$^5$)—(CH$_2$)$_q$, or —NH—CH(R$^5$)—; or
when $Ar^1$ and $R^1$ are both unsubstituted phenyl, X is CH$_2$, n is 2, $L^1$ is CH$_2$C(O)—, $L^2$ is —N(CH$_3$)—(CH$_2$)$_3$—, Y is CR$^2$R$^3$, Ar$^2$ is unsubstituted phenyl, and $R^4$ is hydrogen, then $R^2$ is other than unsubstituted phenyl; or
when $Ar^1$ is phenyl, $R^1$ is hydrogen or methyl, X is CH$_2$, n is 1, $L^1$-$L^2$=====Y taken together are S(O)$_r$, r is 2, then Ar$^2$ is other than 4-methylphenyl; or
when the bond connecting $L^2$ to Y is a double bond, Y is CR$^2$; or
when X is other than CH$_2$, n is 2.

Another aspect of the invention relates to pharmaceutical compositions comprising therapeutically effective amount of compound(s) of the invention or pharmaceutically acceptable salts thereof, in combination with one or more pharmaceutically acceptable carrier. Such compositions can be administered in accordance with a method of the invention, typically as part of a therapeutic regimen for treatment or prevention of conditions and disorders related to calcium channels. More particularly, the method is useful for treating conditions related to a method of treating pain in a subject in need thereof. The method comprises administering to the subject a therapeutically suitable amount of a compound of formula (I), or a pharmaceutically acceptable salt thereof. Conditions related to pain include acute pain, chronic pain, neuropathic pain, inflammatory pain, visceral pain, cancer pain, allodynia, fibromyalgia, sciatica, back pain, and headache pain including migraine, or combinations thereof.

Another aspect of the invention provides a method of treating disorders of the central nervous system in a subject in need thereof. The method comprising the step of: administering a therapeutically suitable amount of a compound of formula (I), or a pharmaceutically acceptable salt thereof. The disorders of the central nervous system include stroke, epilepsy, manic depression, bipolar disorders, depression, anxiety, schizophrenia, migraine, and psychoses; neural degenerative disorders including Alzheimer's disease, AIDS related dementia, Parkinson's disease, neuropathy caused by head injury, and dementia caused by cerebrovascular disorders; disorders of the lower urinary tract including overactive bladder, prostatis, prostadynia, interstitial cystitis, and benign prostatic hyperplasia; disorders caused by psychogenic stress including bronchial asthma, unstable angina, and hypersensitive colon inflammation; cardiovascular disorders including hypertension, atherosclerosis, heart failure, and cardiac arrhythmias; drug addiction withdrawal symptoms, including ethanol addiction withdrawal symptoms; skin disorders including pruritis and allergic dermatitis, inflammatory bowel disease; cancer; diabetes; and infertility and sexual dysfunction, or combinations thereof.

The compounds, compositions comprising the compounds, and methods for treating or preventing conditions and disorders by administering the compounds are further described herein.

These and other objects of the invention are described in the following paragraphs. These objects should not be deemed to narrow the scope of the invention.

DETAILED DESCRIPTION OF THE INVENTION

Compounds of formula (I) are disclosed in this invention

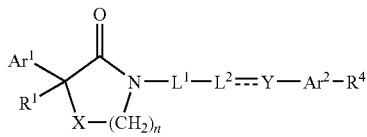

(I)

wherein $Ar^1$, $Ar^2$, $L^1$, $L^2$, n, $R^1$, $R^4$, X and Y are as defined above in the Summary of the Invention. Compositions comprising such compounds and methods for treating conditions and disorders using such compounds and compositions are also disclosed.

In various embodiments, the present invention provides at least one variable that occurs more than one time in any substituent or in the compound of the invention or any other formulae herein. Definition of a variable on each occurrence is independent of its definition at another occurrence. Further, combinations of substituents are permissible only if such combinations result in stable compounds. Stable compounds are compounds, which can be isolated from a reaction mixture.

A. DEFINITIONS

As used in the specification and the appended claims, unless specified to the contrary, the following terms have the meaning indicated:

The term "alkenyl" as used herein, means a straight or branched hydrocarbon chain containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" denotes a divalent group derived from a straight or branched chain hydrocarbon of 2 to 4 carbon atoms and contains at least one carbon-carbon double. Representative examples of alkylene include, but are not limited to, —CH=CH— and —CH$_2$CH=CH—.

The term "alkyl" as used herein, means a straight or branched, saturated hydrocarbon chain containing from 1 to 10 carbon atoms. The term "lower alkyl" or "$C_{1-6}$ alkyl" means a straight or branched chain hydrocarbon containing 1 to 6 carbon atoms. The term "$C_{1-3}$ alkyl" means a straight or branched chain hydrocarbon containing 1 to 3 carbon atoms. Representative examples of alkyl include, but are not limited to, methyl, ethyl, n-propyl, isopropyl, n-butyl, sec-butyl, isobutyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylene" denotes a divalent group derived from a straight or branched chain hydrocarbon 1 to 10 carbon atoms. Representative examples of alkylene include, but are not limited to, —CH$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl" as used herein, means phenyl or a bicyclic aryl. The bicyclic aryl is naphthyl, or a phenyl fused to a monocyclic cycloalkyl, or a phenyl fused to a monocyclic cycloalkenyl. Representative examples of the aryl groups include, but are not limited to, dihydroindenyl, indenyl, naphthyl, dihydronaphthalenyl, and tetrahydronaphthalenyl. The bicyclic aryl is attached to the parent molecular moiety through any carbon atom contained within the bicyclic ring system. The aryl groups of the present invention can be unsubstituted or substituted.

The term "cycloalkyl" or "cycloalkane" as used herein, means a monocyclic, a bicyclic, or a tricyclic cycloalkyl. The monocyclic cycloalkyl is a carbocyclic ring system containing three to eight carbon atoms, zero heteroatoms and zero double bonds. Examples of monocyclic ring systems include cyclopropyl, cyclobutyl, cyclopentyl, cyclohexyl, cycloheptyl, and cyclooctyl. The bicyclic cycloalkyl is a monocyclic cycloalkyl fused to a monocyclic cycloalkyl ring, or a bridged monocyclic ring system in which two non-adjacent carbon atoms of the monocyclic ring are linked by an alkylene bridge containing one, two, three, or four carbon atoms. Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Tricyclic cycloalkyls are exemplified by a bicyclic cycloalkyl fused to a monocyclic cycloalkyl, or a bicyclic cycloalkyl in which two non-adjacent carbon atoms of the ring systems are linked by an alkylene bridge of 1, 2, 3, or 4 carbon atoms. Representative examples of tricyclic-ring systems include, but are not limited to, tricyclo[3.3.1.0$^{3,7}$]nonane (octahydro-2,5-methanopentalene or noradamantane), and tricyclo[3.3.1.1$^{3,7}$]decane (adamantane). The monocyclic, bicyclic, and tricyclic cycloalkyls can be unsubstituted or substituted, and are attached to the parent molecular moiety through any substitutable atom contained within the ring system.

The term "cycloalkenyl" or "cycloalkene" as used herein, means a monocyclic or a bicyclic hydrocarbon ring system. The monocyclic cycloalkenyl has four-, five-, six-, seven- or eight carbon atoms and zero heteroatoms. The four-membered ring systems have one double bond, the five- or six-membered ring systems have one or two double bonds, and the seven- or eight-membered ring systems have one, two or three double bonds. Representative examples of monocyclic cycloalkenyl groups include, but are not limited to, cyclobutenyl, cyclopentenyl, cyclohexenyl, cycloheptenyl and cyclooctenyl. The bicyclic cycloalkenyl is a monocyclic cycloalkenyl fused to a monocyclic cycloalkyl group, or a monocyclic cycloalkenyl fused to a monocyclic cycloalkenyl group. The monocyclic or bicyclic cycloalkenyl ring may contain one or two alkylene bridges, each consisting of one, two or three carbon atoms, each linking two non-adjacent carbon atoms of the ring system. Representative examples of the bicyclic cycloalkenyl groups include, but are not limited to, 4,5,6,7-tetrahydro-3aH-indene, octahydronaphthalenyl and 1,6-dihydro-pentalene. The monocyclic and bicyclic cycloalkenyl can be attached to the parent molecular moiety through any substitutable atom contained within the ring systems, and can be unsubstituted or substituted.

The term "halo" or "halogen" as used herein, means Cl, Br, I, or F.

The term "haloalkyl" as used herein, means an alkyl group, as defined herein, in which one, two, three, four, five or six hydrogen atoms are replaced by halogen. Representative examples of haloalkyl include, but are not limited to, chloromethyl, 2-fluoroethyl, 2,2,2-trifluoroethyl, trifluoromethyl, difluoromethyl, pentafluoroethyl, 2-chloro-3-fluoropentyl, and trifluoropropyl such as 3,3,3-trifluoropropyl.

The term "heterocycle" or "heterocyclic" as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a bridged monocyclic heterocycle ring system in which two non adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, azabicyclo[2.2.1]heptyl (including 2-azabicyclo[2.2.1]hept-2-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.1$^{3,7}$]decane), and oxa-adamantane (2-oxatricyclo[3.3.1.1$^{3,7}$]decane). The monocyclic, bicyclic, and tricyclic heterocycles are connected to the parent molecular moiety through any carbon atom or any nitrogen atom contained within the rings, and can be unsubstituted or substituted.

The term "heteroaryl" as used herein, means a monocyclic heteroaryl or a bicyclic heteroaryl. The monocyclic heteroaryl is a five- or six-membered ring. The five-membered ring contains two double bonds. The five-membered ring may contain one heteroatom selected from O or S; or one, two, three, or four nitrogen atoms and optionally one oxygen or sulfur atom. The six-membered ring contains three double bonds and one, two, three or four nitrogen atoms. Representative examples of monocyclic heteroaryl include, but are not limited to, furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The bicyclic heteroaryl consists of a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl groups include, but are not limited to, benzofuranyl, benzothienyl, benzoxazolyl, benzimidazolyl, benzoxadiazolyl, 6,7-dihydro-1,3-benzothiazolyl, benzotriazolyl, imidazo[1,2-a]pyridinyl, indazolyl, indolyl, isoindolyl, isoquinolinyl, naphthyridinyl, pyridoimidazolyl, quinolinyl, thiazolo[5,4-b]pyridin-2-yl, thiazolo[5,4-d]pyrimidin-2-yl, and 5,6,7,8-tetrahydroquinolin-5-yl. The monocyclic and bicyclic heteroaryl groups of the present invention can be substituted or unsubstituted and are connected to the parent molecular moiety through any carbon atom or any nitrogen atom contained within the ring systems.

The term "heteroatom" as used herein, means a nitrogen, oxygen, or sulfur atom.

The term "hydroxyl" or "hydroxy" as used herein, means an —OH group.

The term "oxo" as used herein, means a =O group.

B. COMPOUNDS

Compounds of the invention have the formula (I) as described above.

Particular values of variable groups in compounds of formula (I) are as follows. Such values may be used where appropriate with any of the other values, definitions, claims or embodiments defined hereinbefore or hereinafter.

More particularly, compounds of formula (I) can include, but are not limited to compounds wherein X is $CH_2$, NC(O)OtBu, NH, or N-alkyl; and n is 1 or 2.

In another embodiment, $Ar^1$ is aryl or heteroaryl; and $R^1$ is aryl, heteroaryl, alkyl or hydrogen, wherein aryl and heteroaryl at each occurrence are independently substituted with 0, 1, 2, or 3, haloalkyl, halogen or —$OR^a$, wherein $R^a$ is alkyl.

In another embodiment, $Ar^2$ is aryl or heteroaryl substituted with 0, 1, 2, 3, or 4 alkyl, haloalkyl, halogen, —CN, $C(O)R^b$, —$C(O)N(R^b)_2$, —$N(R^b)_2$, —$N(R^b)C(O)O(R^b)$, —$OR^a$ wherein $R^a$ is hydrogen, alkyl, haloalkyl, or —CH=CH-heteroaryl-$(CR^dR^e)_m$—O(alkyl) wherein heteroaryl is a 5-membered heteroaryl, $R^b$ is hydrogen, alkyl, haloalkyl, or $G^1$; $R^d$ and $R^e$ are each hydrogen; and m is 1 or 2.

In another embodiment, $L^1$ is —$(CH_2)_pC(O)$—, wherein p is 1; $L^2$ is —$N(R^5)$— or —$N(R^5)$—$(CH_2)_q$; and Y is a bond or $CR_2R_3$; wherein $R^5$ is hydrogen or alkyl; q is 1 or 2; $R^2$ is hydrogen or phenyl; $R^3$ is hydrogen, alkyl, or cycloalkyl; or $R^2$ and $R^3$ taken together with the carbon atom to which they are attached form a cycloalkyl.

Yet in another embodiment, $L^1$ is —$(CH_2)_p$—; $L^2$ is —$N(R^5)$—, —$N(R^5)$—$(CH_2)_q$—, or —$N(R^5)$—$CH_2CH(OH)CH_2$—; p is 2; q is 3; and Y is O or C(O).

In a further embodiment, $L^1$ is —$(CH_2)_pC(O)$—; $L^2$ is —$N(R^5)$—, —$N(R^5)$—$(CH_2)_q$—, —NH—$CH(R^5)$—$(CH_2)_q$—, —NH—$CH(R^5)$—, (i), (ii), (iii), (iv), (v), (vi), (vii), (viii), (ix), or (xii); p is 1, 2, or 3; q is 1, 2, or 3; Y is a bond, $CR^2$, $CH_2CR^2R^3$, or $CR^2R^3$; $R^2$ is hydrogen or phenyl, wherein the phenyl is either unsubstituted or further substituted with 1, 2, or 3 substituents selected from the group consisting of alkyl, halogen, and haloalkyl; and $R^3$ is hydrogen, alkyl, or hydroxyl.

In another embodiment, $L^1$ is —$(CH_2)_pC(O)$; $L^2$ is —$N(R^5)$—, —$N(R^5)$—$(CH_2)_q$—, —NH—CH($R^5$)—$(CH_2)_q$—, —NH—CH($R^5$)—; p is 1, 2, or 3; q is 1, 2, or 3; Y is a bond, $CR^2$, $CH_2CR^2R^3$, or $CR^2R^3$; $R^2$ is hydrogen or phenyl, wherein the phenyl is either unsubstituted or further substituted with 1, 2, or 3 substituents selected from the group consisting of alkyl, halogen, and haloalkyl; and $R^3$ and $R^5$ taken together are —$(CH_2)_p$—.

In yet another embodiment, $L^1$ is —$(CH_2)_pC(O)$—; $L^2$ is —$N(R^5)$—, —$N(R^5)$—$(CH_2)_q$—, —NH—CH($R^5$)—$(CH_2)_q$—, —NH—CH($R^5$)—; p is 1, 2, or 3; q is 1, 2, or 3; Y is a bond, $CR^2$, $CH_2CR^2R^3$, or $CR^2R^3$; $R^2$ is hydrogen or phenyl, wherein the phenyl is either unsubstituted or further substituted with 1, 2, or 3 substituents selected from the group consisting of alkyl, halogen, and haloalkyl; $R^4$ and $R^5$ taken together are a bond or —$(CH_2)_s$—; and s is 1.

In one embodiment, $L^1$ is —$(CH_2)_p$—; —$N(R^5)$—$(CH_2)_q$—; p is 1, 2, or 3; q is 1 or 2; Y is a bond or $CR^2R^3$; $R^4$ and $R^5$ taken together are —$(CH_2)_s$—; and s is 1.

In another embodiment, $L^1$ is —$(CH_2)_p$—; —$N(R^5)$—CH($R^6$)—; p is 1, 2, or 3; Y is a bond or $CR^2R^3$; $R^4$ and $R^6$ taken together are $CH_2$; $R^5$ is hydrogen or alkyl.

In another embodiment, $L^1$ is —$(CH_2)_p$—, wherein in p is 1, 2 or 3; $L^2$ is (i), (ii), or (x); Y is a bond, $CR^2R^3$, or $CH_2CR^2R^3$, wherein $R^2$ is hydrogen or phenyl, and $R^3$ is hydrogen.

Yet in another embodiment, $L^1$ is —$(CH_2)_p$—; $L^2$ is —$N(R^5)$— or —$N(R^5)$—$(CH_2)_q$—; p is 2 or 3; q is 1 or 3; $R^5$ is hydrogen or alkyl; and Y is O or $CR^2R^3$, wherein $R^2$ and $R^3$ are each hydrogen.

In one embodiment, $L^1$ is —$(CH_2)_pC(O)$—; $L^2$ is —$N(R^5)$—, —$N(R^5)$—$(CH_2)_q$— or —NH—CH($R^5$)—$(CH_2)_q$—; p is 1, 2, 3 or 4; q is 1, 2, or 3; Y is a bond, $CR^2R^3$, O, or $S(O)_2$; $R^2$ is hydrogen or phenyl, wherein the phenyl is either unsubstituted or further substituted with 1, 2, or 3 halogen substituents; $R^3$ is hydrogen, alkyl, or hydroxyl; or $R^3$ and $R^5$ taken together are —$(CH_2)_p$— or —$OCH_2CH_2$—.

In one embodiment, $L^1$ is —$(CH_2)_pC(O)$—, wherein p is 1; $L^2$ is —$N(R^5)$—, —$N(R^5)$—$(CH_2)_q$— or —NH—CH($R^5$)—$(CH_2)_q$—; p is 1, 2, 3 or 4; q is 1, 2, or 3; $R^5$ is hydrogen, alkyl, or $G^1$; Y is a bond, $CR^2R^3$, O, or $S(O)_2$; $R^2$ is hydrogen or phenyl, wherein the phenyl is either unsubstituted or further substituted with 1, 2, or 3 halogen substituents; $R^3$ is hydrogen, alkyl, or hydroxyl; or $R^4$ and $R^5$ taken together are a bond or —$(CH_2)_s$— or —O—$(CH_2)_s$—, wherein s is 1.

In one embodiment, $L^1$ is —$(CH_2)_pC(O)$—, wherein p is 1; $L^2$ is (i), (iii), (iv), (v), (vi), or (viii); Y is a bond, $CR^2R^3$, $C(O)OCR^2R^3$; N—O—$CR^2R^3$, O, or $S(O)_2$; $R^2$ is hydrogen or phenyl, wherein the phenyl is either unsubstituted or further substituted with 1, 2, or 3 halogen substituents; and $R^3$ is hydrogen, alkyl, or hydroxyl.

In another embodiment, $L^1$ is —$(CH_2)_p$—, wherein in p is 1, 2 or 3; $L^2$ is —$N(R^5)$—CH($R^6$)—; Y is a bond or $CR^2R^3$, wherein $R^2$ and $R^3$ are each hydrogen; $R^5$ is alkyl; and $R^4$ and $R^6$ taken together are $CH_2$. In another embodiment, $L^1$ is —$(CH_2)_p$—, wherein in p is 1, 2 or 3; $L^2$ is (x); Y is a bond, $CR^2R^3$, $CH_2CR^2R^3$, or $CR^2R^3O$, wherein $R^2$ and $R^3$ are each hydrogen. In one embodiment, $L^1$-$L^2$====Y taken together are $S(O)_r$, wherein r is 1 or 2.

In another embodiment, $L^1$-$L^2$====Y taken together are $S(O)_2$.

Specific embodiments of compounds contemplated as part of the invention include, but are not limited to:
1-[2-(4-benzhydrylpiperazin-1-yl)-2-oxoethyl]-3,3-diphenylpyrrolidin-2-one;
2-(2-oxo-3,3-diphenylpyrrolidin-1-yl)-N-{[6-(trifluoromethyl)pyridin-3-yl]methyl}acetamide;
2-(2-oxo-3,3-diphenylpyrrolidin-1-yl)-N-(1,3-thiazol-2-ylmethyl)acetamide;
N-[(1-methyl-1H-pyrazol-3-yl)methyl]-2-(2-oxo-3,3-diphenylpyrrolidin-1-yl)acetamide;
N-(5-chloropyridin-2-yl)-2-(2-oxo-3,3-diphenylpyrrolidin-1-yl)acetamide;
N-benzyl-2-(2-oxo-3,3-diphenylpyrrolidin-1-yl)acetamide;
2-(2-oxo-3,3-diphenylpyrrolidin-1-yl)-N-[3-(trifluoromethyl)benzyl]acetamide;
2-(2-oxo-3,3-diphenylpyrrolidin-1-yl)-N-[4-(trifluoromethyl)benzyl]acetamide;
N-[cyclopropyl(phenyl)methyl]-2-(2-oxo-3,3-diphenylpyrrolidin-1-yl)acetamide;
2-(2-oxo-3,3-diphenylpyrrolidin-1-yl)-N-{2-[3-(trifluoromethyl)phenyl]ethyl}acetamide;
2-(2-oxo-3,3-diphenylpyrrolidin-1-yl)-N-(1-phenylcyclobutyl)acetamide;
N-(4-fluorobenzyl)-2-(2-oxo-3,3-diphenylpyrrolidin-1-yl)acetamide;
N-(3,3-diphenylpropyl)-2-(2-oxo-3,3-diphenylpyrrolidin-1-yl)acetamide;
N-benzhydryl-2-(2-oxo-3,3-diphenylpyrrolidin-1-yl)acetamide;
N-(2,2-diphenylethyl)-2-(2-oxo-3,3-diphenylpyrrolidin-1-yl)acetamide;
N-(2,2-diphenylpropyl)-2-(2-oxo-3,3-diphenylpyrrolidin-1-yl)acetamide;
1-[2-(3,3-diphenylpyrrolidin-1-yl)-2-oxoethyl]-3,3-diphenylpyrrolidin-2-one;
1-[2-(3-benzylpiperazin-1-yl)-2-oxoethyl]-3,3-diphenylpyrrolidin-2-one;
1-[2-(3,4-dihydroisoquinolin-2(1H)-yl)-2-oxoethyl]-3,3-diphenylpyrrolidin-2-one;
1-{2-oxo-2-[5-(trifluoromethyl)-1,3-dihydro-2H-isoindol-2-yl]ethyl}-3,3-diphenylpyrrolidin-2-one;
1-[2-oxo-2-(3-phenylpyrrolidin-1-yl)ethyl]-3,3-diphenylpyrrolidin-2-one;
N-2,3-dihydro-1H-inden-2-yl-2-(2-oxo-3,3-diphenylpyrrolidin-1-yl)acetamide;
1-[2-(2,2-diphenylmorpholin-4-yl)-2-oxoethyl]-3,3-diphenylpyrrolidin-2-one;
1-[2-(3,3-diphenylpiperidin-1-yl)-2-oxoethyl]-3,3-diphenylpyrrolidin-2-one;
1-[2-(4,4-diphenylpiperidin-1-yl)-2-oxoethyl]-3,3-diphenylpyrrolidin-2-one;
1-[2-(5-fluoro-1,3-dihydro-2H-isoindol-2-yl)-2-oxoethyl]-3,3-diphenylpyrrolidin-2-one;
2-(2-oxo-3,3-diphenylpyrrolidin-1-yl)-N-1,2,3,4-tetrahydronaphthalen-1-ylacetamide;
4-[(2-oxo-3,3-diphenylpyrrolidin-1-yl)acetyl]-1-[3-(trifluoromethyl)benzyl]piperazin-2-one;
1-benzhydryl-4-[(2-oxo-3,3-diphenylpyrrolidin-1-yl)acetyl]piperazin-2-one;
1-[2-(4-benzhydrylpiperidin-1-yl)-2-oxoethyl]-3,3-diphenylpyrrolidin-2-one;
1-{2-[4-(diphenylmethylene)piperidin-1-yl]-2-oxoethyl}-3,3-diphenylpyrrolidin-2-one;
1-(2-{4-[bis(4-fluorophenyl)(hydroxy)methyl]piperidin-1-yl}-2-oxoethyl)-3,3-diphenylpyrrolidin-2-one;
1-{2-[4-(hydroxy{bis[3-(trifluoromethyl)phenyl]}methyl)piperidin-1-yl]-2-oxoethyl}-3,3-diphenylpyrrolidin-2-one;

1-(2-{4-[hydroxy(diphenyl)methyl]piperidin-1-yl}-2-oxoethyl)-3,3-diphenylpyrrolidin-2-one;
1-{2-[4-(5-methoxy-1H-indol-3-yl)-3,6-dihydropyridin-1(2H)-yl]-2-oxoethyl}-3,3-diphenylpyrrolidin-2-one;
1-{2-[4-(2,6-dichlorobenzyl)piperazin-1-yl]-2-oxoethyl}-3,3-diphenylpyrrolidin-2-one;
1-(2-oxo-2-{4-[3-(trifluoromethyl)benzyl]piperazin-1-yl}ethyl)-3,3-diphenylpyrrolidin-2-one;
1-{2-[4-(4-fluorobenzyl)piperazin-1-yl]-2-oxoethyl}-3,3-diphenylpyrrolidin-2-one;
N-[(1-benzylpyrrolidin-3-yl)methyl]-2-(2-oxo-3,3-diphenylpyrrolidin-1-yl)acetamide;
N-(1-benzyl-3-methylpyrrolidin-3-yl)-2-(2-oxo-3,3-diphenylpyrrolidin-1-yl)acetamide;
2-(2-oxo-3,3-diphenylpyrrolidin-1-yl)-N-{1-[3-(trifluoromethyl)benzyl]piperidin-4-yl}acetamide;
1-[2-oxo-2-(4-{[3-(trifluoromethyl)benzyl]amino}piperidin-1-yl)ethyl]-3,3-diphenylpyrrolidin-2-one;
1-{2-[4-(2,4-dichlorobenzyl)piperazin-1-yl]-2-oxoethyl}-3,3-diphenylpyrrolidin-2-one;
1-[2-oxo-2-(4-{1-[3-(trifluoromethyl)phenyl]ethyl}piperazin-1-yl)ethyl]-3,3-diphenylpyrrolidin-2-one;
1-(2-{4-[bis(4-fluorophenyl)methyl]piperazin-1-yl}-2-oxoethyl)-3,3-diphenylpyrrolidin-2-one;
1-(2-{4-[(4-fluorophenyl)(phenyl)methyl]piperazin-1-yl}-2-oxoethyl)-3,3-diphenylpyrrolidin-2-one;
1-(2-{4-[(4-chlorophenyl)(phenyl)methyl]piperazin-1-yl}-2-oxoethyl)-3,3-diphenylpyrrolidin-2-one;
N-(1-benzhydrylpiperidin-4-yl)-2-(2-oxo-3,3-diphenylpyrrolidin-1-yl)acetamide;
1-{2-[(2R)-4-benzhydryl-2-methylpiperazin-1-yl]-2-oxoethyl}-3,3-diphenylpyrrolidin-2-one;
1-{2-[(4aS,7aS)-6-benzhydryloctahydro-1H-pyrrolo[3,4-b]pyridin-1-yl]-2-oxoethyl}-3,3-diphenylpyrrolidin-2-one;
1-{2-[(4aR,7aR)-6-benzhydryloctahydro-1H-pyrrolo[3,4-b]pyridin-1-yl]-2-oxoethyl}-3,3-diphenylpyrrolidin-2-one;
1-(2-{4-[(2,2-diphenylethyl)amino]piperidin-1-yl}-2-oxoethyl)-3,3-diphenylpyrrolidin-2-one;
1-{2-[4-(5-chloropyridin-2-yl)piperazin-1-yl]-2-oxoethyl}-3,3-diphenylpyrrolidin-2-one;
1-{2-[4-(4-fluorophenyl)piperazin-1-yl]-2-oxoethyl}-3,3-diphenylpyrrolidin-2-one;
1-{2-oxo-2-[7-(trifluoromethyl)-3,4-dihydroisoquinolin-2(1H)-yl]ethyl}-3,3-diphenylpyrrolidin-2-one;
2-(2-oxo-3,3-diphenylpyrrolidin-1-yl)-N-{(3aS*,4S*,6aR*)-2-[3-(trifluoromethyl)benzyl]octahydrocyclopenta[c]pyrrol-4-yl}acetamide;
2-(2-oxo-3,3-diphenylpyrrolidin-1-yl)-N-{(3aS*,4R*,6aR*)-2-[3-(trifluoromethyl)benzyl]octahydrocyclopenta[c]pyrrol-4-yl}acetamide;
1-[2-(4-benzhydrylpiperazin-1-yl)-2-oxoethyl]-3,3-bis(4-fluorophenyl)pyrrolidin-2-one;
2-[3,3-bis(4-fluorophenyl)-2-oxopyrrolidin-1-yl]-N-(2,2-diphenylpropyl)acetamide;
3,3-bis(4-fluorophenyl)-1-(2-oxo-2-{4-[3-(trifluoromethyl)benzyl]piperazin-1-yl}ethyl)pyrrolidin-2-one;
1-[2-(3,3-diphenylpyrrolidin-1-yl)-2-oxoethyl]-3,3-bis(4-fluorophenyl)pyrrolidin-2-one;
3,3-diphenyl-1-({3-[4-(trifluoromethyl)phenyl]-1,2,4-oxadiazol-5-yl}methyl)pyrrolidin-2-one;
1-{2-[4-(3,5-dimethoxybenzyl)piperazin-1-yl]ethyl}-3,3-bis(4-fluorophenyl)pyrrolidin-2-one;
4-benzhydryl-1-[2-(2-oxo-3,3-diphenylpyrrolidin-1-yl)ethyl]piperazin-2-one;
3,3-dimethyl-1-[2-(2-oxo-3,3-diphenylpyrrolidin-1-yl)ethyl]-4-(thien-2-ylmethyl)piperazin-2-one;
1-benzhydryl-4-[2-(2-oxo-3,3-diphenylpyrrolidin-1-yl)ethyl]piperazin-2-one;
3,3-diphenyl-1-{2-[7-(trifluoromethyl)-3,4-dihydroisoquinolin-2(1H)-yl]ethyl}pyrrolidin-2-one;
1-[2-(4-benzhydrylpiperazin-1-yl)-2-oxoethyl]-3,3-diphenylpiperidin-2-one;
1-[2-(2,2-diphenylmorpholin-4-yl)-2-oxoethyl]-3,3-diphenylpiperidin-2-one;
1-[2-oxo-2-(2-phenylmorpholin-4-yl)ethyl]-3,3-diphenylpiperidin-2-one;
1-[2-(3,3-diphenylpiperidin-1-yl)-2-oxoethyl]-3,3-diphenylpiperidin-2-one;
1-[2-(4,4-diphenylpiperidin-1-yl)-2-oxoethyl]-3,3-diphenylpiperidin-2-one;
1-{2-[2-(4-fluorophenyl)pyrrolidin-1-yl]-2-oxoethyl}-3,3-diphenylpiperidin-2-one;
1-{2-[2-(4-fluorophenyl)piperidin-1-yl]-2-oxoethyl}-3,3-diphenylpiperidin-2-one;
N-(6-fluoro-3,4-dihydro-2H-chromen-4-yl)-2-(2-oxo-3,3-diphenylpiperidin-1-yl)acetamide;
1-[2-(4-benzhydrylpiperidin-1-yl)-2-oxoethyl]-3,3-diphenylpiperidin-2-one;
N-(2,2-diphenylpropyl)-2-(2-oxo-3,3-diphenylpiperidin-1-yl)acetamide;
1-(2-{4-[hydroxy(diphenyl)methyl]piperidin-1-yl}-2-oxoethyl)-3,3-diphenylpiperidin-2-one;
1-(2-oxo-2-{4-[3-(trifluoromethyl)benzyl]piperazin-1-yl}ethyl)-3,3-diphenylpiperidin-2-one;
1-(2-oxo-2-{4-[4-(trifluoromethyl)benzyl]piperazin-1-yl}ethyl)-3,3-diphenylpiperidin-2-one;
1-{2-[4-(3-chlorobenzyl)piperazin-1-yl]-2-oxoethyl}-3,3-diphenylpiperidin-2-one;
1-(2-{4-[bis(4-fluorophenyl)methyl]piperazin-1-yl}-2-oxoethyl)-3,3-diphenylpiperidin-2-one;
1-benzhydryl-4-[(2-oxo-3,3-diphenylpiperidin-1-yl)acetyl]piperazin-2-one;
1-[2-oxo-2-(4-{[3-(trifluoromethyl)phenyl]sulfonyl}piperazin-1-yl)ethyl]-3,3-diphenylpiperidin-2-one;
N-(1-benzhydrylpiperidin-4-yl)-2-(2-oxo-3,3-diphenylpiperidin-1-yl)acetamide;
N-(1-benzhydryl-3-methylpyrrolidin-3-yl)-2-(2-oxo-3,3-diphenylpiperidin-1-yl)acetamide;
1-{2-[4-(benzhydrylamino)piperidin-1-yl]-2-oxoethyl}-3,3-diphenylpiperidin-2-one;
1-{2-[(4aS,7aS)-1-benzhydryloctahydro-6H-pyrrolo[3,4-b]pyridin-6-yl]-2-oxoethyl}-3,3-diphenylpiperidin-2-one;
N-(1-benzyl-3-methylpyrrolidin-3-yl)-2-(2-oxo-3,3-diphenylpiperidin-1-yl)acetamide;
1-[2-(4-benzhydrylpiperazin-1-yl)-2-oxoethyl]-3,3-bis(4-fluorophenyl)piperidin-2-one;
1-[2-(4-benzhydrylpiperazin-1-yl)-2-oxoethyl]-3-phenylpiperidin-2-one;
1-(2-{4-[bis(4-fluorophenyl)methyl]piperazin-1-yl}-2-oxoethyl)-3-phenylpiperidin-2-one;
1-(2-oxo-2-{4-[3-(trifluoromethyl)benzyl]piperazin-1-yl}ethyl)-3-phenylpiperidin-2-one;
1-{2-[4-(2,4-dichlorobenzyl)piperazin-1-yl]-2-oxoethyl}-3-phenylpiperidin-2-one;
1-[2-(5-fluoro-1,3-dihydro-2H-isoindol-2-yl)-2-oxoethyl]-3-phenylpiperidin-2-one;
1-{2-oxo-2-[7-(trifluoromethyl)-3,4-dihydroisoquinolin-2(1H)-yl]ethyl}-3-phenylpiperidin-2-one;
N-[1-(4-fluorophenyl)cyclobutyl]-2-(2-oxo-3-phenylpiperidin-1-yl)acetamide;

1-[2-(5-fluoro-1,3-dihydro-2H-isoindol-2-yl)-2-oxoethyl]-3-methyl-3-phenylpiperidin-2-one;
3,3-diphenyl-1-({3-[4-(trifluoromethyl)phenyl]-1,2,4-oxadiazol-5-yl}methyl)piperidin-2-one;
1-{[3-(4-fluorophenyl)-1,2,4-oxadiazol-5-yl]methyl}-3,3-diphenylpiperidin-2-one;
tert-butyl 4-[2-(4-benzhydrylpiperazin-1-yl)-2-oxoethyl]-3-oxo-2-phenylpiperazine-1-carboxylate;
1-[2-(4-benzhydrylpiperazin-1-yl)-2-oxoethyl]-3-phenylpiperazin-2-one;
1-(2-{4-[bis(4-fluorophenyl)methyl]piperazin-1-yl}-2-oxoethyl)-3-phenylpiperazin-2-one;
1-(2-{4-[bis(4-fluorophenyl)methyl]piperazin-1-yl}-2-oxoethyl)-4-methyl-3-phenylpiperazin-2-one;
1-{2-[[3-(3,5-dimethoxyphenoxy)propyl](methyl)amino]ethyl}-3,3-bis(4-fluorophenyl)pyrrolidin-2-one;
1-{2-[[2-hydroxy-3-(quinolin-5-yloxy)propyl](methyl)amino]ethyl}-3,3-bis(4-methoxyphenyl)pyrrolidin-2-one;
3,3-bis(4-fluorophenyl)-1-{2-[[2-hydroxy-3-(2-{(E)-2-[3-(methoxymethyl)isoxazol-5-yl]vinyl}phenoxy)propyl](methyl)amino]ethyl}pyrrolidin-2-one;
3,3-bis(4-fluorophenyl)-1-{2-[[2-hydroxy-3-(quinolin-5-yloxy)propyl](methyl)amino]ethyl}pyrrolidin-2-one;
3,3-bis(4-fluorophenyl)-1-{2-[4-(3,4,5-trimethoxybenzyl)piperazin-1-yl]ethyl}pyrrolidin-2-one;
3,3-bis(4-fluorophenyl)-1-{3-[4-(3,4,5-trimethoxybenzyl)piperazin-1-yl]propyl}pyrrolidin-2-one;
3,3-bis(4-fluorophenyl)-1-(2-{4-[3-(trifluoromethyl)phenyl]piperazin-1-yl}ethyl)pyrrolidin-2-one;
N-{2-[3,3-bis(4-methoxyphenyl)-2-oxopyrrolidin-1-yl]ethyl}benzamide;
1-{2-[2,3-dihydro-1H-inden-2-yl(methyl)amino]ethyl}-3,3-bis(4-methoxyphenyl)piperidin-2-one;
1-{3-[2,3-dihydro-1H-inden-2-yl(methyl)amino]propyl}-3,3-bis(4-fluorophenyl)pyrrolidin-2-one;
1-{2-[[3-(3,5-dimethoxyphenoxy)propyl](methyl)amino]ethyl}-3,3-bis(4-methoxyphenyl)piperidin-2-one;
1-{3-[[3-(3,5-dimethoxyphenoxy)propyl](methyl)amino]propyl}-3,3-bis(4-methoxyphenyl)piperidin-2-one;
1-{3-[methyl(2-phenylethyl)amino]propyl}-3,3-diphenylpiperidin-2-one;
1-{2-[[2-(3,4-dimethoxyphenyl)ethyl](methyl)amino]ethyl}-3,3-diphenylpiperidin-2-one;
1-{3-[[2-(3,5-dimethoxyphenyl)ethyl](methyl)amino]propyl}-3,3-bis(4-methoxyphenyl)piperidin-2-one;
3,3-bis(4-fluorophenyl)-1-{2-[[2-(3-methoxyphenyl)ethyl](methyl)amino]ethyl}piperidin-2-one;
3,3-bis(4-fluorophenyl)-1-{3-[[2-(3-methoxyphenyl)ethyl](methyl)amino]propyl}piperidin-2-one;
3,3-bis(4-fluorophenyl)-1-{2-[methyl(2-phenylethyl)amino]ethyl}piperidin-2-one;
3,3-bis(4-fluorophenyl)-1-{3-[methyl(2-phenylethyl)amino]propyl}piperidin-2-one;
3,3-bis(4-methoxyphenyl)-1-{2-[[2-(3-methoxyphenyl)ethyl](methyl)amino]ethyl}piperidin-2-one;
3,3-bis(4-methoxyphenyl)-1-{3-[[2-(3-methoxyphenyl)ethyl](methyl)amino]propyl}piperidin-2-one;
1-{2-[[2-(2,4-dimethoxyphenyl)ethyl](methyl)amino]ethyl}-3,3-bis(4-methoxyphenyl)piperidin-2-one;
1-{3-[(3,5-dimethoxybenzyl)(methyl)amino]propyl}-3,3-bis(4-methoxyphenyl)piperidin-2-one;
3-isopropyl-3-(3-methoxyphenyl)-1-{3-[[2-(3-methoxyphenyl)ethyl](methyl)amino]propyl}piperidin-2-one;
1-{3-[[2-(4-fluorophenyl)ethyl](methyl)amino]propyl}-3-isopropyl-3-(3-methoxyphenyl)piperidin-2-one;
3-isopropyl-3-(3-methoxyphenyl)-1-{2-[[2-(4-methoxyphenyl)ethyl](methyl)amino]ethyl}piperidin-2-one;
1-{3-[4-(3,5-dimethoxybenzyl)piperazin-1-yl]propyl}-3,3-bis(4-methoxyphenyl)piperidin-2-one;
1-{2-[4-(3,5-dimethoxybenzyl)piperazin-1-yl]ethyl}-3,3-bis(4-methoxyphenyl)piperidin-2-one;
1-{3-[4-(3,5-dimethoxybenzyl)piperazin-1-yl]propyl}-3-isopropyl-3-(3-methoxyphenyl)piperidin-2-one;
3,3-diphenyl-1-[2-(4-pyrimidin-2-ylpiperazin-1-yl)ethyl]piperidin-2-one;
3,3-bis(4-fluorophenyl)-1-[3-(4-pyrimidin-2-ylpiperazin-1-yl)propyl]piperidin-2-one;
3,3-bis(4-fluorophenyl)-1-[2-(4-pyrimidin-2-ylpiperazin-1-yl)ethyl]piperidin-2-one;
3,3-bis(4-fluorophenyl)-1-{2-[4-(2-methoxyphenyl)piperazin-1-yl]ethyl}piperidin-2-one;
3,3-bis(4-fluorophenyl)-1-{3-[4-(2-methoxyphenyl)piperazin-1-yl]propyl}piperidin-2-one;
3,3-bis(4-fluorophenyl)-1-(2-{4-[3-(trifluoromethyl)phenyl]piperazin-1-yl}ethyl)piperidin-2-one;
3,3-diphenyl-1-(3-{4-[3-(trifluoromethyl)phenyl]piperazin-1-yl}propyl)piperidin-2-one;
3,3-diphenyl-1-(2-{4-[3-(trifluoromethyl)phenyl]piperazin-1-yl}ethyl)piperidin-2-one;
3,3-bis(4-fluorophenyl)-1-(3-{4-[3-(trifluoromethyl)phenyl]piperazin-1-yl}propyl)piperidin-2-one;
N-[2-(3,4-dimethoxyphenyl)ethyl]-N-methyl-2-(2-oxo-3,3-diphenylpiperidin-1-yl)acetamide;
3,3-diphenyl-1-{[3-(trifluoromethyl)phenyl]sulfonyl}pyrrolidin-2-one;
3,3-bis(4-fluorophenyl)-1-{[3-(trifluoromethyl)phenyl]sulfonyl}pyrrolidin-2-one;
3,3-diphenyl-1-{[3-(trifluoromethyl)phenyl]sulfonyl}piperidin-2-one;
1-[(3-{[(cis-2,6-dimethylmorpholin-4-yl]carbonyl}phenyl)sulfonyl]-3,3-diphenylpyrrolidin-2-one;
3,3-diphenyl-1-{[2-(trifluoromethyl)phenyl]sulfonyl}pyrrolidin-2-one;
3,3-diphenyl-1-{[4-(trifluoromethyl)phenyl]sulfonyl}pyrrolidin-2-one;
N-cyclopropyl-3-[(2-oxo-3,3-diphenylpyrrolidin-1-yl)sulfonyl]benzamide;
1-{[2-chloro-4-(trifluoromethyl)phenyl]sulfonyl}-3,3-diphenylpyrrolidin-2-one;
1-[2-(7-benzyl-2,7-diazaspiro[3.5]non-2-yl)-2-oxoethyl]-3,3-bis(4-fluorophenyl)pyrrolidin-2-one;
3,3-bis(4-fluorophenyl)-1-(2-oxo-2-{7-[4-(trifluoromethyl)benzyl]-2,7-diazaspiro[3.5]non-2-yl}ethyl)pyrrolidin-2-one;
1-{[3-(1H-indazol-5-yl)-1,2,4-oxadiazol-5-yl]methyl}-3,3-diphenylpiperidin-2-one;
3,3-diphenyl-1-(3-{3-[4-(trifluoromethyl)phenyl]-1,2,4-oxadiazol-5-yl}propyl)pyrrolidin-2-one;
1-({4-methyl-2-[4-(trifluoromethyl)phenyl]-1,3-thiazol-5-yl}methyl)-3,3-diphenylpyrrolidin-2-one;
1-({4-methyl-2-[3-(trifluoromethyl)phenyl]-1,3-thiazol-5-yl}methyl)-3,3-diphenylpyrrolidin-2-one;
1-{2-[4-(4-chlorophenoxy)piperidin-1-yl]-2-oxoethyl}-3,3-diphenylpiperidin-2-one;
1-{2-[4-(3-chlorophenoxy)piperidin-1-yl]-2-oxoethyl}-3,3-diphenylpiperidin-2-one;
1-{2-[4-(3,4-difluorophenoxy)piperidin-1-yl]-2-oxoethyl}-3,3-diphenylpiperidin-2-one;
1-{2-[4-(4-methoxyphenoxy)piperidin-1-yl]-2-oxoethyl}-3,3-diphenylpiperidin-2-one;
1-(2-oxo-2-{4-[3-(trifluoromethyl)phenoxy]piperidin-1-yl}ethyl)-3,3-diphenylpiperidin-2-one;
1-(2-{4-[(benzyloxy)imino]piperidin-1-yl}-2-oxoethyl)-3,3-diphenylpiperidin-2-one;

1-(2-oxo-2-{4-[5-(trifluoromethyl)-1H-1,2,3-benzotriazol-1-yl]piperidin-1-yl}ethyl)-3,3-diphenylpiperidin-2-one;
1-({3-[2-(4-chlorophenyl)ethyl]-1,2,4-oxadiazol-5-yl}methyl)-3,3-bis(4-fluorophenyl)pyrrolidin-2-one;
2-(2-oxo-3,3-diphenylpiperidin-1-yl)-N-piperidin-4-yl-N-[4-(trifluoromethyl)phenyl]acetamide;
1-{2-[3-(3,4-dimethoxybenzyl)-3-methylpiperazin-1-yl]-2-oxoethyl}-3,3-diphenylpyrrolidin-2-one;
N-(1,3-oxazol-2-ylmethyl)-2-(2-oxo-3,3-diphenylpyrrolidin-1-yl)acetamide;
1-{2-[4-(2,4-dichlorobenzyl)piperazin-1-yl]-2-oxoethyl}-3,3-diphenylpiperidin-2-one;
1-{[3-(4-chlorophenyl)-1,2,4-oxadiazol-5-yl]methyl}-3,3-diphenylpiperidin-2-one;
1-(2-{4-[bis(4-fluorophenyl)methylene]piperidin-1-yl}-2-oxoethyl)-3,3-diphenylpiperidin-2-one;
1-[2-(3,3-diphenylpyrrolidin-1-yl)-2-oxoethyl]-3,3-bis(4-fluorophenyl)piperidin-2-one;
1-[2-(4,4-diphenylpiperidin-1-yl)-2-oxoethyl]-3,3-bis(4-fluorophenyl)piperidin-2-one;
1-[2-(3,3-diphenylpyrrolidin-1-yl)-2-oxoethyl]-3,3-diphenylpiperidin-2-one;
3,3-bis(4-fluorophenyl)-1-(2-oxo-2-{-4-[3-(trifluoromethyl)benzyl]piperazin-1-yl}ethyl)piperidin-2-one;
N-(1-benzhydrylazetidin-3-yl)-2-(2-oxo-3,3-diphenylpiperidin-1-yl)acetamide;
3,3-diphenyl-1-({3-[6-(trifluoromethyl)pyridin-3-yl]-1,2,4-oxadiazol-5-yl}methyl)piperidin-2-one;
1-{2-oxo-2-[5-(trifluoromethyl)-1,3-dihydro-2H-isoindol-2-yl]ethyl}-3-phenylpiperidin-2-one;
3,3-diphenyl-1-({3-[3-(trifluoromethyl)phenyl]-1,2,4-oxadiazol-5-yl}methyl)piperidin-2-one;
2-(2-oxo-3,3-diphenylpiperidin-1-yl)-N-{1-[3-(trifluoromethyl)benzyl]azetidin-3-yl}acetamide;
3-phenyl-1-({3-[4-(trifluoromethyl)phenyl]-1,2,4-oxadiazol-5-yl}methyl)piperidin-2-one;
benzyl 4-[(2-oxo-3,3-diphenylpiperidin-1-yl)acetyl]piperazine-1-carboxylate;
N-{1-[4-fluoro-3-(trifluoromethyl)benzyl]piperidin-4-yl}-2-(2-oxo-3,3-diphenylpiperidin-1-yl)acetamide;
1-(2-{4-[4-fluoro-3-(trifluoromethyl)benzyl]piperazin-1-yl}-2-oxoethyl)-3,3-diphenylpiperidin-2-one;
2-(2-oxo-3,3-diphenylpiperidin-1-yl)-N-{(3S)-1-[3-(trifluoromethyl)benzyl]pyrrolidin-3-yl}acetamide;
2-(2-oxo-3,3-diphenylpiperidin-1-yl)-N-{(3R)-1-[3-(trifluoromethyl)benzyl]pyrrolidin-3-yl}acetamide;
(3S)-1-[2-(5-fluoro-1,3-dihydro-2H-isoindol-2-yl)-2-oxoethyl]-3-phenylpiperidin-2-one;
(3R)-1-[2-(5-fluoro-1,3-dihydro-2H-isoindol-2-yl)-2-oxoethyl]-3-phenylpiperidin-2-one;
3-(4-fluorophenyl)-1-({3-[4-(trifluoromethyl)phenyl]-1,2,4-oxadiazol-5-yl}methyl)pyrrolidin-2-one;
3,3-bis(4-fluorophenyl)-1-({3-[4-(trifluoromethyl)phenyl]-1,2,4-oxadiazol-5-yl}methyl)pyrrolidin-2-one;
3,3-bis(4-fluorophenyl)-1-({3-[4-(trifluoromethyl)phenyl]-1,2,4-oxadiazol-5-yl}methyl)piperidin-2-one;
N-(5-chloropyridin-2-yl)-2-(2-oxo-3-phenylpiperidin-1-yl)acetamide;
1-{[3-(4-chlorophenyl)-1,2,4-oxadiazol-5-yl]methyl}-3,3-diphenylpyrrolidin-2-one;
1-{[3-(4-fluorophenyl)-1,2,4-oxadiazol-5-yl]methyl}-3,3-diphenylpyrrolidin-2-one;
1-{[3-(4-methylphenyl)-1,2,4-oxadiazol-5-yl]methyl}-3,3-diphenylpyrrolidin-2-one;
3,3-diphenyl-1-({5-[4-(trifluoromethyl)phenyl]-1,2,4-oxadiazol-3-yl}methyl)pyrrolidin-2-one;
N-methyl-2-(2-oxo-3,3-diphenylpiperidin-1-yl)-N-{1-[3-(trifluoromethyl)benzyl]piperidin-4-yl}acetamide;
N-{1-[4-fluoro-3-(trifluoromethyl)benzyl]azetidin-3-yl}-2-(2-oxo-3,3-diphenylpiperidin-1-yl)acetamide;
3,3-diphenyl-1-({3-[4-(trifluoromethoxy)phenyl]-1,2,4-oxadiazol-5-yl}methyl)piperidin-2-one;
2-(2-oxo-3,3-diphenylpiperidin-1-yl)-N-{1-[3-(trifluoromethyl)benzyl]piperidin-4-yl}acetamide;
N-{1-[2-fluoro-3-(trifluoromethyl)benzyl]azetidin-3-yl}-2-(2-oxo-3,3-diphenylpiperidin-1-yl)acetamide;
1-{[3-(4-tert-butylphenyl)-1,2,4-oxadiazol-5-yl]methyl}-3,3-diphenylpyrrolidin-2-one;
1-{2-[3,3-bis(4-fluorophenyl)pyrrolidin-1-yl]-2-oxoethyl}-3,3-diphenylpyrrolidin-2-one;
1-{2-[3,3-bis(4-fluorophenyl)pyrrolidin-1-yl]-2-oxoethyl}-3,3-bis(4-fluorophenyl)pyrrolidin-2-one;
1-{2-[3,3-bis(4-fluorophenyl)pyrrolidin-1-yl]-2-oxoethyl}-3,3-diphenylpiperidin-2-one;
1-{[3-(4-hydroxyphenyl)-1,2,4-oxadiazol-5-yl]methyl}-3,3-diphenylpiperidin-2-one;
1-{[3-(4-chlorobenzyl)-1,2,4-oxadiazol-5-yl]methyl}-3,3-diphenylpiperidin-2-one;
2-[3,3-bis(4-fluorophenyl)-2-oxopyrrolidin-1-yl]-N-{1-[3-(trifluoromethyl)benzyl]piperidin-4-yl}acetamide;
1-{[3-(4-isobutoxyphenyl)-1,2,4-oxadiazol-5-yl]methyl}-3,3-diphenylpiperidin-2-one;
3,3-bis(4-fluorophenyl)-1-(2-oxo-2-{(4aS,7aS)-1-[3-(trifluoromethyl)benzyl]octahydro-6H-pyrrolo[3,4-b]pyridin-6-yl}ethyl)pyrrolidin-2-one;
3,3-diphenyl-1-({3-[6-(trifluoromethyl)pyridin-3-yl]-1,2,4-oxadiazol-5-yl}methyl)pyrrolidin-2-one;
3,3-bis(4-fluorophenyl)-1-({3-[6-(trifluoromethyl)pyridin-3-yl]-1,2,4-oxadiazol-5-yl}methyl)pyrrolidin-2-one;
1-({3-[2-(4-chlorophenyl)ethyl]-1,2,4-oxadiazol-5-yl}methyl)-3,3-diphenylpiperidin-2-one;
1-{[3-(6-chloropyridin-3-yl)-1,2,4-oxadiazol-5-yl]methyl}-3,3-diphenylpyrrolidin-2-one;
1-{[3-(3,5-difluorophenyl)-1,2,4-oxadiazol-5-yl]methyl}-3,3-diphenylpyrrolidin-2-one;
3-(4-fluorophenyl)-1-{2-oxo-2-[5-(trifluoromethyl)-1,3-dihydro-2H-isoindol-2-yl]ethyl}pyrrolidin-2-one;
2-[3,3-bis(4-fluorophenyl)-2-oxopyrrolidin-1-yl]-N-[5-(trifluoromethyl)pyridin-2-yl]acetamide;
2-[3,3-bis(4-fluorophenyl)-2-oxopyrrolidin-1-yl]-N-[4-(trifluoromethyl)phenyl]acetamide;
3,3-diphenyl-1-({3-[5-(trifluoromethyl)pyridin-3-yl]-1,2,4-oxadiazol-5-yl}methyl)pyrrolidin-2-one;
3,3-diphenyl-1-({3-[4-(trifluoromethyl)pyridin-3-yl]-1,2,4-oxadiazol-5-yl}methyl)pyrrolidin-2-one;
3,3-diphenyl-1-[(3-pyridin-3-yl-1,2,4-oxadiazol-5-yl)methyl]pyrrolidin-2-one;
3,3-diphenyl-1-[(3-pyridin-4-yl-1,2,4-oxadiazol-5-yl)methyl]pyrrolidin-2-one;
1-{4-oxo-4-[5-(trifluoromethyl)-1,3-dihydro-2H-isoindol-2-yl]butyl}-3,3-diphenylpyrrolidin-2-one;
2-[3,3-bis(4-fluorophenyl)-2-oxopyrrolidin-1-yl]-N-[6-(trifluoromethyl)pyridin-3-yl]acetamide;
2-[3,3-bis(4-fluorophenyl)-2-oxopyrrolidin-1-yl]-N-(5-chloropyridin-2-yl)acetamide;
2-[3,3-bis(4-fluorophenyl)-2-oxopyrrolidin-1-yl]-N-[6-(trifluoromethyl)pyridin-2-yl]acetamide;
1-[2-(5-fluoro-1,3-dihydro-2H-isoindol-2-yl)-2-oxoethyl]-3-(4-fluorophenyl)pyrrolidin-2-one;
3,3-bis(4-fluorophenyl)-1-{2-oxo-2-[5-(trifluoromethyl)-1,3-dihydro-2H-isoindol-2-yl]ethyl}pyrrolidin-2-one;
2-[3-(4-fluorophenyl)-2-oxopyrrolidin-1-yl]-N-[5-(trifluoromethyl)pyridin-2-yl]acetamide;

3,3-diphenyl-1-[(3-pyrazin-2-yl-1,2,4-oxadiazol-5-yl)methyl]pyrrolidin-2-one;
tert-butyl 5-{5-[(2-oxo-3,3-diphenylpyrrolidin-1-yl)methyl]-1,2,4-oxadiazol-3-yl}pyridin-2-ylcarbamate;
3,3-bis(4-fluorophenyl)-1-[(3-pyrazin-2-yl-1,2,4-oxadiazol-5-yl)methyl]pyrrolidin-2-one;
1-{[3-(4-bromophenyl)-1,2,4-oxadiazol-5-yl]methyl}-3,3-bis(4-fluorophenyl)pyrrolidin-2-one;
1-{[3-(6-aminopyridin-3-yl)-1,2,4-oxadiazol-5-yl]methyl}-3,3-diphenylpyrrolidin-2-one;
4-(5-{[3,3-bis(4-fluorophenyl)-2-oxopyrrolidin-1-yl]methyl}-1,2,4-oxadiazol-3-yl)benzonitrile;
(3S)-3-(4-fluorophenyl)-1-({3-[4-(trifluoromethyl)phenyl]-1,2,4-oxadiazol-5-yl}methyl)pyrrolidin-2-one;
(3R)-3-(4-fluorophenyl)-1-({3-[4-(trifluoromethyl)phenyl]-1,2,4-oxadiazol-5-yl}methyl)pyrrolidin-2-one;
3-(4-fluorophenyl)-1-({3-[6-(trifluoromethyl)pyridin-3-yl]-1,2,4-oxadiazol-5-yl}methyl)pyrrolidin-2-one;
2-[3,3-bis(4-fluorophenyl)-2-oxopyrrolidin-1-yl]-N-{1-[3-fluoro-4-(trifluoromethyl)benzyl]azetidin-3-yl}acetamide;
1-(2-oxo-2-{3-[4-(trifluoromethyl)phenyl]azetidin-1-yl}ethyl)-3,3-diphenylpiperidin-2-one;
4-{1-[(2-oxo-3,3-diphenylpiperidin-1-yl)acetyl]azetidin-3-yl}benzonitrile;
N-(1-benzylazetidin-3-yl)-2-[3,3-bis(4-fluorophenyl)-2-oxopyrrolidin-1-yl]acetamide;
1-(2-oxo-2-{4-[3-(trifluoromethyl)phenyl]piperidin-1-yl}ethyl)-3,3-diphenylpiperidin-2-one;
1-{2-[4-(4-fluorophenyl)piperidin-1-yl]-2-oxoethyl}-3,3-diphenylpiperidin-2-one;
1-(2-oxo-2-{4-[4-(trifluoromethyl)phenyl]piperidin-1-yl}ethyl)-3,3-diphenylpiperidin-2-one;
2-(2-oxo-3,3-diphenylpyrrolidin-1-yl)-N-[5-(trifluoromethyl)pyridin-2-yl]acetamide;
2-(2-oxo-3,3-diphenylpyrrolidin-1-yl)-N-[6-(trifluoromethyl)pyridin-2-yl]acetamide;
2-(2-oxo-3,3-diphenylpyrrolidin-1-yl)-N-[6-(trifluoromethyl)pyridin-3-yl]acetamide;
N-[3-chloro-5-(trifluoromethyl)pyridin-2-yl]-2-(2-oxo-3,3-diphenylpyrrolidin-1-yl)acetamide;
1-(2-{4-[4-chloro-3-(trifluoromethyl)phenyl]-4-hydroxypiperidin-1-yl}-2-oxoethyl)-3,3-diphenylpiperidin-2-one;
N-(5-cyanopyridin-2-yl)-2-(2-oxo-3,3-diphenylpyrrolidin-1-yl)acetamide;
2-[3,3-bis(4-fluorophenyl)-2-oxopyrrolidin-1-yl]-N-(5-cyanopyridin-2-yl)acetamide;
1-[2-(3,4-dihydroisoquinolin-2(1H)-yl)-2-oxoethyl]-3-(4-fluorophenyl)pyrrolidin-2-one;
3-(4-fluorophenyl)-1-{2-oxo-2-[7-(trifluoromethyl)-3,4-dihydroisoquinolin-2(1H)-yl]ethyl}pyrrolidin-2-one;
1-[2-(7-fluoro-3,4-dihydroisoquinolin-2(1H)-yl)-2-oxoethyl]-3-(4-fluorophenyl)pyrrolidin-2-one;
1-[2-(7-chloro-3,4-dihydroisoquinolin-2(1H)-yl)-2-oxoethyl]-3-(4-fluorophenyl)pyrrolidin-2-one;
1-[2-(6-chloro-3,4-dihydroisoquinolin-2(1H)-yl)-2-oxoethyl]-3-(4-fluorophenyl)pyrrolidin-2-one;
1-[2-(3,4-dihydroisoquinolin-2(1H)-yl)-2-oxoethyl]-3,3-bis(4-fluorophenyl)pyrrolidin-2-one;
3,3-bis(4-fluorophenyl)-1-{2-oxo-2-[7-(trifluoromethyl)-3,4-dihydroisoquinolin-2(1H)-yl]ethyl}pyrrolidin-2-one;
1-[2-(3,4-dihydroisoquinolin-2(1H)-yl)-2-oxoethyl]-3,3-diphenylpiperidin-2-one;
1-{2-oxo-2-[7-(trifluoromethyl)-3,4-dihydroisoquinolin-2(1H)-yl]ethyl}-3,3-diphenylpiperidin-2-one;
1-({3-[2-(2-chlorophenyl)ethyl]-1,2,4-oxadiazol-5-yl}methyl)-3,3-diphenylpiperidin-2-one;
1-({3-[(4-chlorophenoxy)methyl]-1,2,4-oxadiazol-5-yl}methyl)-3,3-diphenylpiperidin-2-one;
(+)-3-(4-fluorophenyl)-1-{2-oxo-2-[5-(trifluoromethyl)-1,3-dihydro-2H-isoindol-2-yl]ethyl}pyrrolidin-2-one;
(−)-3-(4-fluorophenyl)-1-{2-oxo-2-[5-(trifluoromethyl)-1,3-dihydro-2H-isoindol-2-yl]ethyl}pyrrolidin-2-one;
1-[2-(5-fluoro-1,3-dihydro-2H-isoindol-2-yl)-2-oxoethyl]-3-[4-(trifluoromethyl)phenyl]pyrrolidin-2-one;
1-{2-oxo-2-[5-(trifluoromethyl)-1,3-dihydro-2H-isoindol-2-yl]ethyl}-3-[4-(trifluoromethyl)phenyl]pyrrolidin-2-one;
3-(2-chloro-4-fluorophenyl)-1-[2-(5-fluoro-1,3-dihydro-2H-isoindol-2-yl)-2-oxoethyl]pyrrolidin-2-one;
3-(2-chloro-4-fluorophenyl)-1-{2-oxo-2-[5-(trifluoromethyl)-1,3-dihydro-2H-isoindol-2-yl]ethyl}pyrrolidin-2-one;
3-(3,4-dichlorophenyl)-1-[2-(5-fluoro-1,3-dihydro-2H-isoindol-2-yl)-2-oxoethyl]pyrrolidin-2-one;
1-(2-{4-[bis(4-fluorophenyl)(hydroxy)methyl]piperidin-1-yl}-2-oxoethyl)-3,3-bis(4-fluorophenyl)pyrrolidin-2-one;
1-(2-{4-[bis(4-fluorophenyl)(hydroxy)methyl]piperidin-1-yl}-2-oxoethyl)-3,3-diphenylpiperidin-2-one; or
1-(2-(4-(bis(4-fluorophenyl)methyl)piperazin-1-yl)-2-oxoethyl)-4-isopropyl-3-phenylpiperazin-2-one.

Compounds of the present application may exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30.

On occasion, the relative stereochemistry of an enantiomeric pair is known, however, the absolute configuration is not known. In that circumstance, the relative stereochemistry descriptor terms "R*" and "S*" are used. The terms "R*" and "S*" used herein are defined in Eliel, E. L.; Wilen, S. H. Stereochemistry of Organic Compounds; John Wiley & Sons, Inc.: New York, 1994; pp 119-120 and 1206. In a particular enantiomeric pair, the relative descriptors are reversed to indicate that this pair of enantiomers is of unknown absolute stereochemistry.

The present application contemplates various stereoisomers and mixtures thereof and these are specifically included within the scope of this application. Stereoisomers include enantiomers and diastereomers, and mixtures of enantiomers or diastereomers. Individual stereoisomers of compounds of the present application may be prepared synthetically from commercially available starting materials which contain asymmetric or chiral centers or by preparation of racemic mixtures followed by resolution which is well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

Geometric isomers may exist in the present compounds. The invention contemplates the various geometric isomers and mixtures thereof resulting from the disposition of substituents around a carbon-carbon double bond, a carbon-nitrogen double bond, a cycloalkyl group, or a heterocycle group. Substituents around a carbon-carbon double bond or a carbon-nitrogen bond are designated as being of Z or E configuration and substituents around a cycloalkyl or a heterocycle are designated as being of cis or trans configuration.

Within the present invention it is to be understood that compounds disclosed herein may exhibit the phenomenon of tautomerism.

Thus, the formulae drawings within this specification can represent only one of the possible tautomeric or stereoisomeric forms. It is to be understood that the invention encompasses any tautomeric or stereoisomeric form, and mixtures thereof, and is not to be limited merely to any one tautomeric or stereoisomeric form utilized within the naming of the compounds or formulae drawings.

Compounds of this invention can exist in an isotopic form containing one or more atoms having an atomic mass or mass number different from the atomic mass or mass number most abundantly found in nature. Isotopes of atoms such as hydrogen, carbon, phosphorous, sulfur fluorine, chlorine, and iodine include, but are not limited to $^2H$, $^3H$, $^{11}C$, $^{14}C$, $^{32}P$, $^{35}S$, $^{18}F$, $^{36}Cl$, and $^{125}I$, respectively. Compounds that contain other isotopes of these and/or other atoms are within the scope of this invention. Compounds containing tritium ($^3H$) and $^{14}C$ radioisotopes are preferred in general for their ease in preparation and detectability for radiolabeled compounds. Isotopically labeled compounds of this invention can be prepared by the general methods well known to persons having ordinary skill in the art. Such Isotopically labeled compounds can be conveniently prepared by carrying out the procedures disclosed in the Examples and Schemes below by substituting a readily available isotopically labeled reagent for a non-isotopically labeled reagent.

C. BIOLOGICAL DATA

Abbreviations which have been used in the descriptions of Biological Data that follow are: EDTA for ethylenediaminetetraacetic acid; FBS for fetal bovine serum; FLIPR for fluorometric imaging plate reader; HBSS for Hank's balanced salt solution; HEPES for 4-(2-hydroxyethyl)-1-piperazineethanesulfonic acid; i.p. for intraperitoneal; MEM for minimum essential medium; MEM NEAA for minimum essential medium non-essential amino acid; p.o. for per orem (by mouth).

(i) In Vitro Methods—Assessment of Calcium Channel Activity Using FLIPR:

IMR32 cells endogenously expressing human $Ca_v2.2$ were assayed for $Ca^{2+}$ influx using a no-wash calcium indicator dye (Calcium 4 dye: Molecular Probes) and FLIPR technology (Lubin, M. L.; Reitz, T. L.; Todd, M. J.; Flores, C. M.; Qin, N.; Xin, H. A nonadherent cell-based HTS assay for N-type calcium channel using calcium 3 dye. Assay and Drug Development Technologies 2006, 4(6), 689-694). The IMR32 cells were maintained in MEM media containing 10% (v/v) FBS, 1% (v/v) antibiotic/antimitotic, 1% (v/v) sodium pyruvate and 1% (v/v) MEM NEAA. Following dissociation in 0.05% (v/v) trypsin/EDTA, cells were seeded into black 1×96-well plates (Corning Cellbind) at a density of 1-1.2×10⁵ cells/well and incubated in the maintenance media above for 48 hours at 37° C. Immediately prior to performing the assay the media was removed and cells were loaded for 1.5 hours with 1× Calcium 4 dye prepared in HBSS (137 mM NaCl, 5.4 mM KCl, 0.25 mM $Na_2HPO_4$, 0.44 mM $KH_2PO_4$, 1.3 mM $CaCl_2$, 1 mM $MgSO_4$, 4.2 mM $NaHCO_3$) containing HEPES pH 7.4 at room temperature. After dye loading and a subsequent 60 minute pre-incubation with compounds (full log dilutions from 10 µM to 0.1 nM) in the presence of 1.3 mM $CaCl_2$ and 2 µM nifedipine to block endogenous L-type channels, the external $Ca^{2+}$ concentration was increased to 5 mM $CaCl_2$ and the cells concomitantly depolarized with 80 mM KCl to assay channel activity. To determine the $IC_{50}$ values, the percent inhibition of the compound at each concentration was determined relative to the activity in the absence of inhibitor, and data was fitted using non-linear regression sigmoidal dose response curve analysis with GraphPad Prism®.

| Example | $IC_{50}$ (µM) |
|---|---|
| 1 | 1.10 |
| 2 | 5.28 |
| 3 | 13.43 |
| 4 | 29.82 |
| 5 | 4.51 |
| 6 | 5.74 |
| 7 | 2.33 |
| 8 | 1.49 |
| 9 | 2.10 |
| 10 | 3.87 |
| 11 | 0.89 |
| 12 | 3.89 |
| 13 | 0.99 |
| 14 | 0.97 |
| 15 | 0.87 |
| 16 | 0.90 |
| 17 | 0.78 |
| 18 | 2.65 |
| 19 | 3.31 |
| 20 | 2.82 |
| 21 | 1.83 |
| 22 | 3.96 |
| 23 | 0.69 |
| 24 | 0.81 |
| 25 | 0.46 |
| 26 | 4.93 |
| 27 | 3.03 |
| 28 | 1.09 |
| 29 | 1.14 |
| 30 | 0.65 |
| 31 | 1.91 |
| 32 | 0.71 |
| 33 | 7.55 |
| 34 | 0.96 |
| 35 | 8.07 |
| 36 | 0.90 |
| 37 | 1.03 |
| 38 | 2.22 |
| 39 | 2.60 |
| 40 | 2.11 |
| 41 | 0.78 |
| 42 | 1.13 |
| 43 | 0.52 |
| 44 | 0.77 |
| 45 | 0.43 |
| 46 | 0.45 |
| 47 | 1.01 |
| 48 | 0.40 |
| 49 | 2.76 |
| 50 | 2.62 |
| 51 | 2.29 |
| 52 | 1.54 |
| 53 | 4.02 |
| 54 | 2.55 |
| 55 | 2.13 |
| 56 | 1.10 |
| 57 | 0.49 |
| 58 | 0.83 |
| 59 | 2.38 |
| 60 | 1.01 |
| 61 | 1.31 |
| 62 | 8.71 |
| 63 | 1.65 |
| 64 | 2.09 |
| 65 | 1.04 |
| 66 | 1.83 |
| 67 | 3.44 |
| 68 | 1.38 |
| 69 | 6.05 |
| 70 | 7.22 |
| 71 | 3.41 |
| 72 | 0.66 |

-continued

| Example | IC$_{50}$ (µM) |
|---|---|
| 73 | 3.46 |
| 74 | 2.68 |
| 75 | 4.61 |
| 76 | 2.61 |
| 77 | 1.71 |
| 78 | 1.74 |
| 79 | 0.93 |
| 80 | 1.38 |
| 81 | 1.32 |
| 82 | 2.36 |
| 83 | 1.23 |
| 84 | 0.41 |
| 85 | 0.41 |
| 86 | 2.20 |
| 87 | 0.76 |
| 88 | 1.64 |
| 89 | 3.00 |
| 90 | 4.61 |
| 91 | 2.18 |
| 92 | 1.01 |
| 93 | 5.90 |
| 94 | 2.20 |
| 95 | 34.84 |
| 96 | 8.90 |
| 97 | 10.00 |
| 98 | 30.00 |
| 99 | 8.65 |
| 100 | 5.29 |
| 101 | 1.77 |
| 102 | 8.39 |
| 103 | 10.64 |
| 104 | 4.70 |
| 105 | 1.65 |
| 106 | 0.73 |
| 107 | 1.88 |
| 108 | 1.00 |
| 109 | 1.76 |
| 110 | 1.47 |
| 111 | 3.94 |
| 112 | 10.01 |
| 113 | 3.19 |
| 114 | 1.53 |
| 115 | 3.12 |
| 116 | 2.01 |
| 117 | 3.46 |
| 118 | 2.46 |
| 119 | 2.68 |
| 120 | 1.67 |
| 121 | 1.63 |
| 122 | 2.35 |
| 123 | 1.45 |
| 124 | 1.90 |
| 125 | 1.68 |
| 126 | 1.49 |
| 127 | 1.53 |
| 128 | 1.12 |
| 129 | 1.14 |
| 130 | 1.13 |
| 131 | 2.30 |
| 132 | 2.30 |
| 133 | 0.67 |
| 134 | 6.48 |
| 135 | 3.01 |
| 136 | 3.32 |
| 137 | 1.10 |
| 138 | 1.42 |
| 139 | 4.77 |
| 140 | 1.25 |
| 141 | 1.56 |
| 142 | 1.23 |
| 143 | 11.64 |
| 144 | 5.48 |
| 145 | 9.64 |
| 146 | 6.78 |
| 147 | 1.84 |
| 148 | 6.88 |
| 149 | 8.13 |
| 150 | 0.86 |

-continued

| Example | IC$_{50}$ (µM) |
|---|---|
| 151 | 18.31 |
| 152 | 0.73 |
| 153 | 0.86 |
| 154 | 5.15 |
| 155 | 4.37 |
| 156 | 6.18 |
| 157 | 5.21 |
| 158 | 4.07 |
| 159 | 3.73 |
| 160 | 3.04 |
| 161 | 5.74 |
| 162 | 1.86 |
| 163 | 3.79 |
| 164 | 2.02 |
| 165 | 3.39 |
| 166 | 3.12 |
| 167 | 2.02 |
| 168 | >30 |
| 169 | 1.80 |
| 170 | 6.70 |
| 171 | 2.45 |
| 172 | 1.77 |
| 173 | 3.88 |
| 174 | 2.43 |
| 175 | 1.25 |
| 176 | 1.03 |
| 177 | 3.37 |
| 178 | 7.73 |
| 179 | 9.41 |
| 180 | 0.94 |
| 181 | 3.27 |
| 182 | 1.37 |
| 183 | 0.96 |
| 184 | 1.27 |
| 185 | 1.15 |
| 186 | 1.37 |
| 187 | >30 |
| 188 | >30 |
| 189 | 5.82 |
| 190 | 7.07 |
| 191 | 6.87 |
| 192 | 11.96 |
| 193 | 4.67 |
| 194 | 4.08 |
| 195 | 3.57 |
| 196 | 4.01 |
| 197 | 1.00 |
| 198 | 0.72 |
| 199 | 5.98 |
| 200 | 1.01 |
| 201 | 0.86 |
| 202 | 10.36 |
| 203 | 2.16 |
| 204 | 3.04 |
| 205 | 3.32 |
| 206 | 4.89 |
| 207 | 5.03 |
| 208 | 2.40 |
| 209 | 10.65 |
| 210 | 0.96 |
| 211 | 3.15 |
| 212 | 2.63 |
| 213 | 1.60 |
| 214 | 2.78 |
| 215 | 6.89 |
| 216 | 9.43 |
| 217 | 2.62 |
| 218 | 6.80 |
| 219 | 2.93 |
| 220 | 1.99 |
| 221 | 5.67 |
| 222 | 5.43 |
| 223 | 2.04 |
| 224 | 3.88 |
| 225 | 2.48 |
| 226 | 2.46 |
| 227 | 12.15 |
| 228 | 1.53 |

-continued

| Example | IC$_{50}$ (μM) |
|---|---|
| 229 | 8.46 |
| 230 | 8.99 |
| 231 | >30 |
| 232 | 1.91 |
| 233 | 6.29 |
| 234 | 6.54 |
| 235 | 3.18 |
| 236 | 2.75 |
| 237 | 2.81 |
| 238 | 12.39 |
| 239 | 1.74 |
| 240 | 3.07 |
| 241 | 8.96 |
| 242 | 3.17 |
| 243 | 4.37 |
| 244 | 3.69 |
| 245 | 4.48 |
| 246 | 3.77 |
| 247 | 4.48 |
| 248 | 8.84 |
| 249 | 6.48 |
| 250 | 4.13 |
| 251 | 8.32 |
| 252 | 2.97 |
| 253 | 10.55 |
| 254 | 4.32 |
| 255 | 9.89 |
| 256 | 7.51 |
| 257 | 6.16 |
| 258 | 4.45 |
| 259 | 2.55 |
| 260 | 7.12 |
| 261 | 4.44 |
| 262 | 3.39 |
| 263 | 3.49 |
| 264 | 14.09 |
| 265 | 11.06 |
| 266 | 10.13 |
| 267 | 7.35 |
| 268 | 11.37 |
| 269 | 3.21 |
| 270 | 5.25 |
| 271 | 2.57 |
| 272 | 1.96 |
| 273 | 2.48 |

(ii) In Vivo Data—Capsaicin Induced Secondary Mechanical Hyperalgesia Model:

Sprague Dawley rats were briefly restrained, and capsaicin was administered at 10 μg in 10 μL of vehicle by intraplantar injection into the center of the right hind paw. Secondary mechanical hyperalgesia (SMH) was measured at the heel away from the site of injection 180 minutes following capsaicin exposure. Compounds and gabapentin (positive control), were administered p.o. 60 minutes before testing (2 hours after capsaicin) or i.p. 30 minutes before testing (2.5 hours after capsaicin). SMH was measured using calibrated von Frey filaments (Stoelting, Woodale, Ill.). Following the 1 hour habituation in the testing room, rats were moved to individual plexiglass chambers that sit on top of a wire mesh to allow for access for stimulation of the plantar surface of the hind paws. Rats were allowed to acclimate to the new chambers for 15 minutes before the onset of testing. The paw withdrawal threshold was determined by increasing and decreasing stimulus intensity (force: g) and calculated using Dixon's up-down method (Chaplan, S. R.; Bach, F. W.; Pogrel, J. W.; Chung, J. M.; Yaksh, T. L.; Quantitative assessment of tactile allodynia in the rat paw. J. Neuroscience Methods 1994, 53(1), 55-63). The filaments (maximum force of 15.0 g) were held in place for 8 seconds or until there was a withdrawal response from the mechanical stimulation.

| Example | % inhibition @ 30 mg/kg p.o. |
|---|---|
| 1 | 61 |
| 17 | 50 |
| 28 | 60 |
| 41 | 75 |
| 45 | 51 |
| 58 | 97 |
| 68 | 71 |
| 72 | 78 |
| 79 | 49 |
| 91 | 58 |
| 264 | 49 |

D. METHODS OF USING THE COMPOUNDS

One embodiment of the present invention provides a method of treating pain in a subject in need thereof. The method comprises administering to the subject, including a mammal, such as a human, a therapeutically suitable amount of a compound of formula (I), or a pharmaceutically acceptable salt thereof. Conditions related to pain include acute pain, chronic pain, neuropathic pain, inflammatory pain, visceral pain, cancer pain, allodynia, fibromyalgia, sciatica, back pain, and headache pain including migraine, or combinations thereof. Preferably, the method comprises administering to the mammal a therapeutically effective amount of any of the compounds as described herein, or a pharmaceutically acceptable salt thereof. In certain embodiments, the method comprises administering to the mammal a therapeutically effective amount of any of the compounds as described herein, or a pharmaceutically acceptable salt thereof, in combination with one or more of the following: nonsteroidal anti-inflammatory drug (NSAID), opioid analgesic, barbiturate, benzodiazapine, histamine antagonist, sedative, skeletal muscle relaxant, transient receptor potential ion channel antagonist, α-adrenergic, tricyclic antidepressant, anticonvulsant, tachykinin antagonist, muscarinic antagonist, cyclooxygenase-2 selective inhibitor, neuroleptic, vanilloid receptor agonist, vanilloid receptor antagonist, β-adrenergic, local anesthetic, corticosteroid, 5-HT receptor agonist, 5-HT receptor antagonist, 5-HT$_{2A}$ receptor antagonist, cholinergic analgesic, α$_2$δ ligand such as gabapentin or pregabalin, cannabinoid receptor ligand, metabotropic glutamate subtype 1 receptor antagonist, serotonin reuptake inhibitor, norepinephrine reuptake inhibitor, dual serotonin-noradrenaline reuptake inhibitor, Rho kinase inhibitor, inducible nitric oxide synthase inhibitor, acetylcholinesterase inhibitor, prostaglandin E$_2$ subtype 4 antagonist, leukotriene B4 antagonist, 5-lipoxygenase inhibitor, sodium channel blocker, 5-HT3 antagonist, N-methyl-D-aspartic acid receptor antagonist, and phosphodiesterase V inhibitor.

Yet another embodiment of the present invention relates to a method for providing a method for treating disorders of the central nervous system including stroke, epilepsy, manic depression, bipolar disorders, depression, anxiety, schizophrenia, migraine, and psychoses; neural degenerative disorders including Alzheimer's disease, AIDS related dementia, Parkinson's disease, neuropathy caused by head injury, and dementia caused by cerebrovascular disorders; disorders of the lower urinary tract including overactive bladder, prostatis, prostadynia, interstitial cystitis, and benign prostatic hyperplasia; disorders caused by psychogenic stress including bronchial asthma, unstable angina, and hypersensitive colon inflammation; cardiovascular disorders including hypertension, atherosclerosis, heart failure, and cardiac arrhythmias; drug addiction withdrawal symptoms, including ethanol addiction withdrawal symptoms; skin disorders including pruritis and allergic dermatitis, inflammatory bowel disease; cancer; diabetes; and infertility and sexual dysfunction in a mammal in need of such treatment. This method comprises administering to the mammal (including human) a therapeutically effective amount of a compound of the invention or a pharmaceutically acceptable salt thereof.

Calcium channel blockers have been associated with a slightly greater decreased risk of stroke compared to other types of antihypertensive agents (Angeli, F.; Verdecchia, P.; Reboldi, G. P.; Gattobigio, R.; Bentivoglio, M.; Staessen, J. A.; Porcellati, C. Calcium channel blockade to prevent stroke in hypertension. American Journal of Hypertension 2004, 17(9), 817-822). The enhanced effect did not correlate with differences in systolic blood pressure and the mechanism of action remains unknown. However, calcium channel blockers have been associated with blockade of central neuronal calcium influx and subsequent ischemic injury in two rodent models (Barone, F. C.; Lysko, P. G.; Price, W. J.; Feuerstein, G.; Al-Baracanji, K. A.; Benham, C. D.; Harrison, D. C.; Harries, M. H.; Bailey, S. J.; Huner, A. J. SB 201823-A antagonizes calcium currents in central neurons and reduces the effects of focal ischemia in rats and mice. Stroke 1995, 26, 1683-1690). In another model of global ischemia, a calcium channel blocker offered neuroprotection although not permanently (Colbourne, F.; Li, H.; Buchan, A. M. Continuing postischemic neuronal death in CA1: Influence of ischemia duration and cytoprotective doses of NBQX and SNX-111 in rats. Stroke 1999, 30(3), 662-668). Additionally, diminished progression of carotid atherosclerosis has been observed with calcium channel blocker use (Zanchetti, A.; Bond, G.; Hennig, M.; Neiss, A.; Mancia, G.; Dal Palu' C.; Hansson, L.; Magnani, B.; Rahn, K. H.; Reid, J. L.; Rodicio, J.; Safar, M.; Eckes, L.; Rizzini, P. Calcium antagonist lacidipine slows down progression of asymptomatic carotid atherosclerosis. Principal results of the European lacidipine study on atherosclerosis (ELSA), a randomized, double-blind, long-term trial. Circulation 2002, 106, r47-r52).

An increase in intracellular calcium concentration has been correlated with seizure activity (Heinemann, U.; Lux, H. D.; Gutnick, M. J. Extracellular free calcium and potassium during paroxysmal activity in the cerebral cortex of the cat. Exp. Brain Res. 1977, 27, 237-243). Several studies have indicated that calcium channel blockers produce anticonvulsant activity (Vezzani, A.; Wu, H. Q.; Stasi, M. A.; Angelico, P.; Samanin, R. Effects of various calcium channel blockers on three different models of limbic seizures in rats. Neuropharmacology 1988, 27(5), 451-458. Otoom, S.; Hasan, Z. Nifedipine inhibits picrotoxin-induced seizure activity: further evidence on the involvement of L-type calcium channel blockers in epilepsy. Fundamental & Clinical Pharmacology 2006, 20, 115-119).

Calcium channel blockers have been evaluated in the treatment of bipolar disorders and manic depression for decades. There are suggestions that the calcium channel subtype has influence on efficacy of these disorders (Gitlin, M. Treatment-resistant bipolar disorder. Molecular Psychiatry 2006, 11, 227-240. Levy, N. A.; Janicak, P. G. Bipolar Disorders 2000, 2, 108-119).

Calcium channel blockers have also been associated with the treatment of anxiety and depression (Saade, S.; Balleine, B. W.; Minor, T. R. The L-type calcium channel blocker nimodipine mitigates "learned helplessness" in rats. Pharmacology, Biochemistry and Behavior 2003, 74, 269-278).

Antischizophrenic drugs have been found to be calcium channel antagonists (Gould, R. J.; Murphy, K. M.; Reynolds, I. J.; Snyder, S. H. Antischizophrenic drugs of the diphenylbutylpiperidine type act as calcium channel antagonists. Proc. Natl. Acad. Sci. USA 1983, 80, 5122-5125). Other calcium channel blockers have been suggested for the treatment of schizophrenia (Tort, A. B. L.; Dall'Igna, O.; de Oliveira, R. V.; Mantese, C. E. A.; Fett, P.; Gomes, M. W. S.; Schuh, J.; Souza, D. O.; Lara, D. R. Atypical antipsychotic profile of flunarizine in animal models. Psychopharmacology 2005, 177, 344-348).

Migraines are treated with calcium channel blockers (Arulmoshi, D. K.; Veeranjaneyulu, A.; Bodhankar, S. L. Migraine: Current concepts and emerging therapies. Vascular Pharmacology 2005, 43, 176-187. Gladstone, J. P.; Dodick, D. W. Current and emerging treatment options for migraine and other primary headache disorders. Expert Rev. Neurotherapeutics 2003, 3(6), 845-872).

Disorders of the lower urinary tract including overactive bladder, prostatis, prostadynia, interstitial cystitis, and benign prostatic hyperplasia can be treated with calcium channel blockers (Fraser, M. O.; Thor, K. B.; Burgard, E. C. US20050148587, 2005).

Ethanol withdrawal syndrome is decreased with calcium channel blockers (Little, H. J.; Dolin, S. J.; Halsey, M. J. Calcium channel antagonists decrease the ethanol withdrawal syndrome. Life Sciences 1986, 39, 2059-2065).

Several cardiac disorders are treated with calcium channel blockers. Atherosclerosis may be reduced by a decrease in free radical-mediated damage as a result of influence on the biophysical properties of membranes (Mason, R. P.; Mak, I. T.; Walter, M. F.; Tulenko, T. N.; Mason, P. E. Antioxidant and cytoprotective activities of the calcium channel blocker mibefradil. Biochemical Pharmacology 1998, 55, 1843-1852). Hypertension and angina are both successfully treated with calcium channel blockers (Croom, K. F.; Wellington, K. Modified-release nifedipine: A review of the use of modified-release formulations in the treatment of hypertension and angina pectoris. Drugs 2006, 66(4), 497-528).

There is data suggesting that calcium channel blockers inhibit the proliferation of cancer cells (Gray, L. S.; MacDonald, T. L.; Haverstick, D. M.; Heady, T. N. WO200059882, 2000).

Calcium channels have been suggested as a target for the treatment of diabetes (Bhattacharjee, A.; Whitehurst, R. M., Jr.; Zhang, M.; Wang, L.; Li, M. T-Type calcium channels facilitate insulin secretion by enhancing general excitability in the insulin-secreting β-cell line, INS-1. Endocrinology 1997, 138(9), 3735-3740).

Ion channels including calcium channels play an important role in sperm physiology and fertilization (Darszon, A.; Labarca, P.; Hishigaki, T.; Espinosa, F. Ion channels in sperm physiology. Physiological Reviews 1999, 79(2), 481-510).

Calcium channel blockers modulate inflammation (Bilici, D.; Akpinar, E.; Gursan, N.; Dengiz, G. O.; Bilici, S.; Altas, S. Protective effect of T-type calcium channel blocker in histamine-induced paw inflammation in rat. Pharmacological Research 2001, 44(6), 527-531).

Increased calcium levels in neurones has been implicated in Alzheimer's disease. Two suggested mechanisms of increased calcium influx are that β-amyloid may form calcium permeable channels (Bhatia, R.; Lin, H.; Lal, R. Fresh and globular amyloid beta protein (1-42) induces rapid cellular degeneration: evidence for AβP channel-mediated cellular toxicity. FASEB J. 2000, 14(9), 1233-1243) or a G-protein-coupled receptor may be activated by β-amyloid (Lorton, D. β-Amyloid induced IL-1β release from an activated human monocyte cell line is calcium- and G-protein-dependent. Mech. Ageing Dev. 1997, 94(1-3), 199-211).

Neurodegenerative diseases, including Parkinson's and Alzheimer's diseases can be modulated by calcium channel blockers (Rodnitzky, R. L. Can calcium antagonists provide a neuroprotective effect in Parkinson's disease. Drugs 1999, 57(6), 845-849. Vagnucci, A. H., Jr.; Li, W. W. Alzheimer's disease and angiogenesis. The Lancet 2003, 361(9357), 605-608. Veng, L. M.; Meches, M. H.; Browning, M. D. Age-related working memory impairment is correlated with increases in the L-type calcium channel protein $\alpha_{1D}$ ($Ca_v1.3$) in area CA1 of the hippocampus and both are ameliorated by chronic nimodipine treatment. Molecular Brain Research 2203, 110, 193-202. Geldenhuys, W. J.; Malan, S. F.; Bloomquist, J. R.; Van der Schyf, C. J. Structure-activity relationships of pentacycloundecylamines at the N-methyl-D-aspartate receptor. Bioorganic and Medicinal Chemistry 2007, 15, 1525-1532. Cavalli, A.; Bolognesi, M. L.; Minarini, A.; Rosini, M.; Tumiatti, V.; Recanatini, M.; Melchiorre, C. Multi-target-directed ligands to combat neurodegenerative diseases. J. Med. Chem. 2008, 51(3), 347-372.)

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

Compounds of the invention can also be administered as a pharmaceutical composition comprising the compounds of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or other animal range from about 0.01 mg/kg body weight to about 100 mg/kg body weight. More preferable doses can be in the range of from about 0.01 mg/kg body weight to about 30 mg/kg body weight. If desired, the effective daily dose can be divided into multiple doses for purposes of administration. Consequently, single dose compositions may contain such amounts or submultiples thereof to make up the daily dose.

E. PHARMACEUTICAL COMPOSITIONS

The present invention further provides pharmaceutical compositions that comprise compounds of the present invention or a pharmaceutically acceptable salt or solvate thereof. The pharmaceutical compositions comprise compounds of the present invention that may be formulated together with one or more non-toxic pharmaceutically acceptable carriers.

Another aspect of the present invention is a pharmaceutical composition comprising compounds of the invention, or a pharmaceutically acceptable salt thereof, and one or more pharmaceutically acceptable carriers, alone or in combination with one or more nonsteroidal anti-inflammatory drugs (NSAID), opioid analgesics, barbiturates, benzodiazepines, histamine antagonists, sedatives, skeletal muscle relaxants, transient receptor potential ion channel antagonists, α-adrenergics, tricyclic antidepressants, anticonvulsants, tachykinin antagonists, muscarinic antagonists, cyclooxygenase-2 selective inhibitors, neuroleptics, vanilloid receptor agonists, vanilloid receptor antagonists, β-adrenergics, local anesthetics, corticosteroids, 5-HT receptor agonists, 5-HT receptor antagonists, $5\text{-}HT_{2A}$ receptor antagonists, cholinergic analgesics, $\alpha_2\delta$ ligands such as gabapentin or pregabalin, cannabinoid receptor ligands, metabotropic glutamate subtype 1 receptor antagonists, serotonin reuptake inhibitors, norepinephrine reuptake inhibitors, dual serotonin-noradrenaline reuptake inhibitors, Rho kinase inhibitors, inducible nitric oxide synthase inhibitors, acetylcholinesterase inhibitors, prostaglandin $E_2$ subtype 4 antagonists, leukotriene B4 antagonists, 5-lipoxygenase inhibitors, sodium channel blockers, 5-HT3 antagonists, N-methyl-D-aspartic acid receptor antagonists, and phosphodiesterase V inhibitors.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

Dosage forms for topical administration of a compound of this invention include powders, sprays, ointments and inhalants. The active compound may be mixed under sterile conditions with a pharmaceutically acceptable carrier and any needed preservatives, buffers or propellants which may be required. Ophthalmic formulations, eye ointments, powders and solutions are also contemplated as being within the scope of this invention.

The compounds of the present invention can be used in the form of pharmaceutically acceptable salts derived from inorganic or organic acids. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio.

Pharmaceutically acceptable salts are well known in the art. For example, S. M. Berge et al. describe pharmaceutically acceptable salts in detail in (J. Pharmaceutical Sciences, 1977, 66: 1 et seq). The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethanesulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts can be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylammonium, dimethylammonium, trimethylammonium, triethylammonium, diethylammonium, ethylammonium and the like. Other representative organic amines useful for the formation of base addition salts include ethylenediamine, ethanolamine, diethanolamine, piperidine, piperazine and the like.

The term "pharmaceutically acceptable prodrug" or "prodrug" as used herein, represents those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use.

The present invention contemplates compounds of the invention formed by synthetic means or formed by in vivo biotransformation of a prodrug.

The compounds of the invention can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

F. GENERAL SYNTHESIS

This invention is intended to encompass compounds of the invention when prepared by synthetic processes or by metabolic processes. Preparation of the compounds by metabolic processes includes those occurring in the human or animal body (in vivo) or processes occurring in vitro.

The compounds of the invention may be prepared by a variety of processes well known for the preparation of compounds of this class. For example, the compounds of the invention wherein the groups $Ar^1$, $Ar^2$, $L^1$, $L^2$, n, $R^1$, $R^4$, X, and Y, have the meanings as set forth in the summary section unless otherwise noted, can be synthesized as shown in Schemes 1-16.

Abbreviations which have been used in the descriptions of the Schemes and the Examples that follow are: Boc for t-butoxy carbonyl; Bu for butyl; Et for ethyl, EtOH for ethanol; DMF or N,N-dimethylformamide; DMSO for dimethyl sulfoxide; KOtBu for potassium tert-butoxide; MeOH for methanol; $NEt_3$ for triethylamine; Ph for phenyl; psi for pounds per square inch; tBu for tert-butyl; and THF for tetrahydrofuran.

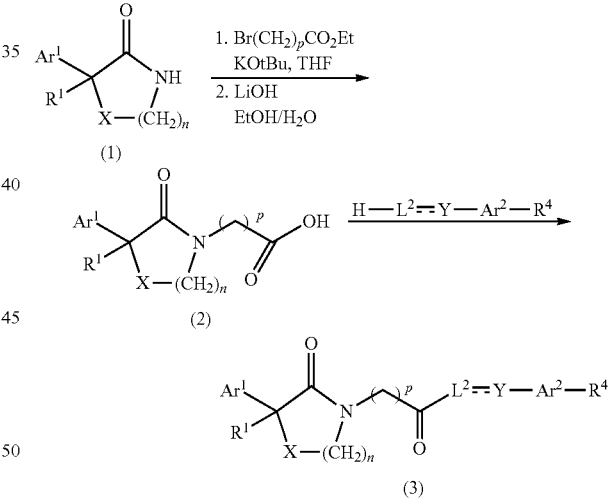

Scheme 1

Compounds of formula (3), wherein $Ar^1$, $Ar^2$, $L^2$, n, p, $R^1$, $R^4$, X and Y are as defined in formula (I), may be prepared as illustrated in Scheme 1. The treatment of compounds of formula (1) with $Br(CH_2)_pCOEt$ in the presence of a base such as potassium t-butoxide, potassium hydride, or sodium ethoxide in a solvent such as tetrahydrofuran or dioxane at a temperatures of 20-100° C. for 4 to 24 hours supplies the corresponding alkylated lactam. Subsequent treatment with a base such as lithium hydroxide, sodium hydroxide, or potassium hydroxide in a mixture of ethanol and water at 20-100° C. for 1 to 12 hours provides the corresponding carboxylic acid of formula (2). Coupling of carboxylic acid (2) with H-$L^2$---Y—$Ar^2$—$R^4$, wherein the H is a hydrogen on a nitrogen atom contained on a primary or secondary amine or as part of a heterocyclic ring, forms an amide bond and yields compounds of formula (3) which are representative of compounds of formula (I). Examples of conditions known to generate amides from a mixture of a carboxylic acid and an amine include but are not limited to adding a coupling reagent such as but not limited to $N^1$-((ethylimino)methylene)-$N^3$, $N^3$-dimethylpropane-1,3-diamine hydrochloride (EDCI), 1,3-dicyclohexylcarbodiimide (DCC), bis(2-oxo-3-oxazolidinyl)phosphinic chloride (BOPCl), O-(7-azabenzotriazol-1-yl)-N,N,N',N'-tetramethyluronium hexafluorophosphate (HATU), O-benzotriazol-1-yl-N,N,N',N'-tetramethyluronium tetrafluoroborate (TBTU), and 2-(1H-benzo[d][1,2,3]triazol-1-yl)-1,1,3,3-tetramethylisouronium hexafluorophosphate(V) (HBTU). The coupling reagents may be added as a solid, a solution or as the reagent bound to a solid support resin. In addition to the coupling reagents, auxiliary-coupling reagents may facilitate the coupling reaction. Auxiliary coupling reagents that are often used in the coupling reactions include but are not limited to N,N-dimethylpyridin-4-amine (DMAP), 1-hydroxy-7-azabenzotriazole (HOAT) and 1-hydroxybenzotriazole hydrate (HOBT). The reaction may be carried out optionally in the presence of a base such as triethylamine or diisopropylethylamine. The coupling reaction may be carried out in solvents such as but not limited to tetrahydrofuran, N,N-dimethylformamide, dichloromethane, and ethyl acetate. The reaction may be conducted at ambient or elevated temperatures.

Alternatively, compounds of formula (3) may be prepared from compounds of formula (2) by first forming the corresponding acid chloride. Compounds of formula (2), may be treated with oxalyl chloride or thionyl chloride in a solvent such as dichloromethane or toluene at room temperature over 1 to 12 hours to form the intermediate acid chloride. Subsequent treatment with H-L$^2$---Y—Ar$^2$—R$^4$ affords compounds of formula (3). Less reactive amines may require elevated temperatures to achieve complete reaction, and this can be realized in a solvent such as dichloroethane or toluene at temperatures of 30-100° C. over 1-12 hours.

A.; Wiesert, W. Chem. Ber. 1981, 114, 32-48) and gradually allowed to warm to room temperature.

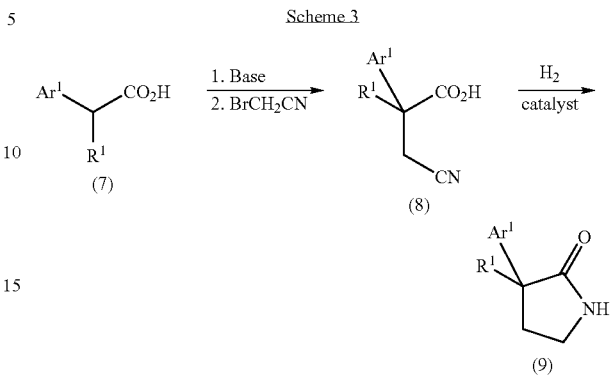

Compounds of formula (9) wherein Ar$^1$ and R$^1$ are as described in formula (I) which are representative of compounds of formula (1) are prepared by the following sequence. Compounds of formula (7), wherein R$^1$ is aryl or heteroaryl, are dissolved in a base such as tetrahydrofuran or dioxane, cooled to a temperature less than −40° C., and treated with a base such as lithium bis(trimethylsilyl)amide or lithium diisopropylamine. After warming to or near 0° C., the reaction mixture is cooled to less than −40° C., and then a solution of bromoacetonitrile is added. After gradually warming to room temperature over 2 or more hours, compounds of formula (8) are obtained. Compounds of formula (8) are hydrogenated (15-100 pounds per square inch) for 4 to 24 hours in a solvent such as acetic acid or ethanol, in the presence of a catalyst such as platinum oxide to supply compounds of formula (9). Alternatively, the reduction and subsequent cyclization from compounds of formula (8) to compounds of formula (9) can be accomplished with hydrogen and a catalyst such as Raney®-nickel in a solvent mixture of ammonia in methanol.

Compounds of formula (5) wherein Ar$^1$ and R$^1$ are as described in formula (I) which are representative of compounds of formula (1) are prepared with the following procedures. Furanones of formula (4) can be treated with ammonia and zinc chloride in an autoclave at temperatures of 150-250° C. for 12 to 36 hours to produce compounds of formula (5) wherein R$^A$ is hydrogen. Alternatively, treatment of compounds of formula (4) with a primary amine such as 2-aminoethanol or 3-aminopropanol at 80-120° C. for 8 to 24 hours supplies compounds of formula (5) wherein R$^A$ is a group such as hydroxyethyl or hydroxypropyl.

Compounds of formula (5) wherein R$^A$ is hydrogen, can also be prepared by combining compounds of formula (6) and formula (7) at or near 0° C., wherein R$^B$ is methyl or ethyl, in the presence of a base such as lithium diisopropylamide or the sodium salt of triphenylmethane in a solvent such as tetrahydrofuran as described in the literature (Stamm, H.; Woderer, Compounds of formula (11) wherein $Ar^1$ and $R^1$ are as described in formula (I) which are representative of compounds of formula (1) are prepared by the following sequence. Compounds of formula (7), wherein $R^1$ is alkyl, aryl, or heteroaryl, are dissolved in ethanol and treated with sulfuric acid at reflux over 4-16 hours. The intermediate ester can be dissolved in a solvent such as dioxane or tetrahydrofuran and treated with a base such as sodium ethoxide, sodium methoxide, or sodium t-butoxide for 30 minutes to 2 hours at a temperature of 20 to 60° C. Addition of acrylonitrile with continued heating at 40-80° C. for an additional 30 minutes to 2 hours furnishes compounds of formula (10). The reduction and subsequent cyclization from compounds of formula (10) to compounds of formula (11) can be accomplished by hydrogenation (15-50 pounds per square inch) in the presence of a catalyst such as Raney®-nickel in a solvent mixture of ammonia in methanol.

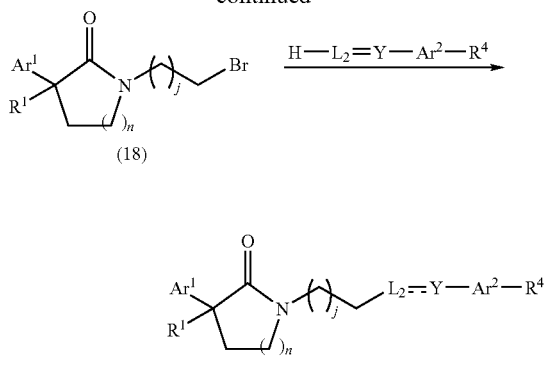

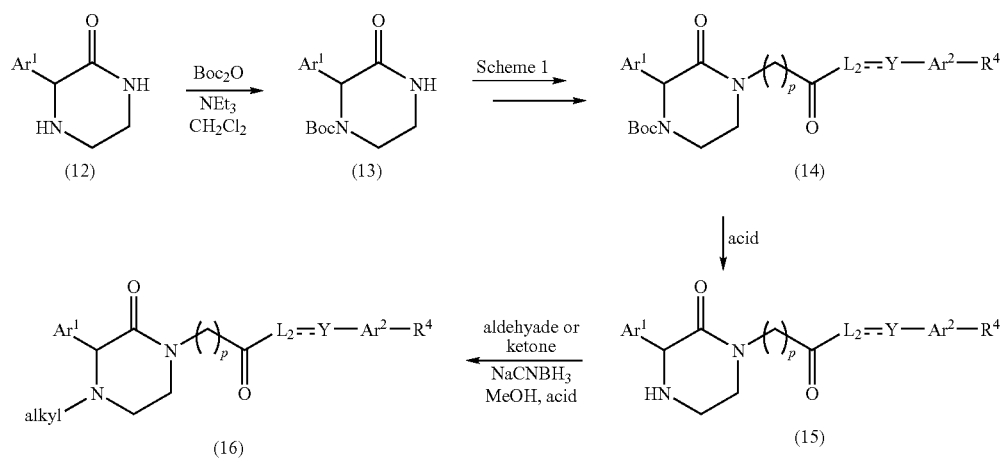

Compounds of formula (14), (15), and (16), wherein $Ar^1$, $Ar^2$, $L^2$, p, $R^4$, and Y are as defined in formula (I) may be prepared as illustrated in Scheme 5. Compounds of formula (12) can be converted to the corresponding carbamate of formula (13) by treating with di-tert-butyl dicarbonate in the presence of a base such as triethylamine in a solvent such as dichloromethane. Compounds of formula (13) are converted to compounds of formula (14) by the methods described in Scheme 1. Compounds of formula (14) give compounds of formula (15) when treated with trifluoroacetic acid in methylene chloride or hydrochloric acid in dioxane. Compounds of formula (16) are prepared from compounds of formula (15) by reacting with an aldehyde or ketone in a solvent such as methanol in the presence of sodium cyanoborohydride or sodium triacetoxyborohydride and an acid such as acetic acid. Compounds of formulas (14), (15), and (16) are representative of compounds of formula (I).

Compounds of formula (19), wherein $Ar^1$, $Ar^2$, $L^2$, n, $R^1$, $R^4$, and Y are as defined in formula (I) and j is 1, 2 or 3 may be prepared as illustrated in Scheme 6. Compounds of formula (17) which may be prepared which can be prepared as described in Scheme 2 are treated with carbon tetrabromide in the presence of triphenylphosphine in a solvent such as dichloromethane to provide compounds of formula (18). Compounds of formula (18) may be treated with H-$L^2$---Y—$Ar^2$—$R^4$, wherein the H is a hydrogen on a nitrogen atom contained on a primary or secondary amine or as part of a heterocyclic ring, in the presence of a base such as sodium hydride, triethylamine, or potassium carbonate optionally with a catalytic amount of potassium iodide in a solvent such as N,N-dimethylformamide, acetonitrile, toluene or ether optionally heated to provide compounds of formula (19). Compounds of formula (19) are representative of compounds of formula (I).

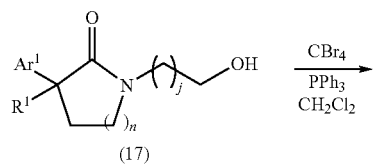

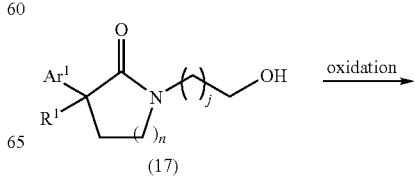

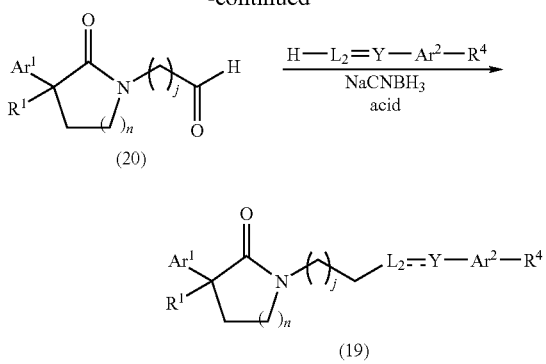

Compounds of formula (19), wherein $Ar^1$, $Ar^2$, $L^2$, n, $R^1$, $R^4$, and Y are as defined in formula (I) and j is 1, 2 or 3 may be prepared as illustrated in Scheme 7. Compounds of formula (17) which can be prepared as described in Scheme 2 are treated with an oxidant such as Dess-Martin periodinane in a solvent such as dichloromethane or under Swern oxidation conditions to give aldehydes of formula (20). Compounds of formula (20) are transformed to compounds of formula (19) by treating with H-$L^2$---Y—$Ar^2$—$R^4$, wherein the H is a hydrogen on a nitrogen atom contained on a primary or secondary amine or as part of a heterocyclic ring, in the presence of a reducing agent such as sodium cyanoborohydride or sodium triacetoxyborohydride and optionally in the presence of an acid such as acetic acid in a solvent such as methanol. Compounds of formula (19) are representative of compounds of formula (I).

temperature of 60-75° C. for 8 to 24 hours to supply compounds of formula (23). The t-butoxy carbonyl protecting group can then be removed with acid (trifluoroacetic acid/dichloromethane or hydrochloric acid/dioxane) to supply compounds of formula (24). Compounds of formula (24) can be reacted with compounds of formula (25) in a solvent such as methanol, dichloromethane or a mixture thereof in the presence of acetic acid and sodium cyanoborohydride, sodium triacetoxyborohydride, or resin-bound-cyanoborohydride at a temperature of 20-50° C. for 8 to 24 hours to supply compounds of formula (26). Compounds of formula (26) are representative of compounds of formula (I).

Scheme 9

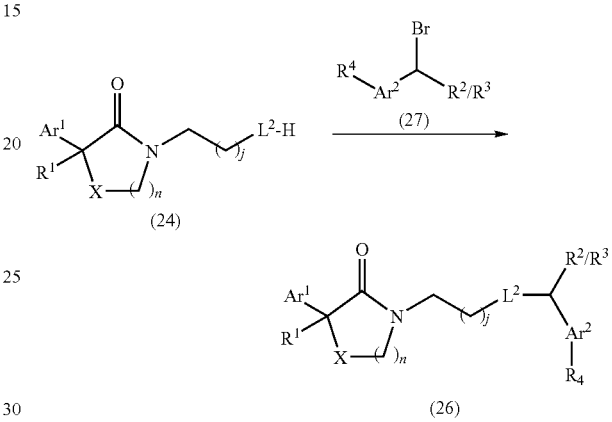

Scheme 8

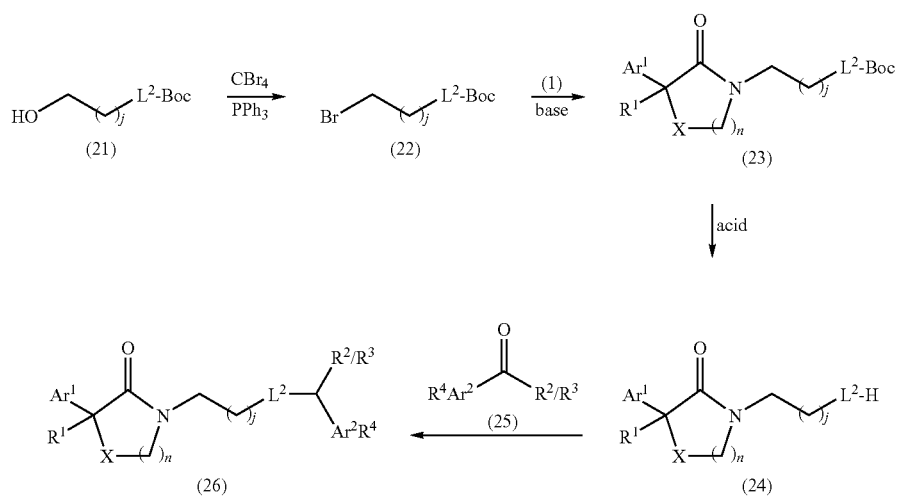

Compounds of formula (26), wherein $Ar^1$, $Ar^2$, $L^2$, n, $R^1$, $R^2$, $R^3$, $R^4$, and X are as defined in formula (I) and j is 1, 2 or 3 can be prepared as illustrated in Scheme 8. Compounds of formula (21); wherein $L^2$ has a primary amine, secondary amine, or amine contained in a heterocycle protected as a carbamate; when treated with carbon tetrabromide in the presence of triphenylphosphine in a solvent such as dichloromethane or tetrahydrofuran provide compounds of formula (22). Compounds of formula (22) can be reacted with compounds of formula (1) in the presence of a base such as potassium t-butoxide in a solvent such as tetrahydrofuran at a Compounds of formula (26), wherein $Ar^1$, $Ar^2$, $L^2$, n, $R^1$, $R^2$, $R^3$, $R^4$, and X are as defined in formula (I) and j is 1, 2 or 3 can be prepared as illustrated in Scheme 9. Compounds of formula (24); wherein the H is attached to $L^2$ as either part of a primary amine, secondary amine, or amine contained in a heterocycle protected as a carbamate; can be heated with bromides of formula (27) in the presence of a base such as sodium carbonate in a solvent such as 2-butanone in a sealed vessel for 24-36 hours to give compounds of formula (26). Compounds of formula (26) are representative of compounds of formula (I).

Scheme 10

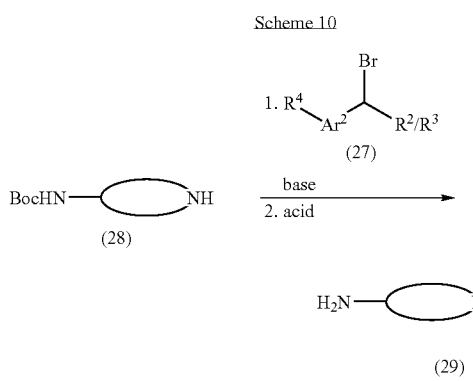

Compounds of formula (29), wherein $Ar^2$, $R^2$, $R^3$ and $R^4$ are as defined in formula (I), can be prepared from compounds of formula (28). Compounds of formula (28) are heterocycles with a pendant amine functionality protected as a carbamate. Compounds of formula (28) can be treated with compounds of formula (27) in the presence of a base such as potassium carbonate optionally with a catalytic amount of potassium iodide present in a solvent such as N,N-dimethylformamide. Subsequent removal of the t-butoxy carbonyl protecting group under acid conditions such as trifluoroacetic acid in dichloromethane or hydrochloric acid in dioxane supplies compounds of formula (29). Compounds of formula (29) can be used in Schemes 1, 5, 6, or 7.

Scheme 11

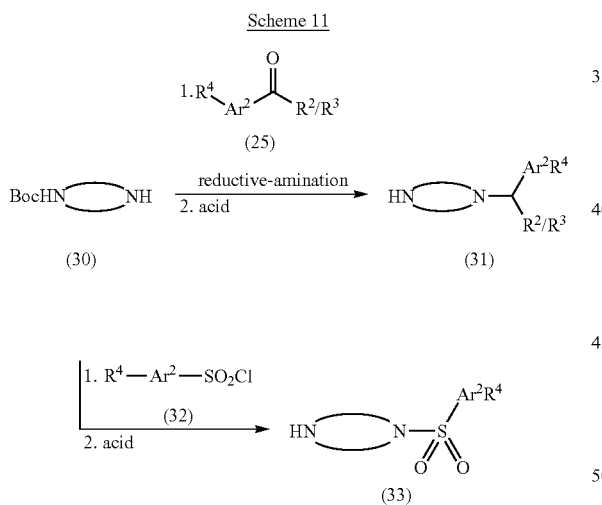

Compounds of formula (31) and (33), wherein $Ar^2$, $R^2$, $R^3$ and $R^4$ are as defined in formula (I), can be prepared from compounds of formula (30). Compounds of formula (30) represent monocyclic or bicyclic heterocycles such as for example piperazine or octahydropyrrolo[3,4-b]pyridine wherein one of the amine moieties is protected as a t-butoxy carbamate. Compounds of formula (30) can be reductively aminated with compounds of formula (25) as described in Scheme 8. Removal of the protecting group under the acidic conditions described in Scheme 10 supplies compounds of formula (31).

Compounds of formula (30) can be reacted with sulfonyl chlorides of formula (32) in the presence of a base such diisopropylethylamine or triethylamine in solvent such as dichloromethane. Removal of the protecting group under the acidic conditions described in Scheme 10 supplies compounds of formula (33).

Compounds of formula (31) and (33) can be used in Schemes 1, 5, 6, or 7.

Scheme 12

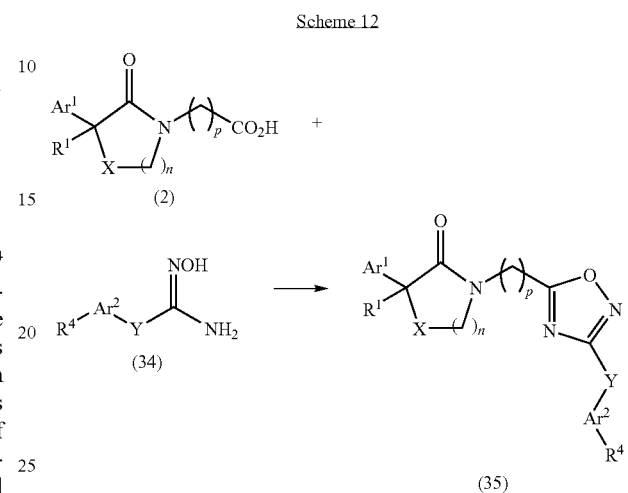

Compounds of formula (35), wherein $Ar^1$, $Ar^2$, n, p, $R^1$, $R^4$, X, and Y are as defined in formula (I), are prepared as described in Scheme 12. Compounds of formula (2) can be reacted with a compound of formula (34) in the presence of a dehydrating agent such as $N^1$-((ethylimino)methylene)-$N^3$, $N^3$-dimethylpropane-1,3-diamine hydrochloride in a solvent such as dichloroethane initially at room temperature for 1 to 4 hours and then heated for 8 to 24 hours to supply compounds of formula (35). Compounds of formula (35) are representative of compounds of formula (I).

Scheme 13

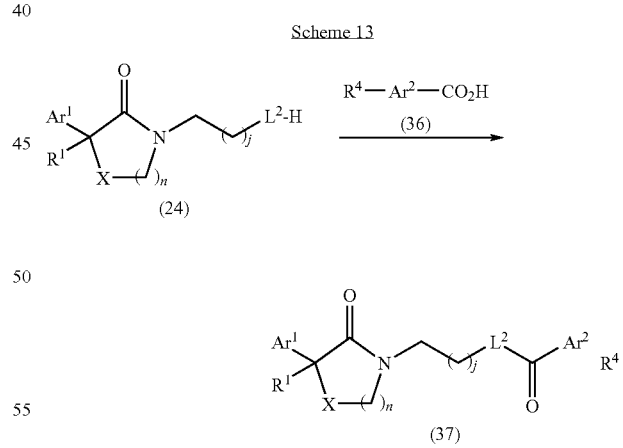

Compounds of formula (37), wherein $Ar^1$, $Ar^2$, $L^2$, n, $R^1$, $R^4$, and X are as defined in formula (I) and j is 1, 2 or 3 can be prepared as illustrated in Scheme 13. Compounds of formula (24); wherein the H is attached to $L^2$ as either part of a primary amine, secondary amine, or amine contained in a heterocycle may be coupled with compounds of formula (36) using the amide bond forming reaction conditions described in Scheme 1. Compounds of formula (37) are representative of compounds of formula (I).

Scheme 14

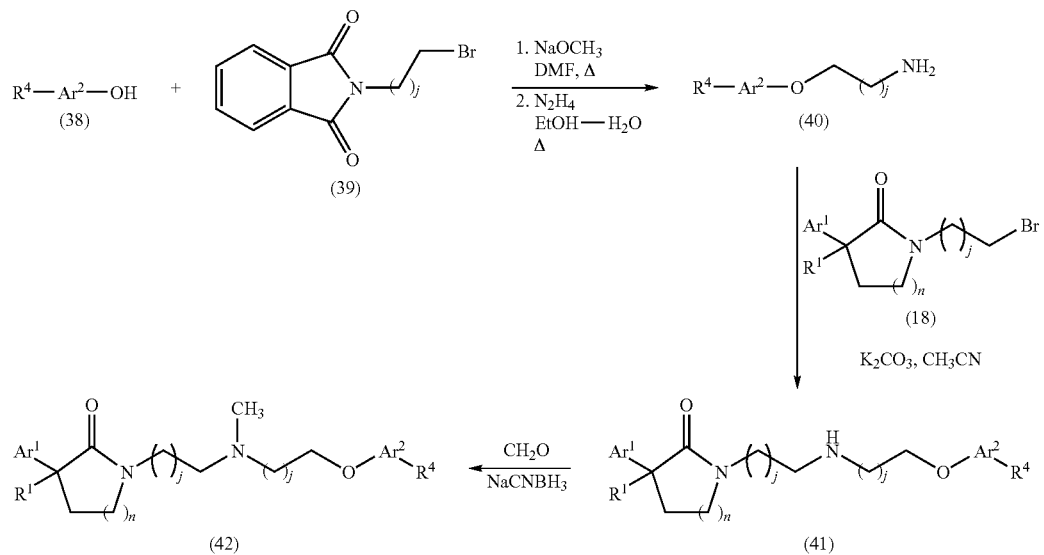

Compounds of formulas (41) and (42), wherein $Ar^1$, $Ar^2$, n, $R^1$, and $R^4$ are as defined in formula (I) and j at each occurrence is independently 1, 2 or 3 can be prepared as illustrated in Scheme 14. Compounds of formula (38) can be treated with compounds of formula (39) in the presence of a base such as sodium methoxide in optionally heated N,N-dimethylformamide. The phthalimide group is subsequently removed by treatment with hydrazine in a heated mixture of ethanol and water to provide compounds of formula (40). Compounds of formula (40) can be treated with compounds of formula (18) in the presence of a base such as potassium carbonate in a heated acetonitrile solution to give compounds of formula (41). Compounds of formula (41) can be reacted with formaldehyde under the reductive amination conditions described in Scheme 5 to provide compounds of formula (42) which are representative of compounds of formula (I).

Scheme 15

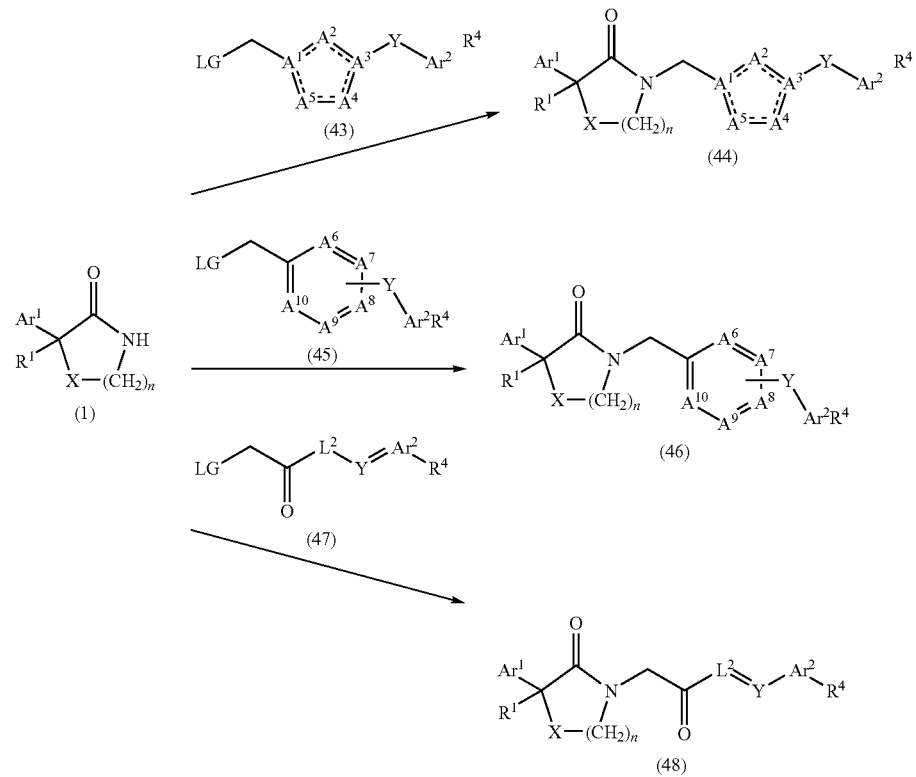

Compounds of formulas (44), (46), and (48), wherein $A^1$, $A^2$, $A^3$, $A^4$, $A^5$, $A^6$, $A^7$, $A^8$, $A^9$, $A^{10}$, $Ar^1$, $Ar^2$, $L^2$, n, $R^1$, $R^4$, X, and Y are as defined in formula (I) can be prepared as illustrated in Scheme 15. Compounds of formula (1) can be reacted with compounds of formulas (43), (44), or (47); wherein LG is a leaving group such as chlorine, bromine, iodine, trifluoromethanesulfonate, or p-toluenesulfonate; in the presence of a base such as sodium hydride, potassium hydride, or potassium t-butoxide in solvents such as tetrahydrofuran or N,N-dimethylformamide to give compounds of formulas (44), (46), or (48), respectively, which are representative of compounds of formula (I).

Scheme 16

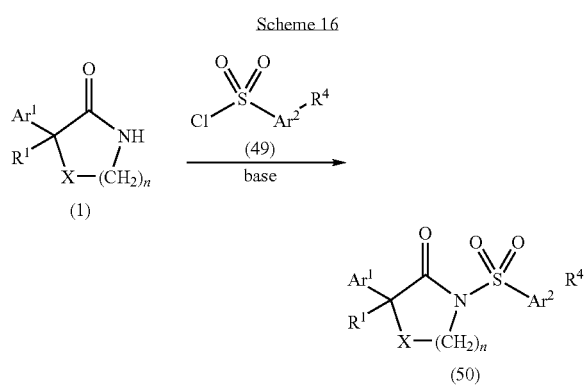

Compounds of formulas (50), wherein $Ar^1$, $Ar^2$, n, $R^1$, $R^4$, and X are as defined in formula (I) can be prepared as illustrated in Scheme 16. Compounds of formula (1) can be reacted with compounds of formula (49) in the presence of a base such as potassium t-buoxide in a solvent such as tetrahydrofuran to give compounds of formula (50) which are representative of compounds of formula (I).

It will be appreciated that the synthetic schemes and specific examples as illustrated in the Examples section are illustrative and are not to be read as limiting the scope of the invention as it is defined in the appended claims. All alternatives, modifications, and equivalents of the synthetic methods and specific examples are included within the scope of the claims.

Optimum reaction conditions and reaction times for each individual step may vary depending on the particular reactants employed and substituents present in the reactants used. Unless otherwise specified, solvents, temperatures and other reaction conditions may be readily selected by one of ordinary skill in the art. Specific procedures are provided in the Examples section. Reactions may be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or may be prepared by one skilled in the art from commercially available materials using methods described in the chemical literature.

Routine experimentations, including appropriate manipulation of the reaction conditions, reagents and sequence of the synthetic route, protection of any chemical functionality that may not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which may be found in T. Greene and P. Wuts, Protecting Groups in Chemical Synthesis (3$^{rd}$ ed.), John Wiley & Sons, NY (1999), which is incorporated herein by reference in its entirety. Synthesis of the compounds of the invention may be accomplished by methods analogous to those described in the synthetic schemes described hereinabove and in specific examples.

Starting materials, if not commercially available, may be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it may be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it may be obtained by carrying out one of the above procedures using a pure geometric isomer as a starting material, or by resolution of a mixture of the geometric isomers of the compound or intermediates using a standard procedure such as chromatographic separation.

G. EXAMPLES

The compounds and processes of the present application will be better understood by reference to the following Examples, which are intended as an illustration of and not a limitation upon the scope of the application. Compounds of the application were named by ACD/ChemSketch version 5.01 (developed by Advanced Chemistry Development, Inc., Toronto, ON, Canada) or were given names consistent with ACD nomenclature or were named by Stuct=Name naming algorithm in ChemDraw Ultra 9.0.7 (developed by CambridgeSoft, Cambridge, Mass., USA).

Example 1

1-[2-(4-benzhydrylpiperazin-1-yl)-2-oxoethyl]-3,3-diphenylpyrrolidin-2-one

Example 1A 3,3-diphenylpyrrolidin-2-one 3,3-Diphenyldihydrofuran-2(3H)-one (3.98 g, 16.70 mmol) and zinc chloride (0.080 g) were placed in an autoclave. Ammonia (8 mL) was added, and the reactor was sealed and heated at 225° C. for 21 hours under an argon atmosphere at an equilibrium pressure of 800 pounds per square inch. The vessel was cooled, the ammonia was vented, and a mixture of solids was obtained. The solid was treated with ethanol (100 mL), filtered and concentrated. Silica gel chromatography eluting with 5% methanol/dichloromethane gave the title compound. MS (DCI+) m/z 238.1 (M+H)$^+$.

Example 1B ethyl 2-(2-oxo-3,3-diphenylpyrrolidin-1-yl)acetate

To a solution of the product from Example 1A (1.0 g, 4.21 mmol) in tetrahydrofuran (20 mL) was added potassium tert-butoxide (1.0 M in tetrahydrofuran, 6.3 mL, 6.3 mmol) via syringe under nitrogen followed by ethyl 2-bromoacetate (0.47 mL, 4.21 mmol). The reaction mixture was heated to 80° C. and stirred overnight. The reaction mixture was cooled to room temperature, concentrated, and then diluted with ethyl acetate. The organic layer was washed with water and brine, dried over magnesium sulfate, filtered, and concentrated. Silica gel chromatography eluting with ethyl acetate/hexane (20:80) gave the title compound. MS (DCI+) m/z 324.2 (M+H)$^+$.

Example 1C 2-(2-oxo-3,3-diphenylpyrrolidin-1-yl)acetic acid

The product from Example 1B (0.92 g, 2.84 mmol) was dissolved in ethanol (20 mL).

A solution of lithium hydroxide (0.57 g, 23.8 mmol) in water (5 mL) was added, and the reaction was heated to 80° C. for 2 hours. The reaction mixture was cooled to room temperature, concentrated, neutralized with 2 N HCl, and then diluted with ethyl acetate. The organic layer was washed with water and brine, dried over magnesium sulfate, filtered and then concentrated to give the title compound. MS (DCI+) m/z 296.1 (M+H)$^+$.

Example 1D

1-[2-(4-benzhydrylpiperazin-1-yl)-2-oxoethyl]-3,3-diphenylpyrrolidin-2-one

To a solution of 1-benzhydrylpiperazine (0.58 g, 2.30 mmol) in dichloromethane (20 mL) under nitrogen was added the product from Example 1C (0.68 g, 2.30 mmol) followed by N$^1$-((ethylimino)methylene)-N$^3$,N$^3$-dimethylpropane-1,3-diamine hydrochloride (0.88 g, 4.60 mmol) and N,N-dimethylpyridin-4-amine (0.014 g, 0.12 mmol). The reaction mixture was stirred overnight at room temperature. The reaction was concentrated and the residue was partitioned in ethyl acetate/water (8:2, 400 mL). The organic layer was washed with water followed by brine, dried over magnesium sulfate, filtered and concentrated. Silica gel chromatography eluting with ethyl acetate/hexane (1:3) gave the title compound. $^1$H NMR (300 MHz, DMSO-d$_6$) δ ppm 7.42-7.46 (m, 4H), 7.19-7.33 (m, 16H), 4.31 (s, 1H), 4.15-4.16 (br s, 2H), 3.38-3.47 (m, 4H), 3.35 (t, J=6.3 Hz, 2H), 2.71 (t, J=6.5 Hz, 2H), 2.23-2.29 (m, 4H); MS (DCI+) m/z 530 (M+H)$^+$.

Example 2

2-(2-oxo-3,3-diphenylpyrrolidin-1-yl)-N-{[6-(trifluoromethyl)pyridin-3-yl]methyl}acetamide N$^1$-((ethylimino)methylene)-N$^3$,N$^3$-dimethylpropane-1,3-diamine hydrochloride (0.049 g, 0.254 mmol), 2-(2-oxo-3,3-diphenylpyrrolidin-1-yl)acetic acid (Example 1C, 0.050 g, 0.169 mmol) and (6-(trifluoromethyl)pyridin-3-yl)methanamine (0.033 g, 0.186 mmol) were combined and stirred together in dichloromethane (0.5 mL) at room temperature. After stirring overnight, the reaction was loaded directly onto a SF15-12 silica gel column (Analogix®, Burlington, Wis.), and the title compound was eluted using a gradient of 5% to 100% ethyl acetate/hexanes over 20 minutes (flow=30 mL/minute). $^1$H NMR (300 MHz, CDCl$_3$) δ ppm 8.48 (s, 1H), 7.53-7.61 (m, 2H), 7.22-7.30 (m, 10H), 6.50-6.56 (m, 1H), 4.32 (d, J=6.1 Hz, 2H), 4.06 (s, 2H), 3.51 (t, J=6.4 Hz, 2H), 2.81 (t, J=6.4 Hz, 2H); MS (ESI−) m/z 452 (M−H)$^-$.

Example 3

2-(2-oxo-3,3-diphenylpyrrolidin-1-yl)-N-(1,3-thiazol-2-ylmethyl)acetamide

N$^1$-((ethylimino)methylene)-N$^3$,N$^3$-dimethylpropane-1,3-diamine hydrochloride (0.049 g, 0.254 mmol), 2-(2-oxo-3,3-diphenylpyrrolidin-1-yl)acetic acid (Example 1C, 0.050 g, 0.169 mmol) and thiazol-2-ylmethanamine (0.021 g, 0.186 mmol) were combined and stirred together in dichloromethane (0.5 mL) at room temperature. After stirring overnight, the reaction was loaded directly onto a SF15-12 silica gel column (Analogix®, Burlington, Wis.), and the title compound was eluted using a gradient of 5% to 100% ethyl acetate/hexanes over 20 minutes (flow=30 mL/minute). $^1$H NMR (300 MHz, CDCl$_3$) δ ppm 7.69 (d, J=3.3 Hz, 1H), 7.19-7.38 (m, 11H), 6.77 (t, J=5.8 Hz, 1H), 4.67 (d, J=5.8 Hz, 2H), 4.09 (s, 2H), 3.53 (t, J=6.5 Hz, 2H), 2.84 (t, J=6.5 Hz, 2H); MS (ESI+) m/z 392 (M+H)$^+$.

Example 4

N-[(1-methyl-1H-pyrazol-3-yl)methyl]-2-(2-oxo-3,3-diphenylpyrrolidin-1-yl)acetamide N$^1$-((ethylimino)methylene)-N$^3$,N$^3$-dimethylpropane-1,3-diamine hydrochloride (0.049 g, 0.254 mmol), 2-(2-oxo-3,3-diphenylpyrrolidin-1-yl)acetic acid (Example 1C, 0.050 g, 0.169 mmol) and (1-methyl-1H-pyrazol-3-yl)methanamine (0.021 g, 0.186 mmol) were combined and stirred together in dichloromethane (0.5 mL) at room temperature. After stirring overnight, the reaction was loaded directly onto a SF10-8 silica gel column (Analogix®, Burlington, Wis.), and the title compound was eluted using a gradient of 0.4% to 7.5% methanol/dichloromethane over 20 minutes (flow=20 mL/minute). $^1$H NMR (300 MHz, CDCl$_3$) δ ppm 7.23-7.34 (m, 11H), 6.40 (t, J=6.0 Hz, 1H), 6.06 (d, J=2.2 Hz, 1H), 4.38 (d, J=5.3 Hz, 2H), 4.05 (s, 2H), 3.82 (s, 3H), 3.50 (t, J=6.4 Hz, 2H), 2.82 (t, J=6.4 Hz, 2H); MS (ESI−) m/z 387 (M−H)$^-$.

Example 5

N-(5-chloropyridin-2-yl)-2-(2-oxo-3,3-diphenylpyrrolidin-1-yl)acetamide

To a solution of 2-(2-oxo-3,3-diphenylpyrrolidin-1-yl)acetic acid (Example 1C, 0.050 g, 0.169 mmol) in dichloromethane (0.5 mL) at room temperature was added a solution of oxalyl chloride in dichloromethane (2.0 M, 0.102 mL, 0.203 mmol). The reaction was stirred for 1 hour and then concentrated under a stream of nitrogen. The resulting acid chloride was dissolved in dichloroethane (0.5 mL), and 5-chloropyridin-2-amine (0.024 g, 0.186 mmol) was added followed by N-methyl morpholine (0.028 mL, 0.254 mmol). The reaction was heated to 70° C. After stirring for 3 hours, the reaction was loaded directly onto a SF15-12 silica gel column (Analogix®, Burlington, Wis.), and the product was eluted using a gradient of 5% ethyl acetate/hexanes to 75% ethyl acetate/hexanes over 25 minutes (flow=30 mL/minute). The product was contaminated with aminopyridine starting material. A second silica gel column chromatography (SF15-24, Analogix®) eluting with a gradient of 5% ethyl acetate/hexanes to 50% ethyl acetate/hexanes over 30 minutes (flow=30 mL/minute) gave the title compound. $^1$H NMR (300

MHz, CDCl$_3$) δ ppm 8.44-8.46 (br s, 1H), 8.22 (dd, J=2.5, 0.7 Hz, 1H), 8.09 (d, J=8.8 Hz, 1H), 7.65 (ddd, J=8.8, 2.6, 0.5 Hz, 1H), 7.21-7.39 (m, 10H), 4.19 (s, 2H), 3.54 (t, J=6.5 Hz, 2H), 2.88 (t, J=6.5 Hz, 2H); MS (ESI+) m/z 406 (M+H)$^+$.

Example 6

N-benzyl-2-(2-oxo-3,3-diphenylpyrrolidin-1-yl)acetamide

To 2-(2-oxo-3,3-diphenylpyrrolidin-1-yl)acetic acid (Example 1C, 0.031 g, 0.105 mmol) and 2-(1H-benzo[d][1,2,3]triazol-1-yl)-1,1,3,3-tetramethylisouronium hexafluorophosphate(V) (0.044 g, 0.115 mmol) in dichloromethane (0.5 mL) was added diisopropylethylamine (0.027 mL, 0.157 mmol) followed by phenylmethanamine (0.014 mL, 0.126 mmol). After stirring overnight, the reaction was loaded onto a silica gel column (Analogix® SF15-12, Burlington, Wis.), and the product was eluted with a gradient of 0.4% to 5.25% methanol/dichloromethane over 20 minutes with a flow rate of 30 mL/minute. The product residue was dissolved in dichloromethane/diethyl ether followed by the addition of hexanes which upon concentration gave the title compound. $^1$H NMR (300 MHz, CDCl$_3$) δ ppm 7.11-7.34 (m, 15H), 6.23 (t, J=5.8 Hz, 1H), 4.32 (d, J=5.8 Hz, 2H), 4.06 (s, 2H), 3.50 (t, J=6.5 Hz, 2H), 2.80 (t, J=6.5 Hz, 2H); MS (ESI–) m/z 383 (M–H)$^-$.

Example 7

2-(2-oxo-3,3-diphenylpyrrolidin-1-yl)-N-[3-(trifluoromethyl)benzyl]acetamide

To 2-(2-oxo-3,3-diphenylpyrrolidin-1-yl)acetic acid (Example 1C, 0.051 g, 0.173 mmol) and 2-(1H-benzo[d][1,2,3]triazol-1-yl)-1,1,3,3-tetramethylisouronium hexafluorophosphate(V) (0.072 g, 0.190 mmol) in dichloromethane (0.5 mL) was added diisopropylethylamine (0.045 mL, 0.259 mmol) followed by (3-(trifluoromethyl)phenyl)methanamine (0.030 mL, 0.207 mmol). After stirring overnight, the reaction was loaded onto a silica gel column (SF15-12, Analogix®, Burlington, Wis.), and the title compound was eluted with a gradient of 0.4% to 4.5% methanol/dichloromethane over 20 minutes with a flow rate of 30 mL/minute. $^1$H NMR (300 MHz, CDCl$_3$) δ ppm 7.50-7.55 (m, 1H), 7.37-7.44 (m, 2H), 7.17-7.34 (m, 11H), 6.30 (t, J=6.0 Hz, 1H), 4.33 (d, J=6.0 Hz, 2H), 4.07 (s, 2H), 3.50 (t, J=6.5 Hz, 2H), 2.81 (t, J=6.5 Hz, 2H); MS (ESI–) m/z 451 (M–H)$^-$.

Example 8

2-(2-oxo-3,3-diphenylpyrrolidin-1-yl)-N-[4-(trifluoromethyl)benzyl]acetamide

A solution of (4-(trifluoromethyl)phenyl)methanamine (0.033 g, 0.186 mmol), 2-(2-oxo-3,3-diphenylpyrrolidin-1-yl)acetic acid (Example 1C, 0.050 g, 0.169 mmol) and N$^1$-((ethylimino)methylene)-N$^3$,N$^3$-dimethylpropane-1,3-diamine hydrochloride (0.049 g, 0.254 mmol) in dichloromethane (0.5 mL) was stirred at room temperature. After stirring overnight, the reaction was loaded directly onto a SF15-12 column (Analogix®, Burlington, Wis.), and the title compound was eluted using a gradient of 5% to 100% ethyl acetate/hexanes over 20 minutes (flow=30 mL/minute). $^1$H NMR (300 MHz, CDCl$_3$) δ ppm 7.50-7.54 (m, 2H), 7.17-7.33 (m, 12H), 6.39 (t, J=6.1 Hz, 1H), 4.34 (d, J=6.1 Hz, 2H), 4.07 (s, 2H), 3.51 (t, J=6.5 Hz, 2H), 2.81 (t, J=6.5 Hz, 2H); MS (ESI–) m/z 451 (M–H)$^-$.

Example 9

N-[cyclopropyl(phenyl)methyl]-2-(2-oxo-3,3-diphenylpyrrolidin-1-yl)acetamide

A solution of cyclopropyl(phenyl)methanamine hydrogen chloride (0.050 g, 0.272 mmol), 2-(2-oxo-3,3-diphenylpyrrolidin-1-yl)acetic acid (Example 1C, 0.073 g, 0.247 mmol) and N$^1$-((ethylimino)methylene)-N$^3$,N$^3$-dimethylpropane-1,3-diamine (0.066 mL, 0.371 mmol) in dichloromethane (0.5 mL) was stirred at room temperature. After stirring overnight, the reaction was loaded directly onto a SF15-12 silica gel column (Analogix®, Burlington, Wis.), and the title compound was eluted using a gradient of 5% to 100% ethyl acetate/hexanes over 20 minutes (flow=30 mL/minute). $^1$H NMR (300 MHz, CDCl$_3$) δ ppm 7.20-7.39 (m, 13H), 7.14-7.18 (m, 2H), 6.44 (d, J=8.1 Hz, 1H), 4.32 (t, J=8.6 Hz, 1H), 4.05 (d, J=15.3 Hz, 1H), 4.03 (d, J=15.6 Hz, 1H), 3.42-3.56 (m, 2H), 2.73-2.88 (m, 2H), 0.81-0.97 (m, 1H), 0.39-0.56 (m, 2H), 0.21-0.37 (m, 2H); MS (ESI–) m/z 423 (M–H)$^-$.

Example 10

2-(2-oxo-3,3-diphenylpyrrolidin-1-yl)-N-{2-[3-(trifluoromethyl)phenyl]ethyl}acetamide A solution of 2-(3-(trifluoromethyl)phenyl)ethanamine (0.021 g, 0.112 mmol), 2-(2-oxo-3,3-diphenylpyrrolidin-1-yl)acetic acid (Example 1C, 0.030 g, 0.102 mmol) and N$^1$-((ethylimino)methylene)-N$^3$,N$^3$-dimethylpropane-1,3-diamine hydrochloride (0.029 g, 0.053 mmol) in dichloromethane (0.5 mL) was stirred at room temperature. After stirring overnight, the reaction was loaded directly onto a SF15-12 silica gel column (Analogix®, Burlington, Wis.), and the title compound was eluted using a gradient of 5% to 100% ethyl acetate/hexanes over 20 minutes (flow=30 mL/minute). $^1$H NMR (300 MHz, CDCl$_3$) δ ppm 7.44-7.50 (m, 1H), 7.23-7.40 (m, 13H), 5.84 (t, J=6.1 Hz, 1H), 3.98 (s, 2H), 3.40 (t, J=6.5 Hz, 2H), 3.32-3.40 (m, 2H), 2.76 (t, J=6.5 Hz, 2H), 2.67 (t, J=7.3 Hz, 2H); MS (ESI–) m/z 465 (M–H)$^-$.

Example 11

2-(2-oxo-3,3-diphenylpyrrolidin-1-yl)-N-(1-phenylcyclobutyl)acetamide

A solution of 1-phenylcyclobutanamine (0.030 g, 0.204 mmol), 2-(2-oxo-3,3-diphenylpyrrolidin-1-yl)acetic acid (0.055 g, 0.185 mmol) and N$^1$-((ethylimino)methylene)-N$^3$,N$^3$-dimethylpropane-1,3-diamine hydrochloride (0.036 g, 0.185 mmol) in dichloromethane (0.5 mL) was stirred at room temperature. After stirring overnight, the reaction was loaded directly onto a SF15-12 silica gel column (Analogix®, Burlington, Wis.), and the title compound was eluted using a gradient of 5% to 100% ethyl acetate/hexanes over 20 minutes (flow=30 mL/minute). $^1$H NMR (300 MHz, CDCl$_3$) δ ppm 7.31-7.39 (m, 7H), 7.17-7.31 (m, 8H), 6.42-6.44 (br s, 1H), 3.94 (s, 2H), 3.46 (t, J=6.5 Hz, 2H), 2.79 (t, J=6.5 Hz, 2H), 2.42-2.52 (m, 2H), 2.19-2.30 (m, 2H), 1.71-1.95 (m, 2H); MS (ESI–) m/z 423 (M–H)$^-$.

Example 12

N-(4-fluorobenzyl)-2-(2-oxo-3,3-diphenylpyrrolidin-1-yl)acetamide

A solution of $N^1$-((ethylimino)methylene)-$N^3,N^3$-dimethylpropane-1,3-diamine hydrochloride (0.049 g, 0.254 mmol), 2-(2-oxo-3,3-diphenylpyrrolidin-1-yl)acetic acid (0.050 g, 0.169 mmol) and (4-fluorophenyl)methanamine (0.023 g, 0.186 mmol) in dichloromethane (0.5 mL) was stirred at room temperature. After stirring overnight, the reaction was loaded directly onto a SF15-12 silica gel column (Analogix®, Burlington, Wis.), and the title compound was eluted using a gradient of 5% to 100% ethyl acetate/hexanes over 20 minutes (flow=30 mL/minute). $^1$H NMR (300 MHz, CDCl$_3$) δ ppm 7.20-7.30 (m, 9H), 7.06-7.12 (m, 2H), 6.93-6.99 (m, 2H), 6.24-6.27 (m, 1H), 4.26 (d, J=5.9 Hz, 2H), 4.04 (s, 3H), 3.49 (t, J=6.5 Hz, 2H), 2.80 (t, J=6.4 Hz, 2H); MS (ESI−) m/z 401 (M−H)$^-$.

Example 13

N-(3,3-diphenylpropyl)-2-(2-oxo-3,3-diphenylpyrrolidin-1-yl)acetamide

To a solution of 3,3-diphenylpropan-1-amine (0.0.21 g, 1.00 mmol) in dichloromethane (20 mL) under nitrogen was added 2-(2-oxo-3,3-diphenylpyrrolidin-1-yl)acetic acid (Example 1C, 0.30 g, 1.00 mmol) followed by $N^1$-((ethylimino)methylene)-$N^3,N^3$-dimethylpropane-1,3-diamine hydrochloride (0.38 g, 2.00 mmol) and N,N-dimethylpyridin-4-amine (0.61 mg, 0.005 mmol). The reaction mixture was stirred overnight at room temperature. The reaction was concentrated and the residue was partitioned in ethyl acetate/water (8:2, 400 mL). The organic layer was washed with water followed by brine, dried over magnesium sulfate, filtered and concentrated. Silica gel chromatography eluting with ethyl acetate/hexane (1:1) gave the title compound. $^1$H NMR (300 MHz, DMSO-d$_6$) δ ppm 8.01 (t, J=5.4 Hz, 1H), 7.12-7.35 (m, 20H), 3.98 (t, J=7.8 Hz, 1H), 3.89 (s, 2H), 3.35 (t, J=6.5 Hz, 2H), 2.94-3.01 (m, 2H), 2.72 (t, J=6.4 Hz, 2H), 2.13-2.21 (m, 2H); MS (DCI+) m/z 489 (M+H)$^+$.

Example 14

N-benzhydryl-2-(2-oxo-3,3-diphenylpyrrolidin-1-yl)acetamide

To a solution of diphenylmethanamine (0.18 g, 1.00 mmol) in dichloromethane (10 mL) under nitrogen was added 2-(2-oxo-3,3-diphenylpyrrolidin-1-yl)acetic acid (Example 1C, 0.30 g, 1.00 mmol) followed by $N^1$-((ethylimino)methylene)-$N^3,N^3$-dimethylpropane-1,3-diamine hydrochloride (0.38 g, 2.00 mmol) and N,N-dimethylpyridin-4-amine (0.61 mg, 0.005 mmol). The reaction mixture was stirred overnight at room temperature. The reaction was concentrated and the residue was partitioned in ethyl acetate/water (8:2, 400 mL). The organic layer was washed with water followed by brine, dried over magnesium sulfate, filtered and concentrated. Silica gel chromatography eluting with ethyl acetate/hexane (1:1) gave the title compound. $^1$H NMR (300 MHz, DMSO-d$_6$) δ ppm 8.96 (d, J=8.5 Hz, 1H), 7.21-7.37 (m, 20H), 6.13 (d, J=8.4 Hz, 1H), 4.08 (s, 2H), 3.37 (t, J=6.5 Hz, 2H), 2.71 (t, J=6.4 Hz, 2H); MS (DCI+) m/z 461 (M+H)$^+$.

Example 15

N-(2,2-diphenylethyl)-2-(2-oxo-3,3-diphenylpyrrolidin-1-yl)acetamide

To a solution of 2,2-diphenylethanamine (0.20 g, 1.00 mmol) in dichloromethane (20 mL) under nitrogen was added 2-(2-oxo-3,3-diphenylpyrrolidin-1-yl)acetic acid (Example 1C, 0.30 g, 1.00 mmol) followed by $N^1$-((ethylimino)methylene)-$N^3,N^3$-dimethylpropane-1,3-diamine hydrochloride (0.38 g, 2.00 mmol) and N,N-dimethylpyridin-4-amine (0.61 mg, 0.005 mmol). The reaction mixture was stirred overnight at room temperature. The reaction was concentrated and the residue was partitioned in ethyl acetate/water (8:2, 400 mL). The organic layer was washed with water followed by brine, dried over magnesium sulfate, filtered and concentrated. Silica gel chromatography eluting with ethyl acetate/hexane (1:1) gave the title compound. $^1$H NMR (300 MHz, DMSO-d$_6$) δ ppm 8.01 (t, J=5.6 Hz, 1H), 7.26-7.32 (m, 16H), 7.15-7.27 (m, 4H), 4.19 (t, J=7.9 Hz, 1H), 3.81 (s, 2H), 3.74 (dd, J=7.9, 5.6 Hz, 2H), 3.15 (t, J=6.4 Hz, 2H), 2.65 (t, J=6.4 Hz, 2H); MS (DCI+) m/z 475 (M+H)$^+$, 492 (M+NH$_4$)$^+$.

Example 16

N-(2,2-diphenylpropyl)-2-(2-oxo-3,3-diphenylpyrrolidin-1-yl)acetamide

To a solution of 2,2-diphenylpropan-1-amine (0.21 g, 1.00 mmol) in dichloromethane (20 mL) under nitrogen was added 2-(2-oxo-3,3-diphenylpyrrolidin-1-yl)acetic acid (Example 1C, 0.30 g, 1.00 mmol) followed by $N^1$-((ethylimino)methylene)-$N^3,N^3$-dimethylpropane-1,3-diamine hydrochloride (0.38 g, 2.00 mmol) and N,N-dimethylpyridin-4-amine (0.61 mg, 0.005 mmol). The reaction mixture was stirred overnight at room temperature. The reaction was concentrated and the residue was partitioned in ethyl acetate/water (8:2, 400 mL). The organic layer was washed with water followed by brine, dried over magnesium sulfate, filtered and concentrated. Silica gel chromatography eluting with ethyl acetate/hexane (1:1) gave the title compound. $^1$H NMR (300 MHz, CDCl$_3$) δ ppm 7.09-7.33 (m, 20H), 5.72-5.77 (m, 1H), 3.95 (d, J=5.9 Hz, 2H), 3.91 (s, 2H), 3.23 (t, J=6.4 Hz, 2H), 2.58 (t, J=6.4 Hz, 2H), 1.57 (s, 3H); MS (DCI+) m/z 489 (M+H)$^+$.

Example 17

1-[2-(3,3-diphenylpyrrolidin-1-yl)-2-oxoethyl]-3,3-diphenylpyrrolidin-2-one

Example 17A

3,3-diphenylpyrrolidine

In a 500 mL flask containing 3,3-diphenylpyrrolidine-2-one (5.00 g, 21 mmol; Example 1A) as a suspension in ether (300 mL) was added lithium aluminum hydride (2.0 M in tetrahydrofuran, 24 mL, 48 mmol) slowly via syringe under nitrogen. The reaction was refluxed overnight, cooled to room temperature, and then carefully quenched by the slow addition of 1 N NaOH (60 mL). The reaction was diluted with ethyl acetate (200 mL) and filtered through a pad of diatomaceous earth. The organic phase was separated, concentrated, and the residue purified over silica gel eluting with 95:5 dichloromethane/methanol to give the title compound. MS (DCI+) m/z 224 (M+H)$^+$.

Example 17B

1-[2-(3,3-diphenylpyrrolidin-1-yl)-2-oxoethyl]-3,3-diphenylpyrrolidin-2-one

To a solution of 3,3-diphenylpyrrolidine (Example 17A, 0.22 g, 1.00 mmol) in dichloromethane (20 mL) under nitrogen was added 2-(2-oxo-3,3-diphenylpyrrolidin-1-yl)acetic acid (Example 1C, 0.30 g, 1.00 mmol) followed by $N^1$-((ethylimino)methylene)-$N^3,N^3$-dimethylpropane-1,3-diamine hydrochloride (0.38 g, 2.00 mmol) and N,N-dimethylpyridin-4-amine (0.61 mg, 0.005 mmol). The reaction mixture was stirred overnight at room temperature. The reaction was concentrated and the residue was partitioned in ethyl acetate/water (8:2, 400 mL). The organic layer was washed with water followed by brine, dried over magnesium sulfate, filtered, and concentrated. Silica gel chromatography eluting with ethyl acetate/hexane (1:1) gave the title compound. $^1$H NMR (300 MHz, CDCl$_3$) δ ppm 7.16-7.40 (m, 20H), 4.14-4.25 (m, 2H), 4.09-4.12 (m, 2H), 3.38-3.61 (m, 4H), 2.75-2.87 (m, 2H), 2.49-2.63 (m, 2H); MS (DCI+) m/z 501 (M+H)$^+$.

Example 18

1-[2-(3-benzylpiperazin-1-yl)-2-oxoethyl]-3,3-diphenylpyrrolidin-2-one

To tert-butyl 2-benzylpiperazine-1-carboxylate (0.052 g, 0.190 mmol), 2-(2-oxo-3,3-diphenylpyrrolidin-1-yl)acetic acid (Example 1C, 0.051 g, 0.173 mmol) and 2-(1H-benzo[d][1,2,3]triazol-1-yl)-1,1,3,3-tetramethylisouronium hexafluorophosphate(V) (0.069 g, 0.181 mmol) in dichloromethane (0.5 mL) was added diisopropylethylamine (0.045 mL, 0.259 mmol), and the reaction was stirred a room temperature. After stirring overnight, the reaction was concentrated, loaded onto a silica gel column (Analogix® SF15-12, Burlington, Wis.) and eluted with a gradient of 5% to 100% ethyl acetate/hexanes. To the resulting product was added HCl (2.0 Min diethyl ether, 3.57 μl, 0.117 mmol), and the reaction was stirred at room temperature overnight. The reaction was centrifuged, and the solvent was decanted away from the solid. Diethyl ether (1 mL) was added, and the suspension was sonicated to give a fine suspension. The reaction was centrifuged, the solvent was decanted and the resulting solid dried to give the title compound as the hydrochloride salt. $^1$H NMR (300 MHz, pyridine-d$_5$) δ ppm 7.05-7.50 (m, 15H), 4.65-4.80 (m, 2H), 4.25-4.55 (m, 2H), 3.95-4.15 (m, 2H), 3.40-3.75 (m, 5H), 2.95-3.27 (m, 2H), 2.75-2.85 (m, 2H); MS (DCI+) m/z 454.2 (M+H)$^+$.

Example 19

1-[2-(3,4-dihydroisoquinolin-2(1H)-yl)-2-oxoethyl]-3,3-diphenylpyrrolidin-2-one

A solution of 1,2,3,4-tetrahydroisoquinoline (0.025 g, 0.186 mmol), 2-(2-oxo-3,3-diphenylpyrrolidin-1-yl)acetic acid (Example 1C, 0.050 g, 0.169 mmol) and $N^1$-((ethylimino)methylene)-$N^3,N^3$-dimethylpropane-1,3-diamine hydrochloride (0.049 g, 0.254 mmol) in dichloromethane (0.5 mL) was stirred at room temperature. After stirring overnight, the reaction was loaded directly onto a SF15-12 silica gel column (Analogix®, Burlington, Wis.), and the title compound was eluted using a gradient of 0.4% to 4.5% methanol/dichloromethane over 20 minutes (flow=30 mL/minute). $^1$H NMR (300 MHz, CDCl$_3$) δ ppm 7.15-7.40 (m, 14H), 4.55-4.80 (m, 2H), 4.25 (s, 2H), 3.60-3.85 (m, 2H), 3.45-3.55 (m, 2H), 2.70-2.90 (m, 4H); MS (ESI+) m/z 411 (M+H)$^+$.

Example 20

1-{2-oxo-2-[5-(trifluoromethyl)-1,3-dihydro-2H-isoindol-2-yl]ethyl}-3,3-diphenylpyrrolidin-2-one A solution of 5-(trifluoromethyl)isoindoline (0.035 g, 0.186 mmol), 2-(2-oxo-3,3-diphenylpyrrolidin-1-yl)acetic acid (0.050 g, 0.169 mmol) and $N^1$-((ethylimino)methylene)-$N^3,N^3$-dimethylpropane-1,3-diamine hydrochloride (0.049 g, 0.254 mmol) in dichloromethane (0.5 mL) was stirred at room temperature. After stirring overnight, the reaction was loaded directly onto a SF15-12 silica gel column (Analogix®, Burlington, Wis.), and the title compound was eluted using a gradient of 5% to 100% ethyl acetate/hexanes over 20 minutes (flow=30 mL/minute). $^1$H NMR (300 MHz, CDCl$_3$) δ ppm 7.54-7.61 (m, 1H), 7.20-7.49 (m, 12H), 4.82-4.88 (m, 4H), 4.24 (s, 2H), 3.61 (td, J=6.5, 1.6 Hz, 2H), 2.85 (t, J=6.6 Hz, 2H); MS (ESI+) m/z 465 (M+H)$^+$.

Example 21

1-[2-oxo-2-(3-phenylpyrrolidin-1-yl)ethyl]-3,3-diphenylpyrrolidin-2-one

A solution of 3-phenylpyrrolidine (0.029 g, 0.194 mmol), 2-(2-oxo-3,3-diphenylpyrrolidin-1-yl)acetic acid (Example 1C, 0.052 g, 0.176 mmol) and $N^1$-((ethylimino)methylene)-$N^3,N^3$-dimethylpropane-1,3-diamine hydrochloride (0.051 g, 0.244 mmol) in dichloromethane (0.5 mL) was stirred at room temperature. After stirring overnight, the reaction was loaded directly onto a SF15-12 silica gel column (Analogix®, Burlington, Wis.), and the title compound was eluted using a gradient of 5% to 100% ethyl acetate/hexanes over 20 minutes (flow=30 mL/minute). $^1$H NMR (300 MHz, CDCl$_3$) δ ppm 7.14-7.43 (m, 15H), 4.09-4.22 (m, 2H), 3.63-4.11 (m, 2H), 3.26-3.63 (m, 5H), 2.77-2.89 (m, 2H), 2.22-2.42 (m, 1H), 1.91-2.13 (m, 1H); MS (ESI+) m/z 425 (M+H)$^+$.

Example 22

N-2,3-dihydro-1H-inden-2-yl-2-(2-oxo-3,3-diphenylpyrrolidin-1-yl)acetamide

A solution of 2,3-dihydro-1H-inden-2-amine (0.020 g, 0.149 mmol), 2-(2-oxo-3,3-diphenylpyrrolidin-1-yl)acetic acid (Example 1C, 0.040 g, 0.135 mmol) and $N^1$-((ethylimino)methylene)-$N^3,N^3$-dimethylpropane-1,3-diamine hydrochloride (0.039 g, 0.203 mmol) in dichloromethane (0.5 mL) was stirred at room temperature. After stirring overnight, the reaction was loaded directly onto a SF15-12 silica gel column (Analogix®, Burlington, Wis.), and the title compound was eluted using a gradient of 5% to 100% ethyl acetate/hexanes over 20 minutes (flow=30 mL/minute). $^1$H NMR (300 MHz, CDCl$_3$) δ ppm 7.18-7.32 (m, 14H), 6.05 (d, J=7.5 Hz, 1H), 4.60 (qt, J=7.5, 5.7 Hz, 1H), 3.99 (s, 2H), 3.49 (t, J=6.5 Hz, 2H), 3.20 (dd, J=15.9, 7.5 Hz, 2H), 2.78 (t, J=6.5 Hz, 2H), 2.52 (dd, J=15.9, 5.8 Hz, 2H); MS (ESI−) m/z 409 (M−H)$^-$.

Example 23

1-[2-(2,2-diphenylmorpholin-4-yl)-2-oxoethyl]-3,3-diphenylpyrrolidin-2-one

A solution of $N^1$-((ethylimino)methylene)-$N^3,N^3$-dimethylpropane-1,3-diamine hydrochloride (0.060 g, 0.313 mmol), 2-(2-oxo-3,3-diphenylpyrrolidin-1-yl)acetic acid (Example 1C, 0.059 g, 0.198 mmol) and 2,2-diphenylmorpholine (0.050 g, 0.209 mmol, CAS 77373-34-3) in dichloromethane (0.5 mL) was stirred at room temperature. After stirring overnight, the reaction was loaded directly onto a SF15-12 silica gel column (Analogix®, Burlington, Wis.), and the title compound was eluted using a gradient of 5% to 100% ethyl acetate/hexanes over 20 minutes (flow=30 mL/minute). $^1$H NMR (300 MHz, CDCl$_3$) δ ppm 7.43 (s, 20H), 4.15 (s, 2H), 4.09 (s, 2H), 3.39-3.44 (m, 2H), 3.28-3.33 (m, 2H), 3.27 (t, J=6.4 Hz, 2H), 2.57 (t, J=6.6 Hz, 2H); MS (ESI+) m/z 517 (M+H)$^+$.

Example 24

1-[2-(3,3-diphenylpiperidin-1-yl)-2-oxoethyl]-3,3-diphenylpyrrolidin-2-one

Example 24A 3,3-diphenylpiperidine

In a 500 mL flask containing 3,3-diphenylpiperidin-2-one (3.77 g, 15 mmol; Example 68C) as a suspension in ether (300 mL) was added lithium aluminum hydride (2.0 Min tetrahydrofuran, 15 mL, 30 mmol) slowly via syringe under nitrogen. The reaction was refluxed overnight, cooled to room temperature, and then carefully quenched by the slow addition of 1 N NaOH (60 mL). The reaction was diluted with ethyl acetate (200 mL) and filtered through a pad or diatomaceous earth. The organic phase was separated, concentrated, and the residue was purified over silica gel eluting with 95:5 dichloromethane/methanol to give the title compound. MS (DCI+) m/z 238 (M+H)$^+$.

Example 24B

1-[2-(3,3-diphenylpiperidin-1-yl)-2-oxoethyl]-3,3-diphenylpyrrolidin-2-one

To a solution of the product from Example 24A (0.48 g, 2.00 mmol) in dichloromethane was added 2-(2-oxo-3,3-diphenylpyrrolidin-1-yl)acetic acid (Example 1C, 0.59 g, 2.00 mmol) under nitrogen. To the reaction was added N$^1$-((ethylimino)methylene)-N$^3$,N$^3$-dimethylpropane-1,3-diamine hydrochloride (0.77 g, 4.00 mmol) and N,N-dimethylpyridin-4-amine (0.024 g, 0.20 mmol), and the reaction mixture was stirred overnight at room temperature. The reaction was concentrated, and the residue was partitioned in ethyl acetate:water (8:2). The organic layer was separated, washed with water and then brine, dried over MgSO4, filtered, and concentrated. Silica gel chromatography eluting with 3% methanol/dichloromethane gave the title compound. $^1$H NMR (300 MHz, CDCl$_3$) δ ppm 7.13-7.37 (m, 20H), 4.16 (s, 2H), 4.11 (s, 2H), 3.33-3.40 (m, 2H), 3.24 (t, J=6.4 Hz, 2H), 2.63 (t, J=6.4 Hz, 2H), 2.39-2.46 (m, 2H), 1.29-1.37 (m, 2H); MS (DCI+) m/z 515 (M+H)$^+$.

Example 25

1-[2-(4,4-diphenylpiperidin-1-yl)-2-oxoethyl]-3,3-diphenylpyrrolidin-2-one

To a solution of 4,4-diphenylpiperidine (Matrix, 0.48 mg, 2.00 mmol) in dichloromethane was added 2-(2-oxo-3,3-diphenylpyrrolidin-1-yl)acetic acid (Example 1C, 0.59 g, 2.00 mmol) under nitrogen. To the reaction was added N$^1$-((ethylimino)methylene)-N$^3$,N$^3$-dimethylpropane-1,3-diamine hydrochloride (0.77 g, 4.00 mmol) and N,N-dimethylpyridin-4-amine (0.024 g, 0.20 mmol), and the reaction mixture was stirred overnight at room temperature. The reaction was concentrated and the residue was partitioned in ethyl acetate:water (8:2). The organic layer was separated, washed with water and then brine, dried over MgSO4, filtered, and concentrated. Silica gel chromatography eluting with 3% methanol/dichloromethane gave the title compound. $^1$H NMR (300 MHz, CDCl$_3$) δ ppm 7.25-7.37 (m, 12H), 7.14-7.24 (m, 8H), 4.20 (s, 2H), 3.61-3.67 (m, 2H), 3.50 (t, J=6.4 Hz, 2H), 3.42-3.47 (m, 2H), 2.80 (t, J=6.6 Hz, 2H), 2.35-2.41 (m, 2H), 2.26-2.31 (m, 2H); MS (DCI+) m/z 515 (M+H)$^+$.

Example 26

1-[2-(5-fluoro-1,3-dihydro-2H-isoindol-2-yl)-2-oxoethyl]-3,3-diphenylpyrrolidin-2-one A solution of N$^1$-((ethylimino)methylene)-N$^3$,N$^3$-dimethylpropane-1,3-diamine (0.067 mL, 0.381 mmol), 2-(2-oxo-3,3-diphenylpyrrolidin-1-yl)acetic acid (Example 1C, 0.075 g, 0.254 mmol) and 5-fluoroisoindoline hydrochloride (0.044 g, 0.254 mmol) in dichloromethane (0.5 mL) was stirred at room temperature. After stirring overnight, the reaction was loaded directly onto a SF15-12 silica gel column (Analogix®, Burlington, Wis.), and the title compound was eluted using a gradient of 5% to 100% ethyl acetate/hexanes over 20 minutes (flow=30 mL/minute). $^1$H NMR (300 MHz, CDCl$_3$) δ ppm 7.13-7.40 (m, 11H), 6.88-7.05 (m, 2H), 4.75-4.81 (m, 4H), 4.23 (s, 2H), 3.60 (t, J=6.6 Hz, 2H), 2.85 (t, J=6.6 Hz, 2H); MS (ESI+) m/z 415 (M+H)$^+$.

Example 27

2-(2-oxo-3,3-diphenylpyrrolidin-1-yl)-N-1,2,3,4-tetrahydronaphthalen-1-ylacetamide A solution of 1,2,3,4-tetrahydronaphthalen-1-amine (0.030 g, 0.204 mmol), 2-(2-oxo-3,3-diphenylpyrrolidin-1-yl)acetic acid (Example 1C, 0.060 g, 0.204 mmol) and N$^1$-((ethylimino)methylene)-N$^3$,N$^3$-dimethylpropane-1,3-diamine hydrochloride (0.059 g, 0.306 mmol) in dichloromethane (0.5 mL) was stirred at room temperature. After stirring overnight, the reaction was loaded onto a SF15-12 silica gel column (Analogix®, Burlington, Wis.), and the title compound was eluted using a gradient of 5% to 100% ethyl acetate/hexanes over 20 minutes (flow=30 mL/minute). $^1$H NMR (300 MHz, CDCl$_3$) δ ppm 7.05-7.31 (m, 14H), 5.98-6.03 (m, 1H), 5.05-5.13 (m, 1H), 4.08 (d, J=15.5 Hz, 1H), 4.05 (d, J=15.5 Hz, 1H), 3.51 (t, J=6.5 Hz, 2H), 2.78 (q, J=6.3 Hz, 2H), 2.71 (t, J=6.5 Hz, 2H), 1.85-1.97 (m, 1H), 1.56-1.78 (m, 2H), 1.45-1.55 (m, 1H); MS (ESI−) m/z 423 (M−H)$^−$.

Example 28

1-benzhydryl-4-[(2-oxo-3,3-diphenylpyrrolidin-1-yl)acetyl]piperazin-2-one

Example 28A 1-benzhydrylpiperazin-2-one

To a solution of tert-butyl 3-oxopiperazine-1-carboxylate (0.75 g, 3.75 mmol) in N,N-dimethylformamide (3 mL) was added a 60% dispersion of sodium hydride in oil (0.18 g, 4.5 mmol). The mixture was stirred at ambient temperature for 1 hour. To the resulting suspension was added bromodiphenylmethane (1.02 g, 4.12 mmol) and stirring was continued at room temperature overnight. The reaction mixture was poured into water and extracted with ethyl acetate. The organic layer was dried over magnesium sulfate, concentrate in vacuo, and chromatographed on silica gel eluting with 20% ethyl acetate/hexane to yield 0.5 g of the t-butoxycarbonyl-protected title compound. The protected material was dissolved in methanol (10 mL) and treated with 4 N HCl/dioxane solution (2 mL) at ambient temperature for 3 hours. Diethyl ether was added to the solution to precipitate the title compound as the hydrochloride salt. $^1$H NMR (300 MHz, DMSO-d$_6$) δ ppm 9.49 (s, 1H), 7.41 (m, 6H), 7.20 (d, J=6.44 Hz, 4H), 6.92 (s, 1H), 3.88 (s, 2H), 3.43 (m, 2H), 3.19 (m, 2H); MS (DCI) m/z 267 (M+H)$^+$.

Example 28B 1-benzhydryl-4-[(2-oxo-3,3-diphenylpyrrolidin-1-yl)acetyl]piperazin-2-one To a solution of 2-(2-oxo-3,3-diphenylpyrrolidin-1-yl)acetic acid (Example 1C, 0.18 g, 0.6 mmol) and the product from Example 28A (0.18 g, 0.6 mmol) in methylene chloride (10 mL) was added O-(7-azabenzotriazol-1-yl)-N,N,N',N'-tetramethyluronium hexafluorophosphate (0.23 g, 0.6 mmol) and diisopropylethylamine (0.5 mL). The reaction mixture was stirred at ambient temperature overnight. The reaction mixture was then diluted with methylene chloride, and then washed with 1 N HCl, water, 1 N NaOH, and water. The organic layer was dried over magnesium sulfate and concentrated in vacuo to yield the title compound. $^1$H NMR (300 MHz, DMSO-d$_6$) δ ppm 7.28 (m, 20H), 6.91 (s, 1H), 4.26 (d, J=21.70 Hz, 2H), 4.18 (d, J=12.88 Hz, 2H), 3.69 (m, 2H), 3.35 (m, 2H), 3.13 (m, 1H), 3.07 (m, 1H), 2.71 (m, 2H), 2.69 (s, 1H); MS (ESI+) m/z 544 (M+H)$^+$.

Example 29

4-[(2-oxo-3,3-diphenylpyrrolidin-1-yl)acetyl]-1-[3-(trifluoromethyl)benzyl]piperazin-2-one Example 29A 1-(3-(trifluoromethyl)benzyl)piperazin-2-one hydrochloride The hydrochloride salt of 1-(3-(trifluoromethyl)benzyl)piperazin-2-one was obtained as described in Example 28A, substituting 1-(bromomethyl)-3-(trifluoromethyl)benzene for bromodiphenylmethane. $^1$H NMR (300 MHz, DMSO-d$_6$) δ ppm 9.64 (s, 1H), 7.63 (m, 4H), 4.68 (s, 2H), 3.81 (s, 2H), 3.51 (m, 2H), 3.39 (t, J=5.55 Hz, 2H); MS (DCI) m/z 259 (M+H)$^+$.

Example 29B

4-[(2-oxo-3,3-diphenylpyrrolidin-1-yl)acetyl]-1-[3-(trifluoromethyl)benzyl]piperazin-2-one The title compound was obtained by the procedure described in Example 28B, replacing 1-benzhydrylpiperazin-2-one hydrochloride with the product from Example 29A. $^1$H NMR (300 MHz, CDCl$_3$) δ ppm 7.58 (m, 1H), 7.49 (m, 3H), 7.32 (m, 10H), 4.63 (d, J=21.36 Hz, 2H), 4.25 (d, J=20.01 Hz, 2H), 4.20 (s, 2H), 3.79 (m, 1H), 3.59 (m, 1H), 3.51 (t, J=6.44 Hz, 2H), 3.30 (m, 1H), 3.02 (m, 1H), 2.83 (m, 2H); MS (ESI+) m/z 536 (M+H)$^+$.

Example 30

1-[2-(4-benzhydrylpiperidin-1-yl)-2-oxoethyl]-3,3-diphenylpyrrolidin-2-one

To a solution of 4-benzhydrylpiperidine (0.25 g, 1.00 mmol) in dichloromethane (20 mL) was added 2-(2-oxo-3,3-diphenylpyrrolidin-1-yl)acetic acid (Example 1C, 0.30 g, 1.00 mmol) under nitrogen. To the reaction was added N$^1$-(ethylimino)methylene)-N$^3$,N$^3$-dimethylpropane-1,3-diamine hydrochloride (0.38 g, 2.00 mmol) and N,N-dimethylpyridin-4-amine (6.1 mg, 0.005 mmol), and the reaction mixture was stirred overnight at room temperature. The reaction was concentrated, and the residue was partitioned in ethyl acetate:water (8:2). The organic layer was separated, washed with water and then brine, dried over MgSO4, filtered and concentrated. Silica gel chromatography eluting with ethyl acetate/hexane (1:1) gave the title compound. $^1$H NMR (300 MHz, DMSO-d$_6$) δ ppm 7.14-7.39 (m, 20H), 4.23-4.31 (m, 1H), 4.19 (d, J=16.5 Hz, 1H), 4.08 (d, J=16.3 Hz, 1H), 3.73-3.80 (m, 1H), 3.58 (d, J=11.0 Hz, 1H), 3.35 (t, J=6.7 Hz, 2H), 2.86-3.00 (m, 1H), 2.71 (t, J=6.5 Hz, 2H), 2.50-2.62 (m, 2H), 1.37-1.47 (m, 2H), 0.81-1.07 (m, 2H); MS (DCI+) m/z 529 (M+H)$^+$.

Example 31

1-{2-[4-(diphenylmethylene)piperidin-1-yl]-2-oxoethyl}-3,3-diphenylpyrrolidin-2-one Example 31A 4-(diphenylmethylene)piperidine trifluoroacetate To a solution of diphenyl(piperidin-4-yl)methanol (J. Med. Chem. 1989, 32(1), 105-118) (0.42 g, 1.57 mmol) in methylene chloride (15 mL) was added trifluoroacetic acid (3 mL), and the reaction mixture was stirred at room temperature overnight. The reaction mixture was concentrated to yield the trifluoroacetic acid salt of the title compound. $^1$H NMR (300 MHz, DMSO-d$_6$) δ ppm 7.35 (tt, J=7.33, 1.65 Hz, 4H), 7.26 (m, 4H), 7.15 (dt, J=6.36, 1.57 Hz, 2H), 3.15 (m, 4H), 2.43 (t, 4H); MS (DCI) m/z 250 (M+H)$^+$.

Example 31B

1-{2-[4-(diphenylmethylene)piperidin-1-yl]-2-oxoethyl}-3,3-diphenylpyrrolidin-2-one The title compound was obtained by the procedure described in Example 28B, replacing 1-benzhydrylpiperazin-2-one hydrochloride with the product from Example 31A. $^1$H NMR (300 MHz, CDCl$_3$) δ ppm 7.18-7.40 (m, 16H), 7.01-7.12 (m, 4H), 4.21 (s, 2H), 3.61 (t, J=5.7 Hz, 2H), 3.53 (t, J=6.5 Hz, 2H), 3.39-3.43 (m, 2H), 2.82 (t, J=6.5 Hz, 2H), 2.35 (t, J=5.7 Hz, 2H), 2.27 (t, J=5.5 Hz, 2H); MS (ESI+) m/z 527 (M+H)$^+$.

Example 32

1-(2-{4-[bis(4-fluorophenyl)(hydroxy)methyl]piperidin-1-yl}-2-oxoethyl)-3,3-diphenylpyrrolidin-2-one

Example 32A bis(4-fluorophenyl)(piperidin-4-yl)methanol

To a solution of 4-bromopyridine (0.78 g, 5.0 mmol) in tetrahydrofuran (5 mL) was added isopropylmagnesium chloride (2.0 Min tetrahydrofuran, 2.5 mL, 5.0 mmol) via syringe under nitrogen at room temperature. The reaction mixture was stirred for one hour. To the reaction mixture was then added bis(4-fluorophenyl)methanone (0.98 g, 4.5 mmol) dissolved in tetrahydrofuran (7 mL) via syringe. The reaction mixture was stirred overnight, quenched with a saturated aqueous solution of ammonium chloride (10 mL), and extracted with diethyl ether. The organic layer was washed with water and brine, dried over magnesium sulfate, filtered, and concentrated. Silica gel chromatography eluting with 5% methanol/dichloromethane gave bis(4-fluorophenyl)(pyridin-4-yl)methanol on (0.73 g, 2.45 mmol).

The above bis(4-fluorophenyl)(pyridin-4-yl)methanol (0.73 g, 2.45 mmol) was hydrogenated (60 pounds per square inch) in the presence of platinum oxide (0.1 g) catalyst in acetic acid (15 mL) for 6 hours at room temperature. The reaction mixture was filtered and concentrated. The concentrated filtrate was diluted with ice/water (20 mL) and neutralized with 10% aqueous sodium carbonate. The title product was collected by filtration. $^1$H NMR (300 MHz, DMSO-$d_6$) δ ppm 7.46-7.54 (m, 4H), 7.051-7.13 (m, 4H), 5.35-5.45 (bs, 1H), 2.87-2.97 (d, J=6.2 Hz, 2H), 2.45-2.56 (m, 3H), 1.24-1.38 (m, 2H), 1.16-1.22 (m, 2H); MS (DCI/NH$_3$) m/z 304 (M+H)$^+$.

Example 32B

1-{2-[4-(diphenylmethylene)piperidin-1-yl]-2-oxoethyl}-3,3-diphenylpyrrolidin-2-one To a solution of bis(4-fluorophenyl)(piperidin-4-yl)methanol (0.30 g, 1.00 mmol, Example 32A) in dichloromethane (20 mL) was added 2-(2-oxo-3,3-diphenylpyrrolidin-1-yl)acetic acid (Example 1C, 0.30 g, 1.00 mmol) under nitrogen. To the mixture was added N$^1$-((ethylimino)methylene)-N$^3$,N$^3$-dimethylpropane-1,3-diamine hydrochloride (0.38 g, 2.00 mmol) and N,N-dimethylpyridin-4-amine (6.1 mg, 0.005 mmol), and the reaction mixture was stirred overnight at room temperature. The reaction was concentrated, and the residue was partitioned in ethyl acetate:water (8:2). The organic layer was separated, washed with water and then brine, dried over MgSO4, filtered and concentrated. Silica gel chromatography eluting with ethyl acetate/hexanes (1:1) gave the title compound. $^1$H NMR (300 MHz, DMSO-$d_6$) δ ppm 7.49-7.57 (m, 4H), 7.17-7.35 (m, 10H), 7.06-7.13 (m, 4H), 5.49 (s, 1H), 4.36 (d, J=14.0 Hz, 1H), 4.17 (d, J=16.6 Hz, 1H), 4.10 (d, J=15.7 Hz, 1H), 3.81 (d, J=14.3 Hz, 1H), 3.34 (t, J=6.7 Hz, 2H), 2.95-2.98 (m, 1H), 2.73-2.85 (m, 1H), 2.72 (t, J=6.6 Hz, 2H), 2.50-2.62 (m, 1H), 1.20-1.39 (m, 4H).

Example 33

1-{2-[4-(hydroxy{bis[3-(trifluoromethyl)phenyl]}methyl)piperidin-1-yl]-2-oxoethyl}-3,3-diphenylpyrrolidin-2-one

Example 33A piperidin-4-ylbis(3-(trifluoromethyl)phenyl)methanol

The title compound was prepared using the procedure described in Example 32A substituting bis(3-(trifluoromethyl)phenyl)methanone for bis(4-fluorophenyl)methanone. $^1$H NMR (300 MHz, DMSO-$d_6$) δ ppm 7.81-7.92 (m, 4H), 7.48-7.58 (m, 4H), 5.75-5.85 (bs, 1H), 2.84-2.95 (d, J=6.2 Hz, 2H), 2.66-2.78 (t, J=6.2 Hz, 1H), 2.43-2.58 (m, 3H), 1.26-1.40 (m, 2H), 1.08-1.18 (m, 2H); MS (DCI/NH$_3$) m/z 404 (M+H)$^+$.

Example 33B

1-{2-[4-(hydroxy{bis[3-(trifluoromethyl)phenyl]}methyl)piperidin-1-yl]-2-oxoethyl}-3,3-diphenylpyrrolidin-2-one To a solution of piperidin-4-ylbis(3-(trifluoromethyl)phenyl)methanol (0.40 mg, 1.00 mmol, Example 33A) in dichloromethane (20 mL) was added 2-(2-oxo-3,3-diphenylpyrrolidin-1-yl)acetic acid (Example 1C, 0.30 g, 1.00 mmol) under nitrogen. To the reaction was added N$^1$-((ethylimino)methylene)-N$^3$,N$^3$-dimethylpropane-1,3-diamine hydrochloride (0.38 g, 2.00 mmol) and N,N-dimethylpyridin-4-amine (6.1 mg, 0.005 mmol), and the reaction mixture was stirred overnight at room temperature. The reaction was concentrated, and the residue was partitioned in ethyl acetate:water (8:2). The organic layer was separated, washed with water and then brine, dried over MgSO4, filtered and concentrated. Silica gel chromatography eluting with ethyl acetate/hexanes (1:1) gave the title compound. $^1$H NMR (300 MHz, DMSO-$d_6$) δ ppm 7.85-7.93 (m, 4H), 7.55-7.57 (m, 4H), 7.18-7.36 (m, 10H), 5.93 (s, 1H), 4.34-4.41 (m, 1H), 4.06-4.23 (m, 2H), 3.82 (d, J=13.5 Hz, 1H), 3.35 (t, J=6.9 Hz, 2H), 2.94-3.11 (m, 2H), 2.72 (t, J=6.4 Hz, 2H), 2.59-2.67 (m, 1H), 1.17-1.50 (m, 4H).

Example 34

1-(2-{4-[hydroxy(diphenyl)methyl]piperidin-1-yl}-2-oxoethyl)-3,3-diphenylpyrrolidin-2-one To a solution of diphenyl(piperidin-4-yl)methanol (0.27 g, 1.00 mmol) in dichloromethane (20 mL) was added 2-(2-oxo-3,3-diphenylpyrrolidin-1-yl)acetic acid (Example 1C, 0.30 g, 1.00 mmol) under nitrogen. To the reaction was added N$^1$-((ethylimino)methylene)-N$^3$,N$^3$-dimethylpropane-1,3-diamine hydrochloride (0.38 g, 2.00 mmol) and N,N-dimethylpyridin-4-amine (6.1 mg, 0.005 mmol), and the reaction mixture was stirred overnight at room temperature. The reaction was concentrated and the residue was partitioned in ethyl acetate:water (8:2). The organic layer was separated, washed with water and then brine, dried over MgSO4, filtered and concentrated. Silica gel chromatography eluting with ethyl acetate/hexanes (1:1) gave the title compound. $^1$H NMR (300 MHz, DMSO-$d_6$) δ ppm 7.50-7.57 (m, 4H), 7.18-7.36 (m, 14H), 7.11-7.16 (m, 2H), 5.35 (s, 1H), 4.33-4.40 (m, 1H), 4.17 (d, J=16.6 Hz, 1H), 4.10 (d, J=15.7 Hz, 1H), 3.77-3.85

(m, 1H), 3.34 (t, J=6.7 Hz, 2H), 2.93-3.02 (m, 1H), 2.75-2.85 (m, 1H), 2.72 (t, J=6.4 Hz, 2H), 2.53-2.64 (m, 1H), 1.19-1.40 (m, 4H).

Example 35

1-{2-[4-(5-methoxy-1H-indol-3-yl)-3,6-dihydropyridin-1(2H)-yl]-2-oxoethyl}-3,3-diphenylpyrrolidin-2-one The title compound was prepared as described in Example 28B substituting 5-methoxy-3-(1,2,3,6-tetrahydro-pyridin-4-yl)-1H-indole (CAS 66611-26-5) for 1-benzhydrylpiperazin-2-one hydrochloride. $^1$H NMR (300 MHz, CDCl$_3$) δ ppm 8.11 (m, 1H), 7.30 (m, 12H), 7.12 (dd, J=26.45, 2.71 Hz, 1H), 6.89 (dt, J=8.90, 1.82 Hz, 1H), 6.07 (d, J=27.13 Hz, 1H), 4.28 (m, J=7.80 Hz, 3H), 4.16 (m 1H), 3.87 (s, 3H), 3.84 (m, 1H), 3.67 (t, J=5.76 Hz, 1H), 3.55 (td, J=6.44, 2.71 Hz, 2H), 2.84 (m, 2H), 2.54 (d, J=27.80 Hz, 2H); MS (ESI+) m/z 506 (M+H)$^+$.

Example 36

1-{2-[4-(2,6-dichlorobenzyl)piperazin-1-yl]-2-oxoethyl}-3,3-diphenylpyrrolidin-2-one To 1-(2,6-dichlorobenzyl)piperazine (0.045 g, 0.183 mmol), 2-(1H-benzo[d][1,2,3]triazol-1-yl)-1,1,3,3-tetramethylisouronium hexafluorophosphate(V) (0.069 g, 0.183 mmol) and 2-(2-oxo-3,3-diphenylpyrrolidin-1-yl)acetic acid (Example 1C, 0.054 g, 0.183 mmol) in dichloromethane (0.5 mL) was added diisopropylethylamine (0.048 mL, 0.274 mmol), and the reaction mixture was stirred at room temperature. After stirring overnight, thin layer chromatography (hexanes/ethyl acetate 1:1) indicated formation of the product. The reaction was loaded directly onto a SF15-12 silica gel column (Analogix®, Burlington, Wis.), and the title compound was eluted using a gradient of 5% to 75% ethyl acetate/hexanes over 20 minutes (flow=30 mL/minute). $^1$H NMR (300 MHz, CDCl$_3$) δ ppm 7.10-7.38 (m, 13H), 4.19 (s, 2H), 3.71 (s, 2H), 3.48-3.59 (m, 4H), 3.33-3.40 (m, 2H), 2.81 (t, J=6.5 Hz, 2H), 2.50-2.58 (m, 2H), 2.41-2.49 (m, 2H); MS (DCI+) m/z 522.1 (M+H)$^+$.

Example 37

1-(2-oxo-2-{4-[3-(trifluoromethyl)benzyl]piperazin-1-yl}ethyl)-3,3-diphenylpyrrolidin-2-one To 1-(3-(trifluoromethyl)benzyl)piperazine (0.090 g, 0.368 mmol), 2-(1H-benzo[d][1,2,3]triazol-1-yl)-1,1,3,3-tetramethylisouronium hexafluorophosphate(V) (0.140 g, 0.368 mmol) and 2-(2-oxo-3,3-diphenylpyrrolidin-1-yl)acetic acid (Example 1C, 0.099 g, 0.335 mmol) in dichloromethane (1.0 mL) was added diisopropylethylamine (0.088 mL, 0.502 mmol), and the reaction mixture was stirred at room temperature overnight. The reaction was concentrated and loaded onto silica gel. The product was eluted using a gradient of 5% to 100% ethyl acetate/hexanes giving incomplete purification. A second chromatography over silica gel using a gradient of 0.5% to 5% methanol/dichloromethane gave the title compound. $^1$H NMR (300 MHz, CDCl$_3$) δ ppm 7.41-7.58 (m, 4H), 7.20-7.37 (m, 10H), 4.19 (s, 2H), 3.60 (t, J=4.8 Hz, 2H), 3.52 (t, J=6.5 Hz, 2H), 3.51 (s, 2H), 3.41 (t, J=4.8 Hz, 2H), 2.81 (t, J=6.5 Hz, 2H), 2.40 (t, J=4.9 Hz, 2H), 2.28 (t, J=4.8 Hz, 2H); MS (ESI−) m/z 520 (M−H)$^-$.

Example 38

1-{2-[4-(4-fluorobenzyl)piperazin-1-yl]-2-oxoethyl}-3,3-diphenylpyrrolidin-2-one To 1-(4-fluorobenzyl)piperazine (0.081 g, 0.416 mmol), 2-(1H-benzo[d][1,2,3]triazol-1-yl)-1,1,3,3-tetramethylisouronium hexafluorophosphate(V) (0.165 g, 0.436 mmol) and 2-(2-oxo-3,3-diphenylpyrrolidin-1-yl)acetic acid (Example 1C, 0.135 g, 0.457 mmol) in dichloromethane (1 mL) was added diisopropylethylamine (0.109 mL, 0.623 mmol), and the reaction mixture was stirred at room temperature overnight. The reaction was concentrated and loaded onto a silica gel column (Analogix® SF25-25) and eluted with a gradient of 5% to 100% ethyl acetate/hexanes to provide the title compound. $^1$H NMR (300 MHz, CDCl$_3$) δ ppm 7.20-7.37 (m, 12H), 6.97-7.04 (m, 2H), 4.18 (s, 2H), 3.59 (t, J=4.7 Hz, 2H), 3.51 (t, J=6.5 Hz, 2H), 3.44 (s, 2H), 3.39-3.44 (m, 2H), 2.81 (t, J=6.5 Hz, 2H), 2.38 (t, J=4.9 Hz, 2H), 2.28-2.32 (m, 2H); MS (ESI+) m/z 472 (M+H)$^+$.

Example 39

N-[(1-benzylpyrrolidin-3-yl)methyl]-2-(2-oxo-3,3-diphenylpyrrolidin-1-yl)acetamide The title compound was obtained by the procedure described for Example 28B substituting 1-benzylpyrrolidin-3-yl)methanamine for 1-benzhydrylpiperazin-2-one hydrochloride. $^1$H NMR (300 MHz, CDCl$_3$) δ ppm 7.26 (m, 15H), 6.37 (br s, 1H), 4.01 (m, 2H), 3.51 (m, 4H), 3.17 (m, 2H), 2.79 (t, J=6.54 Hz, 2H), 2.59 (m, 1H), 2.43 (m, 2H), 2.23 (m, 2H), 1.86 (m, 1H), 1.38 (m, 1H); MS (ESI+) m/z 468 (M+H)$^+$.

Example 40

N-(1-benzyl-3-methylpyrrolidin-3-yl)-2-(2-oxo-3,3-diphenylpyrrolidin-1-yl)acetamide The title compound was obtained using the procedure described in Example 28B, replacing 1-benzhydrylpiperazin-2-one hydrochloride with 1-benzyl-3-methylpyrrolidin-3-amine dihydrochloride. (CAS 181114-76-1). $^1$H NMR (300 MHz, DMSO-d$_6$) δ ppm 7.91 (s, 1H), 7.30 (m, J=5.55 Hz, 6H), 7.30 (m, J=5.55 Hz, 12H), 7.23 (m, 3H), 3.88 (s, 2H), 3.54 (s, 2H), 3.35 (m, 2H), 2.72 (m, 4H), 1.35 (s, 3H); MS (ESI+) m/z 468 (M+H)$^+$.

Example 41

2-(2-oxo-3,3-diphenylpyrrolidin-1-yl)-N-{1-[3-(trifluoromethyl)benzyl]piperidin-4-yl}acetamide

Example 41A tert-butyl 1-(3-(trifluoromethyl)benzyl)piperidin-4-ylcarbamate

To a solution of tert-butyl piperidin-4-ylcarbamate (0.15 g, 0.75 mmol) and 3-(trifluoromethyl)benzaldehyde (0.12 mL, 0.156 mmol) in dichloroethane (5 mL) was added sodium triacetoxyborohydride (0.24 g, 1.12 mmol) and a few drops of acetic acid, and the reaction mixture was stirred at ambient temperature overnight. The reaction mixture was diluted with dichloroethane and washed with saturated aqueous NaHCO$_3$ solution. The organic layer was separated, dried over MgSO$_4$, and chromatographed on silica gel, eluting with 30% ethyl acetate/hexane to yield the title compound. $^1$H NMR (300 MHz, CDCl$_3$) δ ppm 7.58 (s, 1H), 7.45 (m, 3H), 4.41 (m, 1H), 3.50 (m, 2H), 3.50 (m, 1H), 2.77 (d, J=12.21 Hz, 2H), 2.11 (t, J=11.70 Hz, 2H), 1.91 (d, J=11.53 Hz, 2H), 1.41 (s, 9H), 1.34 (m, 2H); MS (DCI) m/z 359 (M+H)$^+$.

Example 41B 1-(3-(trifluoromethyl)benzyl)piperidin-4-amine

The product from the Example 41A (0.14 g) was dissolved in methanol (5 mL) and treated with a 4 N solution of HCl in dioxane (1 mL) at room temperature for 2 hours. The reaction mixture was concentrated to yield the dihydrochloride salt of the title compound. MS (DCI) m/z 259 (M+H)$^+$.

Example 41C 2-(2-oxo-3,3-diphenylpyrrolidin-1-yl)-N-{1-[3-(trifluoromethyl)benzyl]piperidin-4-yl}acetamide The title compound was obtained as described for Example 28B replacing 1-benzhydrylpiperazin-2-one hydrochloride with the product from Example 41B. $^1$H NMR (300 MHz, CDCl$_3$) δ ppm 7.59-7.61 (br s, 1H), 7.40-7.53 (m, 3H), 7.29-7.35 (m, 10H), 5.78 (d, J=7.9 Hz, 1H), 3.99 (s, 2H), 3.61-3.75 (m, 1H), 3.49 (t, J=6.3 Hz, 2H), 3.48 (s, 2H), 2.81 (t, J=6.5 Hz, 2H), 2.61-2.66 (m, 2H), 2.07 (td, J=11.2, 2.6 Hz, 2H), 1.66-1.73 (m, 2H), 1.10-1.28 (m, 2H); MS (ESI+) m/z 536 (M+H)$^+$.

Example 42

1-[2-oxo-2-(4-{[3-(trifluoromethyl)benzyl] amino}piperidin-1-yl)ethyl]-3,3-diphenylpyrrolidin-2-one Example 42A tert-butyl 1-(2-(2-oxo-3,3-diphenylpyrrolidin-1-yl) acetyl)piperidin-4-ylcarbamate The title compound was obtained as described in the Example 28B substituting tert-butyl piperidin-4-ylcarbamate (CAS73874-95-0) for 1-benzhydrylpiperazin-2-one hydrochloride. $^1$H NMR (300 MHz, CDCl$_3$) δ ppm 7.33 (m, 10H), 4.39 (m, 2H), 4.33 (d, J=15.60 Hz, 1H), 4.04 (d, 1H), 3.77 (d, J=12.89 Hz, 1H), 3.53 (m, 3H), 3.02 (t, 1H), 2.77 (m, 4H), 1.89 (m, 2H), 1.45 (m, 9H), 1.17 (m, 2H).

Example 42B 1-(2-(4-aminopiperidin-1-yl)-2-oxoethyl)-3,3-diphenylpyrrolidin-2-one The product from example 42A (0.32 g, 0.67 mmol) was dissolved in dichloromethane (5 mL) and treated with trifluoroacetic acid (2 mL) at ambient temperature for 1 hour. The reaction mixture was concentrated in vacuo to yield the trifluoroacetate salt of the title compound. $^1$H NMR (300 MHz, DMSO-d$_6$) δ ppm 7.84 (br s, 2H), 7.26 (m, 10H), 3.88 (m, 4H), 3.31 (m, 2H), 3.07 (m, 1H), 2.72 (m, 4H), 1.86 (m, 2H), 1.41 (m, 2H); MS (ESI+) m/z 379 (M+H)$^+$.

Example 42C

1-[2-oxo-2-(4-{[3-(trifluoromethyl)benzyl] amino}piperidin-1-yl)ethyl]-3,3-diphenylpyrrolidin-2-one To a solution of product from the Example 42B (0.24 g, 0.48 mmol) in methylene chloride (25 mL) was added 3-(trifluoromethyl)benzaldehyde (0.128 g, 0.73 mmol) and sodium triacetoxyborohydride (0.23 g, 1.1 mmol), and the reaction mixture was stirred at room temperature for 16 hours. The reaction mixture was diluted with methylene chloride and washed with the dilute aqueous NaHCO$_3$ solution. The organic layer was separated, dried over MgSO$_4$ and concentrated. The obtained residue was chromatographed, eluting with 5-10% methanol/dichloromethane. $^1$H NMR (300 MHz, CDCl$_3$) δ ppm 7.44-7.65 (m, 5H), 7.18-7.40 (m, 10H), 4.30-4.39 (m, 1H), 4.23 (d, J=15.5 Hz, 1H), 4.17 (d, J=15.5 Hz, 1H), 3.85 (s, 2H), 3.74-3.81 (m, 1H), 3.52 (t, J=6.5 Hz, 2H), 2.97-3.06 (m, 1H), 2.78-2.88 (m, 3H), 2.67-2.77 (m, 1H), 1.82-1.93 (m, 2H), 1.12-1.37 (m, 2H); MS (ESI+) m/z 536 (M+H)$^+$.

Example 43

1-{2-[4-(2,4-dichlorobenzyl)piperazin-1-yl]-2-oxoethyl}-3,3-diphenylpyrrolidin-2-one A mixture of N$^1$-((ethylimino)methylene)-N$^3$,N$^3$-dimethylpropane-1,3-diamine hydrochloride (0.049 g, 0.254 mmol), 2-(2-oxo-3,3-diphenylpyrrolidin-1-yl)acetic acid (Example 1C, 0.050 g, 0.169 mmol) and 1-(2,4-dichlorobenzyl)piperazine (0.046 g, 0.186 mmol) in dichloromethane (0.5 mL) was stirred at room temperature. After stirring overnight, the reaction was loaded directly onto a SF15-12 silica gel column (Analogix®, Burlington, Wis.), and the title compound was eluted using a gradient of 5% to 100% ethyl acetate/hexanes over 20 minutes (flow=30 mL/minute). $^1$H NMR (300 MHz, CDCl$_3$) δ ppm 7.20-7.39 (m, 13H), 4.19 (s, 2H), 3.59 (t, J=4.8 Hz, 2H), 3.53 (s, 2H), 3.52 (t, J=6.4 Hz, 2H), 3.42 (t, J=4.9 Hz, 2H), 2.81 (t, J=6.5 Hz, 2H), 2.43 (t, J=4.9 Hz, 2H), 2.32 (t, J=4.9 Hz, 2H); MS (ESI+) m/z 522 (M+H)$^+$.

Example 44

1-[2-oxo-2-(4-{1-[3-(trifluoromethyl)phenyl] ethyl}piperazin-1-yl)ethyl]-3,3-diphenylpyrrolidin-2-one Example 44A tert-butyl 4-(1-(3-(trifluoromethyl)phenyl)ethyl)piperazine-1-carboxylate A suspension of 1-(3-(trifluoromethyl)phenyl)ethanone (0.100 g, 0.532 mmol), tert-butyl piperazine-1-carboxylate (0.148 g, 0.797 mmol), acetic acid (0.046 mL, 0.797 mmol) and sodium cyanoborohydride (0.050 g, 0.797 mmol) in ethanol (0.5 mL) was heated under nitrogen at 75° C. After stirring overnight the reaction was concentrated, saturated sodium bicarbonate (0.7 mL) was added, and the product was extracted into ethyl acetate (2×0.7 mL). The combined organic layers were concentrated, dissolved in a minimal amount of dichloromethane, loaded directly onto a SF15-12 silica gel column (Analogix®, Burlington, Wis.), and the title compound was eluted using a gradient of 2% to 20% ethyl acetate/hexanes over 20 minutes (flow=30 mL/minute).

Example 44B 1-(1-(3-(trifluoromethyl)phenyl)ethyl)piperazine dihydrochloride

The product from Example 44A (0.071 g, 0.198 mmol) was added to HCl (2.0 M in dioxane) (0.991 mL, 1.981 mmol), and methanol was added dropwise until the reaction became nearly homogeneous. As the reaction was stirred, a precipitate formed. The reaction was concentrated to give the title compound (0.066 g, 0.256 mmol) as the dihydrochloride salt. MS (APCI) m/z 259 (M+H)+.

Example 44C

1-[2-oxo-2-(4-{1-[3-(trifluoromethyl)phenyl] ethyl}piperazin-1-yl)ethyl]-3,3-diphenylpyrrolidin-2-one A solution of $N^1$-((ethylimino)methylene)-$N^3,N^3$-dimethylpropane-1,3-diamine (0.074 mL, 0.416 mmol), 2-(2-oxo-3,3-diphenylpyrrolidin-1-yl)acetic acid (Example 1C, 0.058 g, 0.198 mmol) and the product from Example 44B (0.066 g, 0.198 mmol) in dichloromethane (0.5 mL) was stirred at room temperature. After stirring overnight, the reaction was loaded directly onto a SF15-12 silica gel column (Analogix®, Burlington, Wis.), and the title compound was eluted using a gradient of 5% to 100% ethyl acetate/hexanes over 20 minutes (flow=30 mL/minute). $^1$H NMR (300 MHz, CDCl$_3$) δ ppm 7.40-7.56 (m, 4H), 7.20-7.37 (m, 10H), 4.10-4.22 (m, 2H), 3.52-3.63 (m, 2H), 3.50 (t, J=6.6 Hz, 2H), 3.34-3.43 (m, 3H), 2.80 (t, J=6.5 Hz, 2H), 2.43-2.51 (m, 1H), 2.16-2.36 (m, 3H), 1.33 (d, J=6.7 Hz, 3H); MS (ESI+) m/z 536 (M+H)+.

Example 45

1-(2-{4-[bis(4-fluorophenyl)methyl]piperazin-1-yl}-2-oxoethyl)-3,3-diphenylpyrrolidin-2-one To a solution of 1-(bis(4-fluorophenyl)methyl)piperazine (0.29 g, 1.00 mmol) in dichloromethane (20 mL) under nitrogen was added 2-(2-oxo-3,3-diphenylpyrrolidin-1-yl)acetic acid (Example 1C, 0.30 g, 1.00 mmol) followed by $N^1$-((ethylimino)methylene)-$N^3,N^3$-dimethylpropane-1,3-diamine hydrochloride (0.38 g, 2.00 mmol) and N,N-dimethylpyridin-4-amine (0.61 mg, 0.005 mmol). The reaction mixture was stirred overnight at room temperature. The reaction was concentrated, and the residue was partitioned in ethyl acetate/water (8:2, 400 mL). The organic layer was washed with water followed by brine, dried over magnesium sulfate, filtered, and concentrated. Silica gel chromatography eluting with ethyl acetate/hexane (1:1) gave the title compound. $^1$H NMR (300 MHz, DMSO-d$_6$) δ ppm 7.42-7.47 (m, 4H), 7.21-7.33 (m, 10H), 7.11-7.17 (m, 4H), 4.41 (s, 1H), 4.14-4.15 (br s, 2H), 3.37-3.47 (m, 4H), 3.35 (t, J=6.6 Hz, 2H), 2.71 (t, J=6.5 Hz, 2H), 2.21-2.26 (m, 4H); MS (DCI+) m/z 566 (M+H)+.

Example 46

1-(2-{4-[(4-fluorophenyl)(phenyl)methyl]piperazin-1-yl}-2-oxoethyl)-3,3-diphenylpyrrolidin-2-one To a solution of 1-((4-fluorophenyl)(phenyl)methyl)piperazine (0.27 g, 1.00 mmol) in dichloromethane (20 mL) under nitrogen was added 2-(2-oxo-3,3-diphenylpyrrolidin-1-yl)acetic acid (Example 1C, 0.30 g, 1.00 mmol) followed by $N^1$-((ethylimino)methylene)-$N^3,N^3$-dimethylpropane-1,3-diamine hydrochloride (0.38 g, 2.00 mmol) and N,N-dimethylpyridin-4-amine (0.61 mg, 0.005 mmol). The reaction mixture was stirred overnight at room temperature. The reaction was concentrated and the residue was partitioned in ethyl acetate/water (8:2, 400 mL). The organic layer was washed with water followed by brine, dried over magnesium sulfate, filtered, and concentrated. Silica gel chromatography eluting with ethyl acetate/hexane (1:1) gave the title compound. $^1$H NMR (300 MHz, DMSO-d$_6$) δ ppm 7.40-7.49 (m, 4H), 7.25-7.35 (m, 10H), 7.17-7.24 (m, 3H), 7.08-7.17 (m, 2H), 4.36 (s, 1H), 4.14-4.15 (br s, 2H), 3.40-3.48 (m, 4H), 3.35 (t, J=6.6 Hz, 2H), 2.71 (t, J=6.5 Hz, 2H), 2.22-2.28 (m, 4H).

Example 47

1-(2-{4-[(4-chlorophenyl)(phenyl)methyl]piperazin-1-yl}-2-oxoethyl)-3,3-diphenylpyrrolidin-2-one To a solution of 1-((4-chlorophenyl)(phenyl)methyl)piperazine (0.29 g, 1.00 mmol) in dichloromethane (20 mL) under nitrogen was added 2-(2-oxo-3,3-diphenylpyrrolidin-1-yl)acetic acid (Example 1C, 0.30 g, 1.00 mmol) followed by $N^1$-((ethylimino)methylene)-$N^3,N^3$-dimethylpropane-1,3-diamine hydrochloride (0.38 g, 2.00 mmol) and N,N-dimethylpyridin-4-amine (0.61 mg, 0.005 mmol). The reaction mixture was stirred overnight at room temperature. The reaction was concentrated, and the residue was partitioned in ethyl acetate/water (8:2, 400 mL). The organic layer was washed with water followed by brine, dried over magnesium sulfate, filtered, and concentrated. Silica gel chromatography eluting with ethyl acetate/hexane (1:1) gave the title compound. $^1$H NMR (300 MHz, DMSO-d$_6$) δ ppm 7.21-7.47 (m, 19H), 4.37 (s, 1H), 4.14-4.15 (br s, 2H), 3.40-3.48 (m, 4H), 3.35 (t, J=6.7 Hz, 2H), 2.71 (t, J=6.5 Hz, 2H), 2.22-2.28 (m, 4H); MS (DCI+) m/z 564 (M+H)+.

Example 48

N-(1-benzhydrylpiperidin-4-yl)-2-(2-oxo-3,3-diphenylpyrrolidin-1-yl)acetamide

Example 48A 1-benzhydrylpiperidin-4-amine

To a solution of tert-butyl piperidin-4-ylcarbamate (0.3 g, 1.5 mmol) in N,N-dimethylformamide (3 mL) was added bromodiphenylmethane (0.45 g, 1.87 mmol), potassium carbonate (0.6 g, 4.5 mmol), and a catalytic amount of potassium iodide. The reaction mixture was stirred at ambient temperature overnight. Then it was concentrated and partitioned between water/methylene chloride. The organic layer was dried over MgSO$_4$, evaporated in vacuo and chromatographed on silica gel eluting with 30% ethyl acetate/hexane to yield t-butoxycarbonyl-protected 1-benzhydrylpiperidin-4-amine. The protected compound was dissolved in methanol and treated with 4 N HCl/dioxane solution for 2 hours at room temperature. The reaction mixture was concentrated, triturated with ether and filtered off to yield the dihydrochloride salt of the title compound. $^1$H NMR (300 MHz, DMSO-d$_6$) δ ppm 8.23 (s, 2H), 7.92 (m, J=7.14 Hz, 4H), 7.42 (m, 6H), 5.44 (d, J=9.12 Hz, 1H), 3.25 (m, J=6.74 Hz, 2H), 3.08 (m, 2H), 2.69 (d, J=4.76 Hz, 1H), 2.33 (m, 2H), 2.06 (m, 2H); MS (ESI+) m/z 266 (M+H)+.

Example 48B

N-(1-benzhydrylpiperidin-4-yl)-2-(2-oxo-3,3-diphenylpyrrolidin-1-yl)acetamide

The title compound was obtained by the procedure described in Example 28B, replacing 1-benzhydrylpiperazin-2-one hydrochloride with the product from Example 48A. $^1$H NMR (300 MHz, CDCl$_3$) δ ppm 7.34 (m, 12H), 7.27 (m, 6H), 7.17 (t, J=7.93 Hz, 2H), 5.79 (d, J=7.93 Hz, 1H), 4.21 (s, 1H), 3.98 (s, 2H), 3.65 (m, 1H), 3.48 (t, J=6.35 Hz, 2H), 2.80 (m, 2H), 2.64 (d, J=11.90 Hz, 2H), 1.94 (t, J=11.50 Hz, 2H), 1.66 (d, J=14.28 Hz, 2H), 1.18 (d, J=9.12 Hz, 2H); MS (ESI+) m/z 544 (M+H)$^+$.

Example 49

1-{2-[(2R)-4-benzhydryl-2-methylpiperazin-1-yl]-2-oxoethyl}-3,3-diphenylpyrrolidin-2-one

Example 49A (R)-1-benzhydryl-3-methylpiperazine

A solution of the dihydrochloride of R-methylpiperazine (Tetrahedron Lett. 1994, 35, 16, 2533-2536)(0.42 g, 2.42 mmol) in N,N-dimethylformamide (3 mL) was treated with bromodiphenylmethane (0.6 g, 2.42 mmol), potassium carbonate (1.17 g, 8.5 mmol), and a catalytic amount of potassium iodide. The resultant reaction mixture was then stirred at ambient temperature overnight. Then the reaction mixture was concentrated and partitioned between water/methylene chloride. The organic layer was dried over magnesium sulfate, concentrated and the residue was purified by preparative HPLC on a Waters Nova-Pak® HR C18 6 um 60 Å Prep-Pak® cartridge column (40 mm×100 mm) using a gradient of 10% to 100% acetonitrile in 10 mM aqueous ammonium acetate over 12 minutes at a flow rate of 70 mL/min to provide the title compound.

Example 49B

1-{2-[(2R)-4-benzhydryl-2-methylpiperazin-1-yl]-2-oxoethyl}-3,3-diphenylpyrrolidin-2-one The title compound was obtained by the procedure described for Example 28B substituting Example 49A for 1-benzhydrylpiperazin-2-one hydrochloride. $^1$H NMR (300 MHz, DMSO-d$_6$) δ ppm 7.45 (m, 4H), 7.25 (m, 16H), 4.25 (m, 2H), 4.06 (m, 2H), 3.38 (m, 2H), 2.73 (m, 3H), 2.61 (m, 1H), 1.95 (m, 1H), 1.82 (m, 1H), 1.23 (m, 4H); MS (ESI+) m/z 544 (M+H)$^+$.

Example 50

1-{2-[(4aS,7aS)-6-benzhydryloctahydro-1H-pyrrolo[3,4-b]pyridin-1-yl]-2-oxoethyl}-3,3-diphenylpyrrolidin-2-one

Example 50A (4aS,7aS)-tert-butyl 6-benzyloctahydro-1H-pyrrolo[3,4-b]pyridine-1-carboxylate To a solution of (4aS,7aS)-6-benzyloctahydro-1H-pyrrolo[3,4-b]pyridine dihydrochloride (CAS 151213-39-7) in methylene chloride was added di-tert-butyl dicarbonate and triethylamine. The reaction mixture was stirred at room temperature overnight, and then it was washed with saturated sodium bicarbonate solution. The organic layer was separated and dried over MgSO$_4$, concentrated, and then chromatographed on silica gel eluting with 30% ethyl acetate/hexane to give the title compound.

Example 50B (4aS,7aS)-tert-butyl octahydro-1H-pyrrolo[3,4-b]pyridine-1-carboxylate The product from Example 50A (0.15 g, 0.5 mmol) in methanol (80 mL) was hydrogenated (4 pounds per square inch) in the presence of palladium hydroxide on carbon (0.42 g) for 3 hours at room temperature. The reaction mixture was filtered and concentrated to yield the title compound. MS (DCI) m/z 227 (M+H)$^+$.

Example 50C (4aS,7aS)-tert-butyl 6-benzhydryloctahydro-1H-pyrrolo[3,4-b]pyridine-1-carboxylate The title compound was obtained using the procedure described for Example 49A substituting Example 50B for the dihydrochloride of R-methylpiperazine. $^1$H NMR (300 MHz, CDCl$_3$) δ ppm 7.53 (m, 10H), 4.65 (m, 1H), 2.79 (m, 3H), 2.41 (m, 1H), 2.13 (m, 1 H), 1.72 (m, 2H), 1.61 (m, 1H), 1.47 (m, 1H), 1.40 (m, 9H), 1.27 (m, 1H), 0.88 (m, 1H); MS (ESI+) m/z 392 (M+H)$^+$.

Example 50D (4aS,7aS)-6-benzhydryloctahydro-1H-pyrrolo[3,4-b]pyridine

The product from Example 50C (0.15 g, 0.38 mmol) was dissolved in methylene chloride (5 mL) and treated with trifluoroacetic acid (1 mL) at ambient temperature for 1 hour. The reaction mixture was concentrated to yield the title compound as the trifluoroacetic acid salt. MS (ESI+) m/z 292 (M+H)$^+$.

Example 50E

1-{2-[(4aS,7aS)-6-benzhydryloctahydro-1H-pyrrolo[3,4-b]pyridin-1-yl]-2-oxoethyl}-3,3-diphenylpyrrolidin-2-one The title compound was obtained as described in Example 28B, substituting Example 50D for 1-benzhydrylpiperazin-2-one hydrochloride. $^1$H NMR (500 MHz, pyridine-d$_5$, 120° C.) δ ppm 7.56-7.62 (m, 4H), 7.48-7.52 (m, 4H), 7.22-7.28 (m, 8H), 7.13-7.19 (m, 4H), 4.78-4.96 (br s, 1H), 4.45 (s, 1H), 4.21-4.39 (br s, 1H), 4.18-4.28 (br s, 1H), 3.48-3.56 (m, 1H), 3.46 (t, J=6.5 Hz, 2H), 2.84-2.92 (br s, 1H), 2.78-2.84 (m, 1H), 2.76 (td, J=6.5, 3.3 Hz, 2H), 2.58 (dd, J=9.7, 5.9 Hz, 1H), 2.43 (dd, J=9.6, 2.0 Hz, 1H), 1.97-2.05 (m, 1H), 1.54-1.64 (m, 3H), 1.26-1.34 (m, 1H), 1.23 (d, J=6.6 Hz, 1H); MS (ESI+) m/z 570 (M+H)$^+$.

Example 51

1-{2-[(4aR,7aR)-6-benzhydryloctahydro-1H-pyrrolo[3,4-b]pyridin-1-yl]-2-oxoethyl}-3,3-diphenylpyrrolidin-2-one The title compound was obtained as described from the procedure in Example 50, substituting (4aS,7aS)-6-benzyloctahydro-1H-pyrrolo[3,4-b]pyridine dihydrochloride with (R,R)-6-benzyl-octahydro-pyrrolo[3,4-b]pyridine dihydrochloride (Astatech). $^1$H NMR (300 MHz, CDCl$_3$) δ ppm 7.38 (m, 19H), 7.14 (m, 2H), 4.35 (m, 2H), 3.90 (m, 1H), 3.51 (m, 2H), 2.76 (m, 3H), 2.53 (m, 2H), 1.73 (m, 2H), 1.38 (m, 2H), 1.26 (m, 1H), 1.15 (m, 2H), 0.88 (m, 1H); MS (ESI+) m/z 570 (M+H)$^+$.

Example 52

1-(2-{4-[(2,2-diphenylethyl)amino]piperidin-1-yl}-2-oxoethyl)-3,3-diphenylpyrrolidin-2-one The title compound was obtained as described for Example 42C substituting 3-(trifluoromethyl)benzaldehyde with 2,2-diphenylacetaldehyde. $^1$H NMR (300 MHz, CDCl$_3$) δ ppm 7.33 (m, 10H), 4.30 (m, 1H), 4.17 (d, J=5.55 Hz, 2H), 4.03 (m, 1H), 3.71 (d, J=13.09 Hz, 1H), 3.49 (m, 2H), 3.22 (d, J=3.17 Hz, 1H), 2.98 (m, 1H), 2.76 (m, 4H), 1.79 (m, 2H), 1.22 (m, 2H); MS (ESI+) m/z 558 (M+H)$^+$.

Example 53

1-{2-[4-(5-chloropyridin-2-yl)piperazin-1-yl]-2-oxoethyl}-3,3-diphenylpyrrolidin-2-one A solution of 1-(5-chloropyridin-2-yl)piperazine (0.037 g, 0.186 mmol), 2-(2-oxo-3,3-diphenylpyrrolidin-1-yl)acetic acid (Example 1C, 0.050 g, 0.169 mmol) and N$^1$-((ethylimino)methylene)-N$^3$,N$^3$-dimethylpropane-1,3-diamine hydrochloride (0.049 g, 0.254 mmol) in dichloromethane (2 mL) was stirred at room temperature. After stirring overnight, the reaction was loaded directly onto a SF15-12 silica gel column (Analogix®, Burlington, Wis.), and the title compound was eluted using a gradient of 5% to 100% ethyl acetate/hexanes over 25 minutes (flow=30 mL/minute). $^1$H NMR (300 MHz, CDCl$_3$) δ ppm 8.12 (dd, J=2.6, 0.7 Hz, 1H), 7.45 (dd, J=9.0, 2.7 Hz, 1H), 7.18-7.38 (m, 10H), 6.54 (dd, J=9.1, 0.7 Hz, 1H), 4.24 (s, 2H), 3.67-3.72 (m, 2H), 3.54 (t, J=6.6 Hz, 2H), 3.51-3.56 (m, 2H), 3.44-3.50 (m, 2H), 3.36-3.42 (m, 2H), 2.82 (t, J=6.6 Hz, 2H); MS (ESI+) m/z 475 (M+H)$^+$.

Example 54

1-{2-[4-(4-fluorophenyl)piperazin-1-yl]-2-oxoethyl}-3,3-diphenylpyrrolidin-2-one A solution of 1-(4-fluorophenyl)piperazine (0.034 g, 0.186 mmol), 2-(2-oxo-3,3-diphenylpyrrolidin-1-yl)acetic acid (Example 1C, 0.050 g, 0.169 mmol) and N$^1$-((ethylimino)methylene)-N$^3$,N$^3$-dimethylpropane-1,3-diamine hydrochloride (0.049 g, 0.254 mmol) in dichloromethane (2 mL) was stirred at room temperature. After stirring overnight, the reaction mixture was loaded directly onto a SF15-12 silica gel column (Analogix®, Burlington, Wis.), and the title compound was eluted using a gradient of 5% to 75% ethyl acetate/hexanes over 25 minutes (flow=30 mL/minute). $^1$H NMR (300 MHz, CDCl$_3$) δ ppm 7.27-7.38 (m, 8H), 7.18-7.25 (m, 2H), 6.94-7.01 (m, 2H), 6.80-6.85 (m, 2H), 4.24 (s, 2H), 3.73 (t, J=4.9 Hz, 2H), 3.54-3.60 (m, 2H), 3.54 (t, J=6.5 Hz, 2H), 3.02 (t, J=5.0 Hz, 2H), 2.89 (t, J=5.2 Hz, 2H), 2.82 (t, J=6.5 Hz, 2H).

Example 55

1-{2-oxo-2-[7-(trifluoromethyl)-3,4-dihydroisoquinolin-2(1H)-yl]ethyl}-3,3-diphenylpyrrolidin-2-one A solution of 7-(trifluoromethyl)-1,2,3,4-tetrahydroisoquinoline (0.037 g, 0.186 mmol), 2-(2-oxo-3,3-diphenylpyrrolidin-1-yl)acetic acid (Example 1C, 0.050 g, 0.169 mmol) and N$^1$-((ethylimino)methylene)-N$^3$,N$^3$-dimethylpropane-1,3-diamine hydrochloride (0.049 g, 0.254 mmol) in dichloromethane (0.5 mL) was stirred at room temperature. After stirring for approximately 60 hours, the reaction was loaded directly onto a SF15-12 silica gel column (Analogix®, Burlington, Wis.), and the title compound was eluted using a gradient of 5% to 100% ethyl acetate/hexanes over 20 minutes (flow=30 mL/minute). $^1$H NMR (300 MHz, CDCl$_3$) δ ppm 7.15-7.40 (m, 13H), 4.55-4.80 (m, 2H), 4.25 (s, 2H), 3.60-3.85 (m, 2H), 3.45-3.55 (m, 2H), 2.70-2.90 (m, 4H); MS (ESI+) m/z 471 (M+H)$^+$.

Example 56

2-(2-oxo-3,3-diphenylpyrrolidin-1-yl)-N-{(3aS*,4S*,6aR*)-2-[3-(trifluoromethyl)benzyl]octahydrocyclopenta[c]pyrrol-4-yl}acetamide Example 56A N-(3-(trifluoromethyl)benzyl)-1-(trimethylsilyl)methanamine (3-(Trifluoromethyl)phenyl)methanamine (25 g, 143 mmol), (chloromethyl)trimethylsilane (19.92 mL, 143 mmol), and triethylamine (23.87 mL, 171 mmol) were combined neat. The resultant reaction mixture was refluxed overnight. The reaction was cooled to room temperature, and heptane (150 mL) was added. The HCl salts were removed by filtration, washing with heptane. The solvent was removed under reduced pressure, and the product was isolated by vacuum distillation (bp 70-90° C./3.2 torr) to give the title compound. $^1$H NMR (300 MHz, CDCl$_3$) δ ppm 7.59 (s, 1H), 7.53-7.38 (m, 3H), 3.86 (s, 2H), 2.04 (s, 2H), 1.34 (s, 1H), 0.06 (s, 9H).

Example 56B 1-methoxy-N-(3-(trifluoromethyl)benzyl)-N-((trimethylsilyl)methyl)methanamine Formaldehyde (4.08 g, 50.2 mmol) was dissolved in methanol (2.032 mL, 50.2 mmol). The reaction was cooled to 0° C. (ice bath) and N-(3-(trifluoromethyl)benzyl)-1-(trimethylsilyl)methanamine (Example 56A, 10.94 g, 41.9 mmol) was added dropwise via addition funnel over 30 minutes. Potassium carbonate (4.63 g, 33.5 mmol) was added, and the mixture was stirred at 0° C. for 2 hours. The reaction solution was decanted from the potassium carbonate. The solution was treated with more potassium carbonate and decanted again. The potassium carbonate solids were sequentially washed with ether and these washes were added to the reaction solution. The solvent was removed in vacuo to give the title compound.

Example 56C 2-(3-(trifluoromethyl)benzyl)hexahydrocyclopenta[c]pyrrol-4(5H)-one Cyclopent-2-enone (3.31 g, 40.4 mmol), and trifluoroacetic acid (0.031 mL, 0.404 mmol) were combined in dichloromethane (40 mL). Then 1-methoxy-N-(3-(trifluoromethyl)benzyl)-N-((trimethylsilyl)methyl)methanamine (Example 56B, 12.33 g, 40.4 mmol) was added as a solution in dichloromethane (10 mL) dropwise via addition funnel over 45 minutes at room temperature under nitrogen. The reaction was quenched with aqueous bicarbonate solution and extracted with dichloromethane (2×100 mL). The organics were combined and washed with brine, and the solvent was removed in vacuo to give the title compound. $^1$H NMR (300 MHz, CDCl$_3$) δ ppm 7.54-7.34 (m, 4H), 3.66 (d, J=13.4, 1H), 3.52 (d, J=13.4, 1H), 3.04 (dd, J=1.8, 8.9, 1H), 2.91 (ddd, J=2.8, 7.4, 11.7, 1H), 2.72-2.65 (m, 1H), 2.62 (d, J=8.9, 1H), 2.52-2.23 (m, 4H), 2.15 (ddd, J=8.1, 12.9, 17.1, 1H), 1.85-1.70 (m, 1H).

Example 56D 2-(3-(trifluoromethyl)benzyl)hexahydrocyclopenta[c]pyrrol-4(5H)-one oxime Hydroxylamine hydrochloride (3.47 g, 50.0 mmol) and sodium acetate (4.27 g, 52.0 mmol) were dissolved in water (15 mL) and added to a solution of 2-(3-(trifluoromethyl)benzyl)hexahydrocyclopenta[c]pyrrol-4(5H)-one (Example 56C, 11.33 g, 40 mmol) in ethanol (80 mL). The reaction was brought to reflux and then allowed to cool to 70° C. After 1 hour, the solvent was removed in vacuo to give the title compound.

Example 56E an 56F (3aS*,4R*,6aR*)-2-(3-(trifluoromethyl)benzyl)octahydrocyclopenta[c]pyrrol-4-amine and (3aS*,4S*,6aR*)-2-(3-(trifluoromethyl)benzyl)octahydrocyclopenta[c]pyrrol-4-amine)

2-(3-(Trifluoromethyl)benzyl)hexahydrocyclopenta[c]pyrrol-4(5H)-one oxime (Example 56D, 11.9 g, 39.9 mmol) in 20% ammonia/methanol (115 mL) was added to methanol-washed Raney®-nickel, water-wet (38.52 g, 295 mmol) in a 500 mL pressure bottle. The vessel was pressurized with hydrogen (30 pounds per square inch), and the mixture was shaken for 16 hours at room temperature. The mixture was filtered through a nylon membrane, the solvent removed in vacuo, and the crude oil adsorbed onto silica gel. Chromatography using an SF65-400 silica gel column (Analogix®, Burlington, Wis.) with 1-10% methanol (2 N NH$_3$)/dichloromethane gave:
Example 56E (3aS*,4R*,6aR*)-2-(3-(trifluoromethyl)benzyl)octahydrocyclopenta[c]pyrrol-4-amine ($^1$H NMR (300 MHz, CDCl$_3$) δ ppm 7.58 (s, 1H), 7.50 (t, J=6.7, 2H), 7.45-7.37 (m, 1H), 3.59 (s, 2H), 3.26 (dt, J=6.3, 12.6, 1H), 2.67-2.50 (m, 4H), 2.38 (dd, J=6.6, 8.4, 1H), 2.31-2.20 (m, 1H), 1.79-1.62 (m, 2H), 1.60-1.33 (m, 4H)); and
Example 56F (3aS*,4S*,6aR*)-2-(3-(trifluoromethyl)benzyl)octahydrocyclopenta[c]pyrrol-4-amine ($^1$H NMR (300 MHz, CDCl$_3$) δ ppm 7.58 (s, 1H), 7.50 (t, J=7.2, 2H), 7.45-7.37 (m, 1H), 3.59 (s, 2H), 3.09 (dd, J=4.9, 11.4, 1H), 2.77-2.57 (m, J=3.9, 1H), 2.52-2.38 (m, 3H), 2.34 (dd, J=3.7, 9.0, 1H), 2.22-2.09 (m, 1H), 2.03-1.85 (m, J=4.7, 7.0, 10.8, 2H), 1.42-1.21 (m, 4H)).

Example 56G 2-(2-oxo-3,3-diphenylpyrrolidin-1-yl)-N-{(3aS*,4S*,6aR*)-2-[3-(trifluoromethyl)benzyl]octahydrocyclopenta[c]pyrrol-4-yl}acetamide To 2-(2-oxo-3,3-diphenylpyrrolidin-1-yl)acetic acid (Example 1C, 171 mg, 0.580 mmol) in dichloromethane (2.0 mL) was added 1H-benzo[d][1,2,3]triazol-1-ol hydrate (89 mg, 0.580 mmol) and N$^1$-((ethylimino)methylene)-N$^3$,N$^3$-dimethylpropane-1,3-diamine hydrochloride (0.126 mL, 0.580 mmol). The reaction mixture was stirred at room temperature for 30 minutes, treated with (3aS*,4S*,6aR*)-2-(3-(trifluoromethyl)benzyl)octahydrocyclopenta[c]pyrrol-4-amine (150 mg, 0.528 mmol, Example 56F), stirred overnight at room temperature, quenched with H$_2$O (2.0 mL), and extracted with dichloromethane (2×2.0 mL). The organic layer was dried (MgSO$_4$), filtered, and concentrated. The residue was loaded onto a silica gel column (SF10-4 g, Analogix®, Burlington, Wis.), eluted with a gradient of 1-10% methanol (2 N NH$_3$)/dichloromethane over 15 minutes with a flow rate of 27 mL/minute. The isolated product was treated with diethyl ether (1.0 mL) and 2 M HCl/diethyl ether solution (1.0 mL). The solid material was collected by filtration and dried to provide the HCl salt of the title compound. $^1$H NMR (500 MHz, pyridine-d$_5$) δ ppm 8.41-8.43 (m, 1H), 7.67-7.69 (m, 5H), 7.55-7.57 (m, 1H), 7.44 (t, J=7.7 Hz, 1H), 7.30-7.37 (m, 4H), 7.24-7.26 (m, 3H), 4.38-4.44 (m, 1H), 4.37 (d, J=15.7 Hz, 1H), 4.26 (d, J=15.6 Hz, 1H), 3.53-3.58 (m, 2H), 3.50 (d, J=13.2 Hz, 1H), 3.40 (d, J=13.2 Hz, 1H), 2.77-2.84 (m, 3H), 2.66 (dd, J=9.6, 3.3 Hz, 1H), 2.41-2.47 (m, 1H), 2.30 (d, J=7.8 Hz, 1H), 2.11-2.27 (m, 2H), 1.75-1.81 (m, 1H), 1.48-1.65 (m, 2H), 1.22-1.29 (m, 1H).

Example 57

2-(2-oxo-3,3-diphenylpyrrolidin-1-yl)-N-{(3aS*,4R*,6aR*)-2-[3-(trifluoromethyl)benzyl]octahydrocyclopenta[c]pyrrol-4-yl}acetamide To 2-(2-oxo-3,3-diphenylpyrrolidin-1-yl)acetic acid (Example 1C, 171 mg, 0.580 mmol) in dichloromethane (2.0 mL) was added 1H-benzo[d][1,2,3]triazol-1-ol hydrate (89 mg, 0.580 mmol) and N$^1$-((ethylimino)methylene)-N$^3$,N$^3$-dimethylpropane-1,3-diamine hydrochloride (0.126 mL, 0.580 mmol). The reaction mixture was stirred for 30 minutes at room temperature, treated with (3aS*,4R*,6aR*)-2-(3-(trifluoromethyl)benzyl)octahydrocyclopenta[c]pyrrol-4-amine (Example 56E, 150 mg, 0.528 mmol), stirred overnight at room temperature, quenched with H$_2$O (2.0 mL) and extracted with dichloromethane (2×2.0 mL). The organic layer was dried (MgSO$_4$), filtered, concentrated, loaded onto a silica gel column (SF10-4 g, Analogix®, Burlington, Wis.) and eluted with a gradient of 1-10% methanol (2 N NH$_3$)/dichloromethane in dichloromethane over 15 minutes with a flow rate of 27 mL/minute. The isolated product was treated with diethyl ether (1.0 mL) and 2 M HCl/diethyl ether solution (1.0 mL). The resultant solid was collected by filtration and dried to provide the HCl salt of the title compound. $^1$HNMR (500 MHz, pyridine-d$_5$) δ ppm 8.58-8.59 (d, 1H), 7.75 (s, 1H), 7.76-7.78 (d, J=7.63 Hz, 4H), 7.6 (s, 1H), 7.43-7.46 (t, J=7.63 Hz, 1H), 7.30-7.33 (m, 4H), 7.25 (d, 3H), 4.34 (m, 3H), 3.60 (d, J=1.68 Hz, 1H), 3.58 (d, J=6.23 Hz, 2H), 3.42-3.45 (d, J=13.58 Hz, 1H), 2.77-2.79 (t, J=6.48, 2H), 2.75 (d, J=7.17 Hz, 1H), 2.42-2.51 (m, 2H), 2.37-2.40 (m, 1H), 2.21-2.28 (m, 2H), 2.20-2.25 (m, 1H), 1.76-1.82 (m, 1H), 1.49-1.56 (m, 1H), 1.31-1.37 (m, 1H).

Example 58

1-[2-(4-benzhydrylpiperazin-1-yl)-2-oxoethyl]-3,3-bis(4-fluorophenyl)pyrrolidin-2-one

Example 58A ethyl 3-cyano-2,2-bis(4-fluorophenyl)propanoate

To a solution of ethyl 2,2-bis(4-fluorophenyl)acetate (0.28 g, 1.00 mmol) in dry tetrahydrofuran at −78° C. was added lithium bis(trimethylsilyl)amide (1.0 M in hexane) (1.00 mL, 1.00 mmol) dropwise via syringe under nitrogen. The reaction was brought to 0° C. and stirred for one hour. The reaction was re-cooled to −78° C. and then bromoacetonitrile (0.69 mL, 1.00 mmol) was added as a solution in tetrahydrofuran (10 mL). The reaction was stirred for 2 hours while the temperature was allowed to reach room temperature. The reaction was quenched with saturated aqueous ammonium chloride solution and extracted with diethyl ether. The organics were washed with brine, dried with $MgSO_4$, filtered, and concentrated. The residue was purified by silica gel chromatography (10% ethyl acetate/hexanes), to obtain the title compound. MS (DCI+) m/z 333 $(M+NH_4)^+$.

Example 58B 3,3-bis(4-fluorophenyl)pyrrolidin-2-one

A solution of the product from Example 58A (20 mg, 0.063 mmol) in acetic acid (4 mL) was added to $PtO_2$ (4.00 mg, 0.018 mmol) in a 50 mL pressure bottle and stirred at room temperature for 12 hours under hydrogen (30 pounds per square inch). The mixture was filtered through a nylon membrane then concentrated to obtain solid. The solid was slurried in 5% ethyl acetate/hexanes, filtered and dried to give the title compound. MS (DCI+) m/z 274 $(M+H)^+$.

Example 58C ethyl 2-(3,3-bis(4-fluorophenyl)-2-oxopyrrolidin-1-yl)acetate

To a solution of the product from Example 58B (0.82 g, 3.00 mmol) in tetrahydrofuran (20 mL) was added potassium tert-butoxide (1.0 M in tetrahydrofuran, 4.5 mL, 4.5 mmol) via syringe under nitrogen followed by ethyl 2-bromoacetate (0.33 mL, 3.00 mmol). The reaction mixture was heated to 80° C. and stirred overnight. The reaction mixture was cooled to room temperature, concentrated and then diluted with ethyl acetate. The reaction mixture was washed with water and brine, dried over magnesium sulfate, filtered and concentrated. The residue was purified with silica gel chromatography eluting with ethyl acetate/hexane (20:80) gave the title compound. MS (APCI+) m/z 359.9 $(M+H)^+$.

Example 58D 2-(3,3-bis(4-fluorophenyl)-2-oxopyrrolidin-1-yl)acetic acid

The product from Example 58C (0.90 g, 2.50 mmol) was dissolved in ethanol (20 mL). A solution of lithium hydroxide (0.57 g, 23.97 mmol) in water (5 mL) was added, and the reaction was heated to 80° C. for 2 hours. The reaction mixture was cooled to room temperature, concentrated, neutralized with 2 N HCl, and then extracted with ethyl acetate. The organic layer was washed with water and brine, dried over magnesium sulfate, filtered, and concentrated to supply the title compound. MS (APCI+) m/z 332.2 $(M+H)^+$.

Example 58E

1-[2-(4-benzhydrylpiperazin-1-yl)-2-oxoethyl]-3,3-bis(4-fluorophenyl)pyrrolidin-2-one To a solution of 1-benzhydrylpiperazine (0.54 g, 2.14 mmol) in dichloromethane (20 mL) under nitrogen was added the product from Example 58D (0.71 g, 2.14 mmol) followed by $N^1$-((ethylimino)methylene)-$N^3$,$N^3$-dimethylpropane-1,3-diamine hydrochloride (0.82 g, 4.29 mmol) and N,N-dimethylpyridin-4-amine (0.013 g, 0.11 mmol). The reaction mixture was stirred overnight at room temperature. The reaction was concentrated and the residue was partitioned in ethyl acetate/water (8:2, 400 mL). The organic layer was washed with water followed by brine, dried over magnesium sulfate, filtered, and concentrated. Silica gel chromatography eluting with ethyl acetate/hexane (1:3) gave the title compound. $^1$H NMR (300 MHz, $CDCl_3$) δ ppm 7.37-7.41 (m, 4H), 7.25-7.33 (m, 8H), 7.16-7.23 (m, 2H), 6.94-7.01 (m, 4H), 4.19 (s, 1H), 4.14 (s, 2H), 3.58 (t, J=4.7 Hz, 2H), 3.49 (t, J=6.5 Hz, 2H), 3.38-3.42 (m, 2H), 2.75 (t, J=6.5 Hz, 2H), 2.36 (t, J=4.8 Hz, 2H), 2.29 (t, J=4.6 Hz, 2H).

Example 59

2-[3,3-bis(4-fluorophenyl)-2-oxopyrrolidin-1-yl]-N-(2,2-diphenylpropyl)acetamide To a solution of 2,2-diphenylpropan-1-amine (0.21 g, 1.00 mmol) in dichloromethane (25 mL) under nitrogen was added 2-(3,3-bis(4-fluorophenyl)-2-oxopyrrolidin-1-yl)acetic acid (Example 58D, 0.33 g, 1.00 mmol) followed by $N^1$-((ethylimino)methylene)-$N^3$,$N^3$-dimethylpropane-1,3-diamine hydrochloride (0.39 g, 2.00 mmol) and N,N-dimethylpyridin-4-amine (0.012 g, 0.10 mmol). The reaction mixture was stirred overnight at room temperature. The reaction was concentrated and the residue was partitioned in ethyl acetate/water (8:2). The organic layer was washed with water followed by brine, dried over magnesium sulfate, filtered, and concentrated. Silica gel chromatography eluting with 3% methanol/dichloromethane gave the title compound. $^1$H NMR (300 MHz, $CDCl_3$) δ ppm 7.10-7.29 (m, 14H), 6.94-7.01 (m, 4H), 5.66 (t, J=5.4 Hz, 1H), 3.95 (d, J=5.8 Hz, 2H), 3.89 (s, 2H), 3.27 (t, J=6.4 Hz, 2H), 2.55 (t, J=6.4 Hz, 2H), 1.59 (s, 3H); MS (DCI+) m/z 525 $(M+H)^+$.

Example 60

3,3-bis(4-fluorophenyl)-1-(2-oxo-2-{4-[3-(trifluoromethyl)benzyl]piperazin-1-yl}ethyl)pyrrolidin-2-one To a solution of 1-(3-(trifluoromethyl)benzyl)piperazine (0.24 g, 1.00 mmol) in dichloromethane (25 mL) under nitrogen was added 2-(3,3-bis(4-fluorophenyl)-2-oxopyrrolidin-1-yl)acetic acid (Example 58D, 0.33 g, 1.00 mmol) followed by $N^1$-((ethylimino)methylene)-$N^3$,$N^3$-dimethylpropane-1,3-diamine hydrochloride (0.39 g, 2.00 mmol) and N,N-dimethylpyridin-4-amine (0.012 g, 0.10 mmol). The reaction

Example 61

1-[2-(3,3-diphenylpyrrolidin-1-yl)-2-oxoethyl]-3,3-bis(4-fluorophenyl)pyrrolidin-2-one To a solution of 3,3-diphenylpyrrolidine (Example 17A, 0.22 g, 1.00 mmol) in dichloromethane (25 mL) under nitrogen was added 2-(3,3-bis(4-fluorophenyl)-2-oxopyrrolidin-1-yl)acetic acid (Example 58D, 0.33 g, 1.00 mmol) followed by $N^1$-((ethylimino)methylene)-$N^3,N^3$-dimethylpropane-1,3-diamine hydrochloride (0.39 g, 2.00 mmol) and N,N-dimethylpyridin-4-amine (0.012 g, 0.10 mmol). The reaction mixture was stirred overnight at room temperature. The reaction was concentrated and the residue was partitioned in ethyl acetate/water (8:2). The organic layer was washed with water followed by brine, dried over magnesium sulfate, filtered, and concentrated. Silica gel chromatography eluting with 3% methanol/dichloromethane gave the title compound. $^1$H NMR (300 MHz, CDCl$_3$) δ ppm 7.14-7.36 (m, 14H), 6.95-7.01 (m, 4H), 4.22 (s, 1H), 4.17 (s, 1H), 4.10 (s, 1H), 4.08 (s, 1H), 3.51-3.60 (m, 3H), 3.42 (t, J=6.7 Hz, 1H), 2.72-2.80 (m, 2H), 2.62 (t, J=6.6 Hz, 1H), 2.53 (t, J=6.8 Hz, 1H); MS (DCI+) m/z 537 (M+H)$^+$.

Example 62

3,3-diphenyl-1-({3-[4-(trifluoromethyl)phenyl]-1,2,4-oxadiazol-5-yl}methyl)pyrrolidin-2-one A solution of (Z)—N-hydroxy-4-(trifluoromethyl)benzimidamide (0.579 g, 2.84 mmol), 2-(2-oxo-3,3-diphenylpyrrolidin-1-yl)acetic acid (Example 1C, 0.762 g, 2.58 mmol) and $N^1$-((ethylimino)methylene)-$N^3,N^3$-dimethylpropane-1,3-diamine hydrochloride (0.594 g, 3.10 mmol) were stirred together in dichloroethane (0.5 mL) at room temperature for 2 hours. The reaction was then heated to 85° C. and stirred overnight. The reaction was cooled, loaded onto a SF25-40 silica gel column (Analogix®, Burlington, Wis.), and the title compound was eluted using a gradient of 5% to 30% ethyl acetate/hexanes over 30 minutes (flow=40 mL/minute). $^1$H NMR (300 MHz, CDCl$_3$) δ ppm 8.09-8.15 (m, 2H), 7.71-7.76 (m, 2H), 7.23-7.43 (m, 10H), 4.91 (s, 2H), 3.58 (t, J=6.5 Hz, 2H), 2.90 (t, J=6.4 Hz, 2H); MS (ESI−) m/z 462 (M−H)$^−$.

Example 63

1-{2-[4-(3,5-dimethoxybenzyl)piperazin-1-yl]ethyl}-3,3-bis(4-fluorophenyl)pyrrolidin-2-one

Example 63A tert-butyl 4-(2-bromoethyl)piperazine-1-carboxylate tert-Butyl 4-(2-hydroxyethyl)piperazine-1-carboxylate (5.76 g, 25.0 mmol) was dissolved in dry tetrahydrofuran (100 mL) and carbon tetrabromide (9.12 g, 27.5 mmol). A solution of triphenyl phosphine (6.62 g, 25.3 mmol) in dry tetrahydrofuran (25 mL) was added dropwise, and the mixture was stirred for 20 hours. The reaction was diluted with n-hexane (100 mL) and washed with a saturated NaHCO$_3$ solution, water and brine, dried with MgSO$_4$, filtered and concentrated. Silica gel chromatography eluting with ethyl acetate/hexanes 1:4 gave the title compound. MS (DCI) m/z 295 (M+H)$^+$.

Example 63B tert-butyl 4-(2-(3,3-bis(4-fluorophenyl)-2-oxopyrrolidin-1-yl)ethyl)piperazine-1-carboxylate To a solution of 3,3-bis(4-fluorophenyl)pyrrolidin-2-one (Example 58B, 1.37 g, 5.00 mmol) in tetrahydrofuran (30 mL) was added potassium t-butoxide (1.0 M in tetrahydrofuran) (7.5 mL, 7.5 mmol) followed by the product from Example 63A (1.47 g, 5.00 mmol). The reaction mixture was heated at 75° C. for 18 hours. The reaction was concentrated, diluted with ethyl acetate, washed with water and brine, dried with MgSO$_4$, filtered and concentrated. The residue was purified with silica gel chromatography eluting with 3% methanol/dichloromethane to give the title compound. MS (DCI) m/z 486.3 (M+H)$^+$.

Example 63C 3,3-bis(4-fluorophenyl)-1-(2-(piperazin-1-yl)ethyl)pyrrolidin-2-one The product from Example 63B (2.00 g, 4.12 mmol) was dissolved in dichloromethane (40 mL) and treated with trifluoroacetic acid (7.40 g, 64.9 mmol) at 0° C. The reaction was allowed to come to room temperature and stirred for 1 hour. The reaction was neutralized with triethylamine and concentrated. The residue was taken into ethyl acetate, and then it was washed with water and brine, dried with MgSO$_4$, filtered and concentrated to give the title compound. MS (DCI) m/z 386.2 (M+H)$^+$.

Example 63D

1-{2-[4-(3,5-dimethoxybenzyl)piperazin-1-yl]ethyl}-3,3-bis(4-fluorophenyl)pyrrolidin-2-one To a solution of the product from Example 63C (1.85 g, 4.80 mmol) in methanol/dichloromethane (50 mL) was added 3,5-dimethoxybenzaldehyde (0.80 g, 4.80 mmol), macroporous-cyanoborohydride resin (8.09 g, 4.80 mmol, 2.24 mol/g) and acetic acid (1.6 mL, 4.80 mmol). The reaction was stirred at 40° C. for 18 hours under an atmosphere of nitrogen. The reaction was cooled to room temperature, filtered and concentrated. Silica gel chromatography eluting with 3% methanol/dichloromethane gave the title compound. The title compound was dissolved in methanol (10 mL) and treated with HCl (1.25 M in methanol, 5.1 mL), concentrated and dried under vacuum to give the title compound as the corresponding hydrochloride salt. MS (DCI) m/z 536.3 (M+H)$^+$.

---

(Top of page, Example continuation:)

mixture was stirred overnight at room temperature. The reaction was concentrated and the residue was partitioned in ethyl acetate/water (8:2). The organic layer was washed with water followed by brine, dried over magnesium sulfate, filtered, and concentrated. Silica gel chromatography eluting with 3% methanol/dichloromethane gave the title compound. $^1$H NMR (300 MHz, CDCl$_3$) δ ppm 7.41-7.59 (m, 4H), 7.27-7.35 (m, 4H), 6.96-7.03 (m, 4H), 4.18 (s, 2H), 3.59-3.63 (m, 2H), 3.53 (s, 2H), 3.51 (t, J=6.6 Hz, 2H), 3.41-3.45 (m, 2H), 2.77 (t, J=6.5 Hz, 2H), 2.40-2.44 (m, 2H), 2.31-2.35 (m, 2H); MS (DCI+) m/z 558 (M+H)$^+$.

Example 64

4-benzhydryl-1-[2-(2-oxo-3,3-diphenylpyrrolidin-1-yl)ethyl]piperazin-2-one

Example 64A 1-(2-hydroxyethyl)-3,3-diphenylpyrrolidin-2-one

A mixture of 3,3-diphenyldihydrofuran-2(3H)-one (0.5 g, 2.098 mmol), 2-aminoethanol (1282 mg, 20.98 mmol) and zinc chloride (0.23 g, 1.679 mmol) was heated neat at 100° C. for 16 hours. The reaction mixture was cooled and partitioned in $H_2O$/ethyl acetate. The organic layer was separated, dried over $MgSO_4$, and concentrated to yield the title compound. $^1$H NMR (400 MHz, $CDCl_3$) δ ppm 7.32 (m, 8H), 7.23 (m, 2H), 3.81 (q, J=5.42 Hz, 2H), 3.52 (t, J=5.42 Hz, 2H), 3.45 (t, J=6.44 Hz, 2H), 2.85 (t, J=5.52 Hz, 1H), 2.79 (t, J=6.44 Hz, 2H); MS (ESI+) m/z 282 (M+H)$^+$.

Example 64B 1-(2-bromoethyl)-3,3-diphenylpyrrolidin-2-one

To a solution of the product from Example 64A (0.3, 1.1 mmol) in methylene chloride was added carbon tetrabromide (0.7 g, 2.13 mmol) and triphenylphosphine (0.56 g, 2.13 mmol) and the reaction mixture was stirred at room temperature overnight. The reaction mixture was concentrated, and the obtained residue was chromatographed on silica gel eluting with 10-30% ethyl acetate/hexane to yield the title compound. $^1$H NMR (300 MHz, $CDCl_3$) δ ppm 7.31 (m, 10H), 3.78 (t, J=6.44 Hz, 2H), 3.54 (t, J=5.59 Hz, 2H), 3.49 (t, J=5.76 Hz, 2H), 2.80 (t, J=6.44 Hz, 2H); MS (ESI+) m/z 345 (M+H)$^+$.

Example 64C 4-benzhydrylpiperazin-2-one tert-Butyl 3-oxopiperazine-1-carboxylate (0.6 g, 3 mmol) in methylene chloride (10 mL) was treated with trifluoroacetic acid (3 mL) at room temperature for 1 hour. The reaction mixture was concentrated and the obtained trifluoroacetic salt of 2-piperazinone was used without purification. To a piperazin-2-one 2,2,2-trifluoroacetate (0.4 g, 1.87 mmol) solution in N,N-dimethylformamide (3 mL) was added bromodiphenylmethane (0.45 g, 1.87 mmol), potassium carbonate (0.78 g, 5.7 mmol) and catalytic amount of potassium iodide and the reaction mixture was stirred at ambient temperature overnight. Then it was evaporated, partitioned in $H_2O$/methylene chloride. The organic layer was dried over $MgSO_4$, evaporated in vacuo and chromatographed on silica gel eluting with 30% ethyl acetate/hexane and then with 10% methanol/dichloromethane/1% ammonium hydroxide to yield the title compound. $^1$H NMR (300 MHz, DMSO-$d_6$) δ ppm 7.80 (s, 1H), 7.46 (m, 4H), 7.31 (m, 4H), 7.21 (m, 2H), 4.37 (s, 1H), 3.17 (m, 2H), 2.79 (s, 2H); MS/DCI 267 (M+H)$^+$.

Example 64D 4-benzhydryl-1-[2-(2-oxo-3,3-diphenylpyrrolidin-1-yl)ethyl]piperazin-2-one To a solution of product from Example 64C (0.11 g, 0.4 mmol)) in N,N-dimethylformamide was added a 60% dispersion of sodium hydride in mineral oil (0.03 g, 0.75 mmol) and the reaction mixture was stirred at room temperature for 1 hour. Then 1-(2-bromoethyl)-3,3-diphenylpyrrolidin-2-one (Example 64B, 0.142 g, 0.4 mmol) was added, and the reaction mixture was stirred at ambient temperature overnight. The reaction mixture was concentrated and partitioned in water/methylene chloride. The organic layer was separated, dried over $MgSO_4$ and concentrated in vacuo. The residue was chromatographed, eluting first with 5% ethyl acetate/hexane and then eluting the title compound with 15% methanol/methylene chloride. $^1$H NMR (300 MHz, $CDCl_3$) δ ppm 7.31 (m, 20H), 3.48 (t, J=6.44 Hz, 2H), 3.42 (m, 2H), 3.28 (m, 2H), 3.12 (s, 2H), 2.70 (m, 2H), 2.66 (m, 2H), 2.42 (m, 2H); MS (ESI+) m/z 530 (M+H)$^+$.

Example 65

3,3-dimethyl-1-[2-(2-oxo-3,3-diphenylpyrrolidin-1-yl)ethyl]-4-(thien-2-ylmethyl)piperazin-2-one The title compound was obtained as described in the Example 64D substituting 4-benzhydrylpiperazin-2-one with 3,3-dimethyl-4-(thiophen-2-ylmethyl)piperazin-2-one that is synthesized from 2-(bromomethyl)thiophene and 3,3-dimethylpiperazino-2-one (CAS 22476-74-0) (Meyers, K. M.; et al. Bioorg. Med. Chem. Lett. 2007, 17(3), 814-818). $^1$H NMR (300 MHz, DMSO-$d_6$) δ ppm 7.14-7.42 (m, 11H), 6.94-6.97 (m, 2H), 3.69 (s, 2H), 3.45-3.46 (m, 4H), 3.36 (t, J=6.3 Hz, 2H), 3.09 (t, J=5.1 Hz, 2H), 2.65 (t, J=6.5 Hz, 2H), 2.51-2.55 (m, 2H), 1.16 (s, 6H); MS (ESI+) m/z 488 (M+H)$^+$.

Example 66

1-benzhydryl-4-[2-(2-oxo-3,3-diphenylpyrrolidin-1-yl)ethyl]piperazin-2-one

To a solution of the product from the Example 28A (0.182 g, 0.6 mmol) in N,N-dimethylformamide (5 mL) was added 1-(2-bromoethyl)-3,3-diphenylpyrrolidin-2-one (Example 64B, 0.2 g, 0.6 mmol), potassium carbonate (0.25 g, 1.8 mmol), and a catalytic amount of potassium iodide. The reaction mixture was stirred at room temperature overnight. The reaction mixture was concentrated in vacuo, and partitioned in $H_2O$/dichloromethane. The organic layer was separated, dried over $MgSO_4$, and concentrated. The obtained residue was chromatographed eluting with 5% methanol/dichloromethane to yield the title compound. $^1$H NMR (300 MHz, $CDCl_3$) δ ppm 7.31 (m, 10H), 7.20 (m, 11H), 3.50 (t, J=6.10 Hz, 2H), 3.38 (t, J=6.44 Hz, 2H), 3.33 (m, 2H), 3.00 (m, 2H), 2.71 (m, 4H), 2.58 (t, J=6.27 Hz, 2H), MS (ESI+) m/z 530 (M+H)$^+$.

Example 67

3,3-diphenyl-1-{2-[7-(trifluoromethyl)-3,4-dihydroisoquinolin-2(1H)-yl]ethyl}pyrrolidin-2-one

Example 67A 1-(2-hydroxyethyl)-3,3-diphenylpyrrolidin-2-one 3,3-Diphenyldihydrofuran-2(3H)-one (1.0 g, 4.20 mmol), 2-aminoethanol (2.56 g, 42.0 mmol) and zinc chloride (0.020 g, 0.147 mmol) were heated together at 100° C. for 18 hours. The reaction was cooled, diluted with ethyl acetate, washed with water and brine, dried with MgSO4, filtered and concentrated. Silica gel chromatography eluting with 5% methanol/dichloromethane gave the title compound. MS (DCI+) m/z 282.2 (M+H)+.

Example 67B 2-(2-oxo-3,3-diphenylpyrrolidin-1-yl)acetaldehyde

To a solution of Dess-Martin periodinane (8.03 g, 18.92 mmol) in dichloromethane (100 mL) was added a solution of the product from Example 67A (4.84 g, 17.20 mmol) in dichloromethane (50 mL) at room temperature. After 30 minutes at room temperature, the reaction is diluted with diethyl ether, filtered and concentrated. Chromatography eluting with a gradient of 50% to 100% ethyl acetate/hexanes using a SF25-40 g (Analogix®, Burlington, Wis.) column gave the title compound. MS (DCI+) m/z 280.1 (M+H)+.

Example 67C 3,3-diphenyl-1-{2-[7-(trifluoromethyl)-3,4-dihydroisoquinolin-2(1H)-yl]ethyl}pyrrolidin-2-one A solution of 7-(trifluoromethyl)-1,2,3,4-tetrahydroisoquinoline hydrochloride (0.153 g, 0.644 mmol), the product from Example 67B (0.120 g, 0.430 mmol) and sodium cyanoborohydride (0.040 g, 0.644 mmol) were stirred together in methanol (0.5 mL) at room temperature. After stirring overnight, the reaction was concentrated, dissolved in minimal dichloromethane and was loaded directly onto a SF15-12 column (Analogix®, Burlington, Wis.), and the title compound was eluted using a gradient of 5% to 100% ethyl acetate/hexanes over 20 minutes (flow=30 mL/minute). $^1$H NMR (300 MHz, CDCl$_3$) δ ppm 7.36-7.42 (m, 1H), 7.29-7.34 (m, 4H), 7.18-7.26 (m, 2H), 7.12-7.18 (m, 6H), 3.66 (s, 2H), 3.63 (t, J=6.2 Hz, 2H), 3.44 (t, J=6.4 Hz, 2H), 2.69-2.84 (m, 8H); MS (ESI+) m/z 465 (M+H)+.

Example 68

1-[2-(4-benzhydrylpiperazin-1-yl)-2-oxoethyl]-3,3-diphenylpiperidin-2-one

Example 68A ethyl 2,2-diphenylacetate 2,2-Diphenylacetic acid (50 g) was dissolved in ethanol (350 mL). Concentrated sulfuric acid (3 mL) was added, and the mixture was refluxed overnight. After cooling to room temperature, the reaction mixture was concentrated and diluted with diethyl ether. The organic solvent solution was then extracted with water, saturated aqueous sodium bicarbonate solution, and brine. The organic layer was then dried with magnesium sulfate, filtered, and concentrated to obtain the title compound. MS (DCI+) m/z 241 (M+H)+.

Example 68B ethyl 4-cyano-2,2-diphenylbutanoate

The product of Example 68A (5.58 g) was dissolved in anhydrous dioxane (15 mL). Sodium ethoxide (1.58 g) was added and the mixture was heated to 40-50° C. for 30 minutes. Acrylonitrile (1.44 mL) was added dropwise with stirring. The mixture was heated at 60-70° C. for one hour. The dioxane was removed in vacuo, and the residue was taken up in diethyl ether, washed with water and brine, dried with magnesium sulfate, filtered, and concentrated. The crude material was purified by silica gel chromatography (3-10% ethyl acetate/hexane) to obtain the title compound. MS (DCI+) m/z 311 (M+NH$_4$)+.

Example 68C 3,3-diphenylpiperidin-2-one

The product of Example 68B (14.4 g, 49.1 mmol) and 7 M ammonia in methanol (150 mL) were added to solvent-washed Raney®-nickel (72.0 g, 1227 mmol), and the mixture was stirred at room temperature for 24 hours under hydrogen (30 pounds per square inch). The mixture was filtered through a nylon membrane. The reaction mixture was concentrated. The residue was dissolved in dichloromethane/methanol (1:1) and filtered through a pad of diatomaceous earth to remove a greenish residue. The filtrate was concentrated to obtain a solid which was slurried in methanol, filtered, and dried to obtain the title compound. MS (DCI+) m/z 251 (M+H)+.

Example 68D ethyl 2-(2-oxo-3,3-diphenylpiperidin-1-yl)acetate

To a solution of the product of Example 68C (2.51 g, 10.00 mmol) in tetrahydrofuran (100 mL) was added potassium tert-butoxide (1.35 g, 12.00 mmol) under nitrogen followed by ethyl 2-bromoacetate (1.22 mL, 11.00 mmol). The reaction mixture was heated to 80° C. and stirred overnight. The reaction mixture was cooled to room temperature, concentrated and then diluted with ethyl acetate. The organic layer was washed with water and brine, dried over magnesium sulfate, filtered and concentrated. Silica gel chromatography eluting with ethyl acetate/hexane (20:80) gave the title compound. MS (DCI+) m/z 338 (M+H)+.

Example 68E 2-(2-oxo-3,3-diphenylpiperidin-1-yl)acetic acid

The product from Example 68D (1.70 g, 5.04 mmol) was dissolved in ethanol (40 mL). A solution of lithium hydroxide (1.20 g, 50.10 mmol) in water (10 mL) was added, and the reaction was heated to 80° C. for 2 hours. The reaction mixture was cooled to room temperature, concentrated, neutralized with 2 N HCl, and then diluted with ethyl acetate. The organic layer was washed with water and brine, dried over magnesium sulfate, filtered, and then concentrated to give the title compound. MS (DCI+) m/z 310 (M+H)+.

Example 68F

1-[2-(4-benzhydrylpiperazin-1-yl)-2-oxoethyl]-3,3-diphenylpiperidin-2-one

To a solution of 1-benzhydrylpiperazine (1.63 g, 6.46 mmol) in dichloromethane (75 mL) under nitrogen was added the product of Example 68E (2.00 g, 6.46 mmol) followed by $N^1$-((ethylimino)methylene)-$N^3$,$N^3$-dimethylpropane-1,3-diamine hydrochloride (2.48 g, 12.93 mmol) and N,N-dimethylpyridin-4-amine (0.079 g, 0.65 mmol). The reaction mixture was stirred overnight at room temperature. The reaction was concentrated and the residue was partitioned in ethyl acetate/water (8:2, 400 mL). The organic layer was washed with water followed by brine, dried over magnesium sulfate, filtered, and concentrated. Silica gel chromatography eluting with ethyl acetate/hexane (1:3) gave the title compound. $^1$H NMR (300 MHz, CDCl$_3$) δ ppm 7.38-7.42 (m, 4H), 7.25-7.31 (m, 12H), 7.16-7.24 (m, 4H), 4.23 (s, 1H), 4.20 (s, 2H), 3.64 (t, J=4.7 Hz, 2H), 3.47 (t, J=6.5 Hz, 2H), 3.41-3.45 (m, 2H), 2.60-2.65 (m, 2H), 2.34-2.42 (m, 4H), 1.78-1.87 (m, 2H); MS (DCI+) m/z 544 (M+H)$^+$.

Example 69

1-[2-(2,2-diphenylmorpholin-4-yl)-2-oxoethyl]-3,3-diphenylpiperidin-2-one

To 2,2-diphenylmorpholine (0.075 g, 0.313 mmol), 2-(2-oxo-3,3-diphenylpiperidin-1-yl)acetic acid (Example 68E, 0.097 g, 0.313 mmol) and 2-(1H-benzo[d][1,2,3]triazol-1-yl)-1,1,3,3-tetramethylisouronium hexafluorophosphate(V) (0.131 g, 0.345 mmol) in dichloromethane (1 mL) was added diisopropylethylamine (0.082 mL, 0.470 mmol), and the reaction mixture was stirred at room temperature overnight. The reaction was loaded directly onto a silica gel column (Analogix®, SF15-24) and the product was eluted with a gradient of 5% to 100% ethyl acetate/hexanes over 25 minutes with a flow rate of 30 mL/minute. $^1$H NMR (300 MHz, CDCl$_3$) δ ppm 7.18-7.60 (m, 20H), 4.43 (s, 2H), 3.50-3.70, m, 6H), 3.05-3.10 (m, 2H), 2.40-2.50 (m, 2H), 1.55-1.70 (m, 2H); MS (DCI+) m/z 531 (M+H)$^+$.

Example 70

1-[2-oxo-2-(2-phenylmorpholin-4-yl)ethyl]-3,3-diphenylpiperidin-2-one

To 2-(2-oxo-3,3-diphenylpiperidin-1-yl)acetic acid (Example 68E, 0.103 g, 0.334 mmol), 2-(1H-benzo[d][1,2,3]triazol-1-yl)-1,1,3,3-tetramethylisouronium hexafluorophosphate(V) (0.155 g, 0.408 mmol) and 2-phenylmorpholine (0.074 g, 0.371 mmol) in dichloromethane (0.5 mL) was added diisopropylethylamine (0.097 mL, 0.556 mmol), and the reaction mixture was stirred at room temperature. After stirring overnight, the reaction was directly loaded onto a silica gel column (Analogix®, SF15-12), and the product was eluted with a gradient of 5% to 100% ethyl acetate/hexanes over 20 minutes with a flow rate of 30 mL/minute. The product eluted with a more polar impurity. The product was rechromatographed over silica gel (Analogix®, SF15-12), and the title compound was eluted with a gradient of 0.4% to 7.5% methanol/dichloromethane over 20 minutes with a flow rate of 30 mL/minute. $^1$H NMR (300 MHz, CDCl$_3$) δ ppm 7.18-7.40 (m, 15H), 4.37-4.68 (m, 3H), 3.98-4.17 (m, 2H), 3.32-3.85 (m, 6H), 2.64-2.70 (m, 2H), 1.82-1.88 (m, 2H); MS (ESI+) m/z 455 (M+H)$^+$.

Example 71

1-[2-(3,3-diphenylpiperidin-1-yl)-2-oxoethyl]-3,3-diphenylpiperidin-2-one

To a solution of 3,3-diphenylpiperidine (Example 24A, 0.24 g, 1.00 mmol) in dichloromethane (20 mL) was added 2-(2-oxo-3,3-diphenylpiperidin-1-yl)acetic acid (Example 68E, 0.308 g, 1.00 mmol), under nitrogen. To the reaction was added N$^1$-((ethylimino)methylene)-N$^3$,N$^3$-dimethylpropane-1,3-diamine hydrochloride (0.38 g, 2.00 mmol) and N,N-dimethylpyridin-4-amine (0.012 g, 0.10 mmol), and the reaction mixture was stirred overnight at room temperature. The reaction was concentrated, and the residue was partitioned in ethyl acetate:water (8:2). The organic layer was separated, washed with water and then brine, dried over MgSO4, filtered and concentrated. Silica gel chromatography eluting with 3% methanol/dichloromethane gave the title compound. $^1$H NMR (300 MHz, CDCl$_3$) δ ppm 7.12-7.33 (m, 20H), 4.23 (s, 2H), 4.13 (s, 2H), 3.35-3.46 (m, 4H), 2.57-2.64 (m, 2H), 2.45-2.51 (m, 2H), 1.72-1.85 (m, 2H), 1.46-1.56 (m, 2H); MS (DCI+) m/z 529 (M+H)$^+$.

Example 72

1-[2-(4,4-diphenylpiperidin-1-yl)-2-oxoethyl]-3,3-diphenylpiperidin-2-one

To a solution of 4,4-diphenylpiperidine (Matrix, 0.24 g, 1.00 mmol) in dichloromethane (20 mL) was added 2-(2-oxo-3,3-diphenylpiperidin-1-yl)acetic acid (Example 68E, 0.308 g, 1.00 mmol), under nitrogen. To the reaction was added N$^1$-((ethylimino)methylene)-N$^3$,N$^3$-dimethylpropane-1,3-diamine hydrochloride (0.38 g, 2.00 mmol) and N,N-dimethylpyridin-4-amine (0.012 g, 0.10 mmol), and the reaction mixture was stirred overnight at room temperature. The reaction was concentrated and the residue was partitioned in ethyl acetate:water (8:2). The organic layer was separated, washed with water and then brine, dried over MgSO4, filtered and concentrated. Silica gel chromatography eluting with 3% methanol/dichloromethane gave the title compound. $^1$H NMR (300 MHz, CDCl$_3$) δ ppm 7.15-7.34 (m, 20H), 4.23 (s, 2H), 3.68-3.73 (m, 2H), 3.45-3.52 (m, 4H), 2.60-2.66 (m, 2H), 2.37-2.45 (m, 4H), 1.78-1.88 (m, 2H); MS (DCI+) m/z 529 (M+H)$^+$.

Example 73

1-{2-[2-(4-fluorophenyl)pyrrolidin-1-yl]-2-oxoethyl}-3,3-diphenylpiperidin-2-one A solution of N$^1$-((ethylimino)methylene)-N$^3$,N$^3$-dimethylpropane-1,3-diamine hydrochloride (0.049 g, 0.254 mmol), 2-(2-oxo-3,3-diphenylpyrrolidin-1-yl)acetic acid (Example 68E, 0.050 g, 0.169 mmol) and 2-(4-fluorophenyl)pyrrolidine (0.028 g, 0.169 mmol) in dichloromethane (0.5 mL) was stirred at room temperature. After stirring overnight, the reaction was loaded directly onto a SF10-4 silica gel column (Analogix®, Burlington, Wis.), and the title compound was eluted using a gradient of 5% to 100% ethyl acetate/hexanes over 20 minutes (flow=30 mL/minute). $^1$H NMR (300 MHz, CDCl$_3$) δ ppm 7.42-6.83 (m, 14H), 5.14 (m, 1H), 4.64-4.10 (m, 1H), 3.97-3.73 (m, 2H), 3.73-3.47 (m, 2H), 3.25-2.91 (m, 1H), 2.78-2.15 (m, 3H), 1.85 (m, 5H)); MS (DCI+) m/z 457 (M+H)$^+$.

Example 74

1-{2-[2-(4-fluorophenyl)piperidin-1-yl]-2-oxoethyl}-3,3-diphenylpiperidin-2-one

A solution of N$^1$-((ethylimino)methylene)-N$^3$,N$^3$-dimethylpropane-1,3-diamine hydrochloride (0.049 g, 0.254 mmol), 2-(2-oxo-3,3-diphenylpyrrolidin-1-yl)acetic acid (Example 68E, 0.050 g, 0.169 mmol) and 2-(4-fluorophenyl)piperidine (0.030 g, 0.169 mmol) in dichloromethane (0.5 mL) was stirred at room temperature. After stirring overnight, the reaction was loaded directly onto a SF10-4 column (Analogix®, Burlington, Wis.), and the title compound was eluted using a gradient of 5% to 70% ethyl acetate/hexanes over 20 minutes (flow=30 mL/minute). ¹H NMR (300 MHz, CDCl₃) δ ppm 7.46-7.09 (m, 12H), 7.03 (m, 2H), 4.58-4.23 (m, 2H), 3.57 (m, 2H), 2.72-2.55 (m, 2H), 2.45-2.23 (m, 2H), 2.02-1.75 (m, 3H), 1.75-1.47 (m, 6H); MS (DCI+) m/z 471 (M+H)⁺.

Example 75

N-(6-fluoro-3,4-dihydro-2H-chromen-4-yl)-2-(2-oxo-3,3-diphenylpiperidin-1-yl)acetamide A solution of 2-(2-oxo-3,3-diphenylpiperidin-1-yl)acetic acid (Example 68E, 0.063 g, 0.204 mmol), N¹-((ethylimino)methylene)-N³,N³-dimethylpropane-1,3-diamine hydrochloride (0.059 g, 0.305 mmol) and 6-fluorochroman-4-amine (0.037 g, 0.224 mmol) in dichloromethane (0.5 mL) was stirred at room temperature. After stirring for approximately 60 hours, the reaction was loaded directly onto a SF15-12 column (Analogix®, Burlington, Wis.), and the title compound was eluted using a gradient of 5% to 75% ethyl acetate/hexanes over 25 minutes (flow=30 mL/minute). ¹H NMR (300 MHz, CDCl₃) δ ppm 7.22-7.31 (m, 2H), 7.15-7.22 (m, 5H), 7.05-7.10 (m, 2H), 6.85-6.94 (m, 3H), 6.75-6.81 (m, 1H), 5.13 (dt, J=8.5, 5.8 Hz, 2H), 4.18 (d, J=14.6 Hz, 1H), 4.10-4.21 (m, 1H), 3.97-4.09 (m, 1H), 4.01 (d, J=14.6 Hz, 1H), 3.54-3.62 (m, 2H), 2.54-2.64 (m, 2H), 2.12-2.25 (m, 1H), 1.91-2.02 (m, 1H), 1.81-1.90 (m, 2H); MS (ESI−) m/z 457 (M−H)⁻.

Example 76

1-[2-(4-benzhydrylpiperidin-1-yl)-2-oxoethyl]-3,3-diphenylpiperidin-2-one

To a solution of 4-benzhydrylpiperidine (0.13 g, 0.5 mmol) in dichloromethane (10 mL) under nitrogen was added 2-(2-oxo-3,3-diphenylpiperidin-1-yl)acetic acid (Example 68E, 0.16 g, 0.50 mmol) followed by N¹-((ethylimino)methylene)-N³,N³-dimethylpropane-1,3-diamine hydrochloride (0.19 g, 1.00 mmol) and N,N-dimethylpyridin-4-amine (6 mg, 0.05 mmol). The reaction mixture was stirred overnight at room temperature. The reaction was concentrated and the residue was partitioned in ethyl acetate/water (8:2, 400 mL). The organic layer was washed with water followed by brine, dried over magnesium sulfate, filtered, and concentrated. Silica gel chromatography eluting with ethyl acetate/hexane (1:3) gave the title compound. ¹H NMR (300 MHz, CDCl₃) δ ppm 7.15-7.34 (m, 20H), 4.52-4.60 (m, 1H), 4.27 (d, J=15.7 Hz, 1H), 4.11 (d, J=15.7 Hz, 1H), 3.64-3.76 (m, 1H), 3.45-3.50 (m, 3H), 2.93-3.02 (m, 1H), 2.54-2.65 (m, 3H), 2.20-2.44 (m, 1H), 1.78-1.87 (m, 2H), 1.55-1.65 (m, 2H), 1.00-1.20 (m, 2H).

Example 77

N-(2,2-diphenylpropyl)-2-(2-oxo-3,3-diphenylpiperidin-1-yl)acetamide

To a solution of 2,2-diphenylpropan-1-amine (0.10 g, 0.5 mmol) in dichloromethane (10 mL) under nitrogen was added 2-(2-oxo-3,3-diphenylpiperidin-1-yl)acetic acid (Example 68E, 0.16 g, 0.50 mmol) followed by N¹-((ethylimino)methylene)-N³,N³-dimethylpropane-1,3-diamine hydrochloride (0.19 g, 1.00 mmol) and N,N-dimethylpyridin-4-amine (6 mg, 0.05 mmol). The reaction mixture was stirred overnight at room temperature. The reaction was concentrated and the residue was partitioned in ethyl acetate/water (8:2, 400 mL). The organic layer was washed with water followed by brine, dried over magnesium sulfate, filtered, and concentrated. Silica gel chromatography eluting with ethyl acetate/hexane (1:3) gave the title compound. ¹H NMR (300 MHz, CDCl₃) δ ppm 7.05-7.35 (m, 20H), 6.0-6.1 (m, 1H), 3.98 (s, 2H), 3.95 (s, 2H), 3.2-3.4 (m, 2H), 2.4-2.5 (m, 2H), 1.65-1.75 (m, 2H), 1.5 (s, 3H); MS (ESI+) m/z 503 (M+H)⁺.

Example 78

1-(2-{4-[hydroxy(diphenyl)methyl]piperidin-1-yl}-2-oxoethyl)-3,3-diphenylpiperidin-2-one To a solution of diphenyl(piperidin-4-yl)methanol (0.13 g, 0.5 mmol) in dichloromethane (10 mL) under nitrogen was added 2-(2-oxo-3,3-diphenylpiperidin-1-yl)acetic acid (Example 68E, 0.16 g, 0.50 mmol) followed by N¹-((ethylimino)methylene)-N³,N³-dimethylpropane-1,3-diamine hydrochloride (0.19 g, 1.00 mmol) and N,N-dimethylpyridin-4-amine (6 mg, 0.05 mmol). The reaction mixture was stirred overnight at room temperature. The reaction was concentrated and the residue was partitioned in ethyl acetate/water (8:2, 400 mL). The organic layer was washed with water followed by brine, dried over magnesium sulfate, filtered, and concentrated. Silica gel chromatography eluting with ethyl acetate/hexane (1:3) gave the title compound. ¹H NMR (300 MHz, CDCl₃) δ ppm 7.42-7.48 (m, 4H), 7.16-7.35 (m, 16H), 4.63-4.71 (m, 1H), 4.20 (d, J=1.5 Hz, 2H), 3.77-3.84 (m, 1H), 3.42-3.54 (m, 2H), 2.97-3.06 (m, 1H), 2.57-2.68 (m, 4H), 1.74-1.87 (m, 2H), 1.46-1.64 (m, 3H), 1.29-1.42 (m, 2H); MS (ESI+) m/z 559 (M+H)⁺.

Example 79

1-(2-oxo-2-{4-[3-(trifluoromethyl)benzyl]piperazin-1-yl}ethyl)-3,3-diphenylpiperidin-2-one A solution of 1-(3-(trifluoromethyl)benzyl)piperazine (0.395 g, 1.616 mmol), 2-(2-oxo-3,3-diphenylpiperidin-1-yl) acetic acid (Example 68E, 0.500 g, 1.616 mmol) and N¹-((ethylimino)methylene)-N³,N³-dimethylpropane-1,3-diamine hydrochloride (0.403 g, 2.101 mmol) in dichloromethane (2 mL) was stirred at room temperature. After stirring overnight, the reaction was loaded directly onto a SF25-40 silica gel column (Analogix®, Burlington, Wis.), and the title compound was eluted using a gradient of 5% to 100% ethyl acetate/hexanes over 35 minutes (flow=35 mL/minute). ¹H NMR (300 MHz, CDCl₃) δ ppm 7.40-7.61 (m, 4H), 7.27-7.34 (m, 8H), 7.18-7.25 (m, 2H), 4.23 (s, 2H), 3.64-3.69 (m, 2H), 3.55 (s, 2H), 3.50 (t, J=6.5 Hz, 2H), 3.43-3.49 (m, 2H), 2.60-2.67 (m, 2H), 2.38-2.49 (m, 4H), 1.79-1.89 (m, 2H); MS (ESI+) m/z 536 (M+H)⁺.

Example 80

1-(2-oxo-2-{4-[4-(trifluoromethyl)benzyl]piperazin-1-yl}ethyl)-3,3-diphenylpiperidin-2-one A solution of 1-(4-(trifluoromethyl)benzyl)piperazine (0.046 g, 0.188 mmol), 2-(2-oxo-3,3-diphenylpiperidin-1-yl) acetic acid (Example 68E, 0.053 g, 0.171 mmol) and N¹-((ethylimino)methylene)-N³,N³-dimethylpropane-1,3-diamine hydrochloride (0.049 g, 0.257 mmol) in dichloromethane (0.5 mL) was stirred at room temperature. After stirring overnight, the reaction was loaded directly onto a SF15-12 silica gel column (Analogix®, Burlington, Wis.), and the title compound was eluted using a gradient of 0.4% to 4.5% methanol/dichloromethane over 20 minutes (flow=30 mL/minute). $^1$H NMR (300 MHz, CDCl$_3$) δ ppm 7.56-7.60 (m, 2H), 7.42-7.46 (m, 2H), 7.27-7.33 (m, 8H), 7.18-7.25 (m, 2H), 4.23 (s, 2H), 3.66 (t, J=4.7 Hz, 2H), 3.55 (s, 2H), 3.50 (t, J=6.5 Hz, 2H), 3.44-3.49 (m, 2H), 2.62-2.66 (m, 2H), 2.35-2.50 (m, 4H), 1.79-1.88 (m, 2H); MS (ESI+) m/z 536 (M+H)$^+$.

Example 81

1-{2-[4-(3-chlorobenzyl)piperazin-1-yl]-2-oxoethyl}-3,3-diphenylpiperidin-2-one

A solution of 1-(3-chlorobenzyl)piperazine (0.014 g, 0.068 mmol), 2-(2-oxo-3,3-diphenylpiperidin-1-yl)acetic acid (Example 68E, 0.019 g, 0.061 mmol) and N$^1$-((ethylimino)methylene)-N$^3$,N$^3$-dimethylpropane-1,3-diamine hydrochloride (0.018 g, 0.092 mmol) in dichloromethane (0.5 mL) was stirred at room temperature. After stirring overnight, the reaction was loaded directly onto a SF15-12 silica gel column (Analogix®, Burlington, Wis.), and the title compound was eluted using a gradient of 0.4% to 4.5% methanol/dichloromethane over 20 minutes (flow=30 mL/minute). $^1$H NMR (300 MHz, CDCl$_3$) δ ppm 7.14-7.34 (m, 14H), 4.23 (s, 2H), 3.63-3.67 (m, 2H), 3.48 (t, J=6.8 Hz, 2 H), 3.47 (s, 2H), 3.43-3.48 (m, 2H), 2.62-2.66 (m, 2H), 2.38-2.46 (m, 4H), 1.79-1.89 (m, 2H); MS (ESI+) m/z 502 (M+H)$^+$.

Example 82

1-(2-{4-[bis(4-fluorophenyl)methyl]piperazin-1-yl}-2-oxoethyl)-3,3-diphenylpiperidin-2-one To a solution of 1-(bis(4-fluorophenyl)methyl)piperazine (0.14 g, 0.5 mmol) in dichloromethane (10 mL) under nitrogen was added 2-(2-oxo-3,3-diphenylpiperidin-1-yl)acetic acid (Example 68E, 0.16 g, 0.50 mmol) followed by N$^1$-((ethylimino)methylene)-N$^3$,N$^3$-dimethylpropane-1,3-diamine hydrochloride (0.19 g, 1.00 mmol) and N,N-dimethylpyridin-4-amine (6 mg, 0.05 mmol). The reaction mixture was stirred overnight at room temperature. The reaction was concentrated and the residue was partitioned in ethyl acetate/water (8:2, 400 mL). The organic layer was washed with water followed by brine, dried over magnesium sulfate, filtered, and concentrated. Silica gel chromatography eluting with ethyl acetate/hexane (1:3) gave the title compound. $^1$H NMR (300 MHz, CDCl$_3$) δ ppm 7.18-7.36 (m, 14H), 6.95-7.01 (m, 4H), 4.22 (s, 1H), 4.19 (s, 2H), 3.63 (t, J=4.7 Hz, 2H), 3.48 (t, J=6.4 Hz, 2H), 3.41-3.46 (m, 2H), 2.60-2.65 (m, 2H), 2.31-2.39 (m, 4H), 1.78-1.87 (m, 2H)); MS (DCI+) m/z 580 (M+H)$^+$.

Example 83

1-benzhydryl-4-[(2-oxo-3,3-diphenylpiperidin-1-yl)acetyl]piperazin-2-one

The title compound was obtained using the procedures described in Example 28B substituting 2-(2-oxo-3,3-diphenylpyrrolidin-1-yl)acetic acid with 2-(2-oxo-3,3-diphenylpiperidin-1-yl)acetic acid (Example 68E). $^1$H NMR (300 MHz, CDCl$_3$) δ ppm 7.35 (m, 21H), 4.33 (d, 2H), 4.17 (s, 2H), 3.75 (m, 1H), 3.75 (m, 1H), 3.52 (m, 2H), 3.19 (m, 2H), 2.63 (m, 2H), 1.84 (m, 2H); MS (ESI+) m/z 558 (M+H)$^+$, 575 (M+NH$_4$)$^+$.

Example 84

1-[2-oxo-2-(4-{[3-(trifluoromethyl)phenyl]sulfonyl}piperazin-1-yl)ethyl]-3,3-diphenylpiperidin-2-one Example 84A tert-butyl 4-(3-(trifluoromethyl)phenylsulfonyl)piperazine-1-carboxylate To tert-butyl piperazine-1-carboxylate (1.39 g, 7.46 mmol) and diisopropylethylamine (1.955 mL, 11.19 mmol) in dichloromethane (10 mL) was added 3-(trifluoromethyl)benzene-1-sulfonyl chloride (1.196 mL, 7.46 mmol) dropwise. The reaction was stirred overnight. Thin layer chromatography indicated formation of a new product (hexanes/ethyl acetate 1:1). The reaction was diluted with dichloromethane (50 mL), washed with 1 N HCl (50 mL) and brine (50 mL), dried over magnesium sulfate, and concentrated to give the title compound.

Example 84B 1-(3-(trifluoromethyl)phenylsulfonyl)piperazine

The product from Example 84A (2.75 g, 6.97 mmol) was dissolved in dioxane (10 mL) with sonication. To the solution was added hydrochloric acid (4.0 M in dioxane) (5.23 mL, 20.92 mmol), and the reaction was allowed to stir at room temperature. After stirring for 4 hours, the reaction was concentrated. This residue was triturated with diethyl ether with sonication to give a solid which was collected by filtration to give the title compound as the hydrochloride salt.

Example 84C

1-[2-oxo-2-(4-{[3-(trifluoromethyl)phenyl]sulfonyl}piperazin-1-yl)ethyl]-3,3-diphenylpiperidin-2-one To 2-(2-oxo-3,3-diphenylpiperidin-1-yl)acetic acid (Example 68E, 0.135 g, 0.436 mmol), 2-(1H-benzo[d][1,2,3]triazol-1-yl)-1,1,3,3-tetramethylisouronium hexafluorophosphate(V) (0.182 g, 0.480 mmol) and the product from Example 84B (0.173 g, 0.524 mmol) in dichloromethane (1 mL) was added diisopropylethylamine (0.229 mL, 1.309 mmol), and the reaction mixture was stirred at room temperature. After stirring overnight, thin layer chromatography (ethyl acetate (100%)) showed product formation. The reaction was concentrated and loaded onto a silica gel column (Analogix®, SF15-24), and the title compound was eluted using a gradient of 5% to 100% ethyl acetate/hexanes over 25 minutes (flow rate=30 mL/minute). $^1$H NMR (300 MHz, CDCl$_3$) δ ppm 8.0 (s, 1H), 7.85-7.93 (m, 2 H), 7.67-7.74 (m, 1H), 7.18-7.40 (m, 10H), 4.12 (s, 2H), 3.71-3.78 (m, 2H), 3.55-3.62 (m, 2H), 3.40-3.49 (m, 2H), 3.03=3.10 (m, 4H), 2.55-2.63 (m, 2H), 1.75-1.85 (m, 2H); MS (DCI+) m/z 586 (M+H)$^+$.

Example 85

N-(1-benzhydrylpiperidin-4-yl)-2-(2-oxo-3,3-diphenylpiperidin-1-yl)acetamide

The title compound was prepared as described in Example 28B, reacting 2-(2-oxo-3,3-diphenylpiperidin-1-yl)acetic acid (Example 68E) with 1-benzhydrylpiperidin-4-amine (Example 48A). $^1$H NMR (300 MHz, CDCl$_3$) δ ppm 7.14-7.43 (m, 20H), 6.58 (d, J=8.1 Hz, 1H), 4.24 (s, 1H), 4.01 (s, 2H), 3.72-3.84 (m, 1H), 3.53 (t, J=6.4 Hz, 2H), 2.70-2.77 (m, 2H), 2.58-2.63 (m, 2H), 1.97-2.08 (m, 2H), 1.76-1.91 (m, 5H), 1.41-1.50 (m, 1H); MS (ESI+) m/z 558 (M+H)$^+$.

Example 86

N-(1-benzhydryl-3-methylpyrrolidin-3-yl)-2-(2-oxo-3,3-diphenylpiperidin-1-yl)acetamide The title compound was obtained as described in Example 28B reacting 2-(2-oxo-3,3-diphenylpiperidin-1-yl)acetic acid (Example 68E) with 1-benzyl-3-methylpyrrolidin-3-amine dihydrochloride (CAS 181114-76-1). $^1$H NMR (300 MHz, CDCl$_3$) δ ppm 7.39-7.45 (m, 4H), 7.09-7.34 (m, 16H), 6.66-6.67 (br s, 1H), 4.22 (s, 1H), 3.96 (s, 2H), 3.55 (t, J=6.5 Hz, 2H), 2.53-2.67 (m, 6H), 2.02-2.14 (m, 1H), 1.86-1.94 (m, 1H), 1.78-1.90 (m, 2H), 1.49 (s, 3H)); MS (ESI+) m/z 482 (M+H)$^+$.

Example 87

1-{2-[4-(benzhydrylamino)piperidin-1-yl]-2-oxoethyl}-3,3-diphenylpiperidin-2-one

Example 87A tert-butyl 1-(2-(2-oxo-3,3-diphenylpiperidin-1-yl)acetyl)piperidin-4-ylcarbamate To a solution of 2-(2-oxo-3,3-diphenylpiperidin-1-yl)acetic acid (Example 68E, 0.31 g, 1 mmol), tert-butyl piperidin-4-ylcarbamate (CAS 73874-95-0, 0.2 g, 1 mmol) and 2-(1H-benzo[d][1,2,3]triazol-1-yl)-1,1,3,3-tetramethylisouronium hexafluorophosphate(V) (0.38 g, 1 mmol) in dichloromethane (10 mL) was added diisopropylethylamine (0.7 mL), and the reaction mixture was stirred at room temperature overnight. The reaction mixture was then diluted with dichloromethane and washed with sequentially with 20 mL of 1 N HCl, water, 20 ml, of 1 N NaOH, and water. The organic phase was dried over magnesium sulfate and concentrated in vacuo to yield the title compound. $^1$H NMR (300 MHz, CDCl$_3$) δ ppm 7.33 (m, 8H), 7.21 (m, 2H), 4.45 (m, 2H), 4.03 (m, 1H), 3.77 (m, 1H), 3.49 (m, 2H), 3.11 (m, 1H), 2.79 (m, 1H), 2.63 (m, 2H), 1.97 (m, 2H), 1.83 (m, 2H), 1.45 (m, 9H), 1.32 (m, 2H).

Example 87B 1-(2-(4-aminopiperidin-1-yl)-2-oxoethyl)-3,3-diphenylpiperidin-2-one The product from Example 87A was dissolved in methylene chloride (5 mL) and treated with trifluoroacetic acid (2 mL) at room temperature for 1 hour. Then the reaction mixture was concentrated, partitioned between methylene chloride and an aqueous solution of sodium bicarbonate. The organic layer was separated, dried over magnesium sulfate, and concentrated to yield the title compound. MS (ESI+) m/z 391 (M+H)$^+$.

Example 87C

1-{2-[4-(benzhydrylamino)piperidin-1-yl]-2-oxoethyl}-3,3-diphenylpiperidin-2-one A mixture of 1-(2-(4-aminopiperidin-1-yl)-2-oxoethyl)-3,3-diphenylpiperidin-2-one (Example 87B, 0.1 g, 0.25 mmol) and benzophenone (0.056 g, 0.3 mmol) is stirred in dichloromethane (3 mL) with titanium(IV) isopropoxide (0.012 g, 0.4 mmol) for 3 hours. The reaction mixture was then diluted with methanol (10 mL) and sodium borohydride (0.4 g, 0.4 mmol) was added. The mixture was stirred at ambient temperature for 16 hours and then concentrated. The residue was partition in ethyl acetate/H$_2$O (100 mL/20 mL). The organic layer was dried over MgSO$_4$ and concentrated. The residue was chromatographed on silica gel eluting with 5-10% methanol/dichloromethane. $^1$H NMR (300 MHz, CDCl$_3$) δ ppm 7.26-7.38 (m, 16H), 7.15-7.24 (m, 4H), 4.99 (s, 1H), 4.36-4.44 (m, 1H), 4.21 (s, 2H), 3.70-3.77 (m, 1H), 3.48 (t, J=6.4 Hz, 2H), 2.93-3.03 (m, 1H), 2.69-2.79 (m, 1H), 2.61-2.69 (m, 3H), 1.89-2.00 (m, 2H), 1.77-1.89 (m, 2H), 1.24-1.41 (m, 3H); MS (ESI+) m/z 558 (M+H)$^+$.

Example 88

1-{2-[(4aS,7aS)-1-benzhydryloctahydro-6H-pyrrolo[3,4-b]pyridin-6-yl]-2-oxoethyl}-3,3-diphenylpiperidin-2-one

Example 88A (4aS,7aS)-tert-butyl 7a-methyl-6-(2-(2-oxo-3,3-diphenylpiperidin-1-yl)acetyl)octahydro-1H-pyrrolo[3,4-b]pyridine-1-carboxylate The title compound was prepared as described in Example 28B reacting 2-(2-oxo-3,3-diphenylpiperidin-1-yl)acetic acid (Example 68E) with (4aS,7aS)-tert-butyl octahydro-1H-pyrrolo[3,4-b]pyridine-1-carboxylate (Example 50B). MS (ESI+) m/z 518 (M+H)$^+$.

Example 88B 1-(2-((4aS,7aS)-7a-methyltetrahydro-1H-pyrrolo[3,4-b]pyridin-6(2H,7H,7aH)-yl)-2-oxoethyl)-3,3-diphenylpiperidin-2-one The product from Example 88A was dissolved in methylene chloride and reacted with trifluoroacetic acid at ambient temperature for 1 hour. The reaction mixture was concentrated to yield the trifluoroacetic salt of the title compound. m/z 418 (M+H)$^+$.

Example 88C

1-{2-[(4aS,7aS)-1-benzhydryloctahydro-6H-pyrrolo[3,4-b]pyridin-6-yl]-2-oxoethyl}-3,3-diphenylpiperidin-2-one To a solution of product from the Example 88B (0.25 g, 0.47 mmol) in 2-butanone was added bromodiphenylmethane (0.139 g, 0.564 mmol) and sodium carbonate. (0.15 g, 1.41 mmol). The reaction mixture was heated to reflux in a closed ampule for 48 hours. The reaction mixture was concentrated and partitioned in H$_2$O/dichloromethane. The organic layer was separated, dried over MgSO$_4$ and concentrated. The obtained residue was chromatographed on silica gel eluting with 50% ethyl acetate/hexane to yield the title compound (two rotameric forms are present in the spectra) δ ppm $^1$H NMR (300 MHz, CDCl$_3$) δ ppm 7.34-7.45 (m, 4H), 7.26-7.35 (m, 10H), 7.14-7.25 (m, 6H), 4.54 (s, 0.5H), 4.49 (s, 0.5H), 4.22 (d, J=15.9 Hz, 0.5H), 3.98-4.14 (m, 1H), 3.88 (d, J=15.9 Hz, 0.5H), 3.53-3.76 (m, 1.5H), 3.43-3.53 (m, 3H), 3.15-3.37 (m, 2H), 3.06-3.13 (m, 0.5H), 2.54-2.67 (m, 3H), 2.20-2.35

(m, 2H), 1.76-1.87 (m, 2H), 1.56-1.71 (m, 2H), 1.20-1.35 (m, 2H); MS (ESI+) m/z 584 (M+H)+. MS (ESI+) m/z 584 (M+H)+.

Example 89

N-(1-benzyl-3-methylpyrrolidin-3-yl)-2-(2-oxo-3,3-diphenylpiperidin-1-yl)acetamide The title compound was prepared as described in Example 28B reacting 2-(2-oxo-3,3-diphenylpiperidin-1-yl)acetic acid (Example 68E) with 1-benzyl-3-methylpyrrolidin-3-amine dihydrochloride. (CAS 181114-76-1). $^1$H NMR (300 MHz, CDCl$_3$) δ ppm 7.33 (m, 15H), 4.08 (d, J=14.67 Hz, 2H), 4.00 (m, 2H), 3.81 (m, 2H), 3.51 (m, 2H), 3.25 (m, J=2.38 Hz, 1H), 3.05 (d, J=13.88 Hz, 1H), 2.67 (m, 2H), 2.26 (m, 2H), 1.85 (m, 2H), 1.49 (s, 3H); MS (ESI+) m/z 482 (M+H)+.

Example 90

1-[2-(4-benzhydrylpiperazin-1-yl)-2-oxoethyl]-3,3-bis(4-fluorophenyl)piperidin-2-one

Example 90A ethyl 4-cyano-2,2-bis(4-fluorophenyl)butanoate

To a solution of ethyl 2,2-bis(4-fluorophenyl)acetate (1.55 g, 5.64 mmol) in anhydrous dioxane (10 mL) was added sodium ethoxide (0.38 g, 5.61 mmol), and the reaction was stirred at a temperature between 40-50° C. for 30 minutes. Acrylonitrile (0.35 mL, 5.61 mmol) was added dropwise with stirring, and the reaction was heated at 60-70° C. for an additional 1 hour. The dioxane was removed in vacuo, and the residue was taken up in ether, washed with water and brine, dried with MgSO$_4$, filtered and concentrated. Silica gel chromatography eluting with a gradient of 3% to 10% ethyl acetate/hexane gave the title compound. MS (DCI) m/z 342 (M+NH$_4$)+.

Example 90B

3,3-bis(4-fluorophenyl)piperidin-2-one

The product from Example 90A (560 mg, 1.700 mmol) as a solution in 7 M ammonia/methanol (20 mL) was added to solvent-washed Raney®-nickel (2800 mg, 47.7 mmol) in a 250 mL stainless steel pressure bottle and stirred at room temperature for 24 hours under hydrogen (30 pounds per square inch). The mixture was filtered through a nylon membrane and was concentrated. The residue was dissolved in methanol/dichloromethane (1:1), filtered and concentrated to give a solid which was slurried in methanol, filtered and dried to give the title compound. MS (DCI) m/z 288 (M+H)+.

Example 90C ethyl 2-(3,3-bis(4-fluorophenyl)-2-oxopiperidin-1-yl)acetate

To the product from Example 90B (0.43 g, 1.50 mmol) as a solution in tetrahydrofuran (20 mL) was added potassium tert-butoxide (1.0 M in tetrahydrofuran) (1.80 mL, 1.80 mmol) via syringe under nitrogen followed by the addition of ethyl 2-bromoacetate (0.18 mL, 1.65 mmol). The reaction mixture heated at 80° C. and stirred overnight. The reaction mixture was cooled to room temperature, concentrated, diluted with ethyl acetate, washed with water and brine, dried with MgSO4, filtered and concentrated. Silica gel chromatography eluting with ethyl acetate/hexane (1:4) gave the title compound. MS (DCI) m/z 374 (M+H)+.

Example 90D

2-(3,3-bis(4-fluorophenyl)-2-oxopiperidin-1-yl)acetic acid

The product from Example 90C (0.40 g, 1.07 mmol) was dissolved in ethanol (20 mL). A solution of lithium hydroxide (0.21 g, 8.57 mmol) in water (5 mL) was added and the reaction was heated to 80° C. for 2 hours. The reaction mixture was cooled to room temperature, concentrated, neutralized with 2 N HCl, and then diluted with ethyl acetate. The organic layer was washed with water and brine, dried over magnesium sulfate, filtered, and then concentrated to give the title compound. MS (DCI) m/z 346 (M+H)+.

Example 90E

1-[2-(4-benzhydrylpiperazin-1-yl)-2-oxoethyl]-3,3-bis(4-fluorophenyl)piperidin-2-one To a solution of 1-benzhydrylpiperazine (0.227 g, 0.90 mmol) in dichloromethane (15 mL) under nitrogen was added the product of Example 90D (0.31 g, 0.90 mmol) followed by $N^1$-((ethylimino)methylene)-$N^3$,$N^3$-dimethylpropane-1,3-diamine hydrochloride (0.344 g, 1.80 mmol) and N,N-dimethylpyridin-4-amine (0.011 g, 0.09 mmol). The reaction mixture was stirred overnight at room temperature. The reaction was concentrated and the residue was partitioned in ethyl acetate/water (8:2, 400 mL). The organic layer was washed with water followed by brine, dried over magnesium sulfate, filtered, and concentrated. Silica gel chromatography eluting with ethyl acetate/hexane (1:3) gave the title compound. $^1$H NMR (300 MHz, CDCl$_3$) δ ppm 7.38-7.42 (m, 4H), 7.15-7.32 (m, 10H), 6.93-7.00 (m, 4H), 4.23 (s, 1H), 4.16 (s, 2H), 3.62-3.66 (m, 2H), 3.47 (t, J=6.4 Hz, 2H), 3.40-3.45 (m, 2H), 2.55-2.65 (m, 2H), 2.36-2.43 (m, 4H), 1.77-1.86 (m, 2H); MS (DCI+) m/z 580 (M+H)+.

Example 91

1-[2-(4-benzhydrylpiperazin-1-yl)-2-oxoethyl]-3-phenylpiperidin-2-one

Example 91A ethyl 4-cyano-2-phenylbutanoate

To a solution of ethyl 2-phenylacetate (5.00 g, 30.5 mmol) in benzene (50 mL) was added Triton-B (40% solution in methanol) (0.240 mL, 0.609 mmol) at 0° C. After stirring for 10 minutes, acrylonitrile (2.005 mL, 30.5 mmol) was added, and the reaction was allowed to warm to room temperature. The reaction was stirred for 3 hours, concentrated, loaded directly onto silica gel (GraceResolv High Resolution Flash Cartridge, 80 g) and eluted using a gradient of 5% to 40% ethyl acetate/hexanes over 40 minutes (flow rate=40 mL/minute). Concentration of product containing fractions provided the title compound. $^1$H NMR (300 MHz, CDCl$_3$) δ ppm 7.44-7.19 (m, 5H), 4.26-4.00 (m, 2H), 3.81-3.59 (m, 1H), 2.50-2.01 (m, 4H), 1.20 (t, J=7.1, 3H).

Example 91B

3-phenylpiperidin-2-one

A solution of the product from Example 91A (2.42 g, 11.14 mmol) in 7 M ammonia/methanol (40 mL) was added to solvent washed Raney®-nickel (24.20 g, 412 mmol) in a 250 mL stainless steel pressure bottle and stirred for 16 hours under hydrogen at 30 pounds per square inch at room temperature. The mixture was filtered through a nylon membrane and concentrated to supply the title compound. $^1$H NMR (300 MHz, CDCl$_3$) δ ppm 7.39-7.17 (m, 5H), 6.00 (s, 1H), 3.65 (dd, J=6.2, 8.3, 1H), 3.54-3.32 (m, 2H), 2.33-2.10 (m, 1H), 2.06-1.70 (m, 3H); MS (ESI+) m/z 176.1 (M+H)$^+$.

Example 91C ethyl 2-(2-oxo-3-phenylpiperidin-1-yl)acetate

To a suspension of the product from Example 91B (1.08 g, 6.16 mmol) in tetrahydrofuran (10 mL) at 0° C. was added potassium tert-butoxide (1.0 M in tetrahydrofuran) (6.78 mL, 6.78 mmol). After stirring for 20 minutes, ethyl 2-bromoacetate (0.750 mL, 6.78 mmol) was added, and the reaction was allowed to warm to room temperature. After stirring for 3 hours, the reaction was poured in ethyl acetate/water (1:1, 200 mL). The organic layer was washed with brine (100 mL), dried over magnesium sulfate and concentrated. Silica gel chromatography using a GraceResolv 80 g silica gel column (Grace Davison Discovery Sciences) eluting with a gradient of 25% ethyl acetate/hexanes to 85% ethyl acetate/hexanes (flow=40 mL/minute) over 30 minutes supplied the title compound. $^1$H NMR (300 MHz, CDCl$_3$) δ ppm 7.39-7.14 (m, 5H), 4.45 (d, J=17.2, 1H), 4.23 (q, J=7.1, 2H), 3.91 (d, J=17.2, 1H), 3.78-3.65 (m, 1H), 3.65-3.49 (m, 1H), 3.41 (dt, J=5.7, 11.3, 1H), 2.32-2.12 (m, 1H), 2.12-1.74 (m, 3H), 1.30 (t, J=7.2, 3H).

Example 91D

2-(2-oxo-3-phenylpiperidin-1-yl)acetic acid

To a solution of the product from Example 91C (2.7 g, 10.33 mmol) in methanol (10 mL) was added sodium hydroxide (2.0 M) (10.33 ml, 20.66 mmol). After stirring for 30 minutes, thin layer chromatography (100% ethyl acetate) showed complete consumption of the starting material. The reaction was diluted with ethyl acetate (50 mL), washed with 1 N HCl (50 mL) and brine (50 mL), dried over magnesium sulfate, and concentrated to supply the title compound. $^1$H NMR (300 MHz, CDCl$_3$) δ ppm 7.41-7.15 (m, 5H), 4.35 (d, J=16.9, 1H), 4.01 (d, J=16.9, 1H), 3.80-3.69 (m, 1H), 3.68-3.51 (m, 1H), 3.44 (dt, J=5.6, 11.3, 2H), 2.31-2.12 (m, 1H), 2.09-1.77 (m, 3H).

Example 91E

1-[2-(4-benzhydrylpiperazin-1-yl)-2-oxoethyl]-3-phenylpiperidin-2-one

To 1-benzhydrylpiperazine (0.238 g, 0.943 mmol), the product from Example 91D (0.200 g, 0.857 mmol) and 2-(1H-benzo[d][1,2,3]triazol-1-yl)-1,1,3,3-tetramethylisouronium hexafluorophosphate(V) (0.358 g, 0.943 mmol) in dichloromethane (1.5 mL) was added diisopropylethylamine (0.225 mL, 1.286 mmol), and the reaction mixture was stirred at room temperature. After stirring overnight, the reaction was concentrated and loaded onto a silica gel column (SF25-25, Analogix®, Burlington, Wis.) and eluted using a gradient of 0.5% to 5% methanol/dichloromethane. The product was isolated along with a slightly lower Rf spot. The mixture was rechromatographed over silica gel using a gradient of 5% to 100% ethyl acetate/hexanes to supply the title compound. $^1$H NMR (300 MHz, CDCl$_3$) δ ppm 7.38-7.43 (m, 4H), 7.14-7.34 (m, 11H), 4.43 (d, J=15.6 Hz, 1H), 4.24 (s, 1H), 4.00 (d, J=15.6 Hz, 1H), 3.70 (dd, J=7.7, 6.0 Hz, 1H), 3.61-3.66 (m, 2H), 3.52-3.59 (m, 1H), 3.44-3.49 (m, 2H), 3.41 (dd, J=11.6, 5.8 Hz, 1H), 2.37-2.43 (m, 4H), 2.15-2.28 (m, 1H), 1.90-2.03 (m, 2H), 1.77-1.89 (m, 1H); MS (ESI+) m/z 468 (M+H)$^+$.

Example 92

1-(2-{4-[bis(4-fluorophenyl)methyl]piperazin-1-yl}-2-oxoethyl)-3-phenylpiperidin-2-one A solution of 2-(2-oxo-3-phenylpiperidin-1-yl)acetic acid (Example 91D, 0.050 g, 0.214 mmol), 1-(bis(4-fluorophenyl)methyl)piperazine (0.068 g, 0.236 mmol) and N$^1$-((ethylimino)methylene)-N$^3$,N$^3$-dimethylpropane-1,3-diamine hydrochloride (0.062 g, 0.322 mmol) in dichloromethane (0.5 mL) was allowed to stir at room temperature. After stirring overnight, the reaction was loaded directly onto a SF15-12 silica gel column (Analogix®, Burlington, Wis.), and the title compound was eluted using a gradient of 5% to 100% ethyl acetate/hexanes over 15 minutes, maintaining 100% ethyl acetate for an additional 10 minutes (flow=30 mL/minute). $^1$H NMR (300 MHz, CDCl$_3$) δ ppm 7.16-7.38 (m, 9H), 6.93-7.04 (m, 4H), 4.42 (d, J=15.5 Hz, 1H), 4.23 (s, 1H), 4.00 (d, J=15.5 Hz, 1H), 3.70 (dd, J=5.8, 4.6 Hz, 1H), 3.59-3.66 (m, 2H), 3.52-3.60 (m, 1H), 3.44-3.50 (m, 2H), 3.37-3.46 (m, 1H), 2.33-2.41 (m, 4H), 2.15-2.27 (m, 1H), 1.92-2.05 (m, 2H), 1.78-1.91 (m, 1H); MS (ESI−) m/z 502 (M−H)$^-$.

Example 93

1-(2-oxo-2-{4-[3-(trifluoromethyl)benzyl]piperazin-1-yl}ethyl)-3-phenylpiperidin-2-one To 2-(2-oxo-3-phenylpiperidin-1-yl)acetic acid (Example 91D, 0.057 g, 0.244 mmol), O-(7-azabenzotriazol-1-yl)-N,N,N',N'-tetramethyluronium hexafluorophosphate (0.098 g, 0.257 mmol) and 1-(3-(trifluoromethyl)benzyl)piperazine (0.066 g, 0.269 mmol) in dichloromethane (0.5 mL) was added diisopropylethylamine (0.064 mL, 0.367 mmol) and the reaction was allowed to stir at room temperature. After stirring overnight, the reaction was loaded directly onto a silica gel column (Analogix®, SF15-12), and the product was eluted using a gradient of 0.4% to 3.75% methanol/dichloromethane over 25 minutes (flow=30 mL/minute). $^1$H NMR (300 MHz, CDCl$_3$) δ ppm 7.58-7.60 (br s, 1H), 7.49-7.55 (m, 2H), 7.41-7.47 (m, 1H), 7.27-7.35 (m, 3H), 7.18-7.26 (m, 2H), 4.47 (d, J=15.7 Hz, 1H), 4.03 (d, J=15.7 Hz, 1H), 3.68-3.73 (m, 1H), 3.59-3.67 (m, 2H), 3.56-3.62 (m, 1H), 3.53-3.59 (m, 2H), 3.47-3.52 (m, 2H), 3.39-3.45 (m, 1H), 2.42-2.49 (m, 4H), 2.17-2.28 (m, 1H), 1.87-2.05 (m, 3H); MS (ESI−) m/z 458 (M−H)$^-$.

Example 94

1-{2-[4-(2,4-dichlorobenzyl)piperazin-1-yl]-2-oxoethyl}-3-phenylpiperidin-2-one A solution of 2-(2-oxo-3-phenylpiperidin-1-yl)acetic acid (Example 91D, 0.050 g, 0.214 mmol), 1-(2,4-dichlorobenzyl)piperazine (0.058 g, 0.236 mmol) and N¹-((ethylimino) methylene)-N³,N³-dimethylpropane-1,3-diamine hydrochloride (0.062 g, 0.322 mmol) in dichloromethane (0.5 mL) was allowed to stir at ambient temperature. After stirring overnight, the reaction was loaded directly onto a SF10-8 silica gel column (Analogix®, Burlington, Wis.), and the title compound was eluted using a gradient of 5% to 100% ethyl acetate/hexanes over 20 minutes, maintaining 100% ethyl acetate for an additional 5 minutes (flow=20 mL/minute). $^1$H NMR (300 MHz, CDCl$_3$) δ ppm 7.36-7.42 (m, 2H), 7.17-7.34 (m, 6H), 4.45 (d, J=15.5 Hz, 1H), 4.05 (d, J=15.5 Hz, 1H), 3.71 (dd, J=7.7, 6.0 Hz, 1H), 3.64 (t, J=4.9 Hz, 2H), 3.58 (s, 2H), 3.53-3.61 (m, 1H), 3.46-3.51 (m, 2H), 3.39-3.48 (m, 1H), 2.48-2.52 (m, 4H), 2.17-2.27 (m, 1H), 1.95-2.08 (m, 2H), 1.80-1.91 (m, 1H); MS (ESI+) m/z 460 (M+H)⁺.

Example 95

1-[2-(5-fluoro-1,3-dihydro-2H-isoindol-2-yl)-2-oxoethyl]-3-phenylpiperidin-2-one To 2-(2-oxo-3-phenylpiperidin-1-yl)acetic acid (Example 91D, 0.168 g, 0.720 mmol) and 5-fluoroisoindoline hydrochloride (0.138 g, 0.792 mmol) in dichloromethane (0.5 mL) was added N¹-((ethylimino)methylene)-N³,N³-dimethylpropane-1,3-diamine (0.191 mL, 1.080 mmol), and the reaction was stirred at ambient temperature overnight. The reaction was loaded directly onto a SF15-12 silica gel column (Analogix®, Burlington, Wis.), and the title compound was eluted using a gradient of 5% to 100% ethyl acetate/hexanes over 20 minutes (flow=30 mL/minute). $^1$H NMR (300 MHz, CDCl$_3$) δ ppm 7.14-7.36 (m, 6H), 6.92-7.02 (m, 2H), 4.85-4.90 (m, 2H), 4.78-4.83 (m, 2H), 4.43 (dd, J=15.6, 1.7 Hz, 1H), 4.06 (d, J=15.7 Hz, 1H), 3.73 (dd, J=7.7, 6.1 Hz, 1H), 3.65-3.71 (m, 1H), 3.57 (dt, J=11.6, 5.8 Hz, 1H), 2.19-2.29 (m, 1H), 1.97-2.11 (m, 2H), 1.83-2.00 (m, 1H); MS (DCI+) m/z 353 (M+H)⁺.

Example 96

1-{2-oxo-2-[7-(trifluoromethyl)-3,4-dihydroisoquinolin-2(1H)-yl]ethyl}-3-phenylpiperidin-2-one To a solution of 7-(trifluoromethyl)-1,2,3,4-tetrahydroisoquinoline hydrochloride (0.056 g, 0.236 mmol) and 2-(2-oxo-3-phenylpiperidin-1-yl)acetic acid (Example 91D, 0.050 g, 0.214 mmol) in dichloromethane (0.5 mL) was added N¹-((ethylimino)methylene)-N³,N³-dimethylpropane-1,3-diamine (0.049 mL, 0.279 mmol), and the reaction was stirred for approximately 39 hours. The reaction was loaded directly onto a SF15-12 silica gel column (Analogix®, Burlington, Wis.), and the title compound was eluted using a gradient of 5% to 100% ethyl acetate/hexane over 20 minutes (flow=30 mL/minute). The product was dissolved in a minimal amount of ethyl acetate, and hexanes were added which caused the product to precipitate. Concentration gave the title compound. $^1$H NMR (300 MHz, CDCl$_3$) δ ppm 7.16-7.48 (m, 8H), 4.80 (s, 1H), 4.71 (s, 1H), 4.48-4.57 (m, 1H), 4.09-4.23 (m, 1H), 3.78-3.99 (m, 1H), 3.68-3.79 (m, 2H), 3.54-3.67 (m, 1H), 3.40-3.54 (m, 1H), 2.90-3.03 (m, 2H), 2.13-2.30 (m, 1H), 1.93-2.11 (m, 2H), 1.76-1.96 (m, 1H); MS (ESI+) m/z 417 (M+H)⁺.

Example 97

N-[1-(4-fluorophenyl)cyclobutyl]-2-(2-oxo-3-phenylpiperidin-1-yl)acetamide

To a solution of 1-(4-fluorophenyl)cyclobutanamine hydrochloride (0.048 g, 0.236 mmol) and 2-(2-oxo-3-phenylpiperidin-1-yl)acetic acid (Example 91D, 0.050 g, 0.214 mmol) in dichloromethane (0.5 mL) was added N¹-((ethylimino)methylene)-N³,N³-dimethylpropane-1,3-diamine (0.049 mL, 0.279 mmol) (0.049 mL, 0.279 mmol), and the reaction was stirred for approximately 60 hours. The reaction was loaded directly onto a SF15-12 silica gel column (Analogix®, Burlington, Wis.), and the title compound was eluted using a gradient of 5% to 100% ethyl acetate/hexanes over 20 minutes (flow=30 mL/minute). The product was dissolved in a minimal ethyl acetate and hexanes was added which caused the product to precipitate from solution. Concentration gave the title compound. $^1$H NMR (300 MHz, CDCl$_3$) δ ppm 7.34-7.43 (m, 2H), 7.22-7.34 (m, 3H), 7.14-7.20 (m, 2H), 7.09-7.11 (br s, 1H), 6.97-7.03 (m, 2H), 4.03 (d, J=14.1 Hz, 1H), 3.87 (d, J=14.1 Hz, 1H), 3.69 (dd, J=7.9, 6.0 Hz, 1H), 3.51-3.60 (m, 1H), 3.39-3.48 (m, 1H), 2.47-2.60 (m, 4H), 1.78-2.17 (m, 6H); MS (ESI−) m/z 379 (M−H)⁻.

Example 98

1-[2-(5-fluoro-1,3-dihydro-2H-isoindol-2-yl)-2-oxoethyl]-3-methyl-3-phenylpiperidin-2-one Example 98A 2-(3-methyl-2-oxo-3-phenylpiperidin-1-yl)acetic acid 3-Methyl-3-phenylpiperidin-2-one is prepared using the procedures described in Examples 91A and 91B substituting ethyl 2-phenylpropionate for ethyl 2-phenylacetate. To 3-methyl-3-phenylpiperidin-2-one (1.01 g, 5.34 mmol) in tetrahydrofuran (3 mL) was added potassium t-butoxide (1.0 M in tetrahydrofuran, 6.40 mL, 6.40 mmol), and the mixture was allowed to stir at room temperature for 30 minutes. To the mixture was added ethyl 2-bromoacetate (0.591 mL, 5.34 mmol). The reaction was heated to 60° C. and stirred for 2 hours. The reaction was cooled, diluted with ethyl acetate (50 mL), washed with 1 N HCl (25 mL) and brine (25 mL), dried over magnesium sulfate and concentrated. The residue was loaded directly onto a SF25-40 silica gel column (Analogix®, Burlington, Wis.), and the intermediate ethyl ester was eluted using a gradient of 5% ethyl acetate/hexanes to 75% ethyl acetate over 30 minutes (flow=30 mL/minute). The ethyl ester was dissolved in ethanol (10 mL) and sodium hydroxide (2.0 M, 5.34 mL, 10.67 mmol) was added. After stirring for 30 minutes, thin layer chromatography (100% ethyl acetate) showed complete consumption of the starting material. The reaction was diluted with ethyl acetate (50 mL), washed with 1 N HCl (50 mL) and brine (50 mL), dried over magnesium sulfate, and concentrated to give the title compound. $^1$H NMR (300 MHz, CDCl$_3$) δ ppm 7.42-7.11 (m, 5H), 4.28 (d, J=16.7, 1H), 4.12 (d, J=16.7, 1H), 3.59-3.33 (m, 2H), 2.23 (dt, J=4.5, 13.5, 1H), 2.07-1.89 (m, 1H), 1.85-1.66 (m, 2H), 1.61 (s, 3H); MS (APCI+) m/z 248 (M+H)⁺.

Example 98B

1-[2-(5-fluoro-1,3-dihydro-2H-isoindol-2-yl)-2-oxoethyl]-3-methyl-3-phenylpiperidin-2-one To the product from Example 98A (0.054 g, 0.218 mmol) and 5-fluoroisoindoline hydrochloride (0.042 g, 0.240 mmol) in dichloromethane (0.5 mL) was added N¹-((ethylimino) methylene)-N³,N³-dimethylpropane-1,3-diamine (0.058 mL, 0.328 mmol), and the reaction was stirred at room temperature overnight. The reaction was loaded directly onto a SF15-12 silica gel column (Analogix®, Burlington, Wis.), and the title compound was eluted using a gradient of 5% ethyl acetate/hexane to 100% ethyl acetate over 20 minutes (flow=30 mL/minute). $^1$H NMR (300 MHz, CDCl$_3$) δ ppm 7.28-7.41 (m, 4H), 7.17-7.24 (m, 2H), 6.93-7.04 (m, 2H), 4.87-4.91 (m, 2H), 4.80-4.85 (m, 2H), 4.29 (d, J=16.1 Hz, 1H), 4.19 (dd, J=15.6, 1.5 Hz, 1H), 3.47-3.64 (m, 2H), 2.22 (dt, J=13.6, 4.6 Hz, 1H), 1.98-2.08 (m, 1H), 1.73-1.82 (m, 2H), 1.62 (s, 3H); MS (ESI+) m/z 367 (M+H)$^+$.

Example 99

3,3-diphenyl-1-({3-[4-(trifluoromethyl)phenyl]-1,2,4-oxadiazol-5-yl}methyl)piperidin-2-one A solution of (Z)—N-hydroxy-4-(trifluoromethyl)benzimidamide (0.033 g, 0.162 mmol), 2-(2-oxo-3,3-diphenylpiperidin-1-yl)acetic acid (Example 68E, 0.050 g, 0.162 mmol) and N$^1$-((ethylimino)methylene)-N$^3$,N$^3$-dimethylpropane-1,3-diamine hydrochloride (0.046 g, 0.242 mmol) were stirred together in 1,2-dichloroethane (0.5 mL) at room temperature. After stirring for 1 hour, the reaction was heated to 85° C. and stirred overnight. The reaction was cooled, loaded directly onto a SF15-12 silica gel column (Analogix®, Burlington, Wis.), and the title compound was eluted using a gradient of 5% ethyl acetate/hexane to 100% ethyl acetate over 20 minutes (flow=30 mL/minute). $^1$H NMR (300 MHz, CDCl$_3$) δ ppm 8.22-8.26 (m, 2H), 7.76-7.80 (m, 2H), 7.21-7.35 (m, 10H), 4.93 (s, 2H), 3.64 (t, J=6.4 Hz, 2H), 2.69-2.74 (m, 2H), 1.88-1.97 (m, 2H); MS (ESI+) m/z 478 (M+H)$^+$.

Example 100

1-{[3-(4-fluorophenyl)-1,2,4-oxadiazol-5-yl]methyl}-3,3-diphenylpiperidin-2-one

A solution of (Z)-4-fluoro-N-hydroxybenzimidamide (0.025 g, 0.162 mmol), 2-(2-oxo-3,3-diphenylpiperidin-1-yl)acetic acid (Example 68E, 0.050 g, 0.162 mmol) and N$^1$-((ethylimino)methylene)-N$^3$,N$^3$-dimethylpropane-1,3-diamine hydrochloride (0.046 g, 0.242 mmol) was stirred in 1,2-dichloroethane (0.5 mL) at room temperature. After stirring for 1 hour, the reaction was heated to 85° C. and stirred overnight. The reaction was cooled, loaded directly onto a SF15-12 silica gel column (Analogix®, Burlington, Wis.), and the title compound was eluted using a gradient of 5% to 100% ethyl acetate/hexanes over 20 minutes (flow=30 mL/minute). $^1$H NMR (300 MHz, CDCl$_3$) δ ppm 8.09-8.15 (m, 2H), 7.24-7.34 (m, 10H), 7.16-7.24 (m, 2H), 4.91 (s, 2H), 3.62 (t, J=6.4 Hz, 2H), 2.68-2.73 (m, 2H), 1.87-1.96 (m, 2H); MS (ESI+) m/z 428 (M+H)$^+$.

Example 101 tert-butyl 4-[2-(4-benzhydrylpiperazin-1-yl)-2-oxoethyl]-3-oxo-2-phenylpiperazine-1-carboxylate Example 101A tert-butyl 3-oxo-2-phenylpiperazine-1-carboxylate To a solution of 3-phenylpiperazin-2-one (CAS 5368-28-5, 0.5 g, 2.84 mmol) in methylene chloride (30 mL) was added di-tert-butyl dicarbonate (0.74 g, 3.4 mmol) and triethylamine (0.6 mL, 4.26 mmol) and the reaction mixture was stirred at ambient temperature overnight. The reaction mixture was diluted with methylene chloride and washed with saturated aqueous NaHCO$_3$ solution. The organic layer was separated, dried over MgSO$_4$ and concentrated to yield the title compound. MS (ESI+) m/z 488 (M+H)$^+$.

Example 101B tert-butyl 4-(2-ethoxy-2-oxoethyl)-3-oxo-2-phenylpiperazine-1-carboxylate To a solution the product from the Example 101A (0.74 g, 2.68 mmol) in tetrahydrofuran (30 mL) was added potassium tert-butoxide (1 M in tetrahydrofuran, 3.21 mL) and ethyl bromoacetate (0.3 mL, 2.68 mmol). The reaction mixture was heated to reflux for 16 hours. The mixture was cooled and partition in methylene chloride/H$_2$O. The organic layer was separated, dried over MgSO$_4$, concentrated and chromatographed on silica gel, eluting with 10-30% ethyl acetate/hexane to yield the title compound. $^1$H NMR (300 MHz, CDCl$_3$) δ ppm 7.44 (m, 2H), 7.33 (m, 3H), 5.78 (s, 1H), 4.43 (d, J=17.29 Hz, 1H), 4.22 (q, J=7.35 Hz, 2H), 4.08 (m, 1H), 3.97 (d, J=17.29 Hz, 1H), 3.59 (m, 1H), 3.39 (m, 3H), 1.46 (m, 9H), 1.29 (t, J=7.12 Hz, 3H).

Example 101C 2-(4-(tert-butoxycarbonyl)-2-oxo-3-phenylpiperazin-1-yl)acetic acid To a solution of Example 101B (0.77 g, 2.12 mmol) in ethanol/water (1:3, 30 mL) was added lithium hydroxide (0.26 g, 6.37 mmol), and the reaction mixture was stirred at ambient temperature overnight. Then the mixture was concentrated and partitioned in cold 1 N HCl/methylene chloride. The organic layer was separated, dried over MgSO$_4$ and concentrated to yield the title compound. $^1$H NMR (300 MHz, DMSO-d$_6$) δ ppm 12.86 (s, 1H), 7.35 (m, 5H), 5.47 (s, 1H), 4.09 (dd, 2H), 3.90 (d, J=15.26 Hz, 1H), 3.53 (m, 1H), 3.28 (m, 1H), 1.40 (s, 9H); MS/DCI 352 (M+NH$_4$)$^+$.

Example 101D tert-butyl 4-[2-(4-benzhydrylpiperazin-1-yl)-2-oxoethyl]-3-oxo-2-phenylpiperazine-1-carboxylate To a solution of 2-(4-(tert-butoxycarbonyl)-2-oxo-3-phenylpiperazin-1-yl)acetic acid (Example 101C, 0.334 g, 1 mmol) and 1-benzhydrylpiperazine (0.252 g, 1 mmol) in methylene chloride (10 mL) was added O-(7-azabenzotriazol-1-yl)-N,N,N',N'-tetramethyluronium hexafluorophosphate (0.38 g, 1 mmol) and diisopropylethylamine (0.8 mL). The reaction mixture was stirred at ambient temperature overnight. The reaction mixture was then diluted with methylene chloride, and then washed sequentially with 1 N HCl, water, 1 N NaOH, and water. The organic layer was dried over magnesium sulfate and concentrated in vacuo to yield the title compound. $^1$H NMR (300 MHz, CDCl$_3$) δ ppm 7.44 (m, 6H), 7.30 (m, 7H), 7.19 (m, 2H), 5.74 (m, 1H), 4.51 (d, J=15.60 Hz, 1H), 4.23 (s, 1H), 4.12 (q, J=7.12 Hz, 1H), 3.96 (d, J=15.94 Hz, 1H), 3.59 (m, 3H), 2.38 (m, 5H), 1.44 (s, 9H); MS (ESI+) m/z 569 (M+H)$^+$.

Example 102

1-[2-(4-benzhydrylpiperazin-1-yl)-2-oxoethyl]-3-phenylpiperazin-2-one

The compound from Example 101D (0.24 g, 0.42 mmol) was dissolved in methanol and treated with 4 N HCl in dioxane at ambient temperature for 2 hours. The reaction mixture was concentrated and then partitioned in 1 N NaOH/methylene chloride. The organic layer was dried over MgSO$_4$, concentrated in vacuo and chromatographed, eluting with 5% MeOH/methylene chloride to yield the title compound. $^1$H NMR (300 MHz, DMSO-d$_6$) δ ppm 7.15-7.48 (m, 15H), 4.30-4.44 (m, 3H), 3.91-4.27 (m, 2H), 3.33-3.55 (m, 4H), 2.80-3.07 (m, 4H), 2.23-2.34 (m, 4H); MS (ESI+) m/z 469 (M+H)$^+$.

Example 103

1-(2-{4-[bis(4-fluorophenyl)methyl]piperazin-1-yl}-2-oxoethyl)-3-phenylpiperazin-2-one Example 103A tert-butyl 4-(2-(4-(bis(4-fluorophenyl)methyl)piperazin-1-yl)-2-oxoethyl)-3-oxo-2-phenylpiperazine-1-carboxylate The title compound was obtained as described in Example 101D replacing 1-benzhydrylpiperazine with 1-(bis(4-fluorophenyl)methyl)piperazine. $^1$H NMR (300 MHz, CDCl$_3$) δ ppm 7.44 (d, J=7.80 Hz, 2H), 7.33 (m, 7H), 6.98 (t, J=8.65 Hz, 4H), 5.74 (s, 1H), 4.50 (d, J=15.94 Hz, 1H), 4.50 (d, J=15.94 Hz, 1H), 4.23 (s, 1H), 4.05 (s, 1H), 3.96 (d, J=15.94 Hz, 1H), 3.60 (m, 2H), 3.39 (m, 4H), 2.35 (m, 4H), 1.45 (s, 9H).

Example 103B 1-(2-{4-[bis(4-fluorophenyl)methyl]piperazin-1-yl}-2-oxoethyl)-3-phenylpiperazin-2-one The title compound was prepared as described in Example 102 replacing compound from Example 101D with the compound from example 103A. $^1$H NMR (300 MHz, CDCl$_3$) δ ppm 7.40-7.47 (m, 2H), 7.26-7.37 (m, 7H), 6.95-7.01 (m, 4H), 4.63 (s, 1H), 4.29 (d, J=15.5 Hz, 1H), 4.23 (s, 1H), 4.13 (d, J=15.5 Hz, 1H), 3.57-3.66 (m, 3H), 3.40-3.47 (m, 3H), 3.10-3.27 (m, 2H), 2.36 (t, J=5.0 Hz, 4H), 1.98-2.00 (m, 1H); MS (ESI+) m/z 505 (M+H)$^+$.

Example 104

1-(2-{4-[bis(4-fluorophenyl)methyl]piperazin-1-yl}-2-oxoethyl)-4-methyl-3-phenylpiperazin-2-one To a solution of 1-(2-{4-[bis(4-fluorophenyl)methyl]piperazin-1-yl}-2-oxoethyl)-3-phenylpiperazin-2-one (Example 103B, 0.1 g, 0.2 mmol) in methanol was added 30% aqueous formaldehyde solution (0.06 mL, 0.3 mmol) and sodium cyanoborohydride (0.02 g, 0.3 mmol). A few drops of acetic acid were added, and the reaction was stirred at ambient temperature overnight. The reaction mixture was diluted with methylene chloride and washed with aqueous bicarbonate solution. The organic layer was separated, dried over MgSO$_4$, evaporated and chromatographed, eluting with 5% methanol/methylene chloride to yield the title compound. $^1$H NMR (300 MHz, CDCl$_3$) δ ppm 7.37-7.42 (m, 2H), 7.26-7.35 (m, 7H), 6.94-7.01 (m, 4H), 4.22 (d, J=15.3 Hz, 1H), 4.21 (s, 1H), 4.09 (d, J=15.5 Hz, 1H), 3.79 (s, 1H), 3.73-3.83 (m, 1H), 3.60 (t, J=4.7 Hz, 2H), 3.34-3.43 (m, 3H), 3.03 (ddd, J=12.0, 4.2, 2.9 Hz, 1H), 2.78 (ddd, J=12.0, 10.7, 3.9 Hz, 1H), 2.29-2.37 (m, 4H), 2.20 (s, 3H); MS (ESI+) m/z 519 (M+H)$^+$.

The following examples, Examples 105-143, can be prepared by the methodologies described in the preceding Examples and Schemes or by methods familiar to once skilled in the art:

Example 105

1-{2-[[3-(3,5-dimethoxyphenoxy)propyl](methyl)amino]ethyl}-3,3-bis(4-fluorophenyl)pyrrolidin-2-one;

Example 106

1-{2-[[2-hydroxy-3-(quinolin-5-yloxy)propyl](methyl)amino]ethyl}-3,3-bis(4-methoxyphenyl)pyrrolidin-2-one;

Example 107

3,3-bis(4-fluorophenyl)-1-{2-[[2-hydroxy-3-(2-{(E)-2-[3-(methoxymethyl)isoxazol-5-yl]vinyl}phenoxy)propyl](methyl)amino]ethyl}pyrrolidin-2-one;

Example 108

3,3-bis(4-fluorophenyl)-1-{2-[[2-hydroxy-3-(quinolin-5-yloxy)propyl](methyl)amino]ethyl}pyrrolidin-2-one;

Example 109

3,3-bis(4-fluorophenyl)-1-{2-[4-(3,4,5-trimethoxybenzyl)piperazin-1-yl]ethyl}pyrrolidin-2-one;

Example 110

3,3-bis(4-fluorophenyl)-1-{3-[4-(3,4,5-trimethoxybenzyl)piperazin-1-yl]propyl}pyrrolidin-2-one;

Example 111

3,3-bis(4-fluorophenyl)-1-(2-{4-[3-(trifluoromethyl)phenyl]piperazin-1-yl}ethyl)pyrrolidin-2-one;

Example 112

N-{2-[3,3-bis(4-methoxyphenyl)-2-oxopyrrolidin-1-yl]ethyl}benzamide;

Example 113

1-{2-[2,3-dihydro-1H-inden-2-yl(methyl)amino]ethyl}-3,3-bis(4-methoxyphenyl)piperidin-2-one;

Example 114

1-{3-[2,3-dihydro-1H-inden-2-yl(methyl)amino]propyl}-3,3-bis(4-fluorophenyl)pyrrolidin-2-one;

Example 115

1-{2-[[3-(3,5-dimethoxyphenoxy)propyl](methyl)amino]ethyl}-3,3-bis(4-methoxyphenyl)piperidin-2-one;

Example 116

1-{3-[[3-(3,5-dimethoxyphenoxy)propyl](methyl)amino]propyl}-3,3-bis(4-methoxyphenyl)piperidin-2-one;

Example 117

1-{3-[methyl(2-phenylethyl)amino]propyl}-3,3-diphenylpiperidin-2-one;

Example 118

1-{2-[[2-(3,4-dimethoxyphenyl)ethyl](methyl)amino]ethyl}-3,3-diphenylpiperidin-2-one;

Example 119

1-{3-[[2-(3,5-dimethoxyphenyl)ethyl](methyl)amino]propyl}-3,3-bis(4-methoxyphenyl)piperidin-2-one;

Example 120

3,3-bis(4-fluorophenyl)-1-{2-[[2-(3-methoxyphenyl)ethyl](methyl)amino]ethyl}piperidin-2-one;

Example 121

3,3-bis(4-fluorophenyl)-1-{3-[[2-(3-methoxyphenyl)ethyl](methyl)amino]propyl}piperidin-2-one;

Example 122

3,3-bis(4-fluorophenyl)-1-{2-[methyl(2-phenylethyl)amino]ethyl}piperidin-2-one;

Example 123

3,3-bis(4-fluorophenyl)-1-{3-[methyl(2-phenylethyl)amino]propyl}piperidin-2-one;

Example 124

3,3-bis(4-methoxyphenyl)-1-{2-[[2-(3-methoxyphenyl)ethyl](methyl)amino]ethyl}piperidin-2-one;

Example 125

3,3-bis(4-methoxyphenyl)-1-{3-[[2-(3-methoxyphenyl)ethyl](methyl)amino]propyl}piperidin-2-one;

Example 126

1-{2-[[2-(2,4-dimethoxyphenyl)ethyl](methyl)amino]ethyl}-3,3-bis(4-methoxyphenyl)piperidin-2-one;

Example 127

1-{3-[(3,5-dimethoxybenzyl)(methyl)amino]propyl}-3,3-bis(4-methoxyphenyl)piperidin-2-one;

Example 128

3-isopropyl-3-(3-methoxyphenyl)-1-{3-[[2-(3-methoxyphenyl)ethyl](methyl)amino]propyl}piperidin-2-one;

Example 129

1-{3-[[2-(4-fluorophenyl)ethyl](methyl)amino]propyl}-3-isopropyl-3-(3-methoxyphenyl)piperidin-2-one;

Example 130

3-isopropyl-3-(3-methoxyphenyl)-1-{2-[[2-(4-methoxyphenyl)ethyl](methyl)amino]ethyl}piperidin-2-one;

Example 131

1-{3-[4-(3,5-dimethoxybenzyl)piperazin-1-yl]propyl}-3,3-bis(4-methoxyphenyl)piperidin-2-one;

Example 132

1-{2-[4-(3,5-dimethoxybenzyl)piperazin-1-yl]ethyl}-3,3-bis(4-methoxyphenyl)piperidin-2-one;

Example 133

1-{3-[4-(3,5-dimethoxybenzyl)piperazin-1-yl]propyl}-3-isopropyl-3-(3-methoxyphenyl)piperidin-2-one;

Example 134

3,3-diphenyl-1-[2-(4-pyrimidin-2-ylpiperazin-1-yl)ethyl]piperidin-2-one;

Example 135

3,3-bis(4-fluorophenyl)-1-[3-(4-pyrimidin-2-ylpiperazin-1-yl)propyl]piperidin-2-one;

Example 136

3,3-bis(4-fluorophenyl)-1-[2-(4-pyrimidin-2-ylpiperazin-1-yl)ethyl]piperidin-2-one;

Example 137

3,3-bis(4-fluorophenyl)-1-{2-[4-(2-methoxyphenyl)piperazin-1-yl]ethyl}piperidin-2-one;

Example 138

3,3-bis(4-fluorophenyl)-1-{3-[4-(2-methoxyphenyl)piperazin-1-yl]propyl}piperidin-2-one;

Example 139

3,3-bis(4-fluorophenyl)-1-(2-{4-[3-(trifluoromethyl)phenyl]piperazin-1-yl}ethyl)piperidin-2-one;

Example 140

3,3-diphenyl-1-(3-{4-[3-(trifluoromethyl)phenyl]piperazin-1-yl}propyl)piperidin-2-one;

Example 141

3,3-diphenyl-1-(2-{4-[3-(trifluoromethyl)phenyl]piperazin-1-yl}ethyl)piperidin-2-one;

Example 142

3,3-bis(4-fluorophenyl)-1-(3-{4-[3-(trifluoromethyl)phenyl]piperazin-1-yl}propyl)piperidin-2-one; and

Example 143

N-[2-(3,4-dimethoxyphenyl)ethyl]-N-methyl-2-(2-oxo-3,3-diphenylpiperidin-1-yl)acetamide

Example 144

3,3-diphenyl-1-{[3-(trifluoromethyl)phenyl]sulfonyl}pyrrolidin-2-one

To a solution of 3,3-diphenylpyrrolidin-2-one (Example 1A, 0.237 g, 1.0 mmol) dissolved in tetrahydrofuran (10 mL) was added potassium t-butoxide (1.0 M in tetrahydrofuran, 1.5 mL, 1.5 mmol) under nitrogen. The reaction mixture was stirred for 15 minutes, and then 3-(trifluoromethyl)benzene-1-sulfonyl chloride (0.294 g, 1.2 mmol) was added. The reaction mixture was stirred for 4 hours at room temperature. The reaction mixture was concentrated and then diluted with ethyl acetate and water. The organic layer was separated, washed with water and brine, dried over magnesium sulfate, filtered, and concentrated. Silica gel chromatography (Analogix®, Burlington, Wis.) eluting with ethyl acetate/hexane (40:60) gave the title compound. $^1$H NMR (300 MHz, DMSO-$d_6$) δ ppm 8.26-8.12 (m, 3H), 7.87 (t, J=7.8, 1H), 7.28-7.16 (m, 6H), 7.08-6.98 (m, 4H), 3.82 (t, J=6.4, 2H), 2.90 (t, J=6.4, 2H); MS (DCI) m/z 446.0 (M+H)$^+$.

Example 145

3,3-bis(4-fluorophenyl)-1-{[3-(trifluoromethyl)phenyl]sulfonyl}pyrrolidin-2-one

The title compound was prepared using the procedure described in Example 144 substituting 3,3-bis(4-fluorophenyl)pyrrolidin-2-one from Example 58B for 3,3-diphenylpyrrolidin-2-one. $^1$H NMR (300 MHz, DMSO-$d_6$) δ ppm 8.31-8.06 (m, 3H), 7.87 (t, J=7.9, 1H), 7.19-6.96 (m, 8H), 3.83 (t, J=6.4, 2H), 2.89 (t, J=6.4, 2H); MS (DCI) m/z 482.0 (M+H)$^+$.

Example 146

3,3-diphenyl-1-{[3-(trifluoromethyl)phenyl]sulfonyl}piperidin-2-one

The title compound was prepared using the procedure described in Example 144 substituting 3,3-diphenylpiperidin-2-one from Example 68C for 3,3-diphenylpyrrolidin-2-one. $^1$H NMR (300 MHz, DMSO-$d_6$) δ ppm 8.37-8.13 (m, 3H), 7.91 (t, J=7.9, 1H), 7.32-7.17 (m, 6H), 6.96-6.85 (m, 4H), 3.99 (t, J=6.4, 2H), 2.66 (dd, J=4.9, 7.2, 2H), 1.93-1.74 (m, 2H); MS (DCI) m/z 460.1 (M+H)$^+$.

Example 147

1-[(3-{[cis-2,6-dimethylmorpholin-4-yl]carbonyl}phenyl)sulfonyl]-3,3-diphenylpyrrolidin-2-one

Example 147A 3-((2S,6R)-2,6-dimethylmorpholine-4-carbonyl)benzene-1-sulfonyl chloride To 3-(chlorosulfonyl)benzoyl chloride (0.167 g 0.7 mmol) in anhydrous dichloromethane (15 mL) was added (3S,5R)-3,5-dimethylmorpholine (0.081 g, 0.7 mmol) in dichloromethane (4 mL) dropwise over 5 minutes at room temperature. Then triethylamine (0.071 g, 0.7 mmol) in dichloromethane (2 mL) was added dropwise. The mixture was stirred at room temperature for 1.5 hours, then concentrated, and used without purification.

Example 147B

1-[(3-{[cis-2,6-dimethylmorpholin-4-yl]carbonyl}phenyl)sulfonyl]-3,3-diphenylpyrrolidin-2-one To 3,3-diphenylpyrrolidin-2-one (166 mg, 0.7 mmol; Example 1A) in anhydrous tetrahydrofuran (6 mL) was added potassium tert-butoxide (1 mL, 1.0 M in tetrahydrofuran) at room temperature followed by stirring for 30 minutes. Then the crude 3-((2S,6R)-2,6-dimethylmorpholine-4-carbonyl)benzene-1-sulfonyl chloride (0.7 mmol; Example 147A) in tetrahydrofuran (8 mL) was added slowly. The mixture was stirred at room temperature for 3 hours. Then the mixture was concentrated. The residue was purified by chromatography on silica gel (hexane/ethyl acetate=1:1) to give crude material. The crude material was dissolved in ether (60 mL), the insoluble solid was removed, and the ether solution was concentrated to give the titled compound. $^1$H NMR (400 MHz, DMSO-$d_6$) δ ppm 0.90 (m, 3H), 1.10 (m, 3H), 2.83 (m, 3H), 3.30-3.60 (m, 4H), 3.80 (m, 2H), 4.37 (m, 1H), 7.00 (m, 4H), 7.20 (m, 6H), 7.71 (t, 1H, J=7 Hz), 7.88 (m, 1H), 8.00 (m, 2H); MS (ESI) m/z 519 (M+H)$^+$.

Example 148

3,3-diphenyl-1-{[2-(trifluoromethyl)phenyl]sulfonyl}pyrrolidin-2-one

The title compound was prepared using the procedure described in Example 144 substituting 2-(trifluoromethyl)benzene-1-sulfonyl chloride for 3-(trifluoromethyl)benzene-1-sulfonyl chloride. $^1$H NMR (300 MHz, CDCl$_3$) δ ppm 8.67-8.58 (m, 1H), 7.85 (dt, J=3.3, 7.9, 1H), 7.79-7.71 (m, 2H), 7.30-7.12 (m, 10H), 3.92 (t, J=6.4, 2H), 2.83 (t, J=6.3, 2H); MS (DCI) m/z 446.0 (M+H)$^+$.

Example 149

3,3-diphenyl-1-{[4-(trifluoromethyl)phenyl]sulfonyl}pyrrolidin-2-one

The title compound was prepared using the procedure described in Example 144 substituting 4-(trifluoromethyl)benzene-1-sulfonyl chloride for 3-(trifluoromethyl)benzene-1-sulfonyl chloride. $^1$H NMR (300 MHz, CDCl$_3$) δ ppm 8.07 (d, J=8.3, 2H), 7.72 (d, J=8.4, 2H), 7.22-7.13 (m, 6H), 7.05 (dt, J=3.4, 4.6, 4H), 3.83 (t, J=6.4, 2H), 2.81 (t, J=6.4, 2H); MS (DCI) m/z 446.0 (M+H)$^+$.

Example 150

N-cyclopropyl-3-[(2-oxo-3,3-diphenylpyrrolidin-1-yl)sulfonyl]benzamide

The title compound was prepared using the procedure described in Example 147 substituting cyclopropanamine for (3S,5R)-3,5-dimethylmorpholine. $^1$H NMR (400 MHz, DMSO-$d_6$) δ ppm 0.60 (m, 2H), 0.72 (m, 2H), 2.88 (m, 3H), 3.80 (m, 2H), 7.01 (m, 4H), 7.21 (m, 6H), 7.70 (t, 1H, J=7 Hz), 8.04 (d, 1H, J=7 Hz), 8.20 (d, 1H, J=7 Hz), 8.55 (s, 1H), 8.77 (br s, 1H); MS (ESI) m/z 461 (M+H)+.

Example 151

1-{[2-chloro-4-(trifluoromethyl)phenyl]sulfonyl}-3,3-diphenylpyrrolidin-2-one

The title compound was prepared using the procedure described in Example 144 substituting 2-chloro-4-(trifluoromethyl)benzene-1-sulfonyl chloride for 3-(trifluoromethyl)benzene-1-sulfonyl chloride. $^1$H NMR (300 MHz, CDCl$_3$) δ ppm 8.48 (d, J=8.4, 1H), 7.72 (d, J=7.8, 2H), 7.37-7.11 (m, 10H), 4.06 (t, J=6.4, 2H), 2.91 (t, J=6.4, 2H); MS (DCI) m/z 480.0 (M+H)+.

Example 152

1-[2-(7-benzyl-2,7-diazaspiro[3.5]non-2-yl)-2-oxoethyl]-3,3-bis(4-fluorophenyl)pyrrolidin-2-one 7-Benzyl-2,7-diazaspiro[3.5]nonane (0.237 g, 0.749 mmol), 2-(3,3-bis(4-fluorophenyl)-2-oxopyrrolidin-1-yl)acetic acid (0.248 g, 0.749 mmol; Example 58D), N$^1$-((ethylimino)methylene)-N$^3$,N$^3$-dimethylpropane-1,3-diamine (0.199 mL, 1.123 mmol) and N-methylmorpholine (0.247 mL, 2.247 mmol) were stirred together in dichloromethane (2 mL). After stirring overnight, the reaction was diluted with dichloromethane (20 mL) and washed with 1 N HCl (10 mL) and brine (10 mL), dried over magnesium sulfate and concentrated. The residue was loaded onto a GraceResolv™ 40 g silica gel column (Grace Davison Discovery Sciences) and the title compound eluted with a gradient of 0.4% methanol/dichloromethane containing 0.2 N NH$_3$ to 6% methanol/dichloromethane containing 0.2 N NH$_3$ (Flow=40 mL/minute) over 40 minutes. $^1$H NMR (300 MHz, CDCl$_3$) δ 7.39-7.15 (m, 9H), 6.99 (t, J=8.2, 4H), 3.97 (s, 2H), 3.72 (d, J=20.0, 4H), 3.53 (t, J=6.5, 2H), 3.46 (s, 2H), 2.75 (t, J=6.4, 2H), 2.32 (s, 4H), 1.73 (s, 4H); MS (ESI+) m/z 530.2 (M+H)+.

Example 153

3,3-bis(4-fluorophenyl)-1-(2-oxo-2-{7-[4-(trifluoromethyl)benzyl]-2,7-diazaspiro[3.5]non-2-yl}ethyl)pyrrolidin-2-one Example 153A 3,3-bis(4-fluorophenyl)-1-(2-oxo-2-(2,7-diazaspiro[3.5]nonan-2-yl)ethyl)pyrrolidin-2-one 1-(2-(7-Benzyl-2,7-diazaspiro[3.5]nonan-2-yl)-2-oxoethyl)-3,3-bis(4-fluorophenyl)pyrrolidin-2-one (Example 152, 0.185 g, 0.349 mmol) and ethanol (20 mL) were added to 20% Pd(OH)$_2$—C, wet (0.037 g, 0.263 mmol) in a 50 mL pressure bottle and stirred for 1 hour at 30 psi and 50° C. The mixture was filtered through a nylon membrane and concentrated to give the title compound.

Example 153B 3,3-bis(4-fluorophenyl)-1-(2-oxo-2-{7-[4-(trifluoromethyl)benzyl]-2,7-diazaspiro[3.5]non-2-yl}ethyl)pyrrolidin-2-one To 3,3-bis(4-fluorophenyl)-1-(2-oxo-2-(2,7-diazaspiro[3.5]nonan-2-yl)ethyl)pyrrolidin-2-one (0.050 g, 0.114 mmol; Example 153A) and 1-(bromomethyl)-4-(trifluoromethyl)benzene (0.030 g, 0.125 mmol) in dichloromethane (0.5 mL) was added N-ethyl-N-isopropylpropan-2-amine (0.030 mL, 0.171 mmol), and the reaction was heated to 40° C. for 1 hour. The reaction was cooled, loaded onto a GraceResolv™ 12 g silica gel column (Grace Davison Discovery Sciences), and the title compound eluted with a gradient of 0.8% methanol/dichloromethane containing 0.2 N NH$_3$ to 5.6% methanol/dichloromethane containing 0.2 N NH$_3$ (Flow=25 mL/minute) over 30 minutes. $^1$H NMR (300 MHz, CDCl$_3$) δ 7.57 (d, J=8.1, 2H), 7.42 (d, J=8.0, 2H), 7.34-7.27 (m, 4H), 7.04-6.94 (m, 4H), 3.97 (s, 2H), 3.72 (d, J=19.3, 4H), 3.52 (dd, J=5.5, 12.0, 4H), 2.75 (t, J=6.5, 2H), 2.31 (s, 4H), 1.74 (d, J=4.9, 4H); MS (ESI+) m/z 598.2 (M+H)+.

Example 154

1-{[3-(1H-indazol-5-yl)-1,2,4-oxadiazol-5-yl]methyl}-3,3-diphenylpiperidin-2-one (Z)—N-hydroxy-1H-indazole-5-carboximidamide (0.055 g, 0.312 mmol), N$^1$-((ethylimino)methylene)-N$^3$,N$^3$-dimethylpropane-1,3-diamine hydrochloride (0.120 g, 0.624 mmol) and 2-(2-oxo-3,3-diphenylpiperidin-1-yl)acetic acid (0.097 g, 0.312 mmol; Example 68E) were stirred together in dichloroethane (1 mL) at room temperature for 20 minutes. N,N-Dimethylformamide (0.2 mL) was added and stirring was continued for 2 hours and a dark solution resulted. The reaction was heated to 85° C. and stirred overnight. The reaction was cooled, concentrated, loaded onto a GraceResolv™ 4 g silica gel column (Grace Davison Discovery Sciences) and the product eluted with a gradient of 5% ethyl acetate/hexanes to 75% ethyl acetate/hexanes (Flow=18 mL/minute) over 30 minutes. The material obtained was subjected to a second chromatography on a GraceResolv™ 4 g silica gel column (Grace Davison Discovery Sciences) and the product eluted with a gradient of 0.5% methanol/dichloromethane to 7.5% methanol/dichloromethane (Flow=18 mL/minute) over 30 minutes to give the title compound. $^1$H NMR (300 MHz, DMSO-d$_6$) δ 8.52 (s, 1H), 8.30 (s, 1H), 8.01 (dd, J=1.2, 8.8, 1H), 7.75 (d, J=8.7, 1H), 7.45-7.07 (m, 10H), 4.92 (s, 2H), 3.66 (t, J=6.3, 2H), 2.76-2.57 (m, 2H), 1.78 (s, 2H).

Example 155

3,3-diphenyl-1-(3-{3-[4-(trifluoromethyl)phenyl]-1,2,4-oxadiazol-5-yl}propyl)pyrrolidin-2-one Example 155A 4-(2-oxo-3,3-diphenylpyrrolidin-1-yl)butanoic acid To a suspension of 3,3-diphenylpyrrolidin-2-one (2.00 g, 8.43 mmol; Example 1A) in tetrahydrofuran (10 mL) was added potassium 2-methylpropan-2-olate (9.27 mL, 9.27 mmol). After stirring for 30 minutes, the reaction was a suspension so the reaction was heated to 40° C. The reaction was cooled to ambient temperature, and then tert-butyl 4-bromobutanoate (2.068 g, 9.27 mmol) as a solution in tetrahydrofuran (3 mL) was added. The reaction was stirred for 3 hours, then poured into ethyl acetate/1 N HCl (1:1, 300 mL). The organic layer was separated, washed with brine (100 mL), dried over magnesium sulfate and concentrated. The residue was loaded onto a GraceResolv™ 40 g silica gel column (Grace Davison Discovery Sciences) and the product eluted with a gradient of 5% ethyl acetate/hexanes to 40% ethyl acetate/hexanes (Flow=40 mL/minute) over 30 minutes. The product was dissolved in 5 mL of dichloromethane then 5 mL of trifluoroacetic acid was added. After stirring for 3 hours, the reaction was concentrated to give the title compound. $^1$H NMR (300 MHz, CDCl$_3$) δ 7.36-7.22 (m, 10H), 3.45 (m, 4H), 2.79 (t, J=6.5, 2H), 2.31 (t, J=7.1, 2H), 1.89 (p, J=7.0, 2H); MS (ESI+) m/z 324.0 (M+H)$^+$.

Example 155B 3,3-diphenyl-1-(3-{3-[4-(trifluoromethyl)phenyl]-1, 2,4-oxadiazol-5-yl}propyl)pyrrolidin-2-one A suspension of (Z)—N-hydroxy-4-(trifluoromethyl)benzimidamide (0.233 g, 1.143 mmol), 4-(2-oxo-3,3-diphenylpyrrolidin-1-yl)butanoic acid (0.336 g, 1.039 mmol) and N$^1$-((ethylimino)methylene)-N$^3$,N$^3$-dimethylpropane-1,3-diamine hydrochloride (0.299 g, 1.559 mmol) were stirred together in dichloroethane (5 mL) for 3 hours then heated to 85° C. for 18 hours. The reaction was cooled and concentrated. The reaction was loaded onto a GraceResolv™ 40 g silica gel column (Grace Davison Discovery Sciences) and the product eluted with a gradient of 5% ethyl acetate/hexanes to 4% ethyl acetate/hexanes (Flow=40 mL/minute) over 40 minutes to give the title compound. $^1$H NMR (300 MHz, CDCl$_3$) δ 8.17 (d, J=8.0, 2H), 7.73 (d, J=8.2, 2H), 7.38-7.20 (m, 10H), 3.56 (t, J=7.0, 2H), 3.41 (t, J=6.4, 2H), 2.92 (t, J=7.6, 2H), 2.77 (t, J=6.4, 2H), 2.22-2.09 (m, 2H); MS (ESI+) m/z 492.1 (M+H)$^+$.

Example 156

1-({4-methyl-2-[4-(trifluoromethyl)phenyl]-1,3-thiazol-5-yl}methyl)-3,3-diphenylpyrrolidin-2-one To a solution of 3,3-diphenylpyrrolidin-2-one (Example 1A) (0.062 g, 0.262 mmol) in N,N-dimethylformamide (2 mL) was added 60% sodium hydride dispersion in oil (0.013 g, 0.314 mmol). The mixture was stirred at room temperature for 1 hour. Then a solution of 5-(bromomethyl)-4-methyl-2-(4-(trifluoromethyl)phenyl)thiazole (CAS 439134-78-8) (0.088 g, 0.262 mmol) in N,N-dimethylformamide (1 mL) was added, and the mixture was stirred at room temperature overnight. The reaction mixture was concentrated and the residue was partitioned between H$_2$O and dichloromethane. The organic layer was separated, dried over MgSO$_4$ and concentrated. The obtained residue was purified by silica gel chromatography eluting with 2-5% methanol/dichloromethane to yield the title compound. $^1$H NMR (300 MHz, CDCl$_3$) δ ppm 7.95-8.00 (m, 2H), 7.65-7.70 (m, 2H), 7.17-7.37 (m, 10H), 4.72 (s, 2H), 3.35 (t, J=6.4 Hz, 2H), 2.76 (t, J=6.3 Hz, 2H), 2.47 (s, 3H); MS (ESI+) m/z 493 (M+H)$^+$.

Example 157

1-({4-methyl-2-[3-(trifluoromethyl)phenyl]-1,3-thiazol-5-yl}methyl)-3,3-diphenylpyrrolidin-2-one Example 157A 5-(bromomethyl)-4-methyl-2-(3-(trifluoromethyl) phenyl)thiazole To a solution of {4-methyl-2-[3-(trifluoromethyl)phenyl]-1,3-thiazol-5-yl}methanol (90.2 g, 0.732 mmol) in dichloromethane (10 mL) was added carbon tetrabromide (0.485 g, 1.464 mmol) and triphenylphosphine (0.384 g, 1.464 mmol). The reaction mixture was then stirred at room temperature for 16 hours. The reaction mixture was concentrated, and the residue was chromatographed on silica gel eluting with 10-20% ethyl acetate/hexane to yield the title compound. $^1$H NMR (300 MHz, CDCl$_3$) δ ppm 8.18 (s, 1H), 8.06 (d, J=7.54 Hz, 1H), 7.67 (d, 1H), 7.56 (t, J=7.73 Hz, 1H), 4.72 (m, 2H), 2.48 (m, 3H).

Example 157B 1-({4-methyl-2-[3-(trifluoromethyl)phenyl]-1,3-thiazol-5-yl}methyl)-3,3-diphenylpyrrolidin-2-one The title compound was obtained by the procedure described in Example 156, replacing 5-(bromomethyl)-4-methyl-2-(4-(trifluoromethyl)phenyl)thiazole with 5-(bromomethyl)-4-methyl-2-(3-(trifluoromethyl)phenyl)thiazole (Example 156A). $^1$H NMR (300 MHz, CDCl$_3$) δ ppm 8.09-8.11 (bs, 1H), 8.00 (d, J=8.5 Hz, 1H), 7.65 (d, J=7.3 Hz, 1H), 7.54 (t, J=7.8 Hz, 1H), 7.21-7.38 (m, 10H), 4.71 (s, 2H), 3.35 (t, J=6.5 Hz, 2H), 2.76 (t, J=6.4 Hz, 2H), 2.45 (s, 3H); MS (ESI+) m/z 493 (M+H)$^+$.

Example 158

1-{2-[4-(4-chlorophenoxy)piperidin-1-yl]-2-oxoethyl}-3,3-diphenylpiperidin-2-one To a solution of the product of Example 68E (117 mg, 0.38 mmol), 4-(4-chlorophenoxy)piperidine (80.0 mg, 0.378 mmol), and 4-(dimethylamino)pyridine (4.6 mg, 0.038 mmol) in CH$_2$Cl$_2$ (2 mL) was added N$^1$-((ethylimino)methylene)-N$^3$,N$^3$-dimethylpropane-1,3-diamine (0.067 mL, 0.378 mmol) via syringe. The reaction was stirred at ambient temperature for 45 hours. The reaction mixture was diluted with 50 mL CH$_2$Cl$_2$, then washed with 1 N aqueous HCl, saturated aqueous NaHCO$_3$ solution and brine, dried with Na$_2$SO$_4$, filtered, and concentrated in vacuo. The crude product was purified by chromatography on silica gel (Analogix® Intelliflash™ 280; SF15-24 g column; 50% ethyl acetate/hexanes) which yielded the title compound. $^1$H NMR (300 MHz, CDCl$_3$) δ ppm 7.36-7.17 (m, 12H), 6.86-6.80 (m, 2H), 4.55-4.45 (m, 1H), 4.40 (d, J=15.6, 1H), 4.09 (d, J=15.6, 1H), 3.80-3.33 (m, 6H), 2.72-2.57 (m, 2H), 2.00-1.74 (m, 6H); MS (ESI$^+$) m/z 503 (M+H)$^+$.

Example 159

1-{2-[4-(3-chlorophenoxy)piperidin-1-yl]-2-oxoethyl}-3,3-diphenylpiperidin-2-one The title compound was obtained by the procedure described in Example 158, replacing 4-(4-chlorophenoxy) piperidine with 4-(3-chlorophenoxy)piperidine and shortening the reaction time to 18 hours. $^1$H NMR (300 MHz, CDCl$_3$) δ ppm 7.36-7.15 (m, 11H), 6.94 (ddd, J=7.9, 1.8, 0.7, 1H), 6.90 (t, J=2.1, 1H), 6.81-6.76 (m, 1H), 4.57-4.47 (m, 1H), 4.41 (d, J=15.6, 1H), 4.10 (d, J=15.7, 1H), 3.83-3.33 (m, 6H), 2.73-2.57 (m, 2H), 2.01-1.75 (m, 6H); MS (ESI$^+$) m/z 503 (M+H)$^+$.

Example 160

1-{2-[4-(3,4-difluorophenoxy)piperidin-1-yl]-2-oxoethyl}-3,3-diphenylpiperidin-2-one To a mixture of the product of Example 68E (225 mg, 0.73 mmol), 4-(3,4-difluorophenoxy)piperidine (155 mg, 0.73 mmol), and 4-(dimethylamino)pyridine (8.9 mg, 0.07 mmol) in CH$_2$Cl$_2$ (3 mL) at ambient temperature was added N$^1$-((ethylimino)methylene)-N$^3$,N$^3$-dimethylpropane-1,3-diamine (0.129 mL, 0.727 mmol) via syringe. The reaction was stirred for 18 hours, then diluted with 50 mL CH$_2$Cl$_2$ and washed with 1 N aqueous HCl, saturated aqueous NaHCO$_3$ solution and brine, dried with Na$_2$SO$_4$, filtered, and concentrated in vacuo. The crude product was purified by chromatography on silica gel (Analogix® Intelliflash™ 280; SF15-24 g column; 50% ethyl acetate/hexanes). Hexanes (20 mL) were added and the flask was placed in an ultrasonic bath for 10 minutes resulting in a milky mixture. Ether (6 mL) was added to help precipitate the solid, which was collected by vacuum filtration and air-dried to give the titled compound. $^1$H NMR (300 MHz, CDCl$_3$) δ ppm 7.39-7.15 (m, 10H), 7.06 (dd, J=19.1, 9.1, 1H), 6.72 (ddd, J=11.9, 6.6, 3.0, 1H), 6.64-6.55 (m, 1H), 4.49-4.32 (m, 2H), 4.11 (d, J=15.6, 1H), 3.80-3.33 (m, 6H), 2.73-2.56 (m, 2H), 2.01-1.72 (m, 6H); MS (ESI$^+$) m/z 505 (M+H)$^+$.

Example 161

1-{2-[4-(4-methoxyphenoxy)piperidin-1-yl]-2-oxoethyl}-3,3-diphenylpiperidin-2-one The title compound was obtained by the procedure described in Example 159, replacing 4-(3-chlorophenoxy)piperidine with 4-(4-methoxyphenoxy)piperidine. $^1$H NMR (300 MHz, CDCl$_3$) δ ppm 7.37-7.16 (m, 10H), 6.89-6.79 (m, 4H), 4.48-4.34 (m, 2H), 4.09 (d, J=16.0, 1H), 3.81-3.31 (m, 6H), 3.77 (s, 3H), 2.73-2.56 (m, 2H), 1.99-1.73 (m, 6H); MS (ESI$^+$) m/z 499 (M+H)$^+$.

Example 162

1-(2-oxo-2-{4-[3-(trifluoromethyl)phenoxy]piperidin-1-yl}ethyl)-3,3-diphenylpiperidin-2-one The title compound was obtained by the procedure described in Example 159, replacing 4-(3-chlorophenoxy)piperidine with 4-(3-(trifluoromethyl)phenoxy)piperidine. $^1$H NMR (300 MHz, CDCl$_3$) δ ppm 7.39 (t, J=8.0, 1H), 7.35-7.17 (m, 11H), 7.14-7.11 (m, 1H), 7.07 (dd, J=8.3, 2.5, 1H), 4.64-4.54 (m, 1H), 4.41 (d, J=15.6, 1H), 4.11 (d, J=15.8, 1H), 3.83-3.36 (m, 6H), 2.70-2.60 (m, 2H), 2.02-1.78 (m, 6H); MS (ESI$^+$) m/z 537 (M+H)$^+$.

Example 163

1-(2-{4-[(benzyloxy)imino]piperidin-1-yl}-2-oxoethyl)-3,3-diphenylpiperidin-2-one Example 163A Piperidin-4-one O-benzyl oxime A solution of tert-butyl 4-oxopiperidine-1-carboxylate (524 mg, 2.63 mmol) and O-benzylhydroxylamine hydrochloride (504 mg, 3.16 mmol) in pyridine (5 mL) was stirred at ambient temperature for 18 hours. The reaction mixture was concentrated in vacuo and the residue was partitioned between ether and H$_2$O. The separated organic phase was washed with 1 N aqueous HCl and brine, dried over MgSO$_4$, filtered, and concentrated in vacuo to yield 816 mg of crude N-tert-butoxycarbonyl intermediate. This material was taken up in CH$_2$Cl$_2$ (5 mL), followed by addition of trifluoroacetic acid (5.0 mL, 65.0 mmol) via syringe. After stirring for 30 minutes at ambient temperature, the reaction was cooled to 0° C. and quenched by slow addition of 2 N aqueous NaOH solution (35 mL). The mixture was diluted with 75 mL CH$_2$Cl$_2$ and the phases were separated. The organic layer was washed with 1 N aqueous NaOH solution and brine, dried over Na$_2$SO$_4$, filtered, and concentrated in vacuo to give the title compound. $^1$H NMR (300 MHz, CDCl$_3$) δ ppm 7.39-7.27 (m, 5H), 5.07 (s, 2H), 3.02-2.94 (m, 2H), 2.94-2.86 (m, 2H), 2.63-2.54 (m, 2H), 2.33-2.23 (m, 2H), 1.58 (bs, 1H); MS (DCI$^+$) m/z 205 (M+H)$^+$.

Example 163B 1-(2-{4-[(benzyloxy)imino]piperidin-1-yl}-2-oxoethyl)-3,3-diphenylpiperidin-2-one The title compound was obtained by the procedure described in Example 159, replacing 4-(3-chlorophenoxy)piperidine with the product of Example 163A. $^1$H NMR (300 MHz, CDCl$_3$) δ ppm 7.40-7.16 (m, 15H), 5.07 (s, 2H), 4.24 (d, J=3.5, 2H), 3.76-3.66 (m, 2H), 3.62-3.46 (m, 4H), 2.71-2.61 (m, 4H), 2.46-2.38 (m, 2H), 1.91-1.78 (m, 2H); MS (ESI$^+$) m/z 496 (M+H)$^+$.

Example 164

1-(2-oxo-2-{4-[5-(trifluoromethyl)-1H-1,2,3-benzotriazol-1-yl]piperidin-1-yl}ethyl)-3,3-diphenylpiperidin-2-one N$^1$-((Ethylimino)methylene)-N$^3$,N$^3$-dimethylpropane-1,3-diamine (0.132 mL, 0.743 mmol) was added via syringe to a mixture of the product of Example 68E (230 mg, 0.743 mmol), 1-(piperidin-4-yl)-5-(trifluoromethyl)-1H-benzo[d][1,2,3]triazole (201 mg, 0.743 mmol), and 4-(dimethylamino)pyridine (9.1 mg, 0.07 mmol) in CH$_2$Cl$_2$ (3 mL). The reaction was allowed to proceed at ambient temperature for 23 hours. The reaction mixture was diluted with CH$_2$Cl$_2$ (50 mL) and washed with 1 N aqueous HCl, saturated aqueous NaHCO$_3$ solution and brine, dried with Na$_2$SO$_4$, filtered, and concentrated in vacuo. The crude product was purified by chromatography on silica gel (Analogix® Intelliflash™ 280; SF15-24 g column; 50%-100% ethyl acetate/hexanes, 0-20 minutes, 30 mL/minute) to yield an amorphous solid which was triturated with 12 mL 1:1 ether/hexanes and 2 mL ether. The solid was collected by vacuum filtration and air-dried to afford the title compound. $^1$H NMR (300 MHz, CDCl$_3$) δ ppm 8.37 (s, 1H), 7.73 (d, J=8.7, 1H), 7.51 (d, J=8.4, 1H), 7.39-7.14 (m, 10H), 5.10-4.95 (m, 1H), 4.82-4.66 (m, 1H), 4.34 (d, J=15.1, 1H), 4.27-4.06 (m, 2H), 3.71-3.50 (m, 2H), 3.46-3.29 (m, 1H), 3.14-2.94 (m, 1H), 2.73-2.63 (m, 2H), 2.64-2.47 (m, 1H), 2.44-2.14 (m, 3H), 1.96-1.82 (m, 2H). MS (ESI$^+$) m/z 562 (M+H)$^+$.

Example 165

1-({3-[2-(4-chlorophenyl)ethyl]-1,2,4-oxadiazol-5-yl}methyl)-3,3-bis(4-fluorophenyl)pyrrolidin-2-one Example 165A (Z)-3-(4-chlorophenyl)-N-hydroxypropanimidamide A mixture of 3-(4-chlorophenyl)propanenitrile (1.45 g, 8.76 mmol), hydroxylamine hydrochloride (0.913 g, 13.1 mmol), and sodium hydrogencarbonate (3.68 g, 43.8 mmol) in methanol (15 mL) was heated to reflux for 18 hours. The cooled reaction mixture was filtered and the filter cake was washed with $CH_2Cl_2$. The filtrate was diluted with $CH_2Cl_2$ (75 mL) and washed with water and brine, dried over $Na_2SO_4$, filtered, and concentrated in vacuo. The crude product was triturated with 5 mL 1:1 ethyl acetate/hexanes and 10 mL pure hexanes, and the resulting solid was collected by vacuum filtration, washed with hexanes, and air-dried to yield the title compound. $^1H$ NMR (300 MHz, DMSO-$d_6$) δ ppm 8.72 (s, 1H), 7.35-7.28 (m, 2H), 7.28-7.20 (m, 2H), 5.40 (bs, 2H), 2.83-2.74 (m, 2H), 2.27-2.18 (m, 2H); MS (DCI$^+$) m/z 199 (M+H)$^+$.

Example 165B 1-({3-[2-(4-chlorophenyl)ethyl]-1,2,4-oxadiazol-5-yl}methyl)-3,3-bis(4-fluorophenyl)pyrrolidin-2-one To a solution of the product of Example 58D (225 mg, 0.679 mmol) and the product of Example 165A (135 mg, 0.679 mmol) in 1,4-dioxane (4 mL) was added $N^1$-((ethylimino)methylene)-$N^3$,$N^3$-dimethylpropane-1,3-diamine (0.120 mL, 0.679 mmol) via syringe. The reaction was stirred at ambient temperature for 2.5 hours, then heated to 60° C. for 44 hours. The reaction was cooled to ambient temperature, diluted with ethyl acetate, and washed with 3 N aqueous HCl resulting in a homogeneous solution. Brine was added to force the phase separation. The organic layer was separated and washed with saturated aqueous $NaHCO_3$ solution and brine, dried over $Na_2SO_4$, filtered, and concentrated in vacuo. Chromatography on silica gel (Analogix® Intelliflash™ 280; SF15-24 g column; 50% ethyl acetate/hexanes) yielded the title compound. $^1H$ NMR (300 MHz, CDCl$_3$) δ ppm 7.36-7.27 (m, 4H), 7.27-7.21 (m, 2H), 7.15-7.07 (m, 2H), 7.07-6.96 (m, 4H), 4.79 (s, 2H), 3.46 (t, J=6.4, 2H), 3.00 (s, 4H), 2.80 (t, J=6.4, 2H); MS (ESI$^+$) m/z 511 (M+NH4)$^+$.

Example 166

2-(2-oxo-3,3-diphenylpiperidin-1-yl)-N-piperidin-4-yl-N-[4-(trifluoromethyl)phenyl]acetamide Example 166A tert-butyl 4-(4-(trifluoromethyl)phenylamino)piperidine-1-carboxylate A solution of 4-(trifluoromethyl)aniline (0.772 mL, 6.21 mmol) and tert-butyl 4-oxopiperidine-1-carboxylate (2.47 g, 12.4 mmol) in acetic acid (30 mL) was treated with anhydrous $Na_2SO_4$ powder (8.82 g, 62.1 mmol). The mixture was stirred at ambient temperature for 20 minutes, and then sodium triacetoxyborohydride (3.95 g, 18.6 mmol) was added in approximately 5 equal portions over 2 minutes. The reaction was allowed to proceed at ambient temperature for 3 hours. The reaction mixture was carefully poured into a well-stirred mixture of 1:1 ethyl acetate/hexanes (100 mL) and saturated $NaHCO_3$ solution (150 mL), and then basified with excess 2 N aqueous NaOH solution. The phases were separated, and the organic layer was washed with water and brine, dried over $Na_2SO_4$, filtered, and concentrated in vacuo. The crude product was triturated with hexanes and the solid was collected by vacuum filtration and air-dried to give the title compound. $^1H$ NMR (300 MHz, DMSO-$d_6$) δ ppm 7.35 (d, J=8.6, 2H), 6.69 (d, J=8.6, 2H), 6.25 (d, J=8.0, 1H), 3.95-3.80 (m, 2H), 3.56-3.40 (m, 1H), 3.02-2.81 (m, 2H), 1.94-1.80 (m, 2H), 1.40 (s, 9H), 1.33-1.18 (m, 2H); MS (DCI$^+$) m/z 345 (M+H)$^+$.

Example 166B tert-butyl 4-(2-bromo-N-(4-(trifluoromethyl)phenyl)acetamido)piperidine-1-carboxylate A solution of the product of Example 166A (480 mg, 1.39 mmol) and N-ethyl-N-isopropylpropan-2-amine (0.486 mL, 2.79 mmol) in anhydrous tetrahydrofuran (10 mL) was cooled in an ice water bath for 10 minutes followed by the dropwise addition of bromoacetyl bromide (0.146 mL, 1.67 mmol) via syringe. The reaction was stirred for 30 minutes at 0° C., then 1 hour at ambient temperature and 3 hours at reflux. The reaction mixture was cooled to ambient temperature and diluted with ethyl acetate. The organic solution was washed with 1 N aqueous HCl and saturated $NaHCO_3$ solution and brine, dried with $Na_2SO_4$, filtered, and concentrated in vacuo. The crude product was chromatographed on silica gel (Analogix® Intelliflash™ 280; SF25-60 g column; 50% ethyl acetate/hexanes) which yielded the title compound. $^1H$ NMR (300 MHz, CDCl$_3$) δ ppm 7.74 (d, J=8.4, 2H), 7.34 (d, J=8.2, 2H), 4.80-4.66 (m, 1H), 4.25-4.04 (m, 2H), 3.49 (s, 2H), 2.79 (t, J=12.4, 2H), 1.87-1.77 (m, 2H), 1.39 (s, 9H), 1.29-1.11 (m, 2H); MS (DCI$^+$) m/z 482/484 (M+NH$_4$)$^+$.

Example 166C tert-butyl 4-(2-(2-oxo-3,3-diphenylpiperidin-1-yl)-N-(4-(trifluoromethyl)phenyl)acetamido)piperidine-1-carboxylate A solution of potassium tert-butoxide (1.0 M in tetrahydrofuran, 0.70 mL, 0.70 mmol) was added dropwise via syringe to a suspension of the product of Example 68C (147 mg, 0.587 mmol) in anhydrous tetrahydrofuran (5 mL) at ambient temperature. The reaction mixture was stirred for 45 minutes, and then a solution of the product of Example 166B (273 mg, 0.587 mmol) in 3 mL tetrahydrofuran was added. The reaction was allowed to proceed for 1 hour at ambient temperature, then poured into brine. The product was extracted with ethyl acetate and the combined organic layer was washed with brine, dried over $Na_2SO_4$, filtered, and concentrated in vacuo. The crude product was purified by chromatography on silica gel (Analogix® Intelliflash™ 280; SF15-24 g column; 25%-75% ethyl acetate/hexanes, 0-15 minutes, 30 mL/minute) to afford the title compound. $^1H$ NMR (300 MHz, CDCl$_3$) δ ppm 7.69 (d, J=8.3, 2H), 7.35 (d, J=8.2, 2H), 7.32-7.15 (m, 10H), 4.86-4.72 (m, 1H), 4.24-4.05 (m, 2H), 3.67 (bs, 2H), 3.45 (t, J=6.3, 2H), 2.80 (t, J=12.6, 2H), 2.67-2.55 (m, 2H), 1.90-1.73 (m, 4H), 1.39 (s, 9H), 1.29-1.11 (m, 2H); MS (DCI$^+$) m/z 636 (M+H)$^+$.

Example 166D 2-(2-oxo-3,3-diphenylpiperidin-1-yl)-N-piperidin-4-yl-N-[4-(trifluoromethyl)phenyl]acetamide Trifluoroacetic acid (3.0 mL, 39 mmol) was added to a solution of the product of Example 166C (279 mg, 0.439 mmol) in $CH_2Cl_2$ (3 mL), and the reaction mixture was stirred at ambient temperature for 1 hour. The reaction was then cooled to 0° C., diluted with $CH_2Cl_2$ (25 mL) and quenched by slow addition of 2 N aqueous NaOH solution (25 mL). The mixture was separated and the aqueous phase was extracted with $CH_2Cl_2$. The combined organic layer was washed with brine, dried over $Na_2SO_4$, filtered, and concentrated in vacuo. Ether was added to the residue which caused a solid to form, which was collected by vacuum filtration and washed with minimal ether and air-dried. The material was then chromatographed on silica gel (Analogix® Intelliflash™ 280; SF10-8 g column; 10% methanol/CH$_2$Cl$_2$) to afford the title compound. $^1$H NMR (300 MHz, CDCl$_3$) δ ppm 7.68 (d, J=8.3, 2H), 7.36 (d, J=8.2, 2H), 7.32-7.15 (m, 10H), 4.85-4.69 (m, 1H), 3.68 (s, 2H), 3.45 (t, J=6.4, 2H), 3.17-3.06 (m, 2H), 2.76 (td, J=12.4, 1.9, 2H), 2.66-2.56 (m, 2H), 2.00-1.65 (m, 5H), 1.40-1.21 (m, 2H); MS (DCI$^+$) m/z 536 (M+H)$^+$.

Example 167

1-{2-[3-(3,4-dimethoxybenzyl)-3-methylpiperazin-1-yl]-2-oxoethyl}-3,3-diphenylpyrrolidin-2-one To 2-(3,4-dimethoxybenzyl)-2-methylpiperazine (0.052 g, 0.208 mmol; German Patent No. DE2438725), 2-(2-oxo-3,3-diphenylpyrrolidin-1-yl)acetic acid (0.061 g, 0.208 mmol; Example 1C) and 2-(1H-benzo[d][1,2,3]triazol-1-yl)-1,1,3,3-tetramethylisouronium hexafluorophosphate(V) (0.079 g, 0.208 mmol) in dichloromethane (0.5 mL) was added diisopropylethylamine (0.054 mL, 0.312 mmol) and the reaction stirred overnight. The reaction was loaded onto silica gel and the product eluted using a gradient of 0.5% methanol/dichloromethane to 5% methanol/dichloromethane containing 7 N NH$_3$ over 30 minutes to provide the title compound. MS (ESI+) m/z 528.2 (M+H)$^+$.

Example 168

N-(1,3-oxazol-2-ylmethyl)-2-(2-oxo-3,3-diphenylpyrrolidin-1-yl)acetamide

A solution of N$^1$-((ethylimino)methylene)-N$^3$,N$^3$-dimethylpropane-1,3-diamine hydrochloride (0.049 g, 0.254 mmol), 2-(2-oxo-3,3-diphenylpyrrolidin-1-yl)acetic acid (0.050 g, 0.169 mmol; Example 1C) and oxazol-2-ylmethanamine (0.018 g, 0.186 mmol) were stirred together in dichloromethane (0.5 mL) at room temperature. After stirring overnight, the reaction was loaded directly onto a SF15-12 (Analogix®) column and the product eluted using a gradient of 5% to 100% ethyl acetate/hexanes over 20 minutes (Flow=30 mL/minute) to give the title compound. $^1$H NMR (300 MHz, CDCl$_3$) δ 7.58 (s, 1H), 7.38-7.19 (m, 10H), 7.05 (s, 1H), 6.68 (s, 1H), 4.48 (d, J=5.6, 2H), 4.08 (s, 2H), 3.53 (t, J=6.5, 2H), 2.83 (t, J=6.5, 2H); MS (ESI+) m/z 376.0 (M+H)$^+$.

Example 169

1-{2-[4-(2,4-dichlorobenzyl)piperazin-1-yl]-2-oxoethyl}-3,3-diphenylpiperidin-2-one A solution of 1-(2,4-dichlorobenzyl)piperazine (0.415 g, 1.693 mmol), 2-(2-oxo-3,3-diphenylpiperidin-1-yl)acetic acid (0.498 g, 1.608 mmol; Example 68E) and N$^1$-((ethylimino)methylene)-N$^3$,N$^3$-dimethylpropane-1,3-diamine hydrochloride (0.389 g, 2.031 mmol) were stirred together in dichloroethane (0.5 mL) at room temperature for 2 hours. The reaction was then heated to 85° C. and stirred overnight. The reaction was cooled, loaded onto a SF25-40 column (Analogix®) and the product eluted using a gradient of 5% ethyl acetate/hexanes to 100% ethyl acetate over 30 minutes, then holding at 100% ethyl acetate for 15 minutes (Flow=45 mL/minute) to yield the title compound. $^1$H NMR (300 MHz, CDCl$_3$) δ 7.42-7.36 (m, 2H), 7.32 (s, 11H), 4.23 (s, 2H), 3.65 (s, 2H), 3.57 (s, 2H), 3.49 (dd, J=6.5, 13.6, 4H), 2.72-2.56 (m, 2H), 2.48 (s, 4H), 1.94-1.74 (m, 2H); MS (ESI+) m/z 536.1 (M+H)$^+$.

Example 170

1-{[3-(4-chlorophenyl)-1,2,4-oxadiazol-5-yl]methyl}-3,3-diphenylpiperidin-2-one

A solution of (Z)-4-chloro-N-hydroxybenzimidamide (0.121 g, 0.711 mmol), 2-(2-oxo-3,3-diphenylpiperidin-1-yl) acetic acid (0.200 g, 0.646 mmol; Example 68E) and N$^1$-((ethylimino)methylene)-N$^3$,N$^3$-dimethylpropane-1,3-diamine hydrochloride (0.161 g, 0.840 mmol) were stirred together in dichloroethane (0.5 mL) at room temperature for 2 hours. The reaction was then heated to 85° C. and stirred overnight. The reaction was cooled, loaded onto a SF15-12 column (Analogix®) and the product eluted using a gradient of 5% ethyl acetate/hexanes to 50% ethyl acetate over 20 minutes (Flow=30 mL/minute) to provide the title compound. $^1$H NMR (300 MHz, CDCl$_3$) δ 8.09-8.02 (m, 2H), 7.52-7.45 (m, 2H), 7.33-7.25 (m, 10H), 4.91 (s, 2H), 3.62 (t, J=6.5, 2H), 2.73-2.67 (m, 2H), 1.98-1.85 (m, 2H); MS (ESI+) m/z 444.0 (M+H)$^+$.

Example 171

1-(2-{4-[bis(4-fluorophenyl)methylene]piperidin-1-yl}-2-oxoethyl)-3,3-diphenylpiperidin-2-one To a solution of 2-(2-oxo-3,3-diphenylpiperidin-1-yl)acetic acid (Example 68E) (0.144 g, 0.47 mmol) and 4-(bis(4-fluorophenyl)methylene)piperidine hydrochloride (European Journal of Medicinal Chemistry; 22, 1987; 243-250) (0.15 g, 0.47 mmol) in methylene chloride (10 mL) was added O-(7-azabenzotriazol-1-yl)-N,N,N',N'-tetramethyluronium hexafluorophosphate (0.177 g, 0.47 mmol) and diisopropylethylamine (0.4 mL). The reaction mixture was stirred at ambient temperature overnight. The reaction mixture was then diluted with methylene chloride, and washed with 1 N HCl, water, 1 N NaOH, and water. The organic layer was dried over magnesium sulfate and concentrated in vacuo. The obtained residue was purified by silica gel flash chromatography, eluting with 5% methanol/dichloromethane. $^1$H NMR (300 MHz, CDCl$_3$) δ ppm 7.17-7.33 (m, 10H), 6.96-7.05 (m, 8H), 4.24 (s, 2H), 3.66 (t, J=5.5 Hz, 2H), 3.51 (t, J=6.4 Hz, 2H), 3.42-3.48 (m, 2H), 2.62-2.67 (m, 2H), 2.29-2.42 (m, 4H), 1.75-1.89 (m, 2H); MS (ESI+) m/z 577 (M+H)$^+$.

Example 172

1-[2-(3,3-diphenylpyrrolidin-1-yl)-2-oxoethyl]-3,3-bis(4-fluorophenyl)piperidin-2-one To a solution of 2-(3,3-bis(4-fluorophenyl)-2-oxopiperidin-1-yl)acetic acid (Example 90D, 0.345 g, 1.0 mmol) in dichloromethane (20 mL) under nitrogen was added 3,3-diphenylpyrrolidine (Example 17A, 0.223 g, 1.0 mmol) followed by N$^1$-((ethylimino)methylene)-N$^3$,N$^3$-dimethylpropane-1,3-diamine hydrochloride (0.383 g, 2.0 mmol) and N,N-dimethylpyridin-4-amine (0.012 g, 0.10 mmol). The reaction mixture was stirred overnight at room temperature. The reaction was concentrated and the residue was partitioned in ethyl acetate/water (8:2, 200 mL). The organic layer was washed with water followed by brine, dried over magnesium sulfate, filtered and concentrated. Silica gel chromatography (Analogix®, Burlington, Wis.) eluting with ethyl acetate/hexane (1:1) gave the title compound. $^1$H NMR (300 MHz, CDCl$_3$) δ ppm 7.32-7.15 (m, 14H), 6.98 (t, J=8.7, 4H), 4.22 (d, J=3.0, 2H), 4.09 (d, J=3.5, 2H), 3.62-3.45 (m, 4H), 2.67-2.49 (m, 4H), 1.84 (d, J=5.6, 2H); MS (DCI) m/z 551.2 (M+H)$^+$.

Example 173

1-[2-(4,4-diphenylpiperidin-1-yl)-2-oxoethyl]-3,3-bis(4-fluorophenyl)piperidin-2-one The title compound was prepared using the procedure described in Example 172 substituting 4,4-diphenylpiperidine for 3,3-diphenylpyrrolidine. $^1$H NMR (300 MHz, CDCl$_3$) δ ppm 7.49-7.14 (m, 14H), 6.97 (ddd, J=2.7, 6.1, 10.6, 4H), 4.20 (s, 2H), 3.77-3.65 (m, 2H), 3.46 (d, J=6.4, 4H), 2.64-2.51 (m, 2H), 2.43 (s, 4H), 1.85-1.76 (m, 2H); MS (DCI) m/z 565.2 (M+H)$^+$.

Example 174

1-[2-(3,3-diphenylpyrrolidin-1-yl)-2-oxoethyl]-3,3-diphenylpiperidin-2-one

The title compound was prepared using the procedure described in Example 172 substituting 2-(2-oxo-3,3-diphenylpiperidin-1-yl)acetic acid from Example 68E for 2-(3,3-bis(4-fluorophenyl)-2-oxopiperidin-1-yl)acetic acid. $^1$H NMR (300 MHz, CDCl$_3$) δ ppm 7.38-7.14 (m, 20H), 4.23 (d, J=13.7, 2H), 4.11 (s, 2H), 3.65-3.44 (m, 4H), 2.69-2.59 (m, 4H), 1.83 (m, 2H); MS (DCI) m/z 515.2 (M+H)$^+$.

Example 175

3,3-bis(4-fluorophenyl)-1-(2-oxo-2-{4-[3-(trifluoromethyl)benzyl]piperazin-1-yl}ethyl)piperidin-2-one The title compound was prepared using the procedure described in Example 172 substituting 1-(3-(trifluoromethyl)benzyl)piperazine for 3,3-diphenylpyrrolidine. $^1$H NMR (300 MHz, CDCl$_3$) δ ppm 7.59 (s, 1H), 7.54-7.40 (m, 3H), 7.34-7.20 (m, 4H), 7.03-6.88 (m, 4H), 4.19 (s, 2H), 3.66 (d, J=4.9, 2H), 3.56 (s, 2H), 3.46 (dd, J=5.6, 12.0, 4H), 2.65-2.52 (m, 2H), 2.45 (dd, J=7.2, 11.4, 4H), 1.91-1.75 (m, 2H); MS (DCI) m/z 572.2 (M+H)$^+$.

Example 176

N-(1-benzhydrylazetidin-3-yl)-2-(2-oxo-3,3-diphenylpiperidin-1-yl)acetamide

The title compound was obtained by the procedure described in Example 171, replacing 4-(bis(4-fluorophenyl)methylene)piperidine hydrochloride with 1-benzhydrylazetidin-3-amine (CAS 40432-52-8). $^1$H NMR (300 MHz, DMSO-d$_6$) δ ppm 8.38 (d, J=7.1 Hz, 1H), 7.38-7.45 (m, 4H), 7.14-7.32 (m, 16H), 4.40 (s, 1H), 4.26-4.39 (m, 1H), 3.93 (s, 2H), 3.34-3.43 (m, 4H), 2.84 (t, J=3.9 Hz, 2H), 2.48-2.53 (m, 2H), 1.59-1.70 (m, 2H); MS (ESI+) m/z 530 (M+H)$^+$.

Example 177

3,3-diphenyl-1-({3-[6-(trifluoromethyl)pyridin-3-yl]-1,2,4-oxadiazol-5-yl}methyl)piperidin-2-one A solution of (Z)—N-hydroxy-6-(trifluoromethyl)nicotinimidamide (0.146 g, 0.711 mmol), 2-(2-oxo-3,3-diphenylpiperidin-1-yl)acetic acid (0.200 g, 0.646 mmol; Example 68E) and N$^1$-((ethylimino)methylene)-N$^3$,N$^3$-dimethylpropane-1,3-diamine hydrochloride (0.161 g, 0.840 mmol) were stirred together in dichloroethane (0.5 mL) at room temperature for 3 hours. The reaction was then heated to 85° C. and stirred overnight. The reaction was cooled, loaded onto a SF15-12 column (Analogix®) and the product eluted using a gradient of 5% ethyl acetate/hexanes to 35% ethyl acetate over 30 minutes (Flow=30 mL/minute) to provide the title compound. $^1$H NMR (300 MHz, CDCl$_3$) δ 9.44 (d, J=1.9, 1H), 8.56 (ddd, J=0.5, 2.0, 8.1, 1H), 7.95-7.75 (m, 1H), 7.43-7.08 (m, 10H), 4.94 (s, 2H), 3.65 (t, J=6.5, 2H), 2.84-2.57 (m, 2H), 1.93 (dtd, J=3.1, 6.4, 9.4, 2H).

Example 178

1-{2-oxo-2-[5-(trifluoromethyl)-1,3-dihydro-2H-isoindol-2-yl]ethyl}-3-phenylpiperidin-2-one To 2-(2-oxo-3-phenylpiperidin-1-yl)acetic acid (0.137 g, 0.587 mmol; Example 91D) and 5-(trifluoromethyl)isoindoline hydrogen bromide (0.173 g, 0.646 mmol) in dichloromethane (0.5 mL) was added N$^1$-((ethylimino)methylene)-N$^3$,N$^3$-dimethylpropane-1,3-diamine (0.156 mL, 0.881 mmol) and the reaction was stirred at room temperature overnight. The reaction was loaded directly onto a SF15-12 column (Analogix®) and the product eluted using a gradient of 50% ethyl acetate/hexanes to 100% ethyl acetate over 15 minutes (Flow=30 mL/minute) to provide the title compound. $^1$H NMR (300 MHz, CDCl$_3$) δ 7.66-7.11 (m, 8H), 4.96 (s, 2H), 4.89 (s, 2H), 4.44 (dd, J=2.6, 15.6, 1H), 4.08 (dt, J=2.3, 6.8, 1H), 3.80-3.65 (m, 2H), 3.59 (dt, J=4.0, 5.6, 1H), 2.39-2.16 (m, 1H), 2.16-1.78 (m, 3H).

Example 179

3,3-diphenyl-1-({3-[3-(trifluoromethyl)phenyl]-1,2,4-oxadiazol-5-yl}methyl)piperidin-2-one A solution of (Z)—N-hydroxy-3-(trifluoromethyl)benzimidamide (0.155 g, 0.761 mmol), 2-(2-oxo-3,3-diphenylpiperidin-1-yl)acetic acid (0.214 g, 0.692 mmol; Example 68E) and N$^1$-((ethylimino)methylene)-N$^3$,N$^3$-dimethylpropane-1,3-diamine hydrochloride (0.172 g, 0.899 mmol) were stirred together in dichloroethane (0.5 mL) at room temperature for 3 hours. The reaction was then heated to 85° C. and stirred overnight. The reaction was cooled, loaded onto a SF15-12 column (Analogix®) and the product eluted using a gradient of 5% ethyl acetate/hexanes to 35% ethyl acetate over 30 minutes (Flow=30 mL/minute) to supply the title compound. $^1$H NMR (300 MHz, CDCl$_3$) δ 8.40 (s, 1H), 8.31 (d, J=7.7, 1H), 7.80 (d, J=7.9, 1H), 7.64 (dd, J=6.4, 14.3, 1H), 7.39-7.10 (m, 10H), 4.89 (d, J=20.0, 2H), 3.70-3.56 (m, 2H), 2.70 (dt, J=11.5, 25.9, 2H), 1.92 (dtd, J=3.1, 6.4, 9.4, 2H).

Example 180

2-(2-oxo-3,3-diphenylpiperidin-1-yl)-N-{1-[3-(trifluoromethyl)benzyl]azetidin-3-yl}acetamide Example 180A tert-butyl 1-[3-(trifluoromethyl)benzyl]azetidin-3-ylcarbamate To a solution of tert-butyl azetidin-3-ylcarbamate (0.34 g, 2 mmol) in dichloroethane was added 3-(trifluoromethyl)

benzaldehyde (0.45 g, 2.6 mmol) and sodium triacetoxyborohydride (0.64 g, 3 mmol). The resultant mixture was stirred at room temperature for 16 hours, and then the mixture was diluted with dichloromethane and washed with aqueous NaHCO$_3$ solution. The organic layer was separated, dried over MgSO$_4$, and concentrated. The residue was purified by flash chromatography on silica gel eluting with 30-70% ethyl acetate/hexane to yield the title compound.

Example 180B 1-(3-(trifluoromethyl)benzyl)azetidin-3-amine hydrochloride

To a solution of product from Example 180A (0.14 g) in methanol (5 mL) was added 4 N HCl in dioxane (1 mL), and the mixture was stirred at room temperature for 2 hours. The reaction mixture was concentrated to yield the title compound. $^1$H NMR (300 MHz, DMSO-d$_6$) δ ppm 8.81 (bs, 2H), 7.95 (m, 1H), 7.84 (m, 2H), 7.71 (t, J=7.73 Hz, 1H), 4.63 (s, 2H), 4.23 (m, 5H); MS (DCI) m/z 231 (M+H)$^+$.

Example 180C 2-(2-oxo-3,3-diphenylpiperidin-1-yl)-N-{1-[3-(trifluoromethyl)benzyl]azetidin-3-yl}acetamide The title compound was obtained by the procedure described in Example 171, replacing 4-(bis(4-fluorophenyl)methylene)piperidine hydrochloride with the product from Example 180B. $^1$H NMR (300 MHz, CDCl$_3$) δ ppm 7.38-7.55 (m, 4H), 7.19-7.33 (m, 10H), 7.03 (d, J=7.8 Hz, 1H), 4.51-4.66 (m, 1H), 4.01 (s, 2H), 3.63-3.68 (m, 2H), 3.63 (s, 2H), 3.55 (t, J=6.5 Hz, 2H), 2.86-2.92 (m, 2H), 2.58-2.65 (m, 2H), 1.76-1.89 (m, 2H); MS (ESI+) m/z 522 (M+H)$^+$.

Example 181

3-phenyl-1-({3-[4-(trifluoromethyl)phenyl]-1,2,4-oxadiazol-5-yl}methyl)piperidin-2-one A solution of (Z)—N-hydroxy-4-(trifluoromethyl)benzimidamide (0.142 g, 0.698 mmol), 2-(2-oxo-3-phenylpiperidin-1-yl)acetic acid (0.148 g, 0.634 mmol; Example 91D) and N$^1$-((ethylimino)methylene)-N$^3$,N$^3$-dimethylpropane-1,3-diamine hydrochloride (0.158 g, 0.825 mmol) were stirred together in dichloroethane (0.5 mL) at room temperature for 2 hours. The reaction was then heated to 85° C. and stirred overnight. The reaction was cooled, loaded onto a SF15-12 column (Analogix®) and the product eluted using a gradient of 5% ethyl acetate/hexanes to 100% ethyl acetate over 25 minutes (Flow=30 mL/minute). The residue was dissolved in ethyl acetate and concentrated to give the title compound. $^1$H NMR (300 MHz, CDCl$_3$) δ 8.23 (d, J=8.2, 2H), 7.77 (d, J=8.3, 2H), 7.42-7.15 (m, 5H), 5.19 (d, J=16.7, 1H), 4.73 (d, J=16.7, 1H), 3.84-3.76 (m, 1H), 3.70 (ddd, J=5.3, 7.6, 12.7, 1H), 3.59 (dt, J=5.5, 11.2, 1H), 2.43-2.18 (m, 1H), 2.18-1.82 (m, 3H); MS (ESI+) m/z 402.0 (M+H)$^+$.

Example 182 benzyl 4-[(2-oxo-3,3-diphenylpiperidin-1-yl)acetyl]piperazine-1-carboxylate

A solution of benzyl piperazine-1-carboxylate (0.196 g, 0.889 mmol), 2-(2-oxo-3,3-diphenylpiperidin-1-yl)acetic acid (0.250 g, 0.808 mmol; Example 68E) and N$^1$-((ethylimino)methylene)-N$^3$,N$^3$-dimethylpropane-1,3-diamine hydrochloride (0.186 g, 0.970 mmol) were stirred together overnight in dichloromethane (5 mL). The reaction was concentrated, loaded directly onto a SF15-silica gel column (Analogix®). The product was eluted using a gradient of 5% to 100% ethyl acetate over 30 minutes to provide the title compound. $^1$H NMR (300 MHz, CDCl$_3$) δ 7.46-7.07 (m, 15H), 5.15 (s, 2H), 4.22 (s, 2H), 3.75-3.30 (m, 10H), 2.73-2.53 (m, 2H), 1.85 (d, J=5.9, 2H); MS (ESI+) m/z 512.2 (M+H)$^+$.

Example 183

N-{1-[4-fluoro-3-(trifluoromethyl)benzyl]piperidin-4-yl}-2-(2-oxo-3,3-diphenylpiperidin-1-yl)acetamide Example 183A 1-[4-fluoro-3-(trifluoromethyl)benzyl]piperidin-4-amine The title compound was obtained by the procedure described in Examples 41A and 41B, replacing 3-(trifluoromethyl)benzaldehyde with 4-fluoro-3-(trifluoromethyl)benzaldehyde. MS (DCI) m/z 263 (M+H)$^+$.

Example 183B

N-{1-[4-fluoro-3-(trifluoromethyl)benzyl]piperidin-4-yl}-2-(2-oxo-3,3-diphenylpiperidin-1-yl)acetamide The title compound was obtained by the procedure described in Example 171, replacing 4-(bis(4-fluorophenyl)methylene)piperidine hydrochloride with 1-[4-fluoro-3-(trifluoromethyl)benzyl]piperidin-4-amine (Example 183A). $^1$H NMR (300 MHz, CDCl$_3$) δ ppm 7.56 (dd, J=7.0, 2.1 Hz, 1H), 7.46-7.51 (m, 1H), 7.19-7.35 (m, 10H), 7.08-7.22 (m, 1H), 6.56-6.60 (m, 1H), 4.02 (s, 2H), 3.75-3.84 (m, 1H), 3.54 (t, J=6.5 Hz, 2H), 2.80 (s, 2H), 2.64-2.74 (m, 2H), 2.56-2.66 (m, 2H), 2.10-2.19 (m, 2H), 1.78-1.92 (m, 4H), 1.43-1.56 (m, 2H); MS (ESI–) m/z 566 (M–H)$^-$.

Example 184

1-(2-{4-[4-fluoro-3-(trifluoromethyl)benzyl]piperazin-1-yl}-2-oxoethyl)-3,3-diphenylpiperidin-2-one Example 184A tert-butyl 4-(4-fluoro-3-(trifluoromethyl)benzyl)piperazine-1-carboxylate The title compound was obtained by the procedure described in Example 180A reacting tert-butyl piperazine-1-carboxylate with 4-fluoro-3-(trifluoromethyl)benzaldehyde. $^1$H NMR (300 MHz, CDCl$_3$) δ ppm 7.56 (d, J=7.12 Hz, 1H), 7.48 (m, 1H), 7.14 (t, 1H), 3.50 (s, 2H), 3.43 (m, 4H), 2.37 (m, 4H), 1.46 (s, 9H); MS (ESI+) m/z 363 (M+H)$^+$.

Example 184B

1-[4-fluoro-3-(trifluoromethyl)benzyl]piperazine hydrochloride

The title compound was obtained as described in Example 180B using product from Example 184A. MS (DCI) m/z 263 (M+H)$^+$.

Example 184C

1-(2-{4-[4-fluoro-3-(trifluoromethyl)benzyl]piperazin-1-yl}-2-oxoethyl)-3,3-diphenylpiperidin-2-one The title compound was obtained by the procedure described in Example 171, replacing 4-(bis(4-fluorophenyl)methylene)piperidine hydrochloride with the product from Example 184B. $^1$H NMR (300 MHz, CDCl$_3$) δ ppm 7.56 (dd, J=6.7, 1.8 Hz, 1H), 7.46-7.52 (m, 1H), 7.27-7.31 (m, 8H), 7.18-7.24 (m, 2H), 7.11-7.18 (m, 1H), 4.23 (s, 2H), 3.62-3.69 (m, 2H), 3.40-3.55 (m, 6H), 2.61-2.67 (m, 2H), 2.37-2.48 (m, 4H), 1.79-1.90 (m, 2H); MS (ESI+) m/z 554 (M+H)$^+$.

Example 185

2-(2-oxo-3,3-diphenylpiperidin-1-yl)-N-{(3S)-1-[3-(trifluoromethyl)benzyl]pyrrolidin-3-yl}acetamide

Example 185A

(S)-tert-butyl 1-(3-(trifluoromethyl)benzyl)pyrrolidin-3-ylcarbamate

To a solution of (S)-tert-butyl pyrrolidin-3-ylcarbamate (0.25 g, 1.34 mmol) in dichloromethane (10 mL) was added 3-(trifluoromethyl)benzaldehyde (0.3 g, 1.745 mmol) and sodium triacetoxyborohydride (0.43 g, 2.01 mmol). The mixture was stirred at room temperature for 16 hours. Then the reaction mixture was diluted with dichloromethane and washed with NaHCO$_3$ solution. The organic layer was dried with MgSO$_4$, concentrated, and purified by flash chromatography, eluting with 50% ethyl acetate/hexane to yield the title compound.

Example 185B

(S)-1-(3-(trifluoromethyl)benzyl)pyrrolidin-3-amine hydrochloride

A solution of product from Example 185A (0.32 g, 0.9 mmol) in methanol (10 mL) was treated with 4 N HCl/dioxane (2 mL) for 2 hours at room temperature. The reaction mixture was concentrated to yield the title compound. $^1$H NMR (300 MHz, DMSO-d$_6$) δ ppm 7.60 (m, 3H), 6.99 (m, 1H), 3.93 (m, 1H), 3.64 (dd, 2H), 2.69 (m, 1H), 2.45 (m, 2H), 2.26 (m, 1H), 1.99 (m, 1H), 1.60 (m, 1H); MS (ESI+) m/z 244 (M+H)$^+$.

Example 185C

2-(2-oxo-3,3-diphenylpiperidin-1-yl)-N-{(3S)-1-[3-(trifluoromethyl)benzyl]pyrrolidin-3-yl}acetamide The title compound was obtained by the procedure described in Example 171, replacing 4-(bis(4-fluorophenyl)methylene)piperidine hydrochloride with the product from Example 185B. $^1$H NMR (300 MHz, CDCl$_3$) δ ppm 7.51-7.56 (bs, 1H), 7.47-7.52 (m, 1H), 7.36-7.43 (m, 1H), 7.19-7.33 (m, 11H), 6.79 (d, J=8.0 Hz, 1H), 4.36-4.50 (m, 1H), 4.00 (s, 2H), 3.60-3.77 (m, 2H), 3.52 (t, J=6.5 Hz, 2H), 2.72-2.80 (m, 1H), 2.58-2.65 (m, 2H), 2.49-2.56 (m, 1H), 2.38-2.48 (m, 1H), 2.21-2.35 (m, 1H), 1.77-1.87 (m, 2H), 1.42-1.49 (m, 2H); MS (ESI+) m/z 536 (M+H)$^+$.

Example 186

2-(2-oxo-3,3-diphenylpiperidin-1-yl)-N-{(3R)-1-[3-(trifluoromethyl)benzyl]pyrrolidin-3-yl}acetamide The title compound was prepared as described in Example 185, replacing (S)-tert-butyl pyrrolidin-3-ylcarbamate with (R)-tert-butyl pyrrolidin-3-ylcarbamate. $^1$H NMR (300 MHz, CDCl$_3$) δ ppm 7.51-7.54 (bs, 1H), 7.47-7.52 (m, 1H), 7.35-7.43 (m, 1H), 7.19-7.32 (m, 11H), 6.79 (d, J=7.8 Hz, 1H), 4.36-4.50 (m, 1H), 4.00 (s, 2H), 3.58-3.73 (m, 2H), 3.53 (t, J=6.5 Hz, 2H), 2.71-2.79 (m, 1H), 2.58-2.66 (m, 2H), 2.48-2.55 (m, 1H), 2.37-2.49 (m, 1H), 2.22-2.36 (m, 1H), 1.77-1.88 (m, 2H), 1.40-1.51 (m, 2H); MS (ESI+) m/z 536 (M+H)$^+$.

Example 187

(3S)-1-[2-(5-fluoro-1,3-dihydro-2H-isoindol-2-yl)-2-oxoethyl]-3-phenylpiperidin-2-one To a suspension of 2-(2-oxo-3-phenylpiperidin-1-yl)acetic acid (4.43 g, 18.99 mmol; Example 91D) and 5-fluoroisoindoline hydrochloride (3.63 g, 20.89 mmol) in dichloromethane (30 mL) was added N$^1$-((ethylimino)methylene)-N$^3$,N$^3$-dimethylpropane-1,3-diamine (5.04 mL, 28.5 mmol). After a few minutes, a dark brown solution resulted. The reaction was stirred overnight then poured into 1 N HCl (100 mL). The product was extracted into dichloromethane (3×100 mL). The combined extracts were washed with brine (100 mL), dried over magnesium sulfate and concentrated. The residue was dissolved in minimal dichloromethane and was loaded onto a GraceResolv™ 80 g silica gel column (Grace Davison Discovery Sciences) and the product eluted with a gradient of 5% ethyl acetate/hexanes to 100% ethyl acetate/hexanes (Flow=40 mL/minute) over 60 minutes to provide the racemic title compound. Supercritical fluid chromatography using a ChiralPak® OD-H 21×250 mm column eluting using 10% to 50% methanol/CO$_2$ over 20 minutes gave the title compound as the first eluting enantiomer. $^1$H NMR (300 MHz, CDCl$_3$) δ 7.40-7.11 (m, 6H), 6.97 (dd, J=8.6, 18.0, 2H), 4.84 (dd, J=8.7, 19.3, 4H), 4.44 (dd, J=1.6, 15.7, 1H), 4.05 (d, J=15.7, 1H), 3.81-3.47 (m, 3H), 2.34-1.83 (m, 4H); MS (ESI+) m/z 353.0 (M+H)$^+$.

Example 188

(3R)-1-[2-(5-fluoro-1,3-dihydro-2H-isoindol-2-yl)-2-oxoethyl]-3-phenylpiperidin-2-one To a suspension of 2-(2-oxo-3-phenylpiperidin-1-yl)acetic acid (4.43 g, 18.99 mmol; Example 91D) and 5-fluoroisoindoline hydrochloride (3.63 g, 20.89 mmol) in dichloromethane (30 mL) was added N$^1$-((ethylimino)methylene)-N$^3$,N$^3$-dimethylpropane-1,3-diamine (5.04 mL, 28.5 mmol). After a few minutes, a dark brown solution resulted. The reaction was stirred overnight then poured into 1 N HCl (100 mL). The product was extracted into dichloromethane (3×100 mL). The combined extracts were washed with brine (100 mL), dried over magnesium sulfate and concentrated to give a brownish foam. The foam was dissolved in minimal dichloromethane and was loaded onto a GraceResolv™ 80 g silica gel column (Grace Davison Discovery Sciences) and the product eluted with a gradient of 5% ethyl acetate/hexanes to 100% ethyl acetate/hexanes (Flow=40 mL/minute) over 60 minutes to provide the racemic title compound. Supercritical fluid chromatography using a ChiralPak® OD-H 21×250 mm column eluting using 10% to 50% methanol/CO$_2$ over 20 minutes gave the title compound as the second eluting enantiomer. $^1$H NMR (300 MHz, CDCl$_3$) δ 7.40-7.11 (m, 6H), 6.97 (dd, J=8.6, 18.0, 2H), 4.84 (dd, J=8.7, 19.3, 4H), 4.44 (dd, J=1.6, 15.7, 1H), 4.05 (d, J=15.7, 1H), 3.81-3.47 (m, 3H), 2.34-1.83 (m, 4H); MS (ESI+) m/z 353.0 (M+H)$^+$.

Example 189

3-(4-fluorophenyl)-1-({3-[4-(trifluoromethyl)phenyl]-1,2,4-oxadiazol-5-yl}methyl)pyrrolidin-2-one Example 189A methyl 3-cyano-2-(4-fluorophenyl)propanoate To lithium bis(trimethylsilyl)amide (1.0 Min tetrahydrofuran) (18.73 mL, 18.73 mmol) at −78° C. was added methyl 2-(4-fluorophenyl)acetate (3.00 g, 17.84 mmol) as a solution in tetrahydrofuran (5 mL) dropwise. During the addition, a white solid precipitated. After the addition, the reaction was placed in an ice bath and stirred for 1 hour. 2-Bromoacetonitrile (2.354 g, 19.62 mmol) was added as a solution in tetrahydrofuran (2 mL) and the reaction was allowed to stir for an additional 1 hour. The reaction was poured into a mixture of 1 N HCl (50 mL) and ethyl acetate (50 mL). The organic layer was separated, washed with brine (50 mL), dried over magnesium sulfate and concentrate. The resulting reside was chromatographed over silica gel (SF40-115, Analogix®) eluting with a gradient of 5% to 50% ethyl acetate/hexanes (Flow=85 mL/minute) to provide the title compound. $^1$H NMR (300 MHz, CDCl$_3$) δ 7.31-7.19 (m, 2H), 7.13-7.01 (m, 2H), 3.93 (t, J=7.6, 1H), 3.73 (s, 3H), 3.02 (dd, J=7.2, 16.8, 1H), 2.81 (dd, J=8.0, 16.9, 1H).

Example 189B 3-(4-fluorophenyl)pyrrolidin-2-one

Methyl 3-cyano-2-(4-fluorophenyl)propanoate (2.09 g, 10.09 mmol; Example 189A) and 7 M NH$_3$-methanol (100 mL) were added to Raney® nickel, solvent washed (20.90 g, 356 mmol) in a 250 mL stainless steel pressure bottle and stirred for 17 hours under hydrogen at 30 psi and room temperature. The mixture was filtered through a nylon membrane and concentrated to give the title compound. $^1$H NMR (300 MHz, CDCl$_3$) δ 7.36-7.16 (m, 2H), 7.12-6.94 (m, 2H), 6.04 (s, 1H), 3.61 (t, J=9.2, 1H), 3.54-3.39 (m, 2H), 2.71-2.53 (m, 1H), 2.23 (ddd, J=8.4, 12.9, 17.7, 1H); MS (ESI+) m/z 179.9 (M+H)$^+$.

Example 189C 3-(4-fluorophenyl)-1-({3-[4-(trifluoromethyl)phenyl]-1,2,4-oxadiazol-5-yl}methyl)pyrrolidin-2-one To 3-(4-fluorophenyl)pyrrolidin-2-one (0.106 g, 0.592 mmol; Example 189B) as suspension in tetrahydrofuran (0.5 mL) was added potassium t-butoxide (1.0 Min tetrahydrofuran) (0.651 mL, 0.651 mmol) dropwise at room temperature. After stirring for 15 minutes, 5-(chloromethyl)-3-(4-(trifluoromethyl)phenyl)-1,2,4-oxadiazole (0.171 g, 0.651 mmol) was added dropwise as a solution in tetrahydrofuran (0.5 mL). The reaction was heated to 50° C. for 1 hour. The reaction was concentrated, loaded onto silica gel SF15-12 g (Analogix®) and the product eluted using a gradient of 5% to 50% ethyl acetate/hexanes over 30 minutes (Flow rate=30 mL/minute) to provide the title compound. $^1$H NMR (300 MHz, CDCl$_3$) δ 8.21 (d, J=8.1, 2H), 7.76 (d, J=8.2, 2H), 7.39-7.23 (m, 2H), 7.17-6.97 (m, 2H), 4.96 (d, J=17.0, 1H), 4.84 (d, J=16.5, 1H), 3.78 (t, J=8.9, 1H), 3.74-3.59 (m, 2H), 2.77-2.57 (m, 1H), 2.25 (ddt, J=8.0, 12.9, 20.7, 1H); MS (ESI+) m/z 406.1 (M+H)$^+$.

Example 190

3,3-bis(4-fluorophenyl)-1-({3-[4-(trifluoromethyl)phenyl]-1,2,4-oxadiazol-5-yl}methyl)pyrrolidin-2-one A solution of (Z)—N-hydroxy-4-(trifluoromethyl)benzimidamide (0.204 g, 1.0 mmol), 2-(3,3-bis(4-fluorophenyl)-2-oxopyrrolidin-1-yl)acetic acid (Example 58D, 0.331 g, 1.0 mmol) and N$^1$-((ethylimino)methylene)-N$^3$,N$^3$-dimethylpropane-1,3-diamine hydrochloride (0.383 g, 2.00 mmol) were stirred together in dichloroethane (5.0 mL) at room temperature for 2 hours under nitrogen. The reaction was then heated to 85° C. and stirred overnight. The reaction mixture was cooled, concentrated, loaded onto a SF25-40 column (Analogix®, Burlington, Wis.) and the product eluted using a gradient of 10% ethyl acetate/hexanes to 70% ethyl acetate over 30 minutes (Flow=30 mL/minute) to give the title compound. $^1$H NMR (300 MHz, CDCl$_3$) δ ppm 8.10 (d, J=8.1, 2H), 7.75 (d, J=8.3, 2H), 7.44-7.31 (m, 4H), 7.08-6.94 (m, 4H), 4.90 (s, 2H), 3.57 (t, J=6.5, 2H), 2.84 (t, J=6.5, 2H); MS (DCI) m/z 500.1 (M+H)$^+$.

Example 191

3,3-bis(4-fluorophenyl)-1-({3-[4-(trifluoromethyl)phenyl]-1,2,4-oxadiazol-5-yl}methyl)piperidin-2-one The title compound was prepared using the procedure described in Example 190 substituting 2-(3,3-bis(4-fluorophenyl)-2-oxopiperidin-1-yl)acetic acid from Example 90D for 2-(3,3-bis(4-fluorophenyl)-2-oxopyrrolidin-1-yl) acetic acid. $^1$H NMR (300 MHz, CDCl$_3$) δ ppm 8.22 (d, J=8.2, 2H), 7.78 (d, J=8.3, 2H), 7.34-7.16 (m, 4H), 7.05-6.91 (m, 4H), 4.91 (s, 2H), 3.64 (t, J=6.5, 2H), 2.65 (dt, J=5.6, 14.2, 2H), 1.96-1.86 (m, 2H); MS (DCI) m/z 514.1 (M+H)$^+$.

Example 192

N-(5-chloropyridin-2-yl)-2-(2-oxo-3-phenylpiperidin-1-yl)acetamide

To a solution of 2-(2-oxo-3-phenylpiperidin-1-yl)acetic acid (0.100 g, 0.429 mmol; Example 91D) in dichloromethane (0.5 mL) was added oxalyl chloride (2.0 Min dichloromethane) (0.322 mL, 0.643 mmol) and a catalytic amount of N,N-dimethylformamide. After stirring for 30 minutes at 0° C., a reddish solution resulted. The reaction was concentrated, the residue was dissolved in dichloromethane (1 mL) and 5-chloropyridin-2-amine (0.047 g, 0.364 mmol) was added followed by N-methylmorpholine (0.071 mL, 0.643 mmol). After stirring for 1 hour, the reaction was loaded onto a silica gel column (SF15-24, Analogix®) and the product was eluted using a gradient of 25% ethyl acetate/hexanes to 70% ethyl acetate/hexanes over 30 minutes (Flow=30 mL/minute). Some color streaked through the column, so a second column was run under identical conditions to give the title compound. $^1$H NMR (300 MHz, CDCl$_3$) δ 8.84 (s, 1H), 8.23 (d, J=2.7, 1H), 8.14 (d, J=8.8, 1H), 7.65 (dd, J=2.6, 8.9, 1H), 7.42-7.13 (m, 5H), 4.34-4.15 (m, 2H), 3.78 (dd, J=6.0, 7.9, 1H), 3.71-3.47 (m, 2H), 2.33-2.14 (m, 1H), 1.99 (m, 3H); MS (ESI+) m/z 344.0 (M+H)$^+$.

Example 193

1-{[3-(4-chlorophenyl)-1,2,4-oxadiazol-5-yl]methyl}-3,3-diphenylpyrrolidin-2-one The title compound was prepared using the procedure described in Example 190 substituting 2-(2-oxo-3,3-diphenylpyrrolidin-1-yl)acetic acid from Example 1C for 2-(3,3-bis(4-fluorophenyl)-2-oxopyrrolidin-1-yl)acetic acid and (Z)-4-chloro-N-hydroxybenzimidamide for (Z)—N-hydroxy-4-(trifluoromethyl)benzimidamide. $^1$H NMR (300 MHz, CDCl$_3$) δ ppm 7.99-7.91 (m, 2H), 7.49-7.14 (m, 12H), 4.88 (s, 2H), 3.57 (t, J=6.5, 2H), 2.89 (t, J=6.5, 2H); MS (DCI) m/z 430.1 (M+H)$^+$.

Example 194

1-{[3-(4-fluorophenyl)-1,2,4-oxadiazol-5-yl]methyl}-3,3-diphenylpyrrolidin-2-one The title compound was prepared using the procedure described in Example 190 substituting 2-(2-oxo-3,3-diphenylpyrrolidin-1-yl)acetic acid from Example 1C for 2-(3,3-bis(4-fluorophenyl)-2-oxopyrrolidin-1-yl)acetic acid and (Z)-4-fluoro-N-hydroxybenzimidamide for (Z)—N-hydroxy-4-(trifluoromethyl)benzimidamide. $^1$H NMR (300 MHz, CDCl$_3$) δ ppm 8.02-7.96 (m, 2H), 7.45-7.27 (m, 10H), 7.18-7.11 (m, 2H), 4.88 (s, 2H), 3.57 (t, J=6.5, 2H), 2.88 (t, J=6.5, 2H); MS (DCI) m/z 414.1 (M+H)$^+$.

Example 195

1-{[3-(4-methylphenyl)-1,2,4-oxadiazol-5-yl]methyl}-3,3-diphenylpyrrolidin-2-one The title compound was prepared using the procedure described in Example 190 substituting 2-(2-oxo-3,3-diphenylpyrrolidin-1-yl)acetic acid from Example 1C for 2-(3,3-bis(4-fluorophenyl)-2-oxopyrrolidin-1-yl)acetic acid and (Z)—N-hydroxy-4-methylbenzimidamide for (Z)—N-hydroxy-4-(trifluoromethyl)benzimidamide. $^1$H NMR (300 MHz, CDCl$_3$) δ ppm 7.93-7.87 (m, 2H), 7.43-7.22 (m, 10H), 7.08 (s, 1H), 6.90-6.81 (m, 1H), 4.88 (s, 2H), 3.56 (t, J=6.5, 2H), 2.88 (t, J=6.5, 2H), 2.42 (s, 3H)); MS (DCI) m/z 410.1 (M+H)$^+$.

Example 196

3,3-diphenyl-1-({5-[4-(trifluoromethyl)phenyl]-1,2,4-oxadiazol-3-yl}methyl)pyrrolidin-2-one 4-(Trifluoromethyl)benzoic acid (0.416 g, 2.187 mmol), (Z)—N-hydroxy-2-(2-oxo-3,3-diphenylpyrrolidin-1-yl)acetimidamide (0.451 g, 1.458 mmol) and N$^1$-((ethylimino)methylene)-N$^3$,N$^3$-dimethylpropane-1,3-diamine hydrochloride (0.559 g, 2.92 mmol) in dichloroethane were stirred together at room temperature for 3 hours. The reaction was then heated to 85° C. and stirred at this temperature for 16 hours. The reaction was cooled, poured in ethyl acetate/1 N HCl (1:1, 200 mL) and the layers separated. The organic layer was washed with brine (100 mL), dried over magnesium sulfate and concentrated. The residue was loaded onto a Grace-eResolv™ 12 g silica gel column (Grace Davison Discovery Sciences) and eluted with a gradient of 5% ethyl acetate/hexanes to 35% ethyl acetate/hexanes (flow=40 mL/minute) over 30 minutes to give the title compound. $^1$H NMR (300 MHz, CDCl$_3$) δ 8.20 (d, J=8.3, 2H), 7.80 (d, J=8.4, 2H), 7.48-7.15 (m, 10H), 4.81 (s, 2H), 3.50 (t, J=6.5, 2H), 2.84 (t, J=6.5, 2H); MS (ESI+) m/z 464.1 (M+H)$^+$.

Example 197

N-methyl-2-(2-oxo-3,3-diphenylpiperidin-1-yl)-N-{1-[3-(trifluoromethyl)benzyl]piperidin-4-yl}acetamide Example 197A N-methyl-1-(3-(trifluoromethyl)benzyl)piperidin-4-amine To a solution of tert-butyl 1-(3-(trifluoromethyl)benzyl)piperidin-4-ylcarbamate (0.358 g, 1 mmol; Example 41A) in tetrahydrofuran (40 mL) was added LiAlH$_4$ (0.056 g, 1.5 mmol) and the resultant mixture was heated to reflux for 16 hours. Then the reaction mixture was cooled in an ice bath and Na$_2$SO$_4$.10H$_2$O (0.1 g) was added. The mixture was stirred for 1 hour at room temperature, and then the inorganic salts were removed by filtration. The filtrate was evaporated, and the obtained residue was chromatographed on silica gel eluting with 5-10% methanol/dichloromethane to yield the title compound. $^1$H NMR (300 MHz, CDCl$_3$) δ ppm 7.58 (s, 1H), 7.51 (m, 2H), 7.42 (m, 1H), 5.36 (Bs, 1H), 3.54 (s, 2H), 2.82 (m, 2H), 2.43 (s, 3H), 2.37 (m, 1H), 2.07 (m, 2H), 1.87 (d, J=12.55 Hz, 2H), 1.38 (m, 2H); MS (DCI+) m/z 273 (M+H)$^+$.

Example 197B

N-methyl-2-(2-oxo-3,3-diphenylpiperidin-1-yl)-N-{1-[3-(trifluoromethyl)benzyl]piperidin-4-yl}acetamide The title compound was obtained by the procedure described in Example 171, replacing 4-(bis(4-fluorophenyl)methylene)piperidine hydrochloride with N-methyl-1-(3-(trifluoromethyl)benzyl)piperidin-4-amine. $^1$H NMR (400 MHz, pyridine-d$_5$, temperature 90° C.) δ ppm 7.70-7.74 (m, 1H), 7.56-7.59 (m, 4H), 7.50-7.57 (m, 2H), 7.41 (t, J=7.6 Hz, 1H), 7.24-7.30 (m, 4H), 7.16-7.21 (m, 2H), 4.31 (s, 2H), 3.50 (t, J=6.4 Hz, 2H), 3.47 (s, 3H), 2.79-2.85 (m, 2H), 2.79 (s, 3H), 2.62-2.67 (m, 2H), 1.97-2.07 (m, 2H), 1.70-1.83 (m, 4H), 1.48-1.55 (m, 2H); MS (ESI+) m/z 564 (M+H)$^+$.

Example 198

N-{1-[4-fluoro-3-(trifluoromethyl)benzyl]azetidin-3-yl}-2-(2-oxo-3,3-diphenylpiperidin-1-yl)acetamide The title compound was obtained by the procedure described in Example 180, replacing 3-(trifluoromethyl)benzaldehyde with 4-fluoro-3-(trifluoromethyl)benzaldehyde. $^1$H NMR (300 MHz, CDCl$_3$) δ ppm 7.48-7.61 (m, 2H), 7.18-7.34 (m, 11H), 7.02 (d, J=7.9 Hz, 1H), 4.73 s, 1H), 4.59 (m, 1H), 3.66-3.73 (m, 4H), 2.97 (t, J=6.5 Hz, 2H), 2.61 (dd, J=7.9, 6.2 Hz, 2H), 1.82 (m, 2H); MS (ESI+) m/z 540 (M+H)$^+$.

Example 199

3,3-diphenyl-1-({3-[4-(trifluoromethoxy)phenyl]-1,2,4-oxadiazol-5-yl}methyl)piperidin-2-one (Z)—N-Hydroxy-4-(trifluoromethoxy)benzimidamide (0.125 g, 0.566 mmol), 2-(2-oxo-3,3-diphenylpiperidin-1-yl)acetic acid (0.175 g, 0.566 mmol; Example 68E) and $N^1$-((ethylimino)methylene)-$N^3$,$N^3$-dimethylpropane-1,3-diamine hydrochloride (0.163 g, 0.849 mmol) were stirred together in dichloroethane (4 mL) at room temperature for 45 minutes, then heated to 85° C. and stirred for 16 hours. The reaction was cooled and concentrated. Silica gel chromatography using a GraceResolv™ 12 g silica gel column (Grace Davison Discovery Sciences) eluting with a gradient of 5% ethyl acetate/hexanes to 35% ethyl acetate/hexanes (Flow=35 mL/minute) over 30 minutes gave the title compound. $^1$H NMR (300 MHz, CDCl$_3$) δ 8.22-8.08 (m, 2H), 7.43-7.16 (m, 12H), 4.92 (s, 2H), 3.62 (t, J=6.5, 2H), 2.80-2.61 (m, 2H), 2.03-1.80 (m, 2H); MS (ESI+) m/z 494.1 (M+H)$^+$.

Example 200

2-(2-oxo-3,3-diphenylpiperidin-1-yl)-N-{1-[3-(trifluoromethyl)benzyl]piperidin-4-yl}acetamide The title compound was obtained by the procedure described in Example 171, replacing 4-(bis(4-fluorophenyl)methylene)piperidine hydrochloride with 1-(3-(trifluoromethyl)benzyl)piperidin-4-amine hydrochloride (Example 41B). $^1$H NMR (300 MHz, CDCl$_3$) δ ppm 7.58-7.60 (bs, 1H), 7.48-7.53 (m, 2H), 7.44 (d, J=7.6 Hz, 1H), 7.19-7.34 (m, 10H), 6.54-6.59 (m, 1H), 4.02 (s, 2H), 3.74-3.86 (m, 1H), 3.54 (t, J=6.5 Hz, 2H), 3.51 (s, 2H), 2.66-2.77 (m, 2H), 2.59-2.63 (m, 2H), 2.10-2.21 (m, 2H), 1.78-1.92 (m, 4H), 1.39-1.52 (m, 2H); MS (ESI−) m/z 548 (M−H)$^−$.

Example 201

N-{1-[2-fluoro-3-(trifluoromethyl)benzyl]azetidin-3-yl}-2-(2-oxo-3,3-diphenylpiperidin-1-yl)acetamide The title compound was obtained by the procedure described in Example 180, replacing 3-(trifluoromethyl)benzaldehyde with 2-fluoro-3-(trifluoromethyl)benzaldehyde. $^1$H NMR (300 MHz, CDCl$_3$) δ ppm 7.48-7.61 (m, 2H), 7.18-7.34 (m, 11H), 7.02 (d, J=7.9 Hz, 1H), 4.52-4.67 (m, 1H), 4.02 (s, 2H), 3.66-3.73 (m, 4H), 3.54 (t, J=6.5 Hz, 2H), 2.94 (dd, J=7.9, 6.2 Hz, 2H), 2.59-2.67 (m, 2H), 1.75-1.88 (m, 2H); MS (ESI+) m/z 540 (M+H)$^+$.

Example 202

1-{[3-(4-tert-butylphenyl)-1,2,4-oxadiazol-5-yl]methyl}-3,3-diphenylpyrrolidin-2-one The title compound was prepared using the procedure described in Example 190 substituting 2-(2-oxo-3,3-diphenylpyrrolidin-1-yl)acetic acid from Example 1C for 2-(3,3-bis(4-fluorophenyl)-2-oxopyrrolidin-1-yl)acetic acid and (Z)-4-tert-butyl-N-hydroxybenzimidamide for (Z)—N-hydroxy-4-(trifluoromethyl)benzimidamide. $^1$H NMR (300 MHz, CDCl$_3$) δ ppm 7.99-7.91 (m, 2H), 7.51-7.46 (m, 2H), 7.42-7.27 (m, 9H), 6.95-6.89 (m, 1H), 4.89 (s, 2H), 3.55 (t, J=6.5, 2H), 2.88 (t, J=6.5, 2H), 1.36 (s, 9H); MS (DCI) m/z 452.2 (M+H)$^+$.

Example 203

1-{2-[3,3-bis(4-fluorophenyl)pyrrolidin-1-yl]-2-oxoethyl}-3,3-diphenylpyrrolidin-2-one

Example 203A

3,3-bis(4-fluorophenyl)pyrrolidine

In a 500 mL flask containing 3,3-bis(4-fluorophenyl)pyrrolidin-2-one (Example 58B, 4.1 g, 15 mmol) as a suspension in ether (300 mL) was added lithium aluminum hydride (2.0 M in tetrahydrofuran, 15 mL, 30 mmol) slowly via syringe under nitrogen. The reaction was refluxed overnight, cooled to room temperature, and then carefully quenched by the slow addition of 1 N NaOH (60 mL). The reaction was diluted with ethyl acetate (200 mL) and filtered through a pad of diatomaceous earth. The organic phase was separated, concentrated, and the residue purified over silica gel eluting with 97:3 dichloromethane/methanol to give the title compound. MS (DCI+) m/z 260 (M+H)$^+$.

Example 203B

1-{2-[3,3-bis(4-fluorophenyl)pyrrolidin-1-yl]-2-oxoethyl}-3,3-diphenylpyrrolidin-2-one The title compound was prepared using the procedure described in Example 172 substituting 2-(2-oxo-3,3-diphenylpyrrolidin-1-yl)acetic acid from Example 1C for 2-(3,3-bis(4-fluorophenyl)-2-oxopiperidin-1-yl)acetic acid and 3,3-bis(4-fluorophenyl)pyrrolidine from Example 203A for 3,3-diphenylpyrrolidine. $^1$H NMR (300 MHz, CDCl$_3$) δ ppm 7.44-6.86 (m, 18H), 4.27-3.98 (m, 4H), 3.55 (dq, J=6.7, 9.6, 3H), 3.41 (t, J=6.7, 1H), 2.82 (q, J=6.5, 2H), 2.50 (dt, J=6.8, 21.3, 2H); MS (DCI) m/z 537.2 (M+H)$^+$.

Example 204

1-{2-[3,3-bis(4-fluorophenyl)pyrrolidin-1-yl]-2-oxoethyl}-3,3-bis(4-fluorophenyl)pyrrolidin-2-one The title compound was prepared using the procedure described in Example 172 substituting 2-(3,3-bis(4-fluorophenyl)-2-oxopyrrolidin-1-yl)acetic acid from Example 58D for 2-(3,3-bis(4-fluorophenyl)-2-oxopiperidin-1-yl)acetic acid and 3,3-bis(4-fluorophenyl)pyrrolidine from Example 203A for 3,3-diphenylpyrrolidine. $^1$H NMR (300 MHz, CDCl$_3$) δ ppm 7.38-7.28 (m, 4H), 7.18-7.09 (m, 4H), 7.03-6.93 (m, 8H), 4.11 (dd, J=5.1, 9.1, 4H), 3.61-3.48 (m, 3H), 3.42 (t, J=6.7, 1H), 2.77 (dd, J=6.4, 11.7, 2H), 2.57 (t, J=6.7, 1H), 2.47 (t, J=6.9, 1H); MS (DCI) m/z 573.2 (M+H)$^+$.

Example 205

1-{2-[3,3-bis(4-fluorophenyl)pyrrolidin-1-yl]-2-oxoethyl}-3,3-diphenylpiperidin-2-one The title compound was prepared using the procedure described in Example 172 substituting 2-(2-oxo-3,3-diphenylpiperidin-1-yl)acetic acid from Example 68E for 2-(3,3-bis(4-fluorophenyl)-2-oxopiperidin-1-yl)acetic acid and 3,3-bis(4-fluorophenyl)pyrrolidine from Example 203A for 3,3-diphenylpyrrolidine. $^1$H NMR (300 MHz, CDCl$_3$) δ ppm 7.30 (d, J=4.4, 8H), 7.25-7.21 (m, 2H), 7.17-7.10 (m, 4H), 6.98-6.88 (m, 4H), 4.14-4.07 (m, 4H), 3.67-3.45 (m, 4H), 2.70-

2.60 (m, 2H), 2.55 (t, J=6.7, 1H), 2.45 (t, J=6.8, 1H), 1.90-1.78 (m, 2H); MS (DCI) m/z 551.2 (M+H)+.

Example 206

1-{[3-(4-hydroxyphenyl)-1,2,4-oxadiazol-5-yl]methyl}-3,3-diphenylpiperidin-2-one (Z)—N',4-Dihydroxybenzimidamide (0.251 g, 1.649 mmol), 2-(2-oxo-3,3-diphenylpiperidin-1-yl)acetic acid (0.510 g, 1.649 mmol; Example 68E) and $N^1$-((ethylimino)methylene)-$N^3$,$N^3$-dimethylpropane-1,3-diamine hydrochloride (0.474 g, 2.473 mmol) were stirred together in dichloroethane at room temperature for 2 hours, then heated to 85° C. for 16 hours. The reaction was cooled and concentrated. The residue was dissolved in dichloromethane (5 mL) and washed with water (3 mL). The organic layer was concentrated and the residue was loaded onto a GraceResolv™ 12 g silica gel column (Grace Davison Discovery Sciences) and the product eluted with a gradient of 5% ethyl acetate/hexanes to 35% ethyl acetate/hexanes (Flow=35 mL/minute) over 30 minutes to give the title compound. $^1$H NMR (300 MHz, CDCl$_3$) δ 7.95-7.78 (m, 2H), 7.40-7.16 (m, 10H), 6.85-6.71 (m, 2H), 5.93 (s, 1H), 4.88 (s, 2H), 3.64 (t, J=6.5, 2H), 2.78-2.66 (m, 2H), 1.99-1.80 (m, 2H); MS (ESI+) m/z 426.1 (M+H)+.

Example 207

1-{[3-(4-chlorobenzyl)-1,2,4-oxadiazol-5-yl]methyl}-3,3-diphenylpiperidin-2-one $N^1$-((Ethylimino)methylene)-$N^3$,$N^3$-dimethylpropane-1,3-diamine hydrochloride (0.160 g, 0.837 mmol), (Z)-2-(4-chlorophenyl)-N-hydroxyacetimidamide (0.103 g, 0.558 mmol) and 2-(2-oxo-3,3-diphenylpiperidin-1-yl)acetic acid (0.173 g, 0.558 mmol; Example 68E) were stirred together in dichloroethane at room temperature for 2 hours, then heated to 85° C. for 16 hours. The reaction was cooled and concentrated. The residue was dissolved in dichloromethane (3 mL) and washed with water (1 mL). The organic layer was concentrated and the residue was loaded onto a GraceResolv™ 12 g silica gel column (Grace Davison Discovery Sciences) and the product eluted with a gradient of 5% ethyl acetate/hexanes to 35% ethyl acetate/hexanes (Flow=35 mL/minute) over 30 minutes to give the title compound. $^1$H NMR (300 MHz, CDCl$_3$) δ 7.38-7.15 (m, 14H), 4.82 (s, 2H), 4.06 (s, 2H), 3.53 (t, J=6.5, 2H), 2.73-2.58 (m, 2H), 1.95-1.76 (m, 2H); MS (ESI+) m/z 458.1 (M+H)+.

Example 208

2-[3,3-bis(4-fluorophenyl)-2-oxopyrrolidin-1-yl]-N-{1-[3-(trifluoromethyl)benzyl]piperidin-4-yl}acetamide The title compound was obtained by the procedure described in Example 171, replacing 2-(2-oxo-3,3-diphenylpiperidin-1-yl)acetic acid (Example 68E) with 2-(3,3-bis(4-fluorophenyl)-2-oxopyrrolidin-1-yl)acetic acid (Example 58D) and 4-(bis(4-fluorophenyl)methylene)piperidine hydrochloride with 1-(3-(trifluoromethyl)benzyl)piperidin-4-amine (Example 41B). $^1$H NMR (300 MHz, CDCl$_3$) δ ppm 7.58 (s, 1H), 7.51 (t, J=6.74 Hz, 2H), 7.43 (m, 1H), 7.30 (m, 4H), 7.01 (m, J=8.72, 8.72 Hz, 4H), 5.79 (d, J=7.93 Hz, 1H), 3.98 (s, 2H), 3.72 (m, 1H), 3.50 (m, 4H), 2.74 (m, 4H), 2.12 (t, J=11.30 Hz, 2H), 1.73 (m, 4H), 1.47 (m, 2H), 1.28 (m, 2H); MS (ESI+) m/z 572 (M+H)+.

Example 209

1-{[3-(4-isobutoxyphenyl)-1,2,4-oxadiazol-5-yl]methyl}-3,3-diphenylpiperidin-2-one To 1-{[3-(4-hydroxyphenyl)-1,2,4-oxadiazol-5-yl]methyl}-3,3-diphenylpiperidin-2-one (Example 206, 0.040 g, 0.094 mmol) and potassium carbonate (0.019 g, 0.141 mmol) in N,N-dimethylformamide (0.5 mL) was added 1-bromo-2-methylpropane (0.012 mL, 0.113 mmol) and the reaction heated to 75° C. for 3 hours. The reaction was cooled, loaded onto a GraceResolv™ 12 g silica gel column (Grace Davison Discovery Sciences) and the product eluted with a gradient of 5% ethyl acetate/hexanes to 40% ethyl acetate/hexanes (Flow=35 mL/minute) over 30 minutes to give the title compound. $^1$H NMR (300 MHz, CDCl$_3$) δ 8.11-7.94 (m, 2H), 7.39-7.13 (m, 10H), 7.06-6.93 (m, 2H), 4.90 (s, 2H), 3.80 (d, J=6.5, 2H), 3.61 (t, J=6.5, 2H), 2.77-2.62 (m, 2H), 2.13 (dp, J=6.8, 13.4, 1H), 2.01-1.80 (m, 2H), 1.04 (t, J=10.1, 6H); MS (ESI+) m/z 482.3 (M+H)+.

Example 210

3,3-bis(4-fluorophenyl)-1-(2-oxo-2-{(4aS,7aS)-1-[3-(trifluoromethyl)benzyl]octahydro-6H-pyrrolo[3,4-b]pyridin-6-yl}ethyl)pyrrolidin-2-one Example 210A 3,3-bis(4-fluorophenyl)-1-(2-oxo-2-((4aS,7aS)-tetrahydro-1H-pyrrolo[3,4-b]pyridin-6(2H,7H,7aH)-yl)ethyl)pyrrolidin-2-one To a solution of 2-(3,3-bis(4-fluorophenyl)-2-oxopyrrolidin-1-yl)acetic acid (Example 58D) (0.331 g, 1 mmol) and (4aS,7aS)-tert-butyl octahydro-1H-pyrrolo[3,4-b]pyridine-1-carboxylate (Example 50B) (0.226 g, 1 mmol) in methylene chloride (20 mL) was added O-(7-azabenzotriazol-1-yl)-N,N,N',N'-tetramethyluronium hexafluorophosphate (0.38 g, 1 mmol) and diisopropylethylamine (0.45 mL). The reaction mixture was stirred at ambient temperature overnight. The reaction mixture was then diluted with methylene chloride, and then washed with 1 N HCl, water, 1 N NaOH, and water. The organic layer was dried over magnesium sulfate and concentrated in vacuo. The obtained residue was purified by silica gel chromatography eluting with ethyl acetate to yield the t-butoxycarbonyl-protected title compound. That material was dissolved in dichloromethane (10 mL) and treated with trifluoroacetic acid (2 mL) for 1 hour at room temperature. The reaction mixture was concentrated and partitioned between saturated aqueous NaHCO$_3$ solution and dichloromethane. The organic layer was separated, dried over MgSO$_4$ and concentrated to give the title compound. $^1$H NMR (300 MHz, CDCl$_3$) δ ppm 7.35 (m, 4H), 7.00 (m, 4H), 4.25 (dd, 1H), 3.96 (t, J=16.78 Hz, 1H), 3.47 (m, 7H), 3.00 (m, 1H), 2.78 (m, 2H), 2.63 (m, 1H), 2.27 (m, 1H), 1.72 (m, 2H) 1.45 (m, 2H); MS (ESI+) m/z 440 (M+H)+.

Example 210B 3,3-bis(4-fluorophenyl)-1-(2-oxo-2-{(4aS,7aS)-1-[3-(trifluoromethyl)benzyl]octahydro-6H-pyrrolo[3,4-b]pyridin-6-yl}ethyl)pyrrolidin-2-one To a solution of product from Example 210A (0.2 g, 0.455 mmol) in dichloroethane (10 mL) was added 3-(trifluoromethyl)benzaldehyde (0.135 g, 0.774 mmol), sodium triacetoxyborohydride (0.145 g, 0.683 mmol), and a few drops of acetic acid. The reaction mixture was stirred at room temperature for 16 hours, then diluted with dichloromethane and washed with saturated aqueous $NaHCO_3$ solution. The organic layer was separated, dried over MgSO4, concentrated and purified by silica gel chromatography eluting with 2-5% methanol/dichloromethane. $^1$H NMR (400 MHz, pyridine-$d_5$, temperature 90° C.) δ ppm 7.63-7.72 (m, 1H), 7.55-7.63 (m, 4H), 7.47-7.58 (m, 2H), 7.33-7.45 (m, 1H), 7.00-7.08 (m, 4H), 4.13-4.33 (m, 2H), 3.66-3.77 (m, 1H), 3.51-3.65 (m, 3H), 3.27-3.65 (m, 4H), 2.87-3.15 (m, 1H), 2.73-2.80 (m, 2H), 2.45-2.57 (m, 1H), 2.06-2.26 (m, 2H), 1.23-1.56 (m, 4H); MS (ESI+) m/z 599 (M+H)$^+$.

Example 211

3,3-diphenyl-1-({3-[6-(trifluoromethyl)pyridin-3-yl]-1,2,4-oxadiazol-5-yl}methyl)pyrrolidin-2-one The title compound was prepared using the procedure described in Example 190 substituting 2-(2-oxo-3,3-diphenylpyrrolidin-1-yl)acetic acid from Example 1C for 2-(3,3-bis(4-fluorophenyl)-2-oxopyrrolidin-1-yl)acetic acid and (Z)—N-hydroxy-6-(trifluoromethyl)nicotinimidamide for (Z)—N-hydroxy-4-(trifluoromethyl)benzimidamide. $^1$H NMR (300 MHz, CDCl$_3$) δ ppm 9.33 (s, 1H), 8.43 (dd, J=1.5, 8.2, 1H), 7.80 (dd, J=0.5, 8.2, 1H), 7.44-7.26 (m, 10H), 4.93 (s, 2H), 3.59 (t, J=6.5, 2H), 2.90 (t, J=6.5, 2H); MS (DCI) m/z 465.1 (M+H)$^+$.

Example 212

3,3-bis(4-fluorophenyl)-1-({3-[6-(trifluoromethyl)pyridin-3-yl]-1,2,4-oxadiazol-5-yl}methyl)pyrrolidin-2-one The title compound was prepared using the procedure described in Example 190 substituting (Z)—N-hydroxy-6-(trifluoromethyl)nicotinimidamide for (Z)—N-hydroxy-4-(trifluoromethyl)benzimidamide. $^1$H NMR (300 MHz, CDCl$_3$) δ ppm 9.35 (d, J=1.4, 1H), 8.41 (dd, J=1.9, 8.0, 1H), 7.82 (d, J=8.2, 1H), 7.34 (ddd, J=2.7, 5.3, 7.1, 4H), 7.08-6.96 (m, 4H), 4.95 (d, J=19.5, 2H), 3.58 (t, J=6.5, 2H), 2.85 (t, J=6.5, 2H); MS (DCI) m/z 501.1 (M+H)$^+$.

Example 213

1-({3-[2-(4-chlorophenyl)ethyl]-1,2,4-oxadiazol-5-yl}methyl)-3,3-diphenylpiperidin-2-one Example 213A (Z)-3-(4-chlorophenyl)-N-hydroxypropanimidamide 3-(4-Chlorophenyl)propanenitrile (0.477 g, 2.88 mmol), hydroxylamine hydrochloride (0.300 g, 4.32 mmol) and sodium hydrogencarbonate (1.210 g, 14.40 mmol) were stirred together in methanol (4 mL) and heated to 60° C. for 16 hours. The reaction was cooled, filtered and concentrated. The reside was dissolved in minimal dichloromethane/methanol and loaded onto a GraceResolv™ 12 g silica gel column (Grace Davison Discovery Sciences) and the product eluted with a gradient of 50% ethyl acetate/hexanes to 100% ethyl acetate (Flow=30 mL/minute) over 20 minutes to supply the title compound.

Example 213B 1-({3-[2-(4-chlorophenyl)ethyl]-1,2,4-oxadiazol-5-yl}methyl)-3,3-diphenylpiperidin-2-one (Z)-3-(4-Chlorophenyl)-N-hydroxypropanimidamide (0.070 g, 0.352 mmol), 2-(2-oxo-3,3-diphenylpiperidin-1-yl)acetic acid (0.109 g, 0.352 mmol; Example 68E) and $N^1$-((ethylimino)methylene)-$N^3,N^3$-dimethylpropane-1,3-diamine hydrochloride (0.135 g, 0.705 mmol) were stirred together in dichloromethane (0.5 mL) at room temperature for 2 hours, then heated to 85° C. overnight. The reaction was cooled, loaded onto a GraceResolv™ 12 g silica gel column (Grace Davison Discovery Sciences) and the product eluted with a gradient of 5% ethyl acetate/hexanes to 50% ethyl acetate/hexanes (Flow=30 mL/minute) over 30 minutes to give the title compound. $^1$H NMR (300 MHz, CDCl$_3$) δ 7.39-7.04 (m, 14H), 4.83 (s, 2H), 3.54 (t, J=6.5, 2H), 3.11-2.99 (m, 4H), 2.74-2.61 (m, 2H), 1.99-1.76 (m, 2H); MS (ESI+) m/z 472.1 (M+H)$^+$.

Example 214

1-{[3-(6-chloropyridin-3-yl)-1,2,4-oxadiazol-5-yl]methyl}-3,3-diphenylpyrrolidin-2-one The title compound was prepared using the procedure described in Example 190 substituting 2-(2-oxo-3,3-diphenylpyrrolidin-1-yl)acetic acid from Example 1C for 2-(3,3-bis(4-fluorophenyl)-2-oxopyrrolidin-1-yl)acetic acid and (Z)-6-chloro-N-hydroxynicotinimidamide for (Z)—N-hydroxy-4-(trifluoromethyl)benzimidamide. $^1$H NMR (300 MHz, CDCl$_3$) δ ppm 9.00 (dd, J=0.7, 2.4, 1H), 8.21 (dd, J=2.4, 8.3, 1H), 7.45 (dd, J=0.7, 8.4, 1H), 7.38-7.24 (m, 10H), 4.90 (s, 2H), 3.58 (t, J=6.5, 2H), 2.90 (t, J=6.5, 2H); MS (DCI) m/z 431.1 (M+H)$^+$.

Example 215

1-{[3-(3,5-difluorophenyl)-1,2,4-oxadiazol-5-yl]methyl}-3,3-diphenylpyrrolidin-2-one The title compound was prepared using the procedure described in Example 190 substituting 2-(2-oxo-3,3-diphenylpyrrolidin-1-yl)acetic acid from Example 1C for 2-(3,3-bis(4-fluorophenyl)-2-oxopyrrolidin-1-yl)acetic acid and (Z)-3,5-difluoro-N-hydroxybenzimidamide for (Z)—N-hydroxy-4-(trifluoromethyl)benzimidamide. $^1$H NMR (300 MHz, CDCl$_3$) δ ppm 7.56-7.49 (m, 2H), 7.42-7.24 (m, 10H), 7.01-6.91 (m, 1H), 4.89 (s, 2H), 3.57 (t, 2H), 2.90 (t, J=6.5, 2H); MS (DCI) m/z 432.1 (M+H)$^+$.

Example 216

3-(4-fluorophenyl)-1-{2-oxo-2-[5-(trifluoromethyl)-1,3-dihydro-2H-isoindol-2-yl]ethyl}pyrrolidin-2-one Example 216A 2-(3-(4-fluorophenyl)-2-oxopyrrolidin-1-yl)acetic acid To a suspension of 3-(4-fluorophenyl)pyrrolidin-2-one (Example 189B, 1.36 g, 7.59 mmol) in tetrahydrofuran was added potassium 2-methylpropan-2-olate (8.35 ml, 8.35 mmol). The reaction was allowed to stir for 30 minutes, during which time a yellow solution resulted. To the reaction was added ethyl 2-bromoacetate (0.92 ml, 8.35 mmol) and stirring was continued at room temperature. After stirring for 3 hours, the reaction was poured into a 1:1 mixture of ethyl acetate/1 N HCl (300 mL). The organic layer was separated, washed with brine (100 mL), dried over magnesium sulfate and concentrated. The residue was dissolved in minimal dichloromethane and loaded onto a GraceResolv 40 g silica gel column (Grace Davison Discovery Sciences) and the product eluted with a gradient of 5% ethyl acetate/hexanes to 100% ethyl acetate/hexanes (Flow=40 mL/minute) over 40 minutes. The resulting ethyl ester intermediate was dissolved in methanol (10 mL) and treated with sodium hydroxide (7.59 mL, 15.18 mmol). After stirring for 1 hour, the reaction was poured into a 1:1 mixture of ethyl acetate/1 N HCl (300 mL). The organic layer was washed with brine (100 mL), dried over magnesium sulfate and concentrated to give the title compound. $^1$H NMR (300 MHz, DMSO-d$_6$) δ 12.87 (s, 1H), 7.34-7.26 (m, 2H), 7.20-7.10 (m, 2H), 4.00 (s, 2H), 3.71 (t, J=9.0, 1H), 3.52-3.43 (m, 2H), 2.59-2.35 (m, 1H), 2.07-1.91 (m, 1H).

Example 216B 3-(4-fluorophenyl)-1-{2-oxo-2-[5-(trifluoromethyl)-1,3-dihydro-2H-isoindol-2-yl]ethyl}pyrrolidin-2-one To a suspension of 2-(3-(4-fluorophenyl)-2-oxopyrrolidin-1-yl)acetic acid (0.102 g, 0.430 mmol; Example 216A) and 5-(trifluoromethyl)isoindoline hydrobromide (0.127 g, 0.473 mmol) in dichloromethane (0.75 mL) was added N$^1$-((ethylimino)methylene)-N$^3$,N$^3$-dimethylpropane-1,3-diamine (0.114 mL, 0.645 mmol) and the reaction was stirred at room temperature. After stirring for 18 hours, the reaction was loaded onto a GraceResolv™ 4 g silica gel column (Grace Davison Discovery Sciences) and the product eluted with a gradient of 5% ethyl acetate/hexanes to 100% ethyl acetate/hexanes (Flow=20 mL/minute) over 30 minutes to give the title compound. $^1$H NMR (300 MHz, CDCl$_3$) δ 7.58 (dd, J=8.5, 12.6, 2H), 7.42 (dd, J=8.1, 15.3, 1H), 7.36-7.21 (m, 2H), 7.12-6.93 (m, 2H), 4.91 (d, J=17.7, 4H), 4.29 (d, J=16.1, 1H), 4.17 (d, J=16.2, 1H), 3.85-3.54 (m, 3H), 2.72-2.50 (m, 1H), 2.19 (ddd, J=8.5, 12.9, 16.3, 1H); MS (ESI+) m/z 407.0 (M+H)$^+$.

Example 217

2-[3,3-bis(4-fluorophenyl)-2-oxopyrrolidin-1-yl]-N-[5-(trifluoromethyl)pyridin-2-yl]acetamide To a suspension of 2-(3,3-bis(4-fluorophenyl)-2-oxopyrrolidin-1-yl)acetic acid (0.158 g, 0.477 mmol; Example 58D) in dichloromethane (2 mL) was added a catalytic amount of N,N-dimethylformamide followed by oxalyl dichloride (2.0 Min dichloromethane) (0.358 mL, 0.715 mmol). After stirring for 30 minutes, the reaction was concentrated. The residue was dissolved in dichloromethane (2 mL) and 5-(trifluoromethyl)pyridin-2-amine (0.066 g, 0.405 mmol) and N-methylmorpholine (0.079 mL, 0.715 mmol) were added. After stirring for 2 hours, the reaction was loaded onto a GraceResolv™ 12 g silica gel column (Grace Davison Discovery Sciences) and the product eluted with a gradient of 5% ethyl acetate/hexanes to 75% ethyl acetate/hexanes (Flow=30 mL/minute) over 30 minutes to give the title compound. $^1$H NMR (300 MHz, CDCl$_3$) δ 8.55 (d, J=12.2, 1H), 8.25 (d, J=8.8, 1H), 7.92 (dd, J=2.2, 8.8, 1H), 7.33 (ddd, J=2.7, 5.3, 7.1, 4H), 7.06-6.96 (m, 4H), 4.22 (s, 2H), 3.55 (t, J=6.5, 2H), 2.83 (t, J=6.5, 2H); MS (ESI+) m/z 467.1 (M+H)$^+$.

Example 218

2-[3,3-bis(4-fluorophenyl)-2-oxopyrrolidin-1-yl]-N-[4-(trifluoromethyl)phenyl]acetamide To a suspension of 2-(3,3-bis(4-fluorophenyl)-2-oxopyrrolidin-1-yl)acetic acid (0.200 g, 0.604 mmol; Example 58D) in dichloromethane (2 mL) was added a catalytic amount of N,N-dimethylformamide followed by oxalyl dichloride (2.0 Min dichloromethane) (0.453 mL, 0.905 mmol). After stirring for 30 minutes, the reaction was concentrated. The residue was dissolved in dichloromethane (2 mL) and 4-(trifluoromethyl)aniline (0.056 mL, 0.453 mmol) followed by 4-methylmorpholine (0.100 mL, 0.905 mmol) were added. After stirring for 1 hour, the reaction was loaded onto a GraceResolv™ 12 g silica gel column (Grace Davison Discovery Sciences) and the product eluted with a gradient of 5% ethyl acetate/hexanes to 65% ethyl acetate/hexanes (Flow=30 mL/minute) over 30 minutes to give the title compound. $^1$H NMR (300 MHz, CDCl$_3$) δ 8.37 (s, 1H), 7.51 (d, J=8.6, 2H), 7.40 (d, J=8.5, 2H), 7.34-7.27 (m, 4H), 7.06-6.96 (m, 4H), 4.16 (s, 2H), 3.60 (t, J=6.5, 2H), 2.82 (t, J=6.5, 2H); MS (ESI+) m/z 474.8 (M+H)$^+$.

Example 219

3,3-diphenyl-1-({3-[5-(trifluoromethyl)pyridin-3-yl]-1,2,4-oxadiazol-5-yl}methyl)pyrrolidin-2-one The title compound was prepared using the procedure described in Example 190 substituting 2-(2-oxo-3,3-diphenylpyrrolidin-1-yl)acetic acid from Example 1C for 2-(3,3-bis(4-fluorophenyl)-2-oxopyrrolidin-1-yl)acetic acid and (Z)—N-hydroxy-5-(trifluoromethyl)nicotinimidamide for (Z)—N-hydroxy-4-(trifluoromethyl)benzimidamide. $^1$H NMR (300 MHz, CDCl$_3$) δ ppm 9.41 (d, J=1.7, 1H), 9.02 (d, J=1.2, 1H), 8.51 (s, 1H), 7.49-7.19 (m, 10H), 4.93 (s, 2H), 3.59 (t, J=6.5, 2H), 2.91 (t, J=6.5, 2H); MS (DCI) m/z 465.1 (M+H)$^+$.

Example 220

3,3-diphenyl-1-({3-[4-(trifluoromethyl)pyridin-3-yl]-1,2,4-oxadiazol-5-yl}methyl)pyrrolidin-2-one The title compound was prepared using the procedure described in Example 190 substituting 2-(2-oxo-3,3-diphenylpyrrolidin-1-yl)acetic acid from Example 1C for 2-(3,3-bis(4-fluorophenyl)-2-oxopyrrolidin-1-yl)acetic acid and (Z)—N-hydroxy-4-(trifluoromethyl)nicotinimidamide for (Z)—N-hydroxy-4-(trifluoromethyl)benzimidamide. $^1$H NMR (300 MHz, CDCl$_3$) δ ppm 9.09 (s, 1H), 8.97 (d, J=5.1, 1H), 7.73 (d, J=5.2, 1H), 7.42-7.18 (m, 10H), 4.95 (s, 2H), 3.59 (t, J=6.5, 2H), 2.89 (t, J=6.5, 2H); MS (DCI) m/z 465.1 (M+H)$^+$.

Example 221

3,3-diphenyl-1-[(3-pyridin-3-yl-1,2,4-oxadiazol-5-yl)methyl]pyrrolidin-2-one

The title compound was prepared using the procedure described in Example 190 substituting 2-(2-oxo-3,3-diphenylpyrrolidin-1-yl)acetic acid from Example 1C for 2-(3,3- bis(4-fluorophenyl)-2-oxopyrrolidin-1-yl)acetic acid and (Z)—N-hydroxynicotinimidamide for (Z)—N-hydroxy-4-(trifluoromethyl)benzimidamide. $^1$H NMR (300 MHz, CDCl$_3$) δ ppm 9.23 (d, J=1.7, 1H), 8.76 (dd, J=1.7, 4.9, 1H), 8.27 (dt, J=1.9, 8.0, 1H), 7.50-7.25 (m, 11H), 4.91 (s, 2H), 3.59 (t, J=6.5, 2H), 2.90 (t, J=6.5, 2H); MS (DCI) m/z 397.1 (M+H)$^+$.

Example 222

3,3-diphenyl-1-[(3-pyridin-4-yl-1,2,4-oxadiazol-5-yl)methyl]pyrrolidin-2-one

The title compound was prepared using the procedure described in Example 190 substituting 2-(2-oxo-3,3-diphenylpyrrolidin-1-yl)acetic acid from Example 1C for 2-(3,3-bis(4-fluorophenyl)-2-oxopyrrolidin-1-yl)acetic acid and (Z)—N-hydroxyisonicotinimidamide for (Z)—N-hydroxy-4-(trifluoromethyl)benzimidamide. $^1$H NMR (300 MHz, CDCl$_3$) δ ppm 8.78 (d, J=5.9, 2H), 7.86 (dd, J=1.6, 4.5, 2H), 7.44-7.28 (m, 10H), 4.92 (s, 2H), 3.58 (t, J=6.5, 2H), 2.90 (t, J=6.5, 2H); MS (DCI) m/z 397.1 (M+H)$^+$.

Example 223

1-{4-oxo-4-[5-(trifluoromethyl)-1,3-dihydro-2H-isoindol-2-yl]butyl}-3,3-diphenylpyrrolidin-2-one To 4-(2-oxo-3,3-diphenylpyrrolidin-1-yl)butanoic acid (Example 155A, 0.039 g, 0.121 mmol) and 5-(trifluoromethyl)isoindoline hydrobromide (0.036 g, 0.133 mmol) in dichloromethane (0.5 mL) was added N$^1$-((ethylimino)methylene)-N$^3$,N$^3$-dimethylpropane-1,3-diamine (0.032 mL, 0.181 mmol) and the reaction stirred for 18 hours. The reaction was loaded onto a GraceResolv™ 4 g silica gel column (Grace Davison Discovery Sciences) and the product eluted with a gradient of 5% ethyl acetate/hexanes to 100% ethyl acetate/hexanes (Flow=20 mL/minute) over 30 minutes to give the title compound. $^1$H NMR (300 MHz, CDCl$_3$) δ 7.55 (d, J=8.0, 1H), 7.45 (d, J=14.3, 1H), 7.36-7.13 (m, 11H), 4.67 (d, J=9.6, 2H), 4.57 (d, J=5.5, 2H), 3.50 (t, J=6.5, 2H), 3.41 (t, J=6.5, 2H), 2.74 (t, J=6.5, 2H), 2.26 (t, J=6.9, 2H), 2.01 (p, J=6.6, 2H); MS (ESI+) m/z 493.1 (M+H)$^+$.

Example 224

2-[3,3-bis(4-fluorophenyl)-2-oxopyrrolidin-1-yl]-N-[6-(trifluoromethyl)pyridin-3-yl]acetamide To a suspension of 2-(3,3-bis(4-fluorophenyl)-2-oxopyrrolidin-1-yl)acetic acid (0.255 g, 0.771 mmol; Example 58D) in dichloromethane (3 mL) was added a catalytic amount of N,N-dimethylformamide followed by oxalyl dichloride (2.0 M in dichloromethane) (0.617 mL, 1.234 mmol). The reaction was stirred for 1 hour, after which a reddish solution resulted. The reaction was concentrated and dried under high vacuum. The residue was dissolved in dichloromethane (3 mL) and 6-(trifluoromethyl)pyridin-3-amine (0.100 g, 0.617 mmol) and 4-methylmorpholine (0.136 mL, 1.234 mmol) were added. After stirring for 1 hour, the reaction was loaded onto a GraceResolv™ 40 g silica gel column (Grace Davison Discovery Sciences) and the product eluted with a gradient of 5% ethyl acetate/hexanes to 60% ethyl acetate/hexanes (Flow=40 mL/minute) over 40 minutes to give the title compound. $^1$H NMR (300 MHz, CDCl$_3$) δ 8.64 (s, 1H), 8.51 (d, J=2.5, 1H), 8.11 (dd, J=2.3, 8.7, 1H), 7.64-7.58 (m, 1H), 7.33-7.23 (m, 4H), 7.06-6.96 (m, 4H), 4.17 (s, 2H), 3.60 (t, J=6.5, 2H), 2.83 (t, J=6.5, 2H); MS (ESI+) m/z 476.0 (M+H)$^+$.

Example 225

2-[3,3-bis(4-fluorophenyl)-2-oxopyrrolidin-1-yl]-N-(5-chloropyridin-2-yl)acetamide To a suspension of 2-(3,3-bis(4-fluorophenyl)-2-oxopyrrolidin-1-yl)acetic acid (0.168 g, 0.506 mmol; Example 58D) was added a catalytic amount of N,N-dimethylformamide followed by oxalyl dichloride (0.404 mL, 0.809 mmol). After stirring for 30 minutes, the reaction was concentrated and dried under high vacuum for 10 minutes. The residue was dissolved in dichloromethane (0.5 mL) and 5-chloropyridin-2-amine (0.052 g, 0.404 mmol) and 4-methylmorpholine (0.089 mL, 0.809 mmol) were added. After 30 minutes, the reaction was loaded onto a GraceResolv™ 40 g silica gel column (Grace Davison Discovery Sciences) and the product eluted with a gradient of 10% ethyl acetate/hexanes to 40% ethyl acetate/hexanes (Flow=40 mL/minute) over 40 minutes to give the title compound. $^1$H NMR (300 MHz, CDCl$_3$) δ 8.29 (s, 1H), 8.24-8.20 (m, 1H), 8.09 (d, J=8.8, 1H), 7.65 (dd, J=2.7, 8.8, 1H), 7.36-7.28 (m, 4H), 7.05-6.96 (m, 4H), 4.19 (s, 2H), 3.54 (t, J=6.5, 2H), 2.82 (t, J=6.5, 2H); MS (ESI+) m/z 442.0 (M+H)$^+$.

Example 226

2-[3,3-bis(4-fluorophenyl)-2-oxopyrrolidin-1-yl]-N-[6-(trifluoromethyl)pyridin-2-yl]acetamide To a suspension of 2-(3,3-bis(4-fluorophenyl)-2-oxopyrrolidin-1-yl)acetic acid (0.192 g, 0.578 mmol; Example 58D) in dichloromethane (3 mL) was added a catalytic amount of N,N-dimethylformamide followed by oxalyl dichloride (2.0 M in dichloromethane) (0.578 mL, 1.157 mmol). The reaction was stirred for 30 minutes than concentrated to give an oil. After drying under high vacuum for 20 minutes, the residue was dissolved in dichloromethane (1 mL) and 6-(trifluoromethyl)pyridin-2-amine (0.075 g, 0.463 mmol) and 4-methylmorpholine (0.102 mL, 0.925 mmol) were added. After stirring for 20 minutes, the reaction was loaded onto a GraceResolv™ 40 g silica gel column (Grace Davison Discovery Sciences) and the product eluted with a gradient of 5% ethyl acetate/hexanes to 35% ethyl acetate/hexanes (Flow=40 mL/minute) over 30 minutes to give the title compound. $^1$H NMR (300 MHz, CDCl$_3$) δ 8.36 (s, 1H), 8.32 (d, J=8.5, 1H), 7.86 (t, J=8.0, 1H), 7.43 (d, J=7.3, 1H), 7.36-7.29 (m, 4H), 7.06-6.96 (m, 4H), 4.22 (s, 2H), 3.54 (t, J=6.5, 2H), 2.83 (t, J=6.5, 2H); MS (ESI+) m/z 476.1 (M+H)$^+$.

Example 227

1-[2-(5-fluoro-1,3-dihydro-2H-isoindol-2-yl)-2-oxoethyl]-3-(4-fluorophenyl)pyrrolidin-2-one To a suspension of 2-(3-(4-fluorophenyl)-2-oxopyrrolidin-1-yl)acetic acid (0.053 g, 0.223 mmol; Example 216A) and 5-fluoroisoindoline hydrogen chloride (0.043 g, 0.246 mmol) in dichloromethane (0.4 mL) was added N$^1$-((ethylimino)methylene)-N$^3$,N$^3$-dimethylpropane-1,3-diamine (0.059 mL, 0.335 mmol) and the reaction stirred for 18 hours. The reaction was loaded onto a GraceResolv™ 12 g silica gel column (Grace Davison Discovery Sciences) and the product eluted with a gradient of 5% ethyl acetate/hexanes to 100% ethyl acetate/hexanes (Flow=20 mL/minute) over 30 minutes to give the title compound. $^1$H NMR (300 MHz, CDCl$_3$) δ 7.34-7.16 (m, 4H), 7.08-6.93 (m, 3H), 4.82 (dd, J=8.6, 16.1, 4H), 4.27 (d, J=16.2, 1H), 4.15 (d, J=16.2, 1H), 3.79-3.59 (m, 3H), 2.67-2.51 (m, 1H), 2.18 (ddd, J=8.5, 12.9, 16.1, 1H); MS (ESI+) m/z 357.0 (M+H)$^+$.

Example 228

3,3-bis(4-fluorophenyl)-1-{2-oxo-2-[5-(trifluoromethyl)-1,3-dihydro-2H-isoindol-2-yl]ethyl}pyrrolidin-2-one To a suspension of 2-(3,3-bis(4-fluorophenyl)-2-oxopyrrolidin-1-yl)acetic acid (0.200 g, 0.604 mmol; Example 58D) and 5-(trifluoromethyl)isoindoline hydrobromide (0.178 g, 0.664 mmol) in dichloromethane (0.5 mL) was added N$^1$-((ethylimino)methylene)-N$^3$,N$^3$-dimethylpropane-1,3-diamine (0.160 mL, 0.905 mmol) and the reaction stirred for 3 days. The reaction was loaded onto a GraceResolv™ 12 g silica gel column (Grace Davison Discovery Sciences) and the product eluted with a gradient of 5% ethyl acetate/hexanes to 50% ethyl acetate/hexanes (Flow=20 mL/minute) over 30 minutes to give the title compound. MS (ESI+) m/z 501.1 (M+H)$^+$.

Example 229

2-[3-(4-fluorophenyl)-2-oxopyrrolidin-1-yl]-N-[5-(trifluoromethyl)pyridin-2-yl]acetamide To a suspension of 2-(3-(4-fluorophenyl)-2-oxopyrrolidin-1-yl)acetic acid (0.088 g, 0.370 mmol; Example 216A) in dichloromethane (1 mL) was added oxalyl dichloride (0.308 mL, 0.617 mmol). After 30 minutes, the reaction was concentrated and dried. This residue was dissolved in dichloromethane (1 mL) and 5-(trifluoromethyl)pyridin-2-amine (0.050 g, 0.308 mmol) was added followed by 4-methylmorpholine (0.068 mL, 0.617 mmol). After stirring for 30 minutes, the reaction was loaded onto a GraceResolv™ 12 g silica gel column (Grace Davison Discovery Sciences) and the product eluted with a gradient of 5% ethyl acetate/hexanes to 100% ethyl acetate/hexanes (Flow=20 mL/minute) over 30 minutes to give the title compound. $^1$H NMR (300 MHz, CDCl$_3$) δ 8.67 (s, 1H), 8.57-8.52 (m, 1H), 8.28 (d, J=8.7, 1H), 7.92 (dd, J=2.3, 8.8, 1H), 7.35-7.21 (m, 2H), 7.09-6.99 (m, 2H), 4.25 (d, J=16.0, 1H), 4.18 (d, J=16.0, 1H), 3.78 (t, J=9.0, 1H), 3.69-3.59 (m, 2H), 2.63 (m, 1H), 2.23 (m, 1H); MS (ESI+) m/z 382.0 (M+H)$^+$.

Example 230

3,3-diphenyl-1-[(3-pyrazin-2-yl-1,2,4-oxadiazol-5-yl)methyl]pyrrolidin-2-one

The title compound was prepared using the procedure described in Example 190 substituting 2-(2-oxo-3,3-diphenylpyrrolidin-1-yl)acetic acid from Example 1C for 2-(3,3-bis(4-fluorophenyl)-2-oxopyrrolidin-1-yl)acetic acid and (Z)—N-hydroxypyrazine-2-carboximidamide for (Z)—N-hydroxy-4-(trifluoromethyl)benzimidamide. $^1$H NMR (300 MHz, DMSO-d$_6$) δ ppm 9.15 (d, J=1.4, 1H), 8.87 (dt, J=2.0, 2.5, 2H), 7.40-7.21 (m, 10H), 5.01 (s, 2H), 3.54 (t, J=6.5, 2H), 2.84 (t, J=6.5, 2H); MS (DCI) m/z 398.3 (M+H)$^+$.

Example 231 tert-butyl 5-{5-[(2-oxo-3,3-diphenylpyrrolidin-1-yl)methyl]-1,2,4-oxadiazol-3-yl}pyridin-2-ylcarbamate The title compound was prepared using the procedure described in Example 190 substituting 2-(2-oxo-3,3-diphenylpyrrolidin-1-yl)acetic acid from Example 1C for 2-(3,3-bis(4-fluorophenyl)-2-oxopyrrolidin-1-yl)acetic acid and (Z)-tert-butyl 5-(N-hydroxycarbamimidoyl)pyridin-2-ylcarbamate for (Z)—N-hydroxy-4-(trifluoromethyl)benzimidamide. $^1$H NMR (300 MHz, CDCl$_3$) δ ppm 8.85 (d, J=1.7, 1H), 8.22 (dd, J=2.2, 8.8, 1H), 8.07 (d, J=8.8, 1H), 7.48-7.28 (m, 10H), 4.89 (s, 2H), 3.57 (t, J=6.5, 2H), 2.89 (t, J=6.5, 2H), 1.55 (s, 9H); MS (DCI) m/z 512.2 (M+H)$^+$.

Example 232

3,3-bis(4-fluorophenyl)-1-[(3-pyrazin-2-yl-1,2,4-oxadiazol-5-yl)methyl]pyrrolidin-2-one The title compound was prepared using the procedure described in Example 190 substituting (Z)—N-hydroxypyrazine-2-carboximidamide for (Z)—N-hydroxy-4-(trifluoromethyl)benzimidamide. $^1$H NMR (300 MHz, DMSO-d$_6$) δ ppm 9.15 (d, J=1.4, 1H), 8.93-8.83 (m, 2H), 7.45-7.33 (m, 4H), 7.25-7.07 (m, 4H), 5.01 (s, 2H), 3.53 (t, J=6.4, 2H), 2.82 (t, J=6.4, 2H); MS (DCI) m/z 434.3 (M+H)$^+$.

Example 233

1-{[3-(4-bromophenyl)-1,2,4-oxadiazol-5-yl]methyl}-3,3-bis(4-fluorophenyl)pyrrolidin-2-one 2-(3,3-Bis(4-fluorophenyl)-2-oxopyrrolidin-1-yl)acetic acid (0.300 g, 0.905 mmol; Example 58D), (Z)-4-bromo-N-hydroxybenzimidamide (0.214 g, 0.996 mmol) and N$^1$-((ethylimino)methylene)-N$^3$,N$^3$-dimethylpropane-1,3-diamine (0.211 g, 1.358 mmol) were stirred together in dichloroethane (5 mL) at room temperature for 3 hours. The reaction was then heated to 85° C. for 18 hours. The reaction was cooled, loaded onto a GraceResolv™ 80 g silica gel column (Grace Davison Discovery Sciences) and the product eluted with a gradient of 5% ethyl acetate/hexanes to 40% ethyl acetate/hexanes (Flow=40 mL/minute) over 40 minutes to give the title compound. $^1$H NMR (300 MHz, CDCl$_3$) δ 7.85 (d, J=8.6, 2H), 7.62 (d, J=8.6, 2H), 7.38-7.30 (m, 4H), 7.07-6.97 (m, 4H), 4.87 (s, 2H), 3.56 (t, J=6.5, 2H), 2.83 (t, J=6.4, 2H). MS (ESI+) m/z 512.0 (M+H)$^+$.

Example 234

1-{[3-(6-aminopyridin-3-yl)-1,2,4-oxadiazol-5-yl]methyl}-3,3-diphenylpyrrolidin-2-one Example 234A tert-butyl 5-(5-((2-oxo-3,3-diphenylpyrrolidin-1-yl)methyl)-1,2,4-oxadiazol-3-yl)pyridin-2-ylcarbamate A solution of (Z)-tert-butyl 5-(N-hydroxycarbamimidoyl)pyridin-2-ylcarbamate (0.131 g, 0.5 mmol), 2-(2-oxo-3,3-diphenylpyrrolidin-1-yl)acetic acid (0.153 g, 0.5 mmol; Example 1C) and N$^1$-((ethylimino)methylene)-N$^3$,N$^3$-dimethylpropane-1,3-diamine hydrochloride (0.199 g, 1.0 mmol) were stirred together in dichloroethane (7.0 mL) at room temperature for 2 hours. The reaction was then heated to 85°

C. and stirred overnight. The reaction was cooled, loaded onto a SF25-40 column (Analogix®) and the product eluted using a gradient of 10% ethyl acetate/hexanes to 70% ethyl acetate over 30 minutes (Flow=30 mL/minute) to supply the title compound.

Example 234B

1-{[3-(6-aminopyridin-3-yl)-1,2,4-oxadiazol-5-yl]methyl}-3,3-diphenylpyrrolidin-2-one To tert-butyl 5-(5-((2-oxo-3,3-diphenylpyrrolidin-1-yl)methyl)-1,2,4-oxadiazol-3-yl)pyridin-2-ylcarbamate (0.110 g, 0.215 mmol; Example 234A) was added HCl (4.0 M in dioxane) (5.0 mL, 20.00 mmol). The reaction was proceeding, but slowly. The reaction was heated to 50° C. for 2 hours. The reaction was concentrated, diethyl ether was added and the resulting suspension sonicated. The resulting solid was collected and dried to give the title compound as the HCl salt. $^1$H NMR (300 MHz, methanol-$d_4$) δ 8.36 (dd, J=2.2, 6.7, 2H), 7.39-7.22 (m, 10H), 7.18-7.10 (m, 1H), 4.94 (s, 2H), 3.68-3.59 (m, 2H), 2.91 (t, J=6.5, 2H); MS (ESI+) m/z 412.0 (M+H)$^+$.

Example 235

4-(5-{[3,3-bis(4-fluorophenyl)-2-oxopyrrolidin-1-yl]methyl}-1,2,4-oxadiazol-3-yl)benzonitrile Example 235A 1-((3-(4-bromophenyl)-1,2,4-oxadiazol-5-yl)methyl)-3,3-bis(4-fluorophenyl)pyrrolidin-2-one 2-(3,3-bis(4-fluorophenyl)-2-oxopyrrolidin-1-yl)acetic acid (0.300 g, 0.905 mmol; Example 58D), (Z)-4-bromo-N-hydroxybenzimidamide (0.214 g, 0.996 mmol) and $N^1$-((ethylimino)methylene)-$N^3$,$N^3$-dimethylpropane-1,3-diamine (0.211 g, 1.358 mmol) were stirred together in dichloroethane (5 mL) at room temperature for 3 hours. The reaction was then heated to 85° C. for 18 hours. The reaction was cooled, loaded onto a GraceResolv 80 g silica gel column (Grace Davison Discovery Sciences) and the product eluted with a gradient of 5% ethyl acetate/hexanes to 40% ethyl acetate/hexanes (Flow=40 mL/minute) over 40 minutes to give the title compound. $^1$H NMR (300 MHz, CDCl$_3$) δ 7.85 (d, J=8.6, 2H), 7.62 (d, J=8.6, 2H), 7.38-7.30 (m, 4H), 7.07-6.97 (m, 4H), 4.87 (s, 2H), 3.56 (t, J=6.5, 2H), 2.83 (t, J=6.4, 2H); MS (ESI+) m/z 512.0 (M+H)$^+$.

Example 235B 4-(5-{[3,3-bis(4-fluorophenyl)-2-oxopyrrolidin-1-yl]methyl}-1,2,4-oxadiazol-3-yl)benzonitrile 1-((3-(4-Bromophenyl)-1,2,4-oxadiazol-5-yl)methyl)-3,3-bis(4-fluorophenyl)pyrrolidin-2-one (233 mg, 0.457 mmol; Example 235A), palladium(II) acetate (1.025 mg, 4.57 μmol), sodium carbonate (48.4 mg, 0.457 mmol) and potassium hexacyanoferrate(II) trihydrate (42.4 mg, 0.100 mmol) in N,N-dimethylacetamide (2 mL) was placed under nitrogen and heated to 120° C. The reaction was cooled, loaded onto a GraceResolv™ 40 g silica gel column (Grace Davison Discovery Sciences) and the product eluted with a gradient of 5% ethyl acetate/hexanes to 40% ethyl acetate/hexanes (Flow=40 mL/minute) over 40 minutes to give the title compound. $^1$H NMR (300 MHz, CDCl$_3$) δ 8.08 (d, J=8.4, 2H), 7.78 (d, J=8.4, 2H), 7.38-7.30 (m, 4H), 7.07-6.98 (m, 4H), 4.89 (s, 2H), 3.57 (t, J=6.5, 2H), 2.84 (t, J=6.4, 2H); MS (ESI–) m/z 455.1 (M–H)$^-$.

Example 236

(3S)-3-(4-fluorophenyl)-1-({3-[4-(trifluoromethyl)phenyl]-1,2,4-oxadiazol-5-yl}methyl)pyrrolidin-2-one The enantiomers of 3-(4-fluorophenyl)-1-((3-(4-(trifluoromethyl)phenyl)-1,2,4-oxadiazol-5-yl)methyl)pyrrolidin-2-one (Example 189, 0.260 g, 0.641 mmol) were separated by preparative supercritical fluid chromatography using a ChiralPak® OD-H column, and eluting with a gradient of 10% to 30% CO$_2$/methanol containing 0.1% diethylamine over 15 minutes. The title compound was obtained as the first eluting enantiomer. $^1$H NMR (300 MHz, CDCl$_3$) δ 8.21 (d, J=8.2, 2H), 7.76 (d, J=8.3, 2H), 7.30 (dd, J=5.3, 8.6, 2H), 7.05 (t, J=8.7, 2H), 4.97 (d, J=17.0, 1H), 4.84 (d, J=16.9, 1H), 3.83-3.59 (m, 3H), 2.74-2.58 (m, 1H), 2.24 (dq, J=8.4, 13.0, 1H).

Example 237

(3R)-3-(4-fluorophenyl)-1-({3-[4-(trifluoromethyl)phenyl]-1,2,4-oxadiazol-5-yl}methyl)pyrrolidin-2-one The enantiomers of 3-(4-fluorophenyl)-1-((3-(4-(trifluoromethyl)phenyl)-1,2,4-oxadiazol-5-yl)methyl)pyrrolidin-2-one (Example 189, 0.260 g, 0.641 mmol) were separated by preparative supercritical fluid chromatography using a ChiralPak® OD-H column, and eluting with a gradient of 10% to 30% CO$_2$/methanol containing 0.1% diethylamine over 15 minutes. The title compound was obtained as the second eluting enantiomer. $^1$H NMR (300 MHz, CDCl$_3$) δ 8.21 (d, J=8.2, 2H), 7.76 (d, J=8.3, 2H), 7.30 (dd, J=5.3, 8.6, 2H), 7.05 (t, J=8.7, 2H), 4.97 (d, J=17.0, 1H), 4.84 (d, J=16.9, 1H), 3.83-3.59 (m, 3H), 2.74-2.58 (m, 1H), 2.24 (dq, J=8.4, 13.0, 1H).

Example 238

3-(4-fluorophenyl)-1-({3-[6-(trifluoromethyl)pyridin-3-yl]-1,2,4-oxadiazol-5-yl}methyl)pyrrolidin-2-one (Z)—N-Hydroxy-6-(trifluoromethyl)nicotinimidamide (0.082 g, 0.399 mmol), 2-(3-(4-fluorophenyl)-2-oxopyrrolidin-1-yl)acetic acid (0.086 g, 0.363 mmol; Example 216A) and $N^1$-((ethylimino)methylene)-$N^3$,$N^3$-dimethylpropane-1,3-diamine hydrochloride (0.104 g, 0.544 mmol) were stirred together in dichloroethane (1 mL) at room temperature for 4 hours. The reaction was heated to 85° C. and heated overnight. The reaction was cooled, loaded onto a GraceResolv™ 12 g silica gel column (Grace Davison Discovery Sciences) and the product eluted with a gradient of 5% ethyl acetate/hexanes to 50% ethyl acetate/hexanes (Flow=36 mL/minute) over 30 minutes to give the title compound. $^1$H NMR (300 MHz, CDCl$_3$) δ 9.41 (d, J=1.7, 1H), 8.58-8.50 (m, 1H), 7.84 (dd, J=0.5, 8.1, 1H), 7.33-7.26 (m, 2H), 7.11-7.01 (m, 2H), 4.98 (d, J=17.0, 1H), 4.87 (d, J=17.0, 1H), 3.78 (t, J=9.0, 1H), 3.74-3.61 (m, 2H), 2.67 (dddd, J=4.3, 7.0, 9.1, 13.2, 1H), 2.26 (ddd, J=8.5, 13.0, 16.5, 1H); MS (ESI+) m/z 407.0 (M+H)$^+$.

Example 239

2-[3,3-bis(4-fluorophenyl)-2-oxopyrrolidin-1-yl]-N-{1-[3-fluoro-4-(trifluoromethyl)benzyl]azetidin-3-yl}acetamide

Example 239A

N-azetidin-3-yl-2-[3,3-bis(4-fluorophenyl)-2-oxopyrrolidin-1-yl]acetamide

The title compound was obtained by the procedure described in Example 210A, replacing (4aS,7aS)-tert-butyl octahydro-1H-pyrrolo[3,4-b]pyridine-1-carboxylate with tert-butyl 3-aminoazetidine-1-carboxylate. $^1$H NMR (300 MHz, CDCl$_3$) δ ppm 7.34 (m, 4H), 6.95 (m, 4H), 5.32 (m, 1H), 4.02 (m, 2H), 3.45 (m, 3H), 2.86 (m, 5H)), MS (APCI+) m/z 386 (M+H)$^+$.

Example 239B

2-[3,3-bis(4-fluorophenyl)-2-oxopyrrolidin-1-yl]-N-{1-[3-fluoro-4-(trifluoromethyl)benzyl]azetidin-3-yl}acetamide To a solution of N-azetidin-3-yl-2-[3,3-bis(4-fluorophenyl)-2-oxopyrrolidin-1-yl]acetamide (0.083 g, 0.215 mmol; Example 239A) in dichloromethane (5 mL) was added 3-fluoro-4-(trifluoromethyl)benzaldehyde (0.062 g, 0.323 mmol), sodium triacetoxyborohydride (0.088 g, 0.323 mmol) and a few drops of acetic acid. The reaction mixture was stirred at ambient temperature for 16 hours. The mixture was then diluted with dichloromethane and washed with saturated aqueous NaHCO$_3$ solution. The separated organic layer was dried over MgSO$_4$, concentrated, and purified by silica gel flash chromatography eluting with 5-10% methanol/dichloromethane. $^1$H NMR (300 MHz, CDCl$_3$) δ ppm 7.54 (t, J=7.6 Hz, 1H), 7.28-7.33 (m, 4H), 7.12-7.16 (m, 2H), 6.98-7.05 (m, 4H), 6.30-6.37 (m, 1H), 4.40-4.59 (m, 1H), 3.99 (s, 2H), 3.54-3.66 (m, 4H), 3.50 (t, J=6.5 Hz, 2H), 2.77 (t, J=6.4 Hz, 4H); MS (ESI+) m/z 562 (M+H)$^+$.

Example 240

1-(2-oxo-2-{3-[4-(trifluoromethyl)phenyl]azetidin-1-yl}ethyl)-3,3-diphenylpiperidin-2-one The title compound was obtained by the procedure described in Example 171, replacing 4-(bis(4-fluorophenyl)methylene)piperidine hydrochloride with 3-(4-(trifluoromethyl)phenyl)azetidine hydrochloride. $^1$H NMR (300 MHz, CDCl$_3$) δ ppm 7.57-7.61 (m, 2H), 7.40-7.44 (m, 2H), 7.20-7.33 (m, 10H), 4.67 (t, J=8.6 Hz, 1H), 4.51 (t, J=9.3 Hz, 1H), 4.27 (dd, J=8.3, 5.8 Hz, 1H), 4.11 (dd, J=9.7, 5.9 Hz, 1H), 4.00 (d, J=3.2 Hz, 2H), 3.80-3.96 (m, 1H), 3.61 (t, J=6.5 Hz, 2H), 2.58-2.67 (m, 2H), 1.80-1.91 (m, 2H); MS (ESI+) m/z 493 (M+H)$^+$.

Example 241

4-{1-[(2-oxo-3,3-diphenylpiperidin-1-yl)acetyl]azetidin-3-yl}benzonitrile

The title compound was obtained by the procedure described in Example 171, replacing 4-(bis(4-fluorophenyl)methylene)piperidine hydrochloride with 4-(azetidin-3-yl)benzonitrile hydrochloride. $^1$H NMR (300 MHz, CDCl$_3$) δ ppm 7.59-7.64 (m, 2H), 7.38-7.44 (m, 2H), 7.19-7.33 (m, 10H), 4.68 (t, J=8.6 Hz, 1H), 4.50 (t, J=9.3 Hz, 1H), 4.28 (dd, J=8.1, 6.1 Hz, 1H), 4.08 (dd, J=9.7, 6.0 Hz, 1H), 3.99 (d, J=15.6 Hz, 1H), 3.95 (d, J=15.0 Hz, 1H), 3.81-3.91 (m, 1H), 3.59-3.66 (m, 2H), 2.60-2.68 (m, 2H), 1.79-1.90 (m, 2H).

Example 242

N-(1-benzylazetidin-3-yl)-2-[3,3-bis(4-fluorophenyl)-2-oxopyrrolidin-1-yl]acetamide The title compound was obtained by the procedure described in Example 171, replacing 2-(2-oxo-3,3-diphenylpiperidin-1-yl)acetic acid (Example 68E) with 2-(3,3-bis(4-fluorophenyl)-2-oxopyrrolidin-1-yl)acetic acid (Example 58D) and 4-(bis(4-fluorophenyl)methylene)piperidine hydrochloride with 1-benzylazetidin-3-amine. $^1$H NMR (300 MHz, CDCl$_3$) δ ppm 7.34 (m, 3H), 7.25 (m, 6H), 6.98 (t, J=8.65 Hz, 4H), 4.52 (m, 1H), 4.01 (s, 2H), 3.91 (m, 4H), 3.47 (t, J=6.61 Hz, 2H), 2.80 (s, 2H), 2.77 (t, J=6.61 Hz, 2H); MS (ESI+) m/z 476 (M+H)$^+$.

Example 243

1-(2-oxo-2-{4-[3-(trifluoromethyl)phenyl]piperidin-1-yl}ethyl)-3,3-diphenylpiperidin-2-one The title compound was obtained by the procedure described in Example 171, replacing 4-(bis(4-fluorophenyl)methylene)piperidine hydrochloride with 4-(3-(trifluoromethyl)phenyl)piperidine hydrochloride. $^1$H NMR (300 MHz, CDCl$_3$) δ ppm 7.17-7.52 (m, 14H), 4.77-4.84 (m, 1H), 4.33-4.39 (m, 1H), 4.17-4.24 (m, 1H), 3.93-4.00 (m, 1H), 3.50-3.57 (m, 2H), 3.10-3.20 (m, 1H), 2.76-2.86 (m, 1H), 2.69-2.72 (m, 1H), 2.63-2.68 (m, 2H), 1.81-2.00 (m, 4H), 1.58-1.75 (m, 2H); MS (ESI+) m/z 521 (M+H)$^+$.

Example 244

1-{2-[4-(4-fluorophenyl)piperidin-1-yl]-2-oxoethyl}-3,3-diphenylpiperidin-2-one

The title compound was obtained by the procedure described in Example 171, replacing 4-(bis(4-fluorophenyl)methylene)piperidine hydrochloride with 4-(4-fluorophenyl)piperidine hydrochloride. $^1$H NMR (300 MHz, CDCl$_3$) δ ppm 7.18-7.35 (m, 10H), 7.13 (dd, J=8.5, 5.4 Hz, 2H), 6.99 (t, J=8.6 Hz, 2H), 4.74-4.81 (m, 1H), 4.33-4.40 (m, 1H), 4.04-4.21 (m, 1H), 3.89-3.97 (m, 1H), 3.50-3.56 (m, 2H), 3.08-3.18 (m, 1H), 2.63-2.76 (m, 4H), 1.78-1.92 (m, 4H), 1.59-1.70 (m, 2H); MS (ESI+) m/z 471 (M+H)$^+$.

Example 245

1-(2-oxo-2-{4-[4-(trifluoromethyl)phenyl]piperidin-1-yl}ethyl)-3,3-diphenylpiperidin-2-one The title compound was obtained by the procedure described in Example 171, replacing 4-(bis(4-fluorophenyl)methylene)piperidine hydrochloride with 4-(4-(trifluoromethyl)phenyl)piperidine hydrochloride. $^1$H NMR (300 MHz, CDCl$_3$) δ ppm 7.54-7.58 (m, 2H), 7.17-7.36 (m, 12H), 4.76-4.84 (m, 1H), 4.35-4.42 (m, 1H), 4.18 (d, J=15.7 Hz, 1H), 3.92-4.00 (m, 1H), 3.50-3.57 (m, 2H), 3.10-3.20 (m, 1H), 2.63-2.86 (m, 4H), 1.79-1.90 (m, 4H), 1.67 (qd, J=12.7, 4.0 Hz, 2H); MS (ESI+) m/z 521 (M+H)$^+$.

Example 246

2-(2-oxo-3,3-diphenylpyrrolidin-1-yl)-N-[5-(trifluoromethyl)pyridin-2-yl]acetamide

Example 246A 2-(2-oxo-3,3-diphenylpyrrolidin-1-yl)acetyl chloride

To a suspension of 2-(2-oxo-3,3-diphenylpyrrolidin-1-yl) acetic acid (1.477 g, 5.0 mmol; Example 1C) in dichloromethane (20 mL) was added catalytic amount of N,N-dimethylformamide followed by oxalyl dichloride (2.0 M in dichloromethane, 3.75 mL, 7.5 mmol). After stirring for 60 minutes, the reaction was concentrated, dried under high vacuum overnight. The resulting material was taken for further reactions without additional purification.

Example 246B 2-(2-oxo-3,3-diphenylpyrrolidin-1-yl)-N-[5-(trifluoromethyl)pyridin-2-yl]acetamide To a solution of 2-(2-oxo-3,3-diphenylpyrrolidin-1-yl) acetyl chloride (Example 246A, 0.157 g, 0.5 mmol) dissolved in dichloromethane (5 mL) was added 5-(trifluoromethyl) pyridin-2-amine (0.081 g, 0.5 mmol) and N-methylmorpholine (0.085 mL, 0.75 mmol) under nitrogen. After stirring for 18 hours, the reaction mixture was concentrated, loaded onto silica gel column (Analogix®, Burlington, Wis.) and the product eluted with a gradient of 5% ethyl acetate/hexanes to 75% ethyl acetate/hexanes (Flow=30 mL/minute) over 30 minutes to give the title compound. $^1$H NMR (300 MHz, CDCl$_3$) δ ppm 8.70 (s, 1H), 8.53 (s, 1H), 8.24 (d, J=8.7, 1H), 7.90 (dd, J=2.3, 8.8, 1H), 7.44-7.18 (m, 10H), 4.21 (s, 2H), 3.55 (t, J=6.5, 2H), 2.88 (t, J=6.5, 2H); MS (DCI) m/z 440.1 (M+H)$^+$.

Example 247

2-(2-oxo-3,3-diphenylpyrrolidin-1-yl)-N-[6-(trifluoromethyl)pyridin-2-yl]acetamide The title compound was prepared using the procedure described in Example 246 substituting 6-(trifluoromethyl) pyridin-2-amine for 5-(trifluoromethyl)pyridin-2-amine. $^1$H NMR (300 MHz, CDCl$_3$) δ ppm 8.41 (s, 1H), 8.33 (d, J=8.4, 1H), 7.85 (t, J=8.0, 1H), 7.43-7.19 (m, 11H), 4.22 (s, 2H), 3.54 (t, J=6.5, 2H), 2.89 (t, J=6.5, 2H); MS (DCI) m/z 440.1 (M+H)$^+$.

Example 248

2-(2-oxo-3,3-diphenylpyrrolidin-1-yl)-N-[6-(trifluoromethyl)pyridin-3-yl]acetamide The title compound was prepared using the procedure described in Example 246 substituting 6-(trifluoromethyl) pyridin-3-amine for 5-(trifluoromethyl)pyridin-2-amine. $^1$H NMR (300 MHz, CDCl$_3$) δ ppm 8.55 (s, 1H), 8.34 (d, J=2.4, 1H), 8.08 (dd, J=2.3, 8.6, 1H), 7.57 (d, J=8.6, 1H), 7.38-7.28 (m, 10H), 4.19 (s, 2H), 3.60 (t, J=6.6, 2H), 2.88 (t, J=6.5, 2H); MS (DCI) m/z 440.1 (M+H)$^+$.

Example 249

N-[3-chloro-5-(trifluoromethyl)pyridin-2-yl]-2-(2-oxo-3,3-diphenylpyrrolidin-1-yl)acetamide The title compound was prepared using the procedure described in Example 246 substituting 3-chloro-5-(trifluoromethyl)pyridin-2-amine for 5-(trifluoromethyl)pyridin-2-amine. $^1$H NMR (300 MHz, CDCl$_3$) δ ppm 8.68 (s, 1H), 8.55 (s, 1H), 7.91 (d, J=1.7, 1H), 7.41-7.19 (m, 10H), 4.52 (s, 2H), 3.59 (t, J=6.5, 2H), 2.87 (t, J=6.5, 2H); MS (DCI) m/z 474.1 (M+H)$^+$.

Example 250

1-(2-{4-[4-chloro-3-(trifluoromethyl)phenyl]-4-hydroxypiperidin-1-yl}-2-oxoethyl)-3,3-diphenylpiperidin-2-one The title compound was obtained by the procedure described in Example 171, replacing 4-(bis(4-fluorophenyl) methylene)piperidine hydrochloride with 4-(4-chloro-3-(trifluoromethyl)phenyl)piperidin-4-ol. $^1$H NMR (300 MHz, CDCl$_3$) δ ppm 7.80 (d, J=2.0 Hz, 1H), 7.38-7.54 (m, 2H), 7.18-7.34 (m, 10H), 4.58-4.66 (m, 1H), 4.47 (d, J=15.6 Hz, 1H), 4.07 (d, J=15.4 Hz, 1H), 3.74-3.80 (m, 1H), 3.42-3.66 (m, 3H), 3.02-3.21 (m, 1H), 2.63-2.68 (m, 2H), 1.95-2.07 (m, 2H), 1.71-1.91 (m, 5H); MS (ESI+) m/z 571 (M+H)$^+$.

Example 251

N-(5-cyanopyridin-2-yl)-2-(2-oxo-3,3-diphenylpyrrolidin-1-yl)acetamide

The title compound was prepared using the procedure described in Example 246 substituting 6-aminonicotinonitrile for 5-(trifluoromethyl)pyridin-2-amine. $^1$H NMR (300 MHz, CDCl$_3$) δ ppm 8.78 (s, 1H), 8.55 (d, J=1.9, 1H), 8.25 (d, J=8.7, 1H), 7.92 (dd, J=2.2, 8.7, 1H), 7.47-7.23 (m, 10H), 4.21 (s, 2H), 3.55 (t, J=6.5, 2H), 2.88 (t, J=6.5, 2H); MS (DCI) m/z 397.1 (M+H)$^+$.

Example 252

2-[3,3-bis(4-fluorophenyl)-2-oxopyrrolidin-1-yl]-N-(5-cyanopyridin-2-yl)acetamide The title compound was prepared using the procedure described in Example 246 substituting 2-(3,3-bis(4-fluorophenyl)-2-oxopyrrolidin-1-yl)acetic acid from Example 58D for 2-(2-oxo-3,3-diphenylpyrrolidin-1-yl)acetic acid and 6-aminonicotinonitrile for 5-(trifluoromethyl)pyridin-2-amine. $^1$H NMR (300 MHz, CDCl$_3$) δ ppm 8.55 (s, 2H), 8.25 (d, J=8.7, 1H), 7.93 (dd, J=2.1, 8.7, 1H), 7.43-7.22 (m, 4H), 7.07-6.98 (m, 4H), 4.21 (s, 2H), 3.55 (t, J=6.5, 2H), 2.83 (t, J=6.5, 2H); MS (DCI) m/z 433.0 (M+H)$^+$.

Example 253

1-[2-(3,4-dihydroisoquinolin-2(1H)-yl)-2-oxoethyl]-3-(4-fluorophenyl)pyrrolidin-2-one The title compound was prepared using the procedure described in Example 172 substituting 2-(3-(4-fluorophenyl)-2-oxopyrrolidin-1-yl)acetic acid from Example 216A for 2-(3,3-bis(4-fluorophenyl)-2-oxopiperidin-1-yl)acetic acid and 1,2,3,4-tetrahydroisoquinoline for 3,3-diphenylpyrrolidine. $^1$H NMR (300 MHz, CDCl$_3$) δ ppm 7.35-6.96 (m, 8H), 4.68 (d, J=27.4, 2H), 4.34 (d, 1H), 4.19 (dd, J=7.4, 15.9, 1H), 3.84 (t, J=6.0, 1H), 3.78-3.52 (m, 4H), 3.02-2.81 (m, 2H), 2.68-2.45 (m, 1H), 2.25-2.06 (m, 1H); MS (DCI) m/z 353.1 (M+H)$^+$.

Example 254

3-(4-fluorophenyl)-1-{2-oxo-2-[7-(trifluoromethyl)-3,4-dihydroisoquinolin-2(1H)-yl]ethyl}pyrrolidin-2-one The title compound was prepared using the procedure described in Example 172 substituting 2-(3-(4-fluorophenyl)-2-oxopyrrolidin-1-yl)acetic acid from Example 216A for 2-(3,3-bis(4-fluorophenyl)-2-oxopiperidin-1-yl)acetic acid and 7-(trifluoromethyl)-1,2,3,4-tetrahydroisoquinoline for 3,3-diphenylpyrrolidine. $^1$H NMR (300 MHz, CDCl$_3$) δ ppm 7.53-7.33 (m, 2H), 7.31-7.18 (m, 3H), 7.02 (td, J=3.4, 8.7, 2H), 4.74 (d, J=23.8, 2H), 4.31 (t, J=18.2, 1H), 4.20-4.02 (m, 1H), 3.86 (t, J=6.0, 1H), 3.78-3.69 (m, 2H), 3.66-3.53 (m, 2H), 3.04-2.87 (m, 2H), 2.66-2.49 (m, 1H), 2.27-2.09 (m, 1H); MS (DCI) m/z 421.1 (M+H)$^+$.

Example 255

1-[2-(7-fluoro-3,4-dihydroisoquinolin-2(1H)-yl)-2-oxoethyl]-3-(4-fluorophenyl)pyrrolidin-2-one The title compound was prepared using the procedure described in Example 172 substituting 2-(3-(4-fluorophenyl)-2-oxopyrrolidin-1-yl)acetic acid from Example 216A for 2-(3,3-bis(4-fluorophenyl)-2-oxopiperidin-1-yl)acetic acid and 7-fluoro-1,2,3,4-tetrahydroisoquinoline for 3,3-diphenylpyrrolidine. $^1$H NMR (300 MHz, CDCl$_3$) δ ppm 7.36-7.20 (m, 2H), 7.16-6.96 (m, 3H), 6.95-6.75 (m, 2H), 4.66 (d, J=26.3, 2H), 4.34 (d, J=16.0, 1H), 4.22-4.03 (m, 1H), 3.83 (dd, J=5.7, 11.4, 1H), 3.75-3.49 (m, 4H), 2.87 (dd, J=5.8, 11.7, 2H), 2.68-2.45 (m, 1H), 2.16 (dd, J=7.7, 13.2, 1H)); MS (DCI) m/z 371.1 (M+H)$^+$.

Example 256

1-[2-(7-chloro-3,4-dihydroisoquinolin-2(1H)-yl)-2-oxoethyl]-3-(4-fluorophenyl)pyrrolidin-2-one The title compound was prepared using the procedure described in Example 172 substituting 2-(3-(4-fluorophenyl)-2-oxopyrrolidin-1-yl)acetic acid from Example 216A for 2-(3,3-bis(4-fluorophenyl)-2-oxopiperidin-1-yl)acetic acid and 7-chloro-1,2,3,4-tetrahydroisoquinoline for 3,3-diphenylpyrrolidine. $^1$H NMR (300 MHz, CDCl$_3$) δ ppm 7.37-7.20 (m, 2H), 7.21-6.93 (m, 5H), 4.65 (d, J=26.2, 2H), 4.33 (d, J=15.9, 1H), 4.24-4.00 (m, 1H), 3.82 (t, 1H), 3.76-3.48 (m, 4H), 2.86 (dt, J=5.9, 11.4, 2H), 2.57 (d, J=3.8, 1H), 2.16 (dd, J=6.2, 14.6, 1H); MS (DCI) m/z 387.1 (M+H)$^+$.

Example 257

1-[2-(6-chloro-3,4-dihydroisoquinolin-2(1H)-yl)-2-oxoethyl]-3-(4-fluorophenyl)pyrrolidin-2-one The title compound was prepared using the procedure described in Example 172 substituting 2-(3-(4-fluorophenyl)-2-oxopyrrolidin-1-yl)acetic acid from Example 216A for 2-(3,3-bis(4-fluorophenyl)-2-oxopiperidin-1-yl)acetic acid and 6-chloro-1,2,3,4-tetrahydroisoquinoline for 3,3-diphenylpyrrolidine. $^1$H NMR (300 MHz, CDCl$_3$) δ ppm 7.41-7.11 (m, 4H), 7.03 (ddd, J=6.1, 10.3, 12.6, 3H), 4.65 (d, J=24.0, 2H), 4.33 (d, 1H), 4.21-4.04 (m, 1H), 3.89-3.44 (m, 5H), 2.87 (dt, J=5.9, 11.7, 2H), 2.66-2.44 (m, 1H), 2.23-2.04 (m, 1H); MS (DCI) m/z 387.1 (M+H)$^+$.

Example 258

1-[2-(3,4-dihydroisoquinolin-2(1H)-yl)-2-oxoethyl]-3,3-bis(4-fluorophenyl)pyrrolidin-2-one The title compound was prepared using the procedure described in Example 172 substituting 2-(3,3-bis(4-fluorophenyl)-2-oxopyrrolidin-1-yl)acetic acid from Example 58D for 2-(3,3-bis(4-fluorophenyl)-2-oxopiperidin-1-yl)acetic acid and 1,2,3,4-tetrahydroisoquinoline for 3,3-diphenylpyrrolidine. $^1$H NMR (300 MHz, CDCl$_3$) δ ppm 7.31 (dt, J=4.4, 5.5, 4H), 7.22-7.11 (m, 3H), 7.06-6.94 (m, 5H), 4.75-4.53 (m, 2H), 4.27 (d, J=4.8, 2H), 3.82 (t, J=6.0, 1H), 3.65 (t, J=6.0, 1H), 3.52 (q, J=6.5, 2H), 2.91-2.67 (m, 4H); MS (DCI) m/z 447.1 (M+H)$^+$.

Example 259

3,3-bis(4-fluorophenyl)-1-{2-oxo-2-[7-(trifluoromethyl)-3,4-dihydroisoquinolin-2(1H)-yl]ethyl}pyrrolidin-2-one The title compound was prepared using the procedure described in Example 172 substituting 2-(3,3-bis(4-fluorophenyl)-2-oxopyrrolidin-1-yl)acetic acid from Example 58D for 2-(3,3-bis(4-fluorophenyl)-2-oxopiperidin-1-yl)acetic acid and 7-(trifluoromethyl)-1,2,3,4-tetrahydroisoquinoline for 3,3-diphenylpyrrolidine. $^1$H NMR (300 MHz, CDCl$_3$) δ ppm 7.51-7.35 (m, 2H), 7.36-7.21 (m, 5H), 6.98 (td, J=5.3, 8.6, 4H), 4.70 (d, J=35.4, 2H), 4.27 (s, 2H), 3.83 (t, J=6.0, 1H), 3.68 (t, J=5.9, 1H), 3.53 (t, J=6.5, 2H), 2.88 (dd, J=8.0, 13.3, 2H), 2.81-2.73 (m, 2H); MS (DCI) m/z 515.1 (M+H)$^+$.

Example 260

1-[2-(3,4-dihydroisoquinolin-2(1H)-yl)-2-oxoethyl]-3,3-diphenylpiperidin-2-one

The title compound was prepared using the procedure described in Example 172 substituting 2-(2-oxo-3,3-diphenylpiperidin-1-yl)acetic acid from Example 68E for 2-(3,3-bis(4-fluorophenyl)-2-oxopiperidin-1-yl)acetic acid and 1,2,3,4-tetrahydroisoquinoline for 3,3-diphenylpyrrolidine. $^1$H NMR (300 MHz, CDCl$_3$) δ ppm 7.44-7.00 (m, 14H), 4.69 (d, J=42.8, 2H), 4.32 (d, J=4.4, 2H), 3.86 (t, J=6.0, 1H), 3.67 (t, J=5.9, 1H), 3.52 (t, J=6.4, 2H), 2.88 (t, J=5.9, 2H), 2.72-2.56 (m, 2H), 1.92-1.76 (m, 2H); MS (DCI) m/z 425.1 (M+H)$^+$.

Example 261

1-{2-oxo-2-[7-(trifluoromethyl)-3,4-dihydroisoquinolin-2(1H)-yl]ethyl}-3,3-diphenylpiperidin-2-one The title compound was prepared using the procedure described in Example 172 substituting 2-(2-oxo-3,3-diphenylpiperidin-1-yl)acetic acid from Example 68E for 2-(3,3- bis(4-fluorophenyl)-2-oxopiperidin-1-yl)acetic acid and 7-(trifluoromethyl)-1,2,3,4-tetrahydroisoquinoline for 3,3-diphenylpyrrolidine. $^1$H NMR (300 MHz, CDCl$_3$) δ ppm 7.43 (d, J=9.3, 2H), 7.36-7.15 (m, 11H), 4.74 (d, J=40.6, 2H), 4.31 (s, 2H), 3.88 (t, J=5.9, 1H), 3.70 (t, J=5.9, 1H), 3.54 (t, J=6.4, 2H), 2.93 (t, J=5.8, 2H), 2.72-2.56 (m, 2H), 1.93-1.81 (m, 2H); MS (DCI) m/z 493.1 (M+H)$^+$.

Example 262

1-({3-[2-(2-chlorophenyl)ethyl]-1,2,4-oxadiazol-5-yl}methyl)-3,3-diphenylpiperidin-2-one Example 262A (Z)-3-(2-chlorophenyl)-N-hydroxypropanimidamide A mixture of 3-(2-chlorophenyl)propanenitrile (1.29 g, 7.79 mmol), hydroxylamine hydrochloride (0.812 g, 11.7 mmol), and sodium hydrogencarbonate (3.27 g, 38.9 mmol) in methanol (10 mL) was heated to reflux. After 15 hours the reaction mixture was cooled to ambient temperature and filtered. The filtrate was concentrated in vacuo and the residue was purified by chromatography on silica gel (Analogix® Intelliflash™ 280; SF25-80 g column; 50%-100% ethyl acetate/hexanes, 0-20 minutes; 100% ethyl acetate, 20-25 minutes, 35 mL/minute), which yielded the title compound. $^1$H NMR (300 MHz, DMSO-d$_6$) δ ppm 8.78 (s, 1H), 7.43-7.33 (m, 2H), 7.32-7.17 (m, 2H), 5.42 (bs, 2H), 2.96-2.85 (m, 2H), 2.31-2.22 (m, 2H); MS (DCI$^+$) m/z 199 (M+H)$^+$.

Example 262B 1-({3-[2-(2-chlorophenyl)ethyl]-1,2,4-oxadiazol-5-yl}methyl)-3,3-diphenylpiperidin-2-one A mixture of the product of Example 262A (180 mg, 0.91 mmol), the product of Example 68E (280 mg, 0.901 mmol), and N$^1$-((ethylimino)methylene)-N$^3$,N$^3$-dimethylpropane-1,3-diamine hydrochloride (347 mg, 1.81 mmol) in 1,2-dichloroethane (4 mL) was stirred at ambient temperature for 3.5 hours and then heated to reflux for 16 hours. The cooled reaction mixture was diluted with CH$_2$Cl$_2$, washed with 1 N aqueous HCl and brine, dried over Na$_2$SO$_4$, filtered, and concentrated in vacuo. The crude product was chromatographed on silica gel twice using ethyl acetate/hexanes as eluant, then finally purified by preparative HPLC on a Phenomenex® Luna® C8(2) 5 um 100 Å AXIA column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A). Samples were injected in 1.5 mL dimethyl sulfoxide:methanol (1:1). The dried down fractions were taken up in CH$_2$Cl$_2$ and combined and concentrated in vacuo. Hexane was added to the residue, which caused the product to solidify. The resulting material was collected by vacuum filtration and dried in the vacuum oven at 50° C. for 4 hours to give the title compound. $^1$H NMR (300 MHz, DMSO-d$_6$) δ ppm 7.46-7.41 (m, 1H), 7.35-7.16 (m, 13H), 4.83 (s, 2H), 3.56 (t, J=6.3, 2H), 3.20-3.10 (m, 2H), 3.09-3.00 (m, 2H), 2.62-2.55 (m, 2H), 1.79-1.67 (m, 2H); MS (ESI$^+$) m/z 472 (M+H)$^+$.

Example 263

1-({3-[(4-chlorophenoxy)methyl]-1,2,4-oxadiazol-5-yl}methyl)-3,3-diphenylpiperidin-2-one Example 263A (Z)-2-(4-chlorophenoxy)-N'-hydroxyacetimidamide A mixture of 2-(4-chlorophenoxy)acetonitrile (1.35 g, 8.06 mmol), hydroxylamine hydrochloride (0.840 g, 12.1 mmol), and sodium hydrogencarbonate (3.38 g, 40.3 mmol) in methanol (15 mL) was heated to reflux. After 16 hours, the reaction mixture was cooled to ambient temperature and filtered. The filtrate was diluted with ethyl acetate (125 mL) and washed with 1 N aqueous HCl and saturated aqueous NaHCO$_3$ solution and brine, dried (Na$_2$SO$_4$), filtered, and concentrated in vacuo to furnish the title compound. $^1$H NMR (300 MHz, DMSO-d$_6$) δ ppm 9.28 (s, 1H), 7.36-7.28 (m, 2H), 7.06-6.98 (m, 2H), 5.60 (bs, 2H), 4.39 (s, 2H); MS (DCI$^+$) m/z 201 (M+H)$^+$.

Example 263B 1-({3-[(4-chlorophenoxy)methyl]-1,2,4-oxadiazol-5-yl}methyl)-3,3-diphenylpiperidin-2-one A mixture of the product of Example 263A (148 mg, 0.738 mmol), the product of Example 68E (228 mg, 0.738 mmol), and N$^1$-((ethylimino)methylene)-N$^3$,N$^3$-dimethylpropane-1,3-diamine hydrochloride (283 mg, 1.48 mmol) in 1,2-dichloroethane (4 mL) was stirred at ambient temperature for 3 hours, then heated to reflux for 24 hours. The cooled reaction mixture was diluted with CH$_2$Cl$_2$ (100 mL) and washed with 1 N aqueous HCl (2×30 mL) and saturated aqueous NaHCO$_3$ solution and brine, dried with Na$_2$SO$_4$, filtered, and concentrated in vacuo. The crude product was chromatographed on silica gel (Analogix® Intelliflash™ 280; SF15-24 g column; 40% ethyl acetate/hexanes) to give a viscous oil which was left standing overnight. Methanol (1 mL) was then added causing a solid to form which was collected by vacuum filtration, washed with hexanes, and air-dried to give the title compound. $^1$H NMR (300 MHz, DMSO-d$_6$) δ ppm 7.40-7.33 (m, 2H), 7.31-7.07 (m, 12H), 5.32 (s, 2H), 4.87 (s, 2H), 3.58 (t, J=6.3, 2H), 2.62-2.54 (m, 2H), 1.78-1.67 (m, 2H); MS (ESI$^+$) m/z 474 (M+H)$^+$.

Example 264

(+)-3-(4-fluorophenyl)-1-{2-oxo-2-[5-(trifluoromethyl)-1,3-dihydro-2H-isoindol-2-yl]ethyl}pyrrolidin-2-one The product of Example 216 (300 mg) was dissolved in methanol, loaded on a ChiralCel® AS-H (21×250 mm) semi-preparative chiral HPLC column (1.5 mL/injection), and eluted with 40% methanol/0.1% diethylamine in supercritical CO$_2$ (100 bar) under supercritical fluid chromatography (SFC) conditions at 35° C. with a flow rate of 40 mL/minute. The early eluting peak was collected and the solvent evaporated to afford the title compound. $^1$H NMR (400 MHz, CDCl$_3$) δ ppm 7.61-7.52 (m, 2H), 7.42 (dd, J=20.2, 8.2, 1H), 7.33-7.24 (m, 2H), 7.03 (t, J=8.6, 2H), 4.93 (bs, 2H), 4.88 (bs, 2H), 4.28 (d, J=16.1, 1H), 4.17 (d, J=16.1, 1H), 3.79-3.61 (m, 3H), 2.66-2.54 (m, 1H), 2.25-2.12 (m, 1H); MS (ESI$^+$) m/z 407 (M+H)$^+$.

Example 265

(−)-3-(4-fluorophenyl)-1-{2-oxo-2-[5-(trifluoromethyl)-1,3-dihydro-2H-isoindol-2-yl]ethyl}pyrrolidin-2-one The product of Example 216 (300 mg) was dissolved in methanol, loaded on a ChiralCel® AS-H (21×250 mm) semi-preparative chiral HPLC column (1.5 mL/injection), and eluted with 40% methanol/0.1% diethylamine in supercritical $CO_2$ (100 bar) under supercritical fluid chromatography (SFC) conditions at 35° C. with a flow rate of 40 mL/minute. The late eluting peak was collected and the solvent evaporated to afford the title compound. $^1$H NMR (500 MHz, $CDCl_3$) δ ppm 7.61-7.52 (m, 2H), 7.41 (dd, J=25.1, 8.1, 1H), 7.33-7.27 (m, 2H), 7.03 (t, J=8.6, 2H), 4.93 (bs, 2H), 4.87 (bs, 2H), 4.28 (d, J=16.1, 1H), 4.17 (d, J=16.3, 1H), 3.79-3.62 (m, 3H), 2.65-2.54 (m, 1H), 2.26-2.10 (m, 1H); MS: $(ESI^+)$ m/z 407 $(M+H)^+$. $[α]_D=-3.0°$ (c=1, methanol).

Example 266

1-[2-(5-fluoro-1,3-dihydro-2H-isoindol-2-yl)-2-oxo-ethyl]-3-[4-(trifluoromethyl)phenyl]pyrrolidin-2-one

Example 266A ethyl 2-(4-(trifluoromethyl)phenyl)acetate 2-(4-(Trifluoromethyl)phenyl)acetic acid (5.0 g, 24.49 mmol) was dissolved in ethanol (100 mL). Concentrated sulfuric acid (1 mL) was added, and the mixture was refluxed overnight. After cooling to room temperature, the reaction mixture was concentrated and diluted with diethyl ether. The organic solvent solution was then extracted with water, saturated aqueous sodium bicarbonate solution, and brine. The organic layer was then dried with magnesium sulfate, filtered, and concentrated to obtain the title compound. MS (DCI+) m/z 250 $(M+NH_4)^+$.

Example 266B ethyl 3-cyano-2-(4-(trifluoromethyl)phenyl)propanoate

To a solution of the product from Example 266A (5.25 g, 23.0 mmol) in dry tetrahydrofuran at −78° C. was added lithium bis(trimethylsilyl)amide (1.0 M in hexane) (23.00 mL, 23.0 mmol) dropwise via syringe under nitrogen. The reaction was brought to 0° C. and stirred for one hour. The reaction was re-cooled to −78° C. and then bromoacetonitrile (1.56 mL, 23.0 mmol) was added as a solution in tetrahydrofuran (10 mL). The reaction was stirred for 2 hours while the temperature was allowed to reach room temperature. The reaction was quenched with saturated aqueous ammonium chloride solution and extracted with diethyl ether. The organics were washed with brine, dried with $MgSO_4$, filtered, and concentrated. The residue was purified by silica gel chromatography (10% ethyl acetate/hexanes), to obtain the title compound. MS (DCI+) m/z 289 $(M+NH_4)^+$.

Example 266C 3-(4-(trifluoromethyl)phenyl)pyrrolidin-2-one

A solution of the product from Example 266B (4.1 g, 15.12 mmol) in methanol (10 mL) was added to 7 M ammonia in methanol (5.00 mL) and Raney® nickel, water wet, A-7000 (12.30 g, 210 mmol) in a 250 mL stainless steel pressure bottle and stirred for 16 hours under hydrogen (30 psi) at room temperature. The mixture was filtered through a nylon membrane and then concentrated to obtain solid. The solid was slurried in 5% ethyl acetate/hexanes, filtered and dried to give the title compound. MS (DCI+) m/z 247 $(M+NH_4)^+$.

Example 266D 2-(2-oxo-3-(4-(trifluoromethyl)phenyl)pyrrolidin-1-yl)acetic acid To a solution of the product from Example 266C (3.1 g, 13.00 mmol) in tetrahydrofuran (40 mL) was added potassium tert-butoxide (1.0 Min tetrahydrofuran, 15.7 mL, 15.7 mmol) via syringe under nitrogen, and the resultant mixture was stirred for 15 minutes. Then ethyl 2-bromoacetate (1.59 mL, 14.4 mmol) was added. The reaction mixture was stirred at room temperature overnight. The reaction mixture was concentrated and then diluted with ethyl acetate, washed with water and brine, dried over magnesium sulfate, filtered and concentrated. The resulting residue was dissolved in ethanol/water (4:1, 60 mL) and treated with lithium hydroxide (1.254 g, 52.4 mmol). After stirring for 2 hours at reflux, the reaction was concentrated, diluted with ice/water (150 mL) and neutralized with 2 N HCl. The precipitate formed was filtered, washed with water (50 mL), and dried under vacuum to obtain the title compound. MS (DCI+) m/z 288.1 $(M+H)^+$.

Example 266E

1-[2-(5-fluoro-1,3-dihydro-2H-isoindol-2-yl)-2-oxo-ethyl]-3-[4-(trifluoromethyl)phenyl]pyrrolidin-2-one The title compound was prepared using the procedure described in Example 172 substituting 2-(2-oxo-3-(4-(trifluoromethyl)phenyl)pyrrolidin-1-yl)acetic acid from Example 266D for 2-(3,3-bis(4-fluorophenyl)-2-oxopiperidin-1-yl)acetic acid and 5-fluoroisoindoline for 3,3-diphenylpyrrolidine. $^1$H NMR (300 MHz, $CDCl_3$) δ ppm 7.61 (d, J=8.2, 2H), 7.46 (d, J=8.2, 2H), 7.32-7.16 (m, 1H), 7.06-6.89 (m, 2H), 4.82 (dd, J=8.7, 15.1, 4H), 4.34-4.13 (m, 2H), 3.83 (t, J=8.9, 1H), 3.77-3.60 (m, 2H), 2.72-2.53 (m, 1H), 2.22 (ddd, J=8.5, 12.9, 16.1, 1H); MS (DCI) m/z 407.1 $(M+H)^+$.

Example 267

1-{2-oxo-2-[5-(trifluoromethyl)-1,3-dihydro-2H-isoindol-2-yl]ethyl}-3-[4-(trifluoromethyl)phenyl]pyrrolidin-2-one The title compound was prepared using the procedure described in Example 172 substituting 2-(2-oxo-3-(4-(trifluoromethyl)phenyl)pyrrolidin-1-yl)acetic acid from Example 266D for 2-(3,3-bis(4-fluorophenyl)-2-oxopiperidin-1-yl)acetic acid and 5-(trifluoromethyl)isoindoline for 3,3-diphenylpyrrolidine. $^1$H NMR (300 MHz, $CDCl_3$) δ ppm 7.58 (t, J=12.0, 4H), 7.42 (dd, J=8.2, 20.4, 3H), 4.91 (d, J=16.7, 4H), 4.23 (dd, J=16.2, 36.5, 2H), 3.83 (t, J=8.3, 1H), 3.77-3.62 (m, 2H), 2.74-2.54 (m, 1H), 2.32-2.16 (m, 1H); MS (DCI) m/z 457.1 $(M+H)^+$.

Example 268

3-(2-chloro-4-fluorophenyl)-1-[2-(5-fluoro-1,3-dihydro-2H-isoindol-2-yl)-2-oxoethyl]pyrrolidin-2-one

Example 268A 2-(3-(2-chloro-4-fluorophenyl)-2-oxopyrrolidin-1-yl) acetic acid The title compound was prepared using the procedures described in Examples 266A through Example 266D substituting 2-(2-chloro-4-fluorophenyl)acetic acid for 2-(4-(trifluoromethyl)phenyl)acetic acid in the procedure described in Example 266A. MS (DCI) m/z 272.0 (M+H)$^+$.

Example 268B 3-(2-chloro-4-fluorophenyl)-1-[2-(5-fluoro-1,3-dihydro-2H-isoindol-2-yl)-2-oxoethyl]pyrrolidin-2-one The title compound was prepared using the procedure described in Example 172 substituting 2-(3-(2-chloro-4-fluorophenyl)-2-oxopyrrolidin-1-yl)acetic acid from Example 268A for 2-(3,3-bis(4-fluorophenyl)-2-oxopiperidin-1-yl) acetic acid and 5-fluoroisoindoline for 3,3-diphenylpyrrolidine. $^1$H NMR (300 MHz, CDCl$_3$) δ ppm 7.36 (dd, J=6.0, 8.7, 1H), 7.28-7.17 (m, 1H), 7.17-7.12 (m, 1H), 7.09-6.91 (m, 3H), 4.84 (dd, J=8.5, 17.8, 4H), 4.34 (d, J=8.0, 1H), 4.24-4.07 (m, 2H), 3.77-3.56 (m, 2H), 2.76-2.55 (m, 1H), 2.03 (ddd, J=8.6, 12.8, 16.4, 1H); MS (DCI) m/z 391.1 (M+H)$^+$.

Example 269

3-(2-chloro-4-fluorophenyl)-1-{2-oxo-2-[5-(trifluoromethyl)-1,3-dihydro-2H-isoindol-2-yl]ethyl}pyrrolidin-2-one The title compound was prepared using the procedure described in Example 172 substituting 2-(3-(2-chloro-4-fluorophenyl)-2-oxopyrrolidin-1-yl)acetic acid from Example 268A for 2-(3,3-bis(4-fluorophenyl)-2-oxopiperidin-1-yl) acetic acid and 5-(trifluoromethyl)isoindoline for 3,3-diphenylpyrrolidine. $^1$H NMR (300 MHz, CDCl$_3$) δ ppm 7.59 (t, J=9.9, 2H), 7.48-7.30 (m, 2H), 7.13 (dd, J=2.7, 8.5, 1H), 7.06-6.94 (m, 1H), 4.92 (d, J=19.6, 4H), 4.36 (d, J=16.2, 1H), 4.24-4.10 (m, 2H), 3.77-3.60 (m, 2H), 2.77-2.56 (m, 1H), 2.04 (dq, J=8.1, 13.4, 1H); MS (DCI) m/z 441.1 (M+H)$^+$.

Example 270

3-(3,4-dichlorophenyl)-1-[2-(5-fluoro-1,3-dihydro-2H-isoindol-2-yl)-2-oxoethyl]pyrrolidin-2-one

Example 270A 2-(3-(3,4-dichlorophenyl)-2-oxopyrrolidin-1-yl)acetic acid

The title compound was prepared using the procedures described in Examples 266A through Example 266D substituting 2-(3,4-dichlorophenyl)acetic acid for 2-(4-(trifluoromethyl)phenyl)acetic acid in the procedure described in Example 266A. MS (DCI) m/z 289.1 (M+H)$^+$.

Example 270B 3-(3,4-dichlorophenyl)-1-[2-(5-fluoro-1,3-dihydro-2H-isoindol-2-yl)-2-oxoethyl]pyrrolidin-2-one The title compound was prepared using the procedure described in Example 172 substituting 2-(3-(2-chloro-4-fluorophenyl)-2-oxopyrrolidin-1-yl)acetic acid from Example 270A for 2-(3,3-bis(4-fluorophenyl)-2-oxopiperidin-1-yl) acetic acid and 5-(trifluoromethyl)isoindoline for 3,3-diphenylpyrrolidine. H NMR (300 MHz, CDCl$_3$) δ ppm 7.47-7.39 (m, 2H), 7.33-7.14 (m, 2H), 6.99 (t, J=10.1, 2H), 4.82 (dd, J=8.7, 14.7, 5H), 4.20 (d, J=6.4, 1H), 3.80-3.58 (m, 3H), 2.60 (d, J=6.5, 1H), 2.28-2.09 (m, 1H); MS (DCI) m/z 407.0 (M+H)$^+$.

Example 271

1-(2-{4-[bis(4-fluorophenyl)(hydroxy)methyl]piperidin-1-yl}-2-oxoethyl)-3,3-bis(4-fluorophenyl)pyrrolidin-2-one A mixture of the product of Example 58D (171 mg, 0.518 mmol), the product of Example 32A (157 mg, 0.518 mmol), 2-(3H-[1,2,3]triazolo[4,5-b]pyridin-3-yl)-1,1,3,3-tetramethylisouronium hexafluorophosphate(V) (197 mg, 0.518 mmol), and N-ethyl-N-isopropylpropan-2-amine (0.361 mL, 2.07 mmol) in CH$_2$Cl$_2$ (5 mL) was stirred at ambient temperature for 36 hours. The reaction mixture was diluted by CH$_2$Cl$_2$, and the organic mixture was washed with 1 N aqueous HCl and saturated NaHCO$_3$ solution and brine, dried with Na$_2$SO$_4$, filtered, and concentrated in vacuo. The crude product was chromatographed on silica gel (Analogix® Intelliflash™ 280; SF15-24 g column; 50% ethyl acetate/hexanes) to afford purified material that was taken up in a minimal amount of ether. Addition of hexanes caused formation of a solid that was collected by vacuum filtration and air-dried to give the title compound. $^1$H NMR (300 MHz, DMSO-d$_6$) δ ppm 7.59-7.47 (m, 4H), 7.40-7.29 (m, 4H), 7.18-7.04 (m, 8H), 5.48 (s, 1H), 4.41-4.29 (m, 1H), 4.19 (d, J=16.5, 1H), 4.09 (d, J=16.6, 1H), 3.86-3.75 (m, 1H), 3.38-3.30 (m, 2H), 3.05-2.89 (m, 1H), 2.85-2.63 (m, 3H), 2.63-2.51 (m, 1H), 1.40-1.17 (m, 4H); MS (DCI$^+$) m/z 617 (M+H)$^+$.

Example 272

1-(2-{4-[bis(4-fluorophenyl)(hydroxy)methyl]piperidin-1-yl}-2-oxoethyl)-3,3-diphenylpiperidin-2-one The title compound was obtained by the procedure described in Example 271, replacing the product of Example 58D with the product of Example 68E. $^1$H NMR (300 MHz, DMSO-d$_6$) δ ppm 7.60-7.47 (m, 4H), 7.32-7.15 (m, 10H), 7.15-7.03 (m, 4H), 5.50 (s, 1H), 4.48-4.36 (m, 1H), 4.24-4.07 (m, 2H), 3.87-3.74 (m, 1H), 3.42-3.31 (m, 2H), 3.05-2.90 (m, 1H), 2.87-2.70 (m, 1H), 2.65-2.50 (m, 3H), 1.75-1.59 (m, 2H), 1.41-1.18 (m, 4H); MS (ESI$^+$) m/z 612 (M+NH$_4$)$^+$.

Example 273

1-(2-(4-(bis(4-fluorophenyl)methyl)piperazin-1-yl)-2-oxoethyl)-4-isopropyl-3-phenylpiperazin-2-one To a solution of the product from Example 103 (0.1 g, 0.198 mmol) in dichloroethane (5 mL), was added acetone (0.03 mL, 0.45 mmol) and sodium triacetoxyborohydride (0.063 g, 0.3 mmol). A few drops of acetic acid were added, and the reaction mixture was stirred at ambient temperature overnight. The mixture was concentrated, and the residue was purified by flash chromatography on silica gel eluting with ethyl acetate. $^1$H NMR (400 MHz, pyridine-$d_5$, temperature 90° C.) δ ppm 7.67-7.70 (m, 2H), 7.35-7.40 (m, 4H), 7.27-7.33 (m, 2H), 7.18-7.25 (m, 1H), 7.00-7.07 (m, 4H), 4.48 (s, 1H), 4.36 (s, 1H), 4.27-4.31 (m, 2H), 3.73 (ddd, J=11.0, 10.1, 4.0 Hz, 1H), 3.49-3.58 (m, 4H), 3.42 (dt, J=11.3, 3.7 Hz, 1H), 2.99 (dt, J=12.0, 3.8 Hz, 1H), 2.83 (h, J=6.6 Hz, 1H), 2.78 (ddd, J=12.0, 9.8, 3.6 Hz, 1H), 2.24-2.29 (m, 4H), 0.95 (d, J=6.7 Hz, 3H), 0.86 (d, J=6.4 Hz, 3H); MS (ESI+) m/z 547 (M+H)$^+$.

Many variations in the invention will suggest themselves to those skilled in the art in light of the foregoing detailed description. All such obvious variations are within the full intended scope of the appended claims.

The invention claimed is:
1. A compound of formula (I),

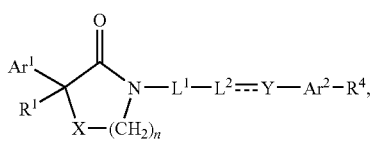
(I)

or a pharmaceutically acceptable salt thereof, wherein
====== is a single or double bond;
n, at each occurrence, is independently 1 or 2;
X is CH$_2$;
r, at each occurrence, is independently 0, 1, or 2;
Ar$^1$ and Ar$^2$ are independently aryl or heteroaryl; wherein each Ar$^1$ and Ar$^2$ is independently unsubstituted or further substituted with 1, 2, 3, 4, or 5 substituents independently selected from the group consisting of alkyl, alkenyl, alkynyl, halogen, —CN, —NO$_2$, —OR$^a$, —S(R$^c$), —S(O)(R$^c$), —S(O)$_2$R$^c$, —S(O)$_2$N(R$^b$)$_2$, —C(O)R$^b$, —C(O)O(R$^b$), —C(O)N(R$^b$)$_2$, —N(R$^b$)$_2$, —N(R$^b$)C(O)R$^b$, —N(R$^b$)C(O)O(R$^b$), —N(R$^b$)S(O)$_2$R$^c$, haloalkyl, —(CR$^d$R$^e$)$_m$—OR$^a$, —(CR$^d$R$^e$)$_m$—S(R$^c$), —(CR$^d$R$^e$)$_m$—S(O)(R$^c$), —(CR$^d$R$^e$)$_m$—S(O)$_2$R$^c$, —(CR$^d$R$^e$)$_m$—S(O)$_2$N(R$^b$)$_2$, —(CR$^d$R$^e$)$_m$—C(O)R$^b$, —(CR$^d$R$^e$)$_m$—C(O)O(R$^b$), —(CR$^d$R$^e$)$_m$—C(O)N(R$^b$)$_2$, —(CR$^d$R$^e$)$_m$—N(R$^b$)$_2$, —(CR$^d$R$^e$)$_m$—N(R$^b$)C(O)R$^b$, —(CR$^d$R$^e$)$_m$—N(R$^b$)C(O)O(R$^b$), —(CR$^d$R$^e$)$_m$—N(R$^b$)S(O)$_2$R$^c$, and —CH=CH-heteroaryl-(CR$^d$R$^e$)$_m$—O(alkyl);
R$^a$, at each occurrence, is independently hydrogen, alkyl, haloalkyl, or —(CR$^d$R$^e$)$_m$—O(alkyl);
R$^b$, at each occurrence, is independently hydrogen, alkyl, haloalkyl, or G$^1$;
R$^c$, at each occurrence, is independently alkyl or haloalkyl;
R$^d$ and R$^e$, at each occurrence, are each independently hydrogen, halogen, alkyl, or haloalkyl;
m, at each occurrence, is independently 1, 2, 3, 4, 5, or 6;
L$^1$ is —(CH$_2$)$_p$C(O)— or —(CH$_2$)$_p$—; wherein
p, at each occurrence, is independently 1, 2, 3, or 4;
L$^2$ is —N(R$^5$)—, —N(R$^5$)—(CH$_2$)$_q$—, —NH—CH(R$^5$)—, —NH—CH(R$^5$)—(CH$_2$)$_q$—, —N(R$^5$)—CH$_2$CH(OH)CH$_2$—, —N(R$^5$)—CH(R$^6$)—, (i), (iv), (v), (vi), (vii), (viii), (ix), (x), (xi) or (xii);

 (i)

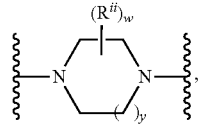 (ii)

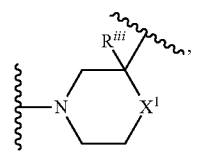 (iii)

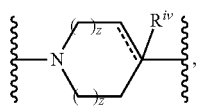 (iv)

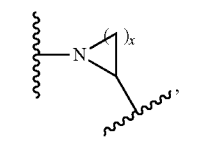 (v)

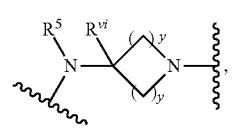 (vi)

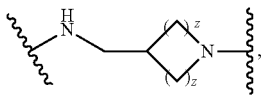 (vii)

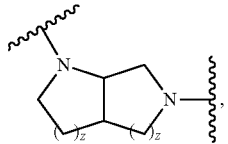 (viii)

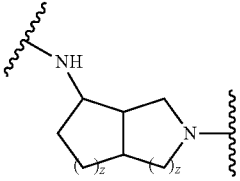 (ix)

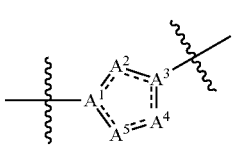 (x)

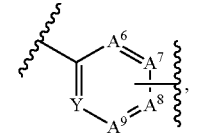 (xi)

-continued

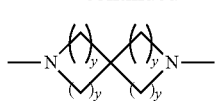
(xii)

q, at each occurrence, is independently 1, 2, or 3;
w is 1, 2, 3, or 4;
x is 2, 3, 4, or 5;
y at each occurrence, is independently 1, 2, or 3;
z at each occurrence, is independently 0, 1, 2, or 3;
$R^5$ at each occurrence, is hydrogen, alkyl, or $G^1$;
$R^{ii}$ at each occurrence, is independently oxo or alkyl;
$R^{iii}$ is hydrogen, alkyl, or aryl;
$R^{iv}$ is hydrogen, aryl, $OR^a$ or part of double bond between $L^2$ and Y;
$R^{vi}$ is hydrogen or alkyl;
$X^1$ is $CH_2$, NH, O, or a bond;
$A^1$ and $A^3$ are independently C or N;
$A^2$, $A^4$, and $A^5$ are each independently CH, $CR^5$, N, O, or S;
one of $A^6$, $A^7$, $A^8$, $A^9$, and $A^{10}$ is C and the others are each independently CH or N;
Y is a bond, $CR^2R^3$, $CH_2CR^2R^3$, $CR^2$, $CR^2R^3O$, C(O), C(O)$OCR^2R^3$, N—O—$CR^2R^3$, O, or S(O)$_r$;
$R^2$ is hydrogen or $G^1$;
$R^3$ is hydrogen, alkyl, cycloalkyl, or hydroxyl; or
$R^2$ and $R^3$ taken together with the carbon atom to which they are attached form a cycloalkyl;
$G^1$, at each occurrence, is independently aryl, heteroaryl, heterocycle, cycloalkyl, or cycloalkenyl; wherein each $G^1$ is independently unsubstituted or further substituted with 1, 2, 3, 4, 5, or 6 substituents independently selected from the group consisting of alkyl, alkenyl, alkynyl, halogen, oxo, —CN, —$NO_2$, —$OR^a$, —S($R^c$), —S(O)($R^c$), —S(O)$_2R^c$, haloalkyl, —$(CR^dR^e)_m$—$OR^a$, —$(CR^dR^e)_m$—S($R^c$), —$(CR^dR^e)_m$—S(O)($R^c$), and —$(CR^dR^e)_m$—S(O)$_2R^c$;
$R^1$ is hydrogen, alkyl, or $G^1$; and
$R^4$ is hydrogen; or
$R^3$ and $R^5$ taken together are —$(CH_2)_p$— or —O—$(CH_2)_p$—; or
$R^4$ and $R^5$ taken together are a bond, —$(CH_2)_s$—, or —O—$(CH_2)_s$—; wherein
s, at each occurrence, is independently 1 or 2; or
$R^4$ and $R^6$ taken together are —$CH_2$—; or
$L^1$-$L^2$------Y taken together are S(O)$_r$;
with the provisos that
$Ar^2$ is other than a pyrazole substituted with 1 or 2 groups independently selected from aryl and heteroaryl; or
when $Ar^1$ is aryl or heteroaryl, $R^1$ is aryl or heteroaryl, X is $CH_2$, n is 1, $L^1$ is —$(CH_2)_p$—, Y is $CR^2R^3$, $Ar^2$ is aryl, and $R^4$ is H, then $L^2$ is other than —N($R^5$)—, —N($R^5$)—$(CH_2)_q$—, or —NH—CH($R^5$)—; or
when $Ar^1$ and $R^1$ are both unsubstituted phenyl, X is $CH_2$, n is 2, $L^1$ is —$CH_2C(O)$—, $L^2$ is —N($CH_3$)—$(CH_2)_3$—, Y is $CR^2R^3$, $Ar^2$ is unsubstituted phenyl, and $R^4$ is hydrogen, then $R^2$ is other than unsubstituted phenyl; or
when $Ar^1$ is phenyl, $R^1$ is hydrogen or methyl, X is $CH_2$, n is 1, $L^1$-$L^2$------Y taken together are S(O)$_r$, r is 2, then $Ar^2$ is other than 4-methylphenyl; or
when the bond connecting $L^2$ to Y is a double bond, Y is $CR^2$; or
when X is other than $CH_2$, n is 2.

2. The compound according to claim 1, wherein
n is 1;
X is $CH_2$;
$Ar^1$ is phenyl; and
$R^1$ is hydrogen or $G^1$, wherein $G^1$ is phenyl;
wherein the phenyl groups of $Ar^1$ and $R^1$ are independently either unsubstituted or further substituted with 1, 2, or 3 substituents selected from the group consisting of halogen, haloalkyl, and —$OR^a$, wherein $R^a$ is alkyl.

3. The compound according to claim 2, wherein
$Ar^2$ is oxazolyl, phenyl, pyridinyl, pyrazolyl, or thiazolyl either unsubstituted or further substituted with 1, 2, or 3 substituents selected from the group consisting of alkyl, —CN, halogen, and haloalkyl;
$L^1$ is —$(CH_2)_pC(O)$—;
$L^2$ is —N($R^5$)— or —N($R^5$)—$(CH_2)_q$—;
$R^5$ is hydrogen;
q is 1 or 2;
Y is a bond or $CR^2R^3$;
$R^2$ is hydrogen or $G^1$, wherein $G^1$ is phenyl; and
$R^3$ is hydrogen, alkyl, or cycloalkyl; or
$R^2$ and $R^3$ taken together with the carbon atom to which they are attached form a cycloalkyl.

4. The compound according to claim 2, wherein
$Ar^2$ is quinolinyl or phenyl, wherein phenyl is either unsubstituted or further substituted with 1, 2, or 3 substituents selected from the group consisting of —$OR^a$ and —CH=CH-heteroaryl-$(CR^dR^e)_m$—O(alkyl), wherein heteroaryl is isoxazolyl;
m is 1;
$R^a$ is alkyl;
$R^d$ and $R^e$ are each hydrogen;
$L^1$ is —$(CH_2)_p$—;
p is 2;
$L^2$ is —N($R^5$)—, —N($R^5$)—$(CH_2)_q$—, or —N($R^5$)—$CH_2CH(OH)CH_2$—;
q is 3; and
Y is O or C(O).

5. The compound according to claim 2, wherein
$Ar^2$ is indolyl, phenyl or pyridyl either unsubstituted or further substituted with 1, 2, or 3 substituents selected from the group consisting of alkyl, halogen, haloalkyl, and —$OR^a$, wherein $R^a$ is alkyl;
$L^1$ is —$(CH_2)_pC(O)$—;
$L^2$ is —N($R^5$)—, —N($R^5$)—$(CH_2)_q$—, —NH—CH($R^5$)—$(CH_2)_q$—, —NH—CH($R^5$)—, (i), (ii), (iii), (iv), (v), (vi), (vii), (viii), (ix), or (xii);
$R^5$ is hydrogen;
q is 1, 2, or 3;
Y is a bond, $CR^2$, $CH_2CR^2R^3$, or $CR^2R^3$; and
$R^2$ is hydrogen or phenyl, wherein the phenyl is either unsubstituted or further substituted with 1, 2, or 3 substituents selected from the group consisting of alkyl, halogen, and haloalkyl;
$R^3$ is hydrogen, alkyl, or hydroxyl; or
$R^3$ and $R^5$ taken together are —$(CH_2)_p$—; wherein,
p, at each occurrence, is independently 1, 2, or 3; or
$R^4$ and $R^5$ taken together are a bond or —$(CH_2)_s$—; wherein,
s is 1.

6. The compound according to claim 2, wherein
$Ar^2$ is thiazolyl, phenyl, pyridyl, or pyrazinyl, wherein phenyl, pyridyl, pyrazinyl and thiazoyl are either unsubstituted or further substituted with 1, 2 or 3 substituents selected from the group consisting of alkyl, —CN, halogen, haloalkyl, —$OR^a$, —N($R^b$)$_2$, and —N($R^b$)C(O)O ($R^b$), wherein $R^a$ is alkyl and $R^b$ at each occurrence, is independently hydrogen or alkyl;

$L^1$ is —$(CH_2)_p$—;

p is 1, 2, or 3;

$L^2$ is —$N(R^5)$—$(CH_2)_q$—, —$N(R^5)$—$CH(R^6)$—, (i), (ii), or (x);

$R^5$ is alkyl;

q is 1 or 2;

Y is a bond, $CR^2R^3$, or $CH_2CR^2R^3$;

$R^2$ is hydrogen or phenyl;

$R^3$ is hydrogen; or $R^4$ and $R^5$ taken together are —$(CH_2)_s$—;

s is 1; or $R^4$ and $R^6$ taken together are $CH_2$.

7. The compound according to claim 1, wherein n is 2;

X is $CH_2$;

$Ar^1$ is phenyl; and $R^1$ is hydrogen, alkyl, or $G^1$, wherein $G^1$ is phenyl;

wherein the phenyl groups of $Ar^1$ and $R^1$ are independently either unsubstituted or further substituted with 1, 2, or 3 substituents selected from the group consisting of halogen and —$OR^a$, wherein $R^a$ is alkyl.

8. The compound according to claim 7, wherein $Ar^2$ is phenyl either unsubstituted or further substituted with 1, 2, or 3 substituents selected from the group consisting of halogen and —$OR^a$, wherein $R^a$ is alkyl;

$L^1$ is —$CH_2C(O)$—;

$L^2$ is —$N(R^5)$— or —$N(R^5)$—$(CH_2)_q$—;

q is 1;

Y is $CR^2R^3$;

$R^2$ is hydrogen; and $R^3$ is hydrogen; or $R^2$ and $R^3$ taken together with the carbon atom to which they are attached form a cycloalkyl.

9. The compound according to claim 7, wherein $Ar^2$ is phenyl, wherein phenyl is either unsubstituted or further substituted with 1, 2 or 3 substituents selected from the group consisting of halogen and —$OR^a$, wherein $R^a$ is alkyl;

$L^1$ is —$(CH_2)_p$—;

p is 2 or 3;

$L^2$ is —$N(R^5)$—, or —$N(R^5)$—$(CH_2)_q$—;

q is 1 or 3;

Y is O or $CR^2R^3$; and $R^2$ and $R^3$ are each hydrogen.

10. The compound according to claim 7, wherein $Ar^2$ is phenyl or heteroaryl, wherein phenyl and heteroaryl are either unsubstituted or further substituted with 1, 2, or 3 substituents selected from the group consisting of alkyl, —CN, halogen, haloalkyl, and —$OR^a$, wherein $R^a$ is alkyl;

$L^1$ is —$CH_2C(O)$—;

$L^2$ is —$N(R^5)$—, —$N(R^5)$—$(CH_2)_q$—, —NH—CH$(R^5)$—$(CH_2)_q$—, (i), (ii), (iii), (iv), (v), (vi), or (viii);

$R^5$ is hydrogen, alkyl, or $G^1$;

q is 1, 2, or 3;

Y is a bond, $CR^2R^3$, O, N—O—$CR^2R^3$, $C(O)OCR^2R^3$, or $S(O)_2$;

$R^2$ is hydrogen or phenyl, wherein the phenyl is either unsubstituted or further substituted with 1, 2, or 3 halogen substituents; and $R^3$ is hydrogen, alkyl, or hydroxyl; or $R^3$ and $R^5$ taken together are —$(CH_2)_p$— or —$OCH_2CH_2$—; wherein p is 1, 2, 3 or 4; or $R^4$ and $R^5$ taken together are a bond or —$(CH_2)_s$—; wherein s is 1.

11. The compound according to claim 7, wherein $Ar^2$ is indazolyl, pyridinyl, pyrimidinyl or phenyl, wherein phenyl is either unsubstituted or further substituted with 1, 2, or 3 substituents selected from the group consisting of halogen, haloalkyl, or —$OR^a$, wherein $R^a$ is hydrogen, alkyl, or haloalkyl;

$L^1$ is —$(CH_2)_p$—;

p is 1, 2, or 3;

$L^2$ is —$N(R^5)$—$CH(R^6)$—, (i), or (x);

$R^5$ is alkyl;

Y is a bond, $CR^2R^3$, $CH_2CR^2R^3$, or $CR^2R^3O$;

$R^2$ is hydrogen; and $R^3$ is hydrogen; or $R^4$ and $R^6$ taken together are $CH_2$.

12. The compound according to claim 7, wherein $Ar^2$ is phenyl either unsubstituted or further substituted with 1, 2, or 3 substituents selected from the group consisting of alkyl, halogen, or haloalkyl; and $L^1$-$L^2$-------Y taken together are $S(O)_r$.

13. The compound according to claim 1, wherein $Ar^1$ and $R^1$ are phenyl optionally substituted with fluorine;

$Ar^2$ is phenyl optionally substituted with haloalkyl;

X is $CH_2$;

$L^1$ is —$CH_2C(O)$—;

$L^2$ is (i);

Y is $CR^2R^3$;

$R^2$ is hydrogen or phenyl; and $R^3$ is hydrogen.

14. The compound according to claim 1 or a pharmaceutically acceptable salt thereof, selected from the group consisting of:

1-[2-(4-benzhydrylpiperazin-1-yl)-2-oxoethyl]-3,3-diphenylpyrrolidin-2-one;

2-(2-oxo-3,3-diphenylpyrrolidin-1-yl)-N-{[6-(trifluoromethyl)pyridin-3-yl]methyl}acetamide;

2-(2-oxo-3,3-diphenylpyrrolidin-1-yl)-N-(1,3-thiazol-2-ylmethyl)acetamide;

N-[(1-methyl-1H-pyrazol-3-yl)methyl]-2-(2-oxo-3,3-diphenylpyrrolidin-1-yl)acetamide;

N-(5-chloropyridin-2-yl)-2-(2-oxo-3,3-diphenylpyrrolidin-1-yl)acetamide;

N-benzyl-2-(2-oxo-3,3-diphenylpyrrolidin-1-yl)acetamide;

2-(2-oxo-3,3-diphenylpyrrolidin-1-yl)-N-[3-(trifluoromethyl)benzyl]acetamide;

2-(2-oxo-3,3-diphenylpyrrolidin-1-yl)-N-[4-(trifluoromethyl)benzyl]acetamide;

N-[cyclopropyl(phenyl)methyl]-2-(2-oxo-3,3-diphenylpyrrolidin-1-yl)acetamide;

2-(2-oxo-3,3-diphenylpyrrolidin-1-yl)-N-{2-[3-(trifluoromethyl)phenyl]ethyl}acetamide;

2-(2-oxo-3,3-diphenylpyrrolidin-1-yl)-N-(1-phenylcyclobutyl)acetamide;

N-(4-fluorobenzyl)-2-(2-oxo-3,3-diphenylpyrrolidin-1-yl)acetamide;

N-(3,3-diphenylpropyl)-2-(2-oxo-3,3-diphenylpyrrolidin-1-yl)acetamide;

N-benzhydryl-2-(2-oxo-3,3-diphenylpyrrolidin-1-yl)acetamide;

N-(2,2-diphenylethyl)-2-(2-oxo-3,3-diphenylpyrrolidin-1-yl)acetamide;

N-(2,2-diphenylpropyl)-2-(2-oxo-3,3-diphenylpyrrolidin-1-yl)acetamide;
1-[2-(3,3-diphenylpyrrolidin-1-yl)-2-oxoethyl]-3,3-diphenylpyrrolidin-2-one;
1-[2-(3-benzylpiperazin-1-yl)-2-oxoethyl]-3,3-diphenylpyrrolidin-2-one;
1-[2-(3,4-dihydroisoquinolin-2(1H)-yl)-2-oxoethyl]-3,3-diphenylpyrrolidin-2-one;
1-{2-oxo-2-[5-(trifluoromethyl)-1,3-dihydro-2H-isoindol-2-yl]ethyl}-3,3-diphenylpyrrolidin-2-one;
1-[2-oxo-2-(3-phenylpyrrolidin-1-yl)ethyl]-3,3-diphenylpyrrolidin-2-one;
N-2,3-dihydro-1H-inden-2-yl-2-(2-oxo-3,3-diphenylpyrrolidin-1-yl)acetamide;
1-[2-(2,2-diphenylmorpholin-4-yl)-2-oxoethyl]-3,3-diphenylpyrrolidin-2-one;
1-[2-(3,3-diphenylpiperidin-1-yl)-2-oxoethyl]-3,3-diphenylpyrrolidin-2-one;
1-[2-(4,4-diphenylpiperidin-1-yl)-2-oxoethyl]-3,3-diphenylpyrrolidin-2-one;
1-[2-(5-fluoro-1,3-dihydro-2H-isoindol-2-yl)-2-oxoethyl]-3,3-diphenylpyrrolidin-2-one;
2-(2-oxo-3,3-diphenylpyrrolidin-1-yl)-N-1,2,3,4-tetrahydronaphthalen-1-ylacetamide;
4-[(2-oxo-3,3-diphenylpyrrolidin-1-yl)acetyl]-1-[3-(trifluoromethyl)benzyl]piperazin-2-one;
1-benzhydryl-4-[(2-oxo-3,3-diphenylpyrrolidin-1-yl)acetyl]piperazin-2-one;
1-[2-(4-benzhydrylpiperidin-1-yl)-2-oxoethyl]-3,3-diphenylpyrrolidin-2-one;
1-{2-[4-(diphenylmethylene)piperidin-1-yl]-2-oxoethyl}-3,3-diphenylpyrrolidin-2-one;
1-(2-{4-[bis(4-fluorophenyl)(hydroxy)methyl]piperidin-1-yl}-2-oxoethyl)-3,3-diphenylpyrrolidin-2-one;
1-{2-[4-(hydroxy{bis[3-(trifluoromethyl)phenyl]}methyl)piperidin-1-yl]-2-oxoethyl}-3,3-diphenylpyrrolidin-2-one;
1-(2-{4-[hydroxy(diphenyl)methyl]piperidin-1-yl}-2-oxoethyl)-3,3-diphenylpyrrolidin-2-one;
1-{2-[4-(5-methoxy-1H-indol-3-yl)-3,6-dihydropyridin-1(2H)-yl]-2-oxoethyl}-3,3-diphenylpyrrolidin-2-one;
1-{2-[4-(2,6-dichlorobenzyl)piperazin-1-yl]-2-oxoethyl}-3,3-diphenylpyrrolidin-2-one;
1-(2-oxo-2-{4-[3-(trifluoromethyl)benzyl]piperazin-1-yl}ethyl)-3,3-diphenylpyrrolidin-2-one;
1-{2-[4-(4-fluorobenzyl)piperazin-1-yl]-2-oxoethyl}-3,3-diphenylpyrrolidin-2-one;
N-[(1-benzylpyrrolidin-3-yl)methyl]-2-(2-oxo-3,3-diphenylpyrrolidin-1-yl)acetamide;
N-(1-benzyl-3-methylpyrrolidin-3-yl)-2-(2-oxo-3,3-diphenylpyrrolidin-1-yl)acetamide;
2-(2-oxo-3,3-diphenylpyrrolidin-1-yl)-N-{1-[3-(trifluoromethyl)benzyl]piperidin-4-yl}acetamide;
1-[2-oxo-2-(4-{[3-(trifluoromethyl)benzyl]amino}piperidin-1-yl)ethyl]-3,3-diphenylpyrrolidin-2-one;
1-{2-[4-(2,4-dichlorobenzyl)piperazin-1-yl]-2-oxoethyl}-3,3-diphenylpyrrolidin-2-one;
1-[2-oxo-2-(4-{1-[3-(trifluoromethyl)phenyl]ethyl}piperazin-1-yl)ethyl]-3,3-diphenylpyrrolidin-2-one;
1-(2-{4-[bis(4-fluorophenyl)methyl]piperazin-1-yl}-2-oxoethyl)-3,3-diphenylpyrrolidin-2-one;
1-(2-{4-[(4-fluorophenyl)(phenyl)methyl]piperazin-1-yl}-2-oxoethyl)-3,3-diphenylpyrrolidin-2-one;
1-(2-{4-[(4-chlorophenyl)(phenyl)methyl]piperazin-1-yl}-2-oxoethyl)-3,3-diphenylpyrrolidin-2-one;
N-(1-benzhydrylpiperidin-4-yl)-2-(2-oxo-3,3-diphenylpyrrolidin-1-yl)acetamide;
1-{2-[(2R)-4-benzhydryl-2-methylpiperazin-1-yl]-2-oxoethyl}-3,3-diphenylpyrrolidin-2-one;
1-{2-[(4aS,7aS)-6-benzhydryloctahydro-1H-pyrrolo[3,4-b]pyridin-1-yl]-2-oxoethyl}-3,3-diphenylpyrrolidin-2-one;
1-{2-[(4aR,7aR)-6-benzhydryloctahydro-1H-pyrrolo[3,4-b]pyridin-1-yl]-2-oxoethyl}-3,3-diphenylpyrrolidin-2-one;
1-(2-{4-[(2,2-diphenylethyl)amino]piperidin-1-yl}-2-oxoethyl)-3,3-diphenylpyrrolidin-2-one;
1-{2-[4-(5-chloropyridin-2-yl)piperazin-1-yl]-2-oxoethyl}-3,3-diphenylpyrrolidin-2-one;
1-{2-[4-(4-fluorophenyl)piperazin-1-yl]-2-oxoethyl}-3,3-diphenylpyrrolidin-2-one;
1-{2-oxo-2-[7-(trifluoromethyl)-3,4-dihydroisoquinolin-2(1H)-yl]ethyl}-3,3-diphenylpyrrolidin-2-one;
2-(2-oxo-3,3-diphenylpyrrolidin-1-yl)-N-{(3aS*,4S*,6aR*)-2-[3-(trifluoromethyl)benzyl]octahydrocyclopenta[c]pyrrol-4-yl}acetamide;
2-(2-oxo-3,3-diphenylpyrrolidin-1-yl)-N-{(3aS*,4R*,6aR*)-2-[3-(trifluoromethyl)benzyl]octahydrocyclopenta[c]pyrrol-4-yl}acetamide;
1-[2-(4-benzhydrylpiperazin-1-yl)-2-oxoethyl]-3,3-bis(4-fluorophenyl)pyrrolidin-2-one;
2-[3,3-bis(4-fluorophenyl)-2-oxopyrrolidin-1-yl]-N-(2,2-diphenylpropyl)acetamide;
3,3-bis(4-fluorophenyl)-1-(2-oxo-2-{4-[3-(trifluoromethyl)benzyl]piperazin-1-yl}ethyl)pyrrolidin-2-one;
1-[2-(3,3-diphenylpyrrolidin-1-yl)-2-oxoethyl]-3,3-bis(4-fluorophenyl)pyrrolidin-2-one;
3,3-diphenyl-1-({3-[4-(trifluoromethyl)phenyl]-1,2,4-oxadiazol-5-yl}methyl)pyrrolidin-2-one;
1-{2-[4-(3,5-dimethoxybenzyl)piperazin-1-yl]ethyl}-3,3-bis(4-fluorophenyl)pyrrolidin-2-one;
4-benzhydryl-1-[2-(2-oxo-3,3-diphenylpyrrolidin-1-yl)ethyl]piperazin-2-one;
3,3-dimethyl-1-[2-(2-oxo-3,3-diphenylpyrrolidin-1-yl)ethyl]-4-(thien-2-ylmethyl)piperazin-2-one;
1-benzhydryl-4-[2-(2-oxo-3,3-diphenylpyrrolidin-1-yl)ethyl]piperazin-2-one;
3,3-diphenyl-1-{2-[7-(trifluoromethyl)-3,4-dihydroisoquinolin-2(1H)-yl]ethyl}pyrrolidin-2-one;
1-[2-(4-benzhydrylpiperazin-1-yl)-2-oxoethyl]-3,3-diphenylpiperidin-2-one;
1-[2-(2,2-diphenylmorpholin-4-yl)-2-oxoethyl]-3,3-diphenylpiperidin-2-one;
1-[2-oxo-2-(2-phenylmorpholin-4-yl)ethyl]-3,3-diphenylpiperidin-2-one;
1-[2-(3,3-diphenylpiperidin-1-yl)-2-oxoethyl]-3,3-diphenylpiperidin-2-one;
1-[2-(4,4-diphenylpiperidin-1-yl)-2-oxoethyl]-3,3-diphenylpiperidin-2-one;
1-{2-[2-(4-fluorophenyl)pyrrolidin-1-yl]-2-oxoethyl}-3,3-diphenylpiperidin-2-one;
1-{2-[2-(4-fluorophenyl)piperidin-1-yl]-2-oxoethyl}-3,3-diphenylpiperidin-2-one;
N-(6-fluoro-3,4-dihydro-2H-chromen-4-yl)-2-(2-oxo-3,3-diphenylpiperidin-1-yl)acetamide;
1-[2-(4-benzhydrylpiperidin-1-yl)-2-oxoethyl]-3,3-diphenylpiperidin-2-one;
N-(2,2-diphenylpropyl)-2-(2-oxo-3,3-diphenylpiperidin-1-yl)acetamide;
1-(2-{4-[hydroxy(diphenyl)methyl]piperidin-1-yl}-2-oxoethyl)-3,3-diphenylpiperidin-2-one;

1-(2-oxo-2-{4-[3-(trifluoromethyl)benzyl]piperazin-1-yl}ethyl)-3,3-diphenylpiperidin-2-one;
1-(2-oxo-2-{4-[4-(trifluoromethyl)benzyl]piperazin-1-yl}ethyl)-3,3-diphenylpiperidin-2-one;
1-{2-[4-(3-chlorobenzyl)piperazin-1-yl]-2-oxoethyl}-3,3-diphenylpiperidin-2-one;
1-(2-{4-[bis(4-fluorophenyl)methyl]piperazin-1-yl}-2-oxoethyl)-3,3-diphenylpiperidin-2-one;
1-benzhydryl-4-[(2-oxo-3,3-diphenylpiperidin-1-yl)acetyl]piperazin-2-one;
1-[2-oxo-2-(4-{[3-(trifluoromethyl)phenyl]sulfonyl}piperazin-1-yl)ethyl]-3,3-diphenylpiperidin-2-one;
N-(1-benzhydrylpiperidin-4-yl)-2-(2-oxo-3,3-diphenylpiperidin-1-yl)acetamide;
N-(1-benzhydryl-3-methylpyrrolidin-3-yl)-2-(2-oxo-3,3-diphenylpiperidin-1-yl)acetamide;
1-{2-[4-(benzhydrylamino)piperidin-1-yl]-2-oxoethyl}-3,3-diphenylpiperidin-2-one;
1-{2-[(4aS,7aS)-1-benzhydryloctahydro-6H-pyrrolo[3,4-b]pyridin-6-yl]-2-oxoethyl}-3,3-diphenylpiperidin-2-one;
N-(1-benzyl-3-methylpyrrolidin-3-yl)-2-(2-oxo-3,3-diphenylpiperidin-1-yl)acetamide;
1-[2-(4-benzhydrylpiperazin-1-yl)-2-oxoethyl]-3,3-bis(4-fluorophenyl)piperidin-2-one;
1-[2-(4-benzhydrylpiperazin-1-yl)-2-oxoethyl]-3-phenylpiperidin-2-one;
1-(2-{4-[bis(4-fluorophenyl)methyl]piperazin-1-yl}-2-oxoethyl)-3-phenylpiperidin-2-one;
1-(2-oxo-2-{4-[3-(trifluoromethyl)benzyl]piperazin-1-yl}ethyl)-3-phenylpiperidin-2-one;
1-{2-[4-(2,4-dichlorobenzyl)piperazin-1-yl]-2-oxoethyl}-3-phenylpiperidin-2-one;
1-[2-(5-fluoro-1,3-dihydro-2H-isoindol-2-yl)-2-oxoethyl]-3-phenylpiperidin-2-one;
1-{2-oxo-2-[7-(trifluoromethyl)-3,4-dihydroisoquinolin-2(1H)-yl]ethyl}-3-phenylpiperidin-2-one;
N-[1-(4-fluorophenyl)cyclobutyl]-2-(2-oxo-3-phenylpiperidin-1-yl)acetamide;
1-[2-(5-fluoro-1,3-dihydro-2H-isoindol-2-yl)-2-oxoethyl]-3-methyl-3-phenylpiperidin-2-one;
3,3-diphenyl-1-({3-[4-(trifluoromethyl)phenyl]-1,2,4-oxadiazol-5-yl}methyl)piperidin-2-one;
1-{[3-(4-fluorophenyl)-1,2,4-oxadiazol-5-yl]methyl}-3,3-diphenylpiperidin-2-one;
1-{2-[[3-(3,5-dimethoxyphenoxy)propyl](methyl)amino]ethyl}-3,3-bis(4-fluorophenyl)pyrrolidin-2-one;
1-{2-[[2-hydroxy-3-(quinolin-5-yloxy)propyl](methyl)amino]ethyl}-3,3-bis(4-methoxyphenyl)pyrrolidin-2-one;
3,3-bis(4-fluorophenyl)-1-{2-[[2-hydroxy-3-(2-{(E)-2-[3-(methoxymethyl)isoxazol-5-yl]vinyl}phenoxy)propyl](methyl)amino]ethyl}pyrrolidin-2-one;
3,3-bis(4-fluorophenyl)-1-{2-[[2-hydroxy-3-(quinolin-5-yloxy)propyl](methyl)amino]ethyl}pyrrolidin-2-one;
3,3-bis(4-fluorophenyl)-1-{2-[4-(3,4,5-trimethoxybenzyl)piperazin-1-yl]ethyl}pyrrolidin-2-one;
3,3-bis(4-fluorophenyl)-1-{3-[4-(3,4,5-trimethoxybenzyl)piperazin-1-yl]propyl}pyrrolidin-2-one;
3,3-bis(4-fluorophenyl)-1-(2-{4-[3-(trifluoromethyl)phenyl]piperazin-1-yl}ethyl)pyrrolidin-2-one;
N-{2-[3,3-bis(4-methoxyphenyl)-2-oxopyrrolidin-1-yl]ethyl}benzamide;
1-{2-[2,3-dihydro-1H-inden-2-ylmethyl)amino]ethyl}-3,3-bis(4-methoxyphenyl)piperidin-2-one;
1-{3-[2,3-dihydro-1H-inden-2-yl(methyl)amino]propyl}-3,3-bis(4-fluorophenyl)pyrrolidin-2-one;
1-{2-[[3-(3,5-dimethoxyphenoxy)propyl](methyl)amino]ethyl}-3,3-bis(4-methoxyphenyl)piperidin-2-one;
1-{3-[[3-(3,5-dimethoxyphenoxy)propyl](methyl)amino]propyl}-3,3-bis(4-methoxyphenyl)piperidin-2-one;
1-{3-[methyl(2-phenylethyl)amino]propyl}-3,3-diphenylpiperidin-2-one;
1-{2-[[2-(3,4-dimethoxyphenyl)ethyl](methyl)amino]ethyl}-3,3-diphenylpiperidin-2-one;
1-{3-[[2-(3,5-dimethoxyphenyl)ethyl](methyl)amino]propyl}-3,3-bis(4-methoxyphenyl)piperidin-2-one;
3,3-bis(4-fluorophenyl)-1-{2-[[2-(3-methoxyphenyl)ethyl](methyl)amino]ethyl}piperidin-2-one;
3,3-bis(4-fluorophenyl)-1-{3-[[2-(3-methoxyphenyl)ethyl](methyl)amino]propyl}piperidin-2-one;
3,3-bis(4-fluorophenyl)-1-{2-[methyl(2-phenylethyl)amino]ethyl}piperidin-2-one;
3,3-bis(4-fluorophenyl)-1-{3-[methyl(2-phenylethyl)amino]propyl}piperidin-2-one;
3,3-bis(4-methoxyphenyl)-1-{2-[[2-(3-methoxyphenyl)ethyl](methyl)amino]ethyl}piperidin-2-one;
3,3-bis(4-methoxyphenyl)-1-{3-[[2-(3-methoxyphenyl)ethyl](methyl)amino]propyl}piperidin-2-one;
1-{2-[[2-(2,4-dimethoxyphenyl)ethyl](methyl)amino]ethyl}-3,3-bis(4-methoxyphenyl)piperidin-2-one;
1-{3-[(3,5-dimethoxybenzyl)(methyl)amino]propyl}-3,3-bis(4-methoxyphenyl)piperidin-2-one;
3-isopropyl-3-(3-methoxyphenyl)-1-{3-[[2-(3-methoxyphenyl)ethyl](methyl)amino]propyl}piperidin-2-one;
1-{3-[[2-(4-fluorophenyl)ethyl](methyl)amino]propyl}-3-isopropyl-3-(3-methoxyphenyl)piperidin-2-one;
3-isopropyl-3-(3-methoxyphenyl)-1-{2-[[2-(4-methoxyphenyl)ethyl](methyl)amino]ethyl}piperidin-2-one;
1-{3-[4-(3,5-dimethoxybenzyl)piperazin-1-yl]propyl}-3,3-bis(4-methoxyphenyl)piperidin-2-one;
1-{2-[4-(3,5-dimethoxybenzyl)piperazin-1-yl]ethyl}-3,3-bis(4-methoxyphenyl)piperidin-2-one;
1-{3-[4-(3,5-dimethoxybenzyl)piperazin-1-yl]propyl}-3-isopropyl-3-(3-methoxyphenyl)piperidin-2-one;
3,3-diphenyl-1-[2-(4-pyrimidin-2-ylpiperazin-1-yl)ethyl]piperidin-2-one;
3,3-bis(4-fluorophenyl)-1-[3-(4-pyrimidin-2-ylpiperazin-1-yl)propyl]piperidin-2-one;
3,3-bis(4-fluorophenyl)-1-[2-(4-pyrimidin-2-ylpiperazin-1-yl)ethyl]piperidin-2-one;
3,3-bis(4-fluorophenyl)-1-{2-[4-(2-methoxyphenyl)piperazin-1-yl]ethyl}piperidin-2-one;
3,3-bis(4-fluorophenyl)-1-{3-[4-(2-methoxyphenyl)piperazin-1-yl]propyl}piperidin-2-one;
3,3-bis(4-fluorophenyl)-1-(2-{4-[3-(trifluoromethyl)phenyl]piperazin-1-yl}ethyl)piperidin-2-one;
3,3-diphenyl-1-(3-{4-[3-(trifluoromethyl)phenyl]piperazin-1-yl}propyl)piperidin-2-one;
3,3-diphenyl-1-(2-{4-[3-(trifluoromethyl)phenyl]piperazin-1-yl}ethyl)piperidin-2-one;
3,3-bis(4-fluorophenyl)-1-(3-{4-[3-(trifluoromethyl)phenyl]piperazin-1-yl}propyl)piperidin-2-one;
N-[2-(3,4-dimethoxyphenyl)ethyl]-N-methyl-2-(2-oxo-3,3-diphenylpiperidin-1-yl)acetamide;
3,3-diphenyl-1-{[3-(trifluoromethyl)phenyl]sulfonyl}pyrrolidin-2-one;
3,3-bis(4-fluorophenyl)-1-{[3-(trifluoromethyl)phenyl]sulfonyl}pyrrolidin-2-one;
3,3-diphenyl-1-{[3-(trifluoromethyl)phenyl]sulfonyl}piperidin-2-one;

1-[(3-{[(cis-2,6-dimethylmorpholin-4-yl]carbonyl}phenyl)sulfonyl]-3,3-diphenylpyrrolidin-2-one;
3,3-diphenyl-1-{[2-(trifluoromethyl)phenyl]sulfonyl}pyrrolidin-2-one;
3,3-diphenyl-1-{[4-(trifluoromethyl)phenyl]sulfonyl}pyrrolidin-2-one;
N-cyclopropyl-3-[(2-oxo-3,3-diphenylpyrrolidin-1-yl)sulfonyl]benzamide;
1-{[2-chloro-4-(trifluoromethyl)phenyl]sulfonyl}-3,3-diphenylpyrrolidin-2-one;
1-[2-(7-benzyl-2,7-diazaspiro[3.5]non-2-yl)-2-oxoethyl]-3,3-bis(4-fluorophenyl)pyrrolidin-2-one;
3,3-bis(4-fluorophenyl)-1-(2-oxo-2-{7-[4-(trifluoromethyl)benzyl]-2,7-diazaspiro[3.5]non-2-yl}ethyl)pyrrolidin-2-one;
1-{[3-(1H-indazol-5-yl)-1,2,4-oxadiazol-5-yl]methyl}-3,3-diphenylpiperidin-2-one;
3,3-diphenyl-1-(3-{3-[4-(trifluoromethyl)phenyl]-1,2,4-oxadiazol-5-yl}propyl)pyrrolidin-2-one;
1-({4-methyl-2-[4-(trifluoromethyl)phenyl]-1,3-thiazol-5-yl}methyl)-3,3-diphenylpyrrolidin-2-one;
1-({4-methyl-2-[3-(trifluoromethyl)phenyl]-1,3-thiazol-5-yl}methyl)-3,3-diphenylpyrrolidin-2-one;
1-{2-[4-(4-chlorophenoxy)piperidin-1-yl]-2-oxoethyl}-3,3-diphenylpiperidin-2-one;
1-{2-[4-(3-chlorophenoxy)piperidin-1-yl]-2-oxoethyl}-3,3-diphenylpiperidin-2-one;
1-{2-[4-(3,4-difluorophenoxy)piperidin-1-yl]-2-oxoethyl}-3,3-diphenylpiperidin-2-one;
1-{2-[4-(4-methoxyphenoxy)piperidin-1-yl]-2-oxoethyl}-3,3-diphenylpiperidin-2-one;
1-(2-oxo-2-{4-[3-(trifluoromethyl)phenoxy]piperidin-1-yl}ethyl)-3,3-diphenylpiperidin-2-one;
1-(2-{4-[(benzyloxy)imino]piperidin-1-yl}-2-oxoethyl)-3,3-diphenylpiperidin-2-one;
1-(2-oxo-2-{4-[5-(trifluoromethyl)-1H-1,2,3-benzotriazol-1-yl]piperidin-1-yl}ethyl)-3,3-diphenylpiperidin-2-one;
1-({3-[2-(4-chlorophenyl)ethyl]-1,2,4-oxadiazol-5-yl}methyl)-3,3-bis(4-fluorophenyl)pyrrolidin-2-one;
2-(2-oxo-3,3-diphenylpiperidin-1-yl)-N-piperidin-4-yl-N-[4-(trifluoromethyl)phenyl]acetamide;
1-{2-[3-(3,4-dimethoxybenzyl)-3-methylpiperazin-1-yl]-2-oxoethyl}-3,3-diphenylpyrrolidin-2-one;
N-(1,3-oxazol-2-ylmethyl)-2-(2-oxo-3,3-diphenylpyrrolidin-1-yl)acetamide;
1-{2-[4-(2,4-dichlorobenzyl)piperazin-1-yl]-2-oxoethyl}-3,3-diphenylpiperidin-2-one;
1-{[3-(4-chlorophenyl)-1,2,4-oxadiazol-5-yl]methyl}-3,3-diphenylpiperidin-2-one;
1-(2-{4-[bis(4-fluorophenyl)methylene]piperidin-1-yl}-2-oxoethyl)-3,3-diphenylpiperidin-2-one;
1-[2-(3,3-diphenylpyrrolidin-1-yl)-2-oxoethyl]-3,3-bis(4-fluorophenyl)piperidin-2-one;
1-[2-(4,4-diphenylpiperidin-1-yl)-2-oxoethyl]-3,3-bis(4-fluorophenyl)piperidin-2-one;
1-[2-(3,3-diphenylpyrrolidin-1-yl)-2-oxoethyl]-3,3-diphenylpiperidin-2-one;
3,3-bis(4-fluorophenyl)-1-(2-oxo-2-{4-[3-(trifluoromethyl)benzyl]piperazin-1-yl}ethyl)piperidin-2-one;
N-(1-benzhydrylazetidin-3-yl)-2-(2-oxo-3,3-diphenylpiperidin-1-yl)acetamide;
3,3-diphenyl-1-({3-[6-(trifluoromethyl)pyridin-3-yl]-1,2,4-oxadiazol-5-yl}methyl)piperidin-2-one;
1-{2-oxo-2-[5-(trifluoromethyl)-1,3-dihydro-2H-isoindol-2-yl]ethyl}-3-phenylpiperidin-2-one;
3,3-diphenyl-1-({3-[3-(trifluoromethyl)phenyl]-1,2,4-oxadiazol-5-yl}methyl)piperidin-2-one;
2-(2-oxo-3,3-diphenylpiperidin-1-yl)-N-{1-[3-(trifluoromethyl)benzyl]azetidin-3-yl}acetamide;
3-phenyl-1-({3-[4-(trifluoromethyl)phenyl]-1,2,4-oxadiazol-5-yl}methyl)piperidin-2-one;
benzyl 4-[(2-oxo-3,3-diphenylpiperidin-1-yl)acetyl]piperazine-1-carboxylate;
N-{1-[4-fluoro-3-(trifluoromethyl)benzyl]piperidin-4-yl}-2-(2-oxo-3,3-diphenylpiperidin-1-yl)acetamide;
1-(2-{4-[4-fluoro-3-(trifluoromethyl)benzyl]piperazin-1-yl}-2-oxoethyl)-3,3-diphenylpiperidin-2-one;
2-(2-oxo-3,3-diphenylpiperidin-1-yl)-N-{(3S)-1-[3-(trifluoromethyl)benzyl]pyrrolidin-3-yl}acetamide;
2-(2-oxo-3,3-diphenylpiperidin-1-yl)-N-{(3R)-1-[3-(trifluoromethyl)benzyl]pyrrolidin-3-yl}acetamide;
(3S)-1-[2-(5-fluoro-1,3-dihydro-2H-isoindol-2-yl)-2-oxoethyl]-3-phenylpiperidin-2-one;
(3R)-1-[2-(5-fluoro-1,3-dihydro-2H-isoindol-2-yl)-2-oxoethyl]-3-phenylpiperidin-2-one;
3-(4-fluorophenyl)-1-({3-[4-(trifluoromethyl)phenyl]-1,2,4-oxadiazol-5-yl}methyl)pyrrolidin-2-one;
3,3-bis(4-fluorophenyl)-1-({3-[4-(trifluoromethyl)phenyl]-1,2,4-oxadiazol-5-yl}methyl)pyrrolidin-2-one;
3,3-bis(4-fluorophenyl)-1-({3-[4-(trifluoromethyl)phenyl]-1,2,4-oxadiazol-5-yl}methyl)piperidin-2-one;
N-(5-chloropyridin-2-yl)-2-(2-oxo-3-phenylpiperidin-1-yl)acetamide;
1-{[3-(4-chlorophenyl)-1,2,4-oxadiazol-5-yl]methyl}-3,3-diphenylpyrrolidin-2-one;
1-{[3-(4-fluorophenyl)-1,2,4-oxadiazol-5-yl]methyl}-3,3-diphenylpyrrolidin-2-one;
1-{[3-(4-methylphenyl)-1,2,4-oxadiazol-5-yl]methyl}-3,3-diphenylpyrrolidin-2-one;
3,3-diphenyl-1-({5-[4-(trifluoromethyl)phenyl]-1,2,4-oxadiazol-3-yl}methyl)pyrrolidin-2-one;
N-methyl-2-(2-oxo-3,3-diphenylpiperidin-1-yl)-N-{1-[3-(trifluoromethyl)benzyl]piperidin-4-yl}acetamide;
N-{1-[4-fluoro-3-(trifluoromethyl)benzyl]azetidin-3-yl}-2-(2-oxo-3,3-diphenylpiperidin-1-yl)acetamide;
3,3-diphenyl-1-({3-[4-(trifluoromethoxy)phenyl]-1,2,4-oxadiazol-5-yl}methyl)piperidin-2-one;
2-(2-oxo-3,3-diphenylpiperidin-1-yl)-N-{1-[3-(trifluoromethyl)benzyl]piperidin-4-yl}acetamide;
N-{1-[2-fluoro-3-(trifluoromethyl)benzyl]azetidin-3-yl}-2-(2-oxo-3,3-diphenylpiperidin-1-yl)acetamide;
1-{[3-(4-tert-butylphenyl)-1,2,4-oxadiazol-5-yl]methyl}-3,3-diphenylpyrrolidin-2-one;
1-{2-[3,3-bis(4-fluorophenyl)pyrrolidin-1-yl]-2-oxoethyl}-3,3-diphenylpyrrolidin-2-one;
1-{2-[3,3-bis(4-fluorophenyl)pyrrolidin-1-yl]-2-oxoethyl}-3,3-bis(4-fluorophenyl)pyrrolidin-2-one;
1-{2-[3,3-bis(4-fluorophenyl)pyrrolidin-1-yl]-2-oxoethyl}-3,3-diphenylpiperidin-2-one;
1-{[3-(4-hydroxyphenyl)-1,2,4-oxadiazol-5-yl]methyl}-3,3-diphenylpiperidin-2-one;
1-{[3-(4-chlorobenzyl)-1,2,4-oxadiazol-5-yl]methyl}-3,3-diphenylpiperidin-2-one;
2-[3,3-bis(4-fluorophenyl)-2-oxopyrrolidin-1-yl]-N-{1-[3-(trifluoromethyl)benzyl]piperidin-4-yl}acetamide;
1-{[3-(4-isobutoxyphenyl)-1,2,4-oxadiazol-5-yl]methyl}-3,3-diphenylpiperidin-2-one;
3,3-bis(4-fluorophenyl)-1-(2-oxo-2-{(4aS,7aS)-1-[3-(trifluoromethyl)benzyl]octahydro-6H-pyrrolo[3,4-b]pyridin-6-yl}ethyl)pyrrolidin-2-one;
3,3-diphenyl-1-({3-[6-(trifluoromethyl)pyridin-3-yl]-1,2,4-oxadiazol-5-yl}methyl)pyrrolidin-2-one;

3,3-bis(4-fluorophenyl)-1-({3-[6-(trifluoromethyl)pyridin-3-yl]-1,2,4-oxadiazol-5-yl}methyl)pyrrolidin-2-one;
1-({3-[2-(4-chlorophenyl)ethyl]-1,2,4-oxadiazol-5-yl}methyl)-3,3-diphenylpiperidin-2-one;
1-{[3-(6-chloropyridin-3-yl)-1,2,4-oxadiazol-5-yl]methyl}-3,3-diphenylpyrrolidin-2-one;
1-{[3-(3,5-difluorophenyl)-1,2,4-oxadiazol-5-yl]methyl}-3,3-diphenylpyrrolidin-2-one;
3-(4-fluorophenyl)-1-{2-oxo-2-[5-(trifluoromethyl)-1,3-dihydro-2H-isoindol-2-yl]ethyl}pyrrolidin-2-one;
2-[3,3-bis(4-fluorophenyl)-2-oxopyrrolidin-1-yl]-N-[5-(trifluoromethyl)pyridin-2-yl]acetamide;
2-[3,3-bis(4-fluorophenyl)-2-oxopyrrolidin-1-yl]-N-[4-(trifluoromethyl)phenyl]acetamide;
3,3-diphenyl-1-({3-[5-(trifluoromethyl)pyridin-3-yl]-1,2,4-oxadiazol-5-yl}methyl)pyrrolidin-2-one;
3,3-diphenyl-1-({3-[4-(trifluoromethyl)pyridin-3-yl]-1,2,4-oxadiazol-5-yl}methyl)pyrrolidin-2-one;
3,3-diphenyl-1-[(3-pyridin-3-yl-1,2,4-oxadiazol-5-yl)methyl]pyrrolidin-2-one;
3,3-diphenyl-1-[(3-pyridin-4-yl-1,2,4-oxadiazol-5-yl)methyl]pyrrolidin-2-one;
1-{4-oxo-4-[5-(trifluoromethyl)-1,3-dihydro-2H-isoindol-2-yl]butyl}-3,3-diphenylpyrrolidin-2-one;
2-[3,3-bis(4-fluorophenyl)-2-oxopyrrolidin-1-yl]-N-[6-(trifluoromethyl)pyridin-3-yl]acetamide;
2-[3,3-bis(4-fluorophenyl)-2-oxopyrrolidin-1-yl]-N-(5-chloropyridin-2-yl)acetamide;
2-[3,3-bis(4-fluorophenyl)-2-oxopyrrolidin-1-yl]-N-[6-(trifluoromethyl)pyridin-2-yl]acetamide;
1-[2-(5-fluoro-1,3-dihydro-2H-isoindol-2-yl)-2-oxoethyl]-3-(4-fluorophenyl)pyrrolidin-2-one;
3,3-bis(4-fluorophenyl)-1-{2-oxo-2-[5-(trifluoromethyl)-1,3-dihydro-2H-isoindol-2-yl]ethyl}pyrrolidin-2-one;
2-[3-(4-fluorophenyl)-2-oxopyrrolidin-1-yl]-N-[5-(trifluoromethyl)pyridin-2-yl]acetamide;
3,3-diphenyl-1-[(3-pyrazin-2-yl-1,2,4-oxadiazol-5-yl)methyl]pyrrolidin-2-one;
tert-butyl 5-{5-[(2-oxo-3,3-diphenylpyrrolidin-1-yl)methyl]-1,2,4-oxadiazol-3-yl}pyridin-2-ylcarbamate;
3,3-bis(4-fluorophenyl)-1-[(3-pyrazin-2-yl-1,2,4-oxadiazol-5-yl)methyl]pyrrolidin-2-one;
1-{[3-(4-bromophenyl)-1,2,4-oxadiazol-5-yl]methyl}-3,3-bis(4-fluorophenyl)pyrrolidin-2-one;
1-{[3-(6-aminopyridin-3-yl)-1,2,4-oxadiazol-5-yl]methyl}-3,3-diphenylpyrrolidin-2-one;
4-(5-{[3,3-bis(4-fluorophenyl)-2-oxopyrrolidin-1-yl]methyl}-1,2,4-oxadiazol-3-yl)benzonitrile;
(3S)-3-(4-fluorophenyl)-1-({3-[4-(trifluoromethyl)phenyl]-1,2,4-oxadiazol-5-yl}methyl)pyrrolidin-2-one;
(3R)-3-(4-fluorophenyl)-1-({3-[4-(trifluoromethyl)phenyl]-1,2,4-oxadiazol-5-yl}methyl)pyrrolidin-2-one;
3-(4-fluorophenyl)-1-({3-[6-(trifluoromethyl)pyridin-3-yl]-1,2,4-oxadiazol-5-yl}methyl)pyrrolidin-2-one;
2-[3,3-bis(4-fluorophenyl)-2-oxopyrrolidin-1-yl]-N-{1-[3-fluoro-4-(trifluoromethyl)benzyl]azetidin-3-yl}acetamide;
1-(2-oxo-2-{3-[4-(trifluoromethyl)phenyl]azetidin-1-yl}ethyl)-3,3-diphenylpiperidin-2-one;
4-{1-[(2-oxo-3,3-diphenylpiperidin-1-yl)acetyl]azetidin-3-yl}benzonitrile;
N-(1-benzylazetidin-3-yl)-2-[3,3-bis(4-fluorophenyl)-2-oxopyrrolidin-1-yl]acetamide;
1-(2-oxo-2-{4-[3-(trifluoromethyl)phenyl]piperidin-1-yl}ethyl)-3,3-diphenylpiperidin-2-one;
1-{2-[4-(4-fluorophenyl)piperidin-1-yl]-2-oxoethyl}-3,3-diphenylpiperidin-2-one;
1-(2-oxo-2-{4-[4-(trifluoromethyl)phenyl]piperidin-1-yl}ethyl)-3,3-diphenylpiperidin-2-one;
2-(2-oxo-3,3-diphenylpyrrolidin-1-yl)-N-[5-(trifluoromethyl)pyridin-2-yl]acetamide;
2-(2-oxo-3,3-diphenylpyrrolidin-1-yl)-N-[6-(trifluoromethyl)pyridin-2-yl]acetamide;
2-(2-oxo-3,3-diphenylpyrrolidin-1-yl)-N-[6-(trifluoromethyl)pyridin-3-yl]acetamide;
N-[3-chloro-5-(trifluoromethyl)pyridin-2-yl]-2-(2-oxo-3,3-diphenylpyrrolidin-1-yl)acetamide;
1-(2-{4-[4-chloro-3-(trifluoromethyl)phenyl]-4-hydroxypiperidin-1-yl}-2-oxoethyl)-3,3-diphenylpiperidin-2-one;
N-(5-cyanopyridin-2-yl)-2-(2-oxo-3,3-diphenylpyrrolidin-1-yl)acetamide;
2-[3,3-bis(4-fluorophenyl)-2-oxopyrrolidin-1-yl]-N-(5-cyanopyridin-2-yl)acetamide;
1-[2-(3,4-dihydroisoquinolin-2(1H)-yl)-2-oxoethyl]-3-(4-fluorophenyl)pyrrolidin-2-one;
3-(4-fluorophenyl)-1-{2-oxo-2-[7-(trifluoromethyl)-3,4-dihydroisoquinolin-2(1H)-yl]ethyl}pyrrolidin-2-one;
1-[2-(7-fluoro-3,4-dihydroisoquinolin-2(1H)-yl)-2-oxoethyl]-3-(4-fluorophenyl)pyrrolidin-2-one;
1-[2-(7-chloro-3,4-dihydroisoquinolin-2(1H)-yl)-2-oxoethyl]-3-(4-fluorophenyl)pyrrolidin-2-one;
1-[2-(6-chloro-3,4-dihydroisoquinolin-2(1H)-yl)-2-oxoethyl]-3-(4-fluorophenyl)pyrrolidin-2-one;
1-[2-(3,4-dihydroisoquinolin-2(1H)-yl)-2-oxoethyl]-3,3-bis(4-fluorophenyl)pyrrolidin-2-one;
3,3-bis(4-fluorophenyl)-1-{2-oxo-2-[7-(trifluoromethyl)-3,4-dihydroisoquinolin-2(1H)-yl]ethyl}pyrrolidin-2-one;
1-[2-(3,4-dihydroisoquinolin-2(1H)-yl)-2-oxoethyl]-3,3-diphenylpiperidin-2-one;
1-{2-oxo-2-[7-(trifluoromethyl)-3,4-dihydroisoquinolin-2(1H)-yl]ethyl}-3,3-diphenylpiperidin-2-one;
1-({3-[2-(2-chlorophenyl)ethyl]-1,2,4-oxadiazol-5-yl}methyl)-3,3-diphenylpiperidin-2-one;
1-({3-[(4-chlorophenoxy)methyl]-1,2,4-oxadiazol-5-yl}methyl)-3,3-diphenylpiperidin-2-one;
(+)-3-(4-fluorophenyl)-1-{2-oxo-2-[5-(trifluoromethyl)-1,3-dihydro-2H-isoindol-2-yl]ethyl}pyrrolidin-2-one;
(−)-3-(4-fluorophenyl)-1-{2-oxo-2-[5-(trifluoromethyl)-1,3-dihydro-2H-isoindol-2-yl]ethyl}pyrrolidin-2-one;
1-[2-(5-fluoro-1,3-dihydro-2H-isoindol-2-yl)-2-oxoethyl]-3-[4-(trifluoromethyl)phenyl]pyrrolidin-2-one;
1-{2-oxo-2-[5-(trifluoromethyl)-1,3-dihydro-2H-isoindol-2-yl]ethyl}-3-[4-(trifluoromethyl)phenyl]pyrrolidin-2-one;
3-(2-chloro-4-fluorophenyl)-1-[2-(5-fluoro-1,3-dihydro-2H-isoindol-2-yl)-2-oxoethyl]pyrrolidin-2-one;
3-(2-chloro-4-fluorophenyl)-1-{2-oxo-2-[5-(trifluoromethyl)-1,3-dihydro-2H-isoindol-2-yl]ethyl}pyrrolidin-2-one;
3-(3,4-dichlorophenyl)-1-[2-(5-fluoro-1,3-dihydro-2H-isoindol-2-yl)-2-oxoethyl]pyrrolidin-2-one;
1-(2-{4-[bis(4-fluorophenyl)(hydroxy)methyl]piperidin-1-yl}-2-oxoethyl)-3,3-bis(4-fluorophenyl)pyrrolidin-2-one; and
1-(2-{4-[bis(4-fluorophenyl)(hydroxy)methyl]piperidin-1-yl}-2-oxoethyl)-3,3-diphenylpiperidin-2-one.

15. A pharmaceutical composition comprising a therapeutically effective amount of a compound of formula (I) according to claim 1 or a pharmaceutically acceptable salt thereof, in combination with a pharmaceutically acceptable carrier.

16. A method of treating pain in a subject in need thereof, comprising: administering to the subject a therapeutically suitable amount of a compound of formula (I) according to claim 1, or a pharmaceutically acceptable salt thereof, wherein the pain is acute pain, chronic pain, neuropathic pain, inflammatory pain, visceral pain, cancer pain, allodynia, fibromyalgia, sciatica, back pain, and headache pain including migraine, or combinations thereof.

17. The compound according to claim 2, wherein
$Ar^2$ is phenyl either unsubstituted or further substituted with 1, 2, or 3 substituents selected from the group consisting of alkyl, halogen, haloalkyl, —C(O)$R^b$, —C(O)N($R^b$)$_2$, wherein $R^b$ at each occurrence, is independently hydrogen, alkyl, or $G^1$; and
$L^1$-$L^2$$\text{------}$Y taken together are S(O)$_r$.

* * * * *